(12) United States Patent
Vasudevan et al.

(10) Patent No.: US 7,468,391 B2
(45) Date of Patent: Dec. 23, 2008

(54) METHODS FOR TREATING RETINOID RESPONSIVE DISORDERS USING SELECTIVE INHIBITORS OF CYP26A AND CYP26B

(75) Inventors: Jayasree Vasudevan, Anaheim, CA (US); Rong Yang, Viejo, CA (US); Liming Wang, Irvine, CA (US); Xiaoxia Liu, Nashua, NH (US); Kwok-Yin Tsang, Irvine, CA (US); Ling Li, Irvine, CA (US); Janet Takeuchi, Anaheim, CA (US); Thong Vu, Garden Grove, CA (US); Richard Beard, Newport Beach, CA (US); Smita Bhat, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 536 days.

(21) Appl. No.: 11/010,953

(22) Filed: Dec. 13, 2004

(65) Prior Publication Data

US 2005/0187298 A1 Aug. 25, 2005

Related U.S. Application Data

(60) Provisional application No. 60/530,601, filed on Dec. 17, 2003.

(51) Int. Cl.
*A01N 31/00* (2006.01)
*A61K 9/00* (2006.01)
*A61K 31/415* (2006.01)
*A61K 9/20* (2006.01)
*A61K 9/48* (2006.01)

(52) U.S. Cl. .................. 514/567; 424/400; 424/404

(58) Field of Classification Search .................. None
See application file for complete search history.

(56) References Cited

U.S. PATENT DOCUMENTS

| 5,648,503 | A | 7/1997 | Vuligonda et al. |
| 5,723,666 | A | 3/1998 | Vuligonda et al. |
| 5,952,345 | A | 9/1999 | Klein et al. |
| 6,252,090 | B1 | 6/2001 | Vasudevan et al. |
| 6,303,785 | B1 | 10/2001 | Vasudevan et al. |
| 6,313,107 | B1 | 11/2001 | Vasudevan et al. |
| 6,359,135 | B1 | 3/2002 | Vasudevan et al. |
| 6,380,256 | B1 | 4/2002 | Vasudevan et al. |
| 6,387,892 | B1 | 5/2002 | Vasudevan et al. |
| 6,387,951 | B1 | 5/2002 | Vasudevan et al. |
| 6,399,774 | B1 | 6/2002 | Vasudevan et al. |
| 6,495,552 | B2 | 12/2002 | Vasudevan et al. |
| 6,531,599 | B2 | 3/2003 | Vasudevan et al. |
| 2002/0132796 | A1 | 9/2002 | Vasudevan et al. |
| 2003/0166932 | A1 | 9/2003 | Beard et al. |

FOREIGN PATENT DOCUMENTS

| WO | WO 01/44443 | 6/2001 |
| WO | WO 02/48334 | 6/2002 |
| WO | WO 03/072769 A1 | 9/2003 |
| WO | WO 2005/007631 A1 | 1/2005 |

OTHER PUBLICATIONS

Johnson, JI et al. "Relationship between drug activity in NCI preclinical in vitro and in vivo models and early clinical trails", British Journal of Cancer, 84(10, p. 1424-1431, 2001.*
Talmadge, et al. "Murine Models to Evaluate Novel and Conventional Strategies for Cancer", American Journal of Pathology, 170(3), p. 793-804, 2007.*
"Prevent"; from dictionary.com accessed Nov. 28, 2007.*
Thacher, et al., "Therapeutic Applications for Ligands of Retinoid Receptors," *Current Pharm. Design* 6:25-58 (2000).
Kuijpers, et al., "The effects of oral liarozole on epidermal proliferation and differentiation in severe plaque psoriasis are comparable with those of acitretin," *British Journal of Dermatology* 139:380-389 (1998).
Bollag, et al., "Retinoids in cancer prevention and therapy," *Ann. Ocol.* 3:513-526 (1992).
Chiesa, et al., "Prevention of Local Relapses and New Localisations of Oral Leukoplakias with the Synthetic Retinoid Fenretinide (4-HPR). Preliminary Results," *Oral Oncol., Eur. J. Cancer* 28(B):97-102 (1992).
Costa, et al., "Prospects of Chemoprevention of Human Cancers with the Synthetic Retinoid Fenretinide," *Cancer Res.* 54:Supp. 54:2032s-2037s (1994).
Verma, "Inhibition of Both Stage I and Stage II Mouse Skin Tumor Promotion by Retinoic Acid and the Dependence of Inhibition of Tumor Promotion on the Duration of Retinoic Treatment," *Cancer Res.* 47:5097-5101 (1987).
Lippman, et al., "13-cis-Retinoic Acid and Interferon alpha-2a: Effective Combination Therapy for Advanced Squamous Cell Carcinoma of the Skin," *J. Natl. Cancer Inst.* 84:235-241 (1992) Text only, no table or figures.
Lippman, et al., "13-cis-Retinoic Acid Plus Interferon alpha-2a: Highly Active Systemic Therapy for Squamous Cell Carcinoma of the Cervix," *J. Natl. Cancer Inst.* 84:241-245 (1992) Text only, no table or figures.
Bonhomme, et al., "Topical treatment of epidemic kaposi's sarcoma with all-trans-retinoic acid," *Ann. Oncol.* 2:234-235 (1991).
Huang, et al., "Use of All-*Trans* Retinoic Acid in the Treatment of Acute Promyelocytic Leukemia," *Blood* 72:567-572 (1988).

(Continued)

*Primary Examiner*—Michael G. Hartley
*Assistant Examiner*—Nissa M Westerberg
(74) *Attorney, Agent, or Firm*—Hamilton, Brook, Smith & Reynolds, P.C.

(57) ABSTRACT

The invention provides methods for treating an individual having a retinoid responsive disorder. In one embodiment, a method involves administering to the individual an effective amount of a selective CYP26B inhibitor, the selective CYP26B inhibitor having at least 10-fold selectivity for CYP26B relative to CYP26A. In another embodiment, a method involves administering to the individual an effective amount of a selective CYP26A inhibitor, the selective CYP26A inhibitor having a chemical formula set forth in the specification. The invention further provides screening methods for identifying a selective CYP26A inhibitor or selective CYP26B inhibitor.

12 Claims, 3 Drawing Sheets

OTHER PUBLICATIONS

Castaigne, et al., "All-Trans Retinoic Acid as a Differentiation Therapy for Acute Promyelocytic Leukemia. I. Clinical Results," *Blood* 76:1704-1709 (1990).

Lo Coco, et al., "Molecular Evaluation of Response to All-Trans-Retinoic Acid Therapy in Patients With Acute Promyelocytic Leukemia," *Blood* 77(8):1657-1659 (1991).

Warrell, et al., Differentiation Therapy of Acute Promyelogytic Leukemia with Tretinoin (All-)(*Trans*)-Retinoic Acid) *N. Engl. J. Med.* 324:1385-1393 (1991).

Chomienne, et al., "Retinoid differentiation therapy in promyelocytic leukemia," *FASEB J.* 10: 1025-1030 (1996).

Conner, et al., "Retinoic Acid Synthesis in Normal and Alzheimer Diseased Brain and Human Neural Cells," *Mol. Chem. Neuropathol.* 30(3):239-252 (1997).

Goodman and Pardee, "Evidence for defective retinoid transport and function in late onset Alzheimer's disease," *Proc. Natl. Acad. Sci. USA*, 100(5):2901-2905 (2003).

Carelli, et al., "Optic nerve degeneration and mitochondrial dysfunction: genetic and acquired optic neuropathies," *Neurochem. Intl.* 40:573-584 (2002).

Olichon, et al., "Loss of OPA1 Perturbates the Mitochondrial Inner Membrane Structure and Integrity, Leading to Cytochrome *c* Release and Apoptosis," *J. Biol. Chem.* 278(10):7743-7746 (2003).

Massaro and Massaro, "Retinoic acid treatment abrogates elastase-induced pulmonary emphysema in rats," *Nature Medicine* 3:675-677 (1997).

Ray, et al., "CYP26, a Novel Mammalian Cytochrome P450, Is Induced by Retinoic Acid and Defines a New Family," *J. Biol. Chem.* 272 (30):18702-18708 (1997).

Loudig, Olivier, et al., "Cytochrome P450RAI(CYP26) Promoter: A Distinct Composite Retinoic Acid Response Element Underlies the Complex Regulation of Retinoic Acid Metabolism," *Mol. Endocrinology*, 14(9):1483-1497 (2000).

White, et al., "Identification of the human cytochrome P450, P450RAI-2, which is predominantly expressed in the adult cerebellum and is responsible for all-trans-retinoic acid metabolism," *Proc. Natl. Acad. Sci. USA* 97(12):6403-6408 (2000).

White, et al., "cDNA Cloning of Huma Retinoic Acid-metabolizing Enzyme (hP450RAI) Identifies a Novel Family of Cytochromes P450 (CYP26)," *J. Biol. Chem.* 272(30):18538-18541 (1997).

Abu-Abed, Suzan, S., "Mouse P40RAI (CYP26) Expression and Retinoic Acid-inducible Retinoic Acid Metabolism in F9 Cells Are Regulated by Retinoic Acid Receptor γ and Retinoid X Receptor α," *J. Biol. Chem.*, 273(4):2409-2415 (1998).

Bligh, et al., "A Rapid Method of Total Lipid Extraction and Purification," *Canadian Journal of Biochemistry and Physiology*, 37(8):911-917 (1959).

Moore, et al., "Homogenous repair of nuclear genes after experimental stroke," *J. Neurochem.* 80:111-118 (2002).

Akasu, et al., "Hyperexcitability of hippocampal CA1 neurons after fluid percussion injury of the rat cerebral cortex," *Neurosci. Lett.* 329:305-308 (2002).

Scheifer, et al., "Rats with chronic spinal cord transection as a possible model for the at-level pain of paraplegic patients," *Neurosci. Lett.* 323:117-120 (2002).

Lewis, et al., "Animal modelss of retinal detachment and reattachment: identifying cellular events that may affect visual recovery," *Eye* 16:375-387 (2002).

Chen, et al., "An Animal Model for Lung Volume Reduction Therapy of Pulmonary Emphysema," *J. Invest Surg* 11:129-137 (1998).

Barlaam, et al., "New α-Substituted Succinate-Based Hydroxamic Acid as TNFα Convertase Inhibitors," *J.Med.Chem.*, 42:4890-4908 (1999).

Floyd, et al., "Cyclic Analog of Ethacrynic Acid," *Journal of Pharmaceutival Sciences*, 59(6):869-870 (1970).

Teng, et al., "Identification of a Retinoic Acid receptor α Subtype Specific Agonist," *Journal of Medicinal Chemistry*, 39(16):3035-3038 (1996).

\* cited by examiner

METHODS FOR TREATING RETINOID RESPONSIVE DISORDERS USING SELECTIVE INHIBITORS OF CYP26A AND CYP26B

RELATED APPLICATION

This application claims the benefit of U.S. Provisional Application No. 60/530,601, filed on Dec. 17, 2003. The entire teachings of this application are incorporated herein by reference.

BACKGROUND OF THE INVENTION

Field of the Invention

This invention relates generally to the treatment of retinoid responsive disorders and, in particular, to the therapeutic use of compounds that selectively inhibit CYP26A (P450RAI-1) or CYP26B(P450RAI-2).

Retinoids, such as retinoic acid (RA), are important modulators of cell division and differentiation, immune response and embryonic development. These molecules function in cells by binding to and activating retinoic acid receptors (RARs), which in turn bind to certain DNA sequences and regulate target gene expression. Retinoid drugs can be used to beneficially modulate the expression of certain target genes to improve or prevent disease conditions. For this reason, over 30 naturally occurring and synthetic analogs of retinoic acid have been developed for use as therapeutics. Current retinoid therapies include differentiation of acute promyelocytic leukemia (APL); treatment of nodulocystic acne, a severe form of inflammatory acne; treatment of psoriasis; prevention of secondary head and neck cancers; topical therapy of acne vulgaris; and reversal of UV-mediated photodamage (Thacher et al., *Current Pharm. Design* 6:25-58 (2000)).

Unfortunately, retinoids can be highly toxic at therapeutic dosages. Therefore, the dosage of retinoids that can be given to a patient is limited by significant side effects, which include irritation and inflammation of skin and mucous membranes, elevation of serum triglycerides, dysregulation of bone formation and resorption, headaches, hypothyroidism, and fetal malformation. Another disadvantage of retinoid therapy is that patients, in particular cancer patients, frequently become resistant to the therapy over time.

Thus, there exists a need to identify new methods for therapeutically increasing or maintaining beneficial levels of retinoic acid and other retinoids in the body to treat disease. The present invention satisfies this need and provides related advantages as well.

SUMMARY OF THE INVENTION

The invention provides methods for treating an individual having a retinoid responsive disorder. In one embodiment, a method involves administering to the individual an effective amount of a selective CYP26B (P450RAI-2) inhibitor, the selective CYP26B inhibitor having at least 10-fold selectivity for CYP26B relative to CYP26A. A selective CYP26B inhibitor used in a method of the invention can have at least 20-fold selectivity for CYP26B relative to CYP26A (P450RAI-1), for example, at least 100-fold, at least 500-fold and at least 1000-fold selectivity for CYP26B relative to CYP26A. Exemplary selective CYP26B inhibitors that can be used in a method of the invention are set forth herein below as Formulas 5, 15 and 30 through 32.

In another embodiment, a method for treating an individual having a retinoid responsive disorder involves administering to the individual an effective amount of a selective CYP26A inhibitor, the selective CYP26A inhibitor having at least 10-fold selectivity for CYP26A relative to CYP26B and having a formula selected from Formulas 1 through 4, 6 through 14, 16, 17 and 18 through 29, as set forth herein below. A selective CYP26A inhibitor used in a method of the invention can have at least 20-fold selectivity for CYP26A relative to CYP26B, for example, at least 100-fold, at least 500-fold and at least 1000-fold selectivity for CYP26A relative to CYP26B.

Exemplary retinoid responsive disorders than can be treated using a method of the invention include a skin disorder, such as acne, an autoimmune disorder, an inflammatory disorder, a proliferative disorder, a neurological disorder, an ocular disorder and a pulmonary disorder. In various embodiments, a selective CYP26A inhibitor or selective CYP26B inhibitor can be administered, for example, peripherally or orally. In an embodiment, a method of the invention can be used to treat a human having a retinoid responsive disorder.

The invention further provides a screening method for identifying a selective CYP26A inhibitor that has at least 10-fold selectivity for CYP26A relative to CYP26B. The method involves contacting a CYP26A with one or more candidate compounds; selecting from the candidate compounds a compound that inhibits CYP26A activity; determining the ability of the selected compound to inhibit CYP26B activity; and identifying a compound having at least 10-fold selectivity for CYP26A relative to CYP26B. The invention also provides screening for identifying a selective CYP26B inhibitor that has at least 10-fold selectivity for CYP26B relative to CYP26A.

DETAILED DESCRIPTION OF THE INVENTION

Figure 1:
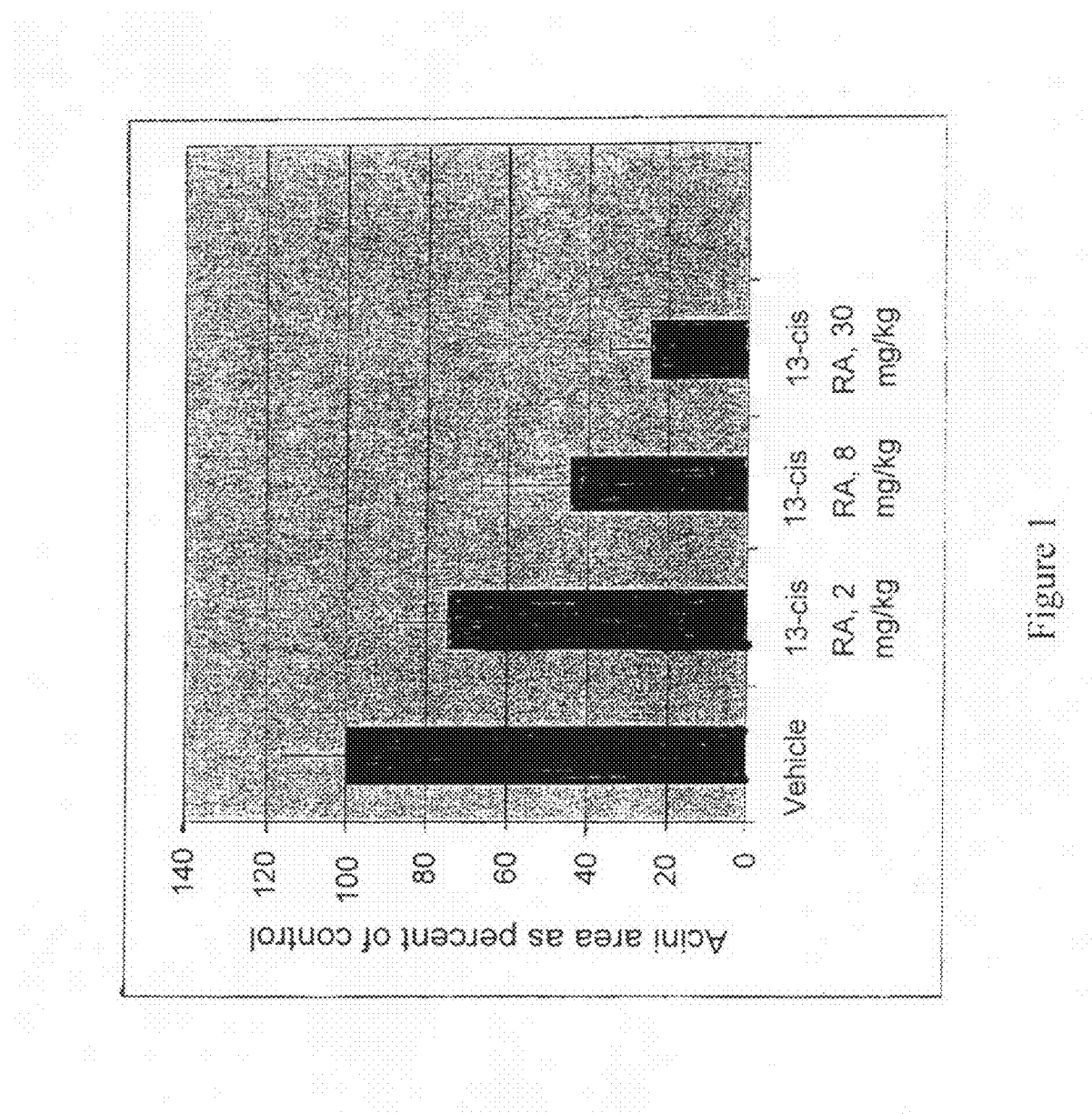
FIG. 1 shows that 13-cis retinoic acid is effective in reducing sebaceous gland differentiation in hamster flank organ.

Retinoids play important roles in regulating gene expression during embryonic development and in the maintenance of adult epithelial tissues. The amount of a retinoid, such as retinoic acid (RA), present in the body at a given time is regulated, in part, by cellular metabolism. The cytochrome P450 molecules CYP26A and CYP26B, also known as P450RAI-1 and P450RAI-2, respectively, metabolize RA into more polar hydroxylated and oxidized derivatives, thus reducing the level of this retinoid in the body. By blocking the RA-destroying activity of CYP26A or CYP26B, the amount of natural or administered RA in a cell can be maintained at a beneficial level. Therefore, an inhibitor of CYP26A or CYP26B can be used to beneficially maintain or increase a level of a retinoid in an individual, either alone or in conjunction with retinoid treatment.

Administration of certain CYP26A inhibitors to mammals has been observed to cause a significant increase in endogenous retinoic acid levels (see, for example, U.S. Pat. Nos. 6,531,599 and 6,495,552). For example, treatment of human patients with the CYP26A inhibitor liarozole results in beneficial effects similar to those observed upon treatment with retinoids, such as amelioration of psoriasis (Kuijpers, et al., *British Journal of Dermatology* 139:380-389 (1998)).

As herein below, selective inhibitors of CYP26A having at least 10-fold selectivity for CYP26A relative to CYP26B have been identified and are referenced as Formulas 1 through 4, 6 through 14, 16, 17 and 18 through 29. A variety of exemplary selective CYP26A inhibitors and selective CYP26B inhibitors are shown in Table 4 below. The selective CYP26A inhibitors shown in Table 4 have selectivity that ranges from at least 10-fold to at least 888-fold selectivity for CYP26A relative to CYP26B. The selective CYP26B inhibitors shown in Table 4 have selectivity that ranges from at least 10-fold to at least 83-fold selectivity for CYP26B relative to CYP26A. Although the selective CYP26A inhibitors disclosed herein are structurally unrelated to previously described CYP26A inhibitors, these compounds can provide similar beneficial effects by reducing destruction of endogenous or administered retinoids, including, without limitation, retinoic acid and retinoic acid analogs. Based on the identification of selective inhibitors of CYP26A and CYP26B, the present invention provides therapeutic methods that involve selective inhibition of CYP26A or CYP26B. The methods are useful for beneficially treating an individual having any of a variety of retinoid responsive disorders disclosed herein below or otherwise known in the art.

As disclosed herein in Example I, compounds that selectively inhibit CYP26A or CYP26B activity were demonstrated to be effective in reducing sebocyte differentiation in an animal model of acne development. In this animal model, which involves observation of sebaceous gland differentiation in hamster flank organ, retinoids and retinoic acid receptor agonists blocked differentiation, which is akin to blocking acne development in a mammal such as a human. Moreover, treatment with a selective CYP26A inhibitor or a selective CYP26B inhibitor reduced sebocyte differentiation as effectively as ACCUTANE™, one of the most widely used commercially available retinoic acid acne medications. Thus, in one embodiment, the present invention provides a method of treating a retinoid responsive disorder by administering an effective amount of a selective CYP26A inhibitor having any of Formulas 1 through 4, 6 through 14, 16, 17 and 18 through 29 or a selective CYP26B inhibitor that has at least 10-fold selectivity for CYP26B relative to CYP26A.

As used herein, the term "retinoid responsive disorder" means a condition or disease that normally has at least one symptom that is improved, alleviated, delayed in onset, or prevented upon administration of retinoic acid (RA) or a synthetic retinoid having RA activity. A variety of retinoid responsive disorders are well known to those skilled in the art and include, without limitation, cancers such as skin cancer, oral cancer and Kaposi's sarcoma; skin disorders such as acne, psoriasis and eczema; and multiple other disorders of diverse etiology, including but not limited to emphysema and Alzheimer's disease.

The ability of RA or a synthetic retinoid having RA activity to improve, alleviate, delay onset of, or prevent at least one symptom of a condition or disease, if not known, can be determined using well known methods, including those described herein below. A synthetic retinoid used for such a determination can be any of a variety of experimental or clinically used retinoids. Exemplary synthetic retinoids currently in clinical use include acitretin, isotretinoin, tretinoin, tazarotene and adapalene.

A variety of retinoid responsive skin disorders can be treated according to a method of the invention. Such skin disorders include, without limitation, inflammatory and non-inflammatory acne, psoriasis, eczema, atopic dermatitis, Pityriasis rubra pilaris, multiple basal cell carcinomasactinic keratoses, arsenic keratoses, ichthyoses and other keratinization and hyperproliferative disorders of the skin, Darriers disease, lichen planus, glucocorticoid damage (steroid atrophy), microbial infection of the skin, excessive pigmentation of the skin, and photodamage of the skin.

In several embodiments, the invention provides methods for treating acne that involve administering a selective CYP26A inhibitor or a selective CYP26B inhibitor. Acne is a common disease of the pilosebaceous glands, and is characterized by comedones, papules, pustules, inflamed nodules, superficial pus-filled cysts, and (in extreme cases) canalizing and deep, inflamed, sometimes purulent sacs.

Multiple categories or types of acne have been defined in the art based on the severity of the condition. For example, "superficial acne" is characterized by blackheads (open comedones) or whiteheads (closed comedones), inflamed papules, pustules, and superficial cysts, with large cysts occurring occasionally. As another example, "deep acne" is similarly characterized except with deep inflamed nodules and pus-filled cysts, which often rupture and become abscesses. Other categories of acne include "acne vulgaris," which is the most common form of acne; "acne conglobata," which is acne that covers the back, chest, and buttocks with pustules and nodules that often connect under the skin; "acne fulminans," which is an extreme form of acne conglobata that involves a sudden onset of pustules and nodules, infected nodules, fever, joint pain, and possible loss of weight or appetite; "acne medicamentosa," which is caused by a drug; "comedonal acne," which is acne characterized by whiteheads and blackheads without other forms of skin lesions, and "cystic acne," which occurs when the infected contents of a pustule or pimple erupt beneath the skin, rather than on the surface. It is understood that a method of the invention can be used to beneficially treat an individual having any form of mild, moderate or severe acne including, but not limited to, those discussed above.

In a further embodiment, the invention provides a method for treating an individual having a proliferative disorder that involves administering to the individual an effective amount of a selective CYP26B inhibitor that has at least 10-fold selectivity for CYP26B relative to CYP26A, or an effective amount of a selective CYP26A inhibitor, which is represented by any of Formulas 1 through 4, 6 through 14, 16, 17 and 18 through 29. As used herein, the term "proliferative disorder" means a disease or abnormal condition that results in unwanted or abnormal cell growth, viability or proliferation. Proliferative disorders include diseases such as cancer, in which the cells are neoplastically transformed, and diseases resulting from overgrowth of normal cells. For example, cell proliferative disorders include diseases associated with the overgrowth of connective tissues, such as various fibrotic diseases, including scleroderma, arthritis, alcoholic liver cirrhosis, keloid, and hypertropic scarring; vascular proliferative disorders, such as atherosclerosis; benign tumors, and the abnormal proliferation of cells mediating autoimmune disease. As used herein, the term "cancer" means a class of diseases characterized by the uncontrolled growth of aberrant cells, including all known cancers, and neoplastic conditions, whether characterized as malignant, benign, soft tissue or solid tumor. Specific cancers that can be treated using a method of the invention include, without limitation, cancers of the skin, breast, eye, prostate, cervix, uterus, colon, bladder, esophagus, stomach, lung, larynx, oral cavity, blood and lymphatic system, metaplasias, dysplasias, neoplasias, leukoplakias, papillomas of the mucous membranes and Kaposi's sarcoma.

A compound that beneficially maintains or increases a level of a retinoid in the body by selective inhibition of CYP26A or CYP26B can be used to treat a variety of cancers. For example, increasing the amount of retinoid in the body of cancer patients has been a successful strategy for treating a variety of cancers. For example, retinoids have been used to reduce or prevent oral, skin and head and neck cancers in individuals at risk for these tumors (see, for example, Bollag et al., *Ann. Oncol.* 3:513-526 (1992); Chiesa et al., *Eur. J. Cancer B. Oral Oncol.* 28:97-102 (1992); Costa et al., *Cancer Res.* 54:Supp. 7, 2032-2037 (1994)). Retinoids have also been used to treat squamous cell carcinoma of the cervix and the skin (see, for example, Verma, *Cancer Res.* 47:5097-5101 (1987); Lippman et al., *J. Natl Cancer Inst.* 84:235-241 (1992); Lippman et al., *J. Natl Cancer Inst.* 84:241-245 (1992)) and Kaposi's sarcoma (see, for example, Bonhomme, et al., *Ann. Oncol.* 2:234-235 (1991)), and have found significant use in the therapy of acute promyelocytic leukemia (see, for example, Huang et al., *Blood* 72:567-572 (1988); Castaigne et al., *Blood* 76:1704-1709 (1990); Lo Coco et al., *Blood* 77:1657-1659 (1991); Warrell et al., *N. Engl. J. Med* 324:1385-1393 (1991); and Chomienne et al., *FASEB J.* 10: 1025-1030 (1996)). Therefore, a compound that beneficially maintains or increases a level of a retinoid in the body by selective inhibition of CYP26A or CYP26B can be used to treat a variety of cancers using a method of the invention.

In another embodiment, the invention provides a method for treating an individual having a retinoid responsive neurological disorder that involves administering to the individual an effective amount of a selective CYP26B inhibitor that has at least 10-fold selectivity for CYP26B relative to CYP26A, or an effective amount of a selective CYP26A inhibitor represented by any of Formulas 1 through 4, 6 through 14, 16, 17 and 18 through 29. Because a selective CYP26A inhibitor or selective CYP26B inhibitor can beneficially maintain or increase a level of a retinoid in a nervous system tissue of an individual, such an inhibitor can be used for treating a variety of neurological disorders that respond beneficially to retinoids. Both CYP26A and CYP26B are highly expressed in the brain, and multiple lines of evidence indicate that retinoids such as RA have important roles in normal neurological function and neurological disease. For example, retinaldehyde, dehydrogenase, the enzyme that forms retinoic acid from retinaldehyde has 1.5 to 2-fold higher activity in the hippocampus and parietal cortex of Alzheimer's diseased brains than in normal controls (Conner and Sidell, *Mol Chem Neuropathol* 30(3):239-52 (1997)). In addition, retinoid hypofunction and impaired retinoid transport have been indicated to be contributing factors in Alzheimer's Disease (Goodman and Pardee, *Proc. Natl. Acad. Sci. USA* 4; 100(5):2901-5 (2003)). Exemplary retinoid responsive neurological disorders that can be treated with a selective CYP26A or selective CYP26B inhibitor according to a method to the invention, include, yet are not limited to, Alzheimer's Disease, schizophrenia, Parkinson's disease, anxiety, depression, drug addiction, disorders of cognition, emesis, eating disorders, attention deficit-hyperactivity disorder, Tourette's Syndrome, Huntington's disease, tardive dyskinesia, Lesch-Nyhan disease, Rett syndrome or any neurological disorder that is retinoid responsive.

In a further embodiment, the invention provides a method for treating an individual having a retinoid responsive inflammatory disorder or autoimmune disorder by administering to the individual an effective amount of a selective CYP26B inhibitor that has at least 10-fold selectivity for CYP26B relative to CYP26A, or an effective amount of a selective CYP26A inhibitor represented by any of Formulas 1 through 4, 6 through 14, 16, 17 and 18 through 29. A method of the invention can be used to treat any of a variety of inflammatory disorders, including, without limitation, those resulting from injury; infection by a bacteria, virus, fungus or other pathogen; autoimmune disorders; and other abnormal conditions. Exemplary retinoid responsive inflammatory disorders that can be treated using a method of the invention include, without limitation, inflammatory skin disorders, for example, psoriasis; inflammatory gastrointestinal disorders, for example, ileitis, irritable bowel syndrome, ulcerative colitis and Crohn's disease; autoimmune disorders such as rheumatoid and other forms of arthritis; organ transplant rejection; and any inflammatory or autoimmune disorder that is retinoid responsive.

In another embodiment, the invention provides a method for treating an individual having a retinoid responsive ocular disorder that involves administering to the individual an effective amount of a selective CYP26B inhibitor that has at least 10-fold selectivity for CYP26B relative to CYP26A, or an effective amount of a selective CYP26A inhibitor represented by any of Formulas 1 through 4, 6 through 14, 16, 17 and 18 through 29. A method of the invention can be used for treating a variety of ocular disorders, including, without limitation, diabetic retinopathy; macular edema such as macular edema associated with diabetes mellitus or other conditions; retinal degeneration such as age-related macular degeneration or retinitis pigmentosa; inflammatory disorders of the retina; vascular occlusive conditions of the retina such as retinal vein occlusions or branch or central retinal artery occlusions; retinopathy of prematurity; retinopathy associated with blood disorders such as sickle cell anemia; damage following retinal detachment; damage or insult due to vitrectomy surgery or retinal surgery; and other retinal damage including therapeutic damage such as that resulting from laser treatment of the retina, for example, pan-retinal photocoagulation for diabetic retinopathy or photodynamic therapy of the retina, for example, for age-related macular degeneration; genetic and acquired optic neuropathies such as optic neuropathies characterized primarily by loss of central vision, for example, Leber's hereditary optic neuropathy (LHON), autosomal dominant optic atrophy (Kjer disease) and other optic neuropathies such as those involving mitochondrial defects, aberrant dynamin-related proteins or inappropriate apoptosis, proliferative vitreoretinopathy (PVR), retinal detachment, dry eye, as well as any ocular disorder that is retinoid responsive. In reference to ocular disorders see, for example, Carelli et al., *Neurochem. Intl.* 40:573-584 (2002); and Olichon et al., *J. Biol. Chem.* 278:7743-7746 (2003).

In yet another embodiment, the invention provides a method for treating an individual having a pulmonary disorder that involves administering to the individual an effective amount of a selective CYP26B inhibitor that has at least 10-fold selectivity for CYP26B relative to CYP26A, or an effective amount of a selective CYP26A inhibitor represented by any of Formulas 1 through 4, 6 through 14, 16, 17 and 18 through 29. Retinoid treatment has been used to successfully treat, for example, emphysema, which is a pulmonary disorder resulting from progressive destruction of alveolar septae that was considered irreversible until it was shown that retinoid acid administration can reverse anatomic and physiologic signs of emphysema in a rat model (Massaro and Massaro, *Nature Medicine* 3:675-7 (1997)). A method of the invention can be used to treat emphysema or another pulmonary disorder that is retinoid responsive. Non-limiting examples of pulmonary disorders include, but are not limited to, obstructive pulmonary disorders such as emphysema, chronic bronchitis, bronchial asthma, bronchiectasis and cystic fibrosis; and restrictive pulmonary disorders such as interstitial fibrosis, pulmonary edema, adult respiratory distress syndrome, rheumatoid spondylitis and pleural effusion.

It is understood that increasing the level of a retinoid in a tissue of an individual can have beneficial effects in individuals having a variety of other retinoid responsive disorders, including cardiovascular disorders such as, without limitation, diseases associated with lipid metabolism including dyslipidemias and post-angioplasty restenosis; and diabetes. Thus, the methods can be useful for treating a variety of retinoid responsive disorders including, but not limited to, skin disorders, autoimmune disorders, inflammatory disorders, proliferative disorders, neurological disorders, ocular disorders and pulmonary disorders.

By specific mention of the above categories of retinoid responsive disorders, those skilled in the art will understand that such terms include all classes and types of these disorders. For example, the term "skin disorder" is intended to include any skin disorder having a symptom that is improved, alleviated, delayed in onset or prevented upon administration of RA or a synthetic retinoid having RA activity; and likewise for other classes of disorders such as proliferative disorders, pulmonary disorders, autoimmune disorders, inflammatory disorders, neurological disorders and ocular disorders. Those skilled in the art will know how to appropriately assess whether a disorder has at least one symptom that is improved, alleviated, delayed in onset or prevented upon administration of RA or a synthetic retinoid having RA activity. Therefore, the methods of the invention are applicable to known retinoid responsive disorders as well as disorders determined to be retinoid responsive, for example, in an animal model that corresponding to a particular disorder.

As disclosed herein below, CYP26A and CYP26B have distinct expression levels in various tissues in humans and other mammals. Thus, a selective CYP26A inhibitor or selective CYP26B inhibitor can be used to inhibit the activity of a particular CYP26, such as CYP26A, for example, in a selected tissue without substantially altering the activity of CYP26B in that tissue, and visa versa. A selective CYP26A inhibitor or selective CYP26B inhibitor also can be used to target inhibition of a CYP26 in a particular tissue, if desired. It is also understood that a selective CYP26A inhibitor or selective CYP26B inhibitor can be beneficially used without targeting particular tissues for CYP26 inhibition.

In humans, CYP26A expression has been observed in liver, brain and placenta (Ray et al. *J. Biol. Chem.* 272:18702-18708 (1997)); CYP26B expression has been observed in brain (White et al. *Proc. Natl. Acad. Sci. USA* 97:6403-6408 (2000)) as well as in kidney, lung, spleen, fetal spleen, skeletal muscle, thymus, peripheral blood leukocyte, lymph node, bone, stomach, placenta, duodenum, small intestine, and pituitary gland (PCT/CA00/01493). It is understood that either or both CYP26A and CYP26B can be present in other tissues in humans or other mammals. For example, as shown in Example I, both CYP26A and CYP26B are expressed in the skin of hamsters.

It is understood that a selective CYP26A or selective CYP26B inhibitor can be useful for treating a retinoid responsive disorder associated with a tissue in which either CYP26A or CYP26B is expressed. For example, an individual having a cancer in a tissue in which CYP26A is expressed can be treated using a selective CYP26A inhibitor, while an individual having a cancer in a tissue in which CYP26B is expressed can be treated using a selective CYP26B inhibitor. Thus, the expression of CYP26A or CYP26B in a particular tissue can be used to assess whether treatment of a particular retinoid responsive disorder with a selective CYP26A or selective CYP26B inhibitor is appropriate. It is understood that a selective CYP26A or selective CYP26B inhibitor can be useful for treating a retinoid responsive disorder even when the target tissue contains a low level of expression of either CYP26A or CYP26B. Methods for determining expression levels of CYP26A or CYP26B mRNA or protein are well known to those skilled in the art and are described, for example, in Sambrook et al., *Molecular Cloning: A Laboratory Manual*, Cold Spring Harbor Laboratory, New York (1992) and Ausubel et al., *Current Protocols in Molecular Biology*, John Wiley and Sons, Baltimore, Md. (1998).

Selective CYP26A and CYP26B Inhibitors

A. Functional Characteristics

The methods of the invention involve administering a selective CYP26A inhibitor or selective CYP26B inhibitor. As used herein, the term "selective CYP26A inhibitor" means a compound that reduces CYP26A expression or activity at least 10-fold more than any reduction affected by the inhibitor on the expression or activity of CYP26B. A selective CYP26A inhibitor can have, for example, at least 10-fold selectivity for CYP26A relative to CYP26B, at least 20-fold, at least 40-fold, at least 80-fold, at least 100-fold, at least 500-fold, at least 800-fold, or at least 1000-fold selectivity for CYP26A relative to CYP26B. As used herein, a "CYP26B inhibitor" means that reduces CYP26B expression or activity at least 10-fold more than any reduction affected by the inhibitor on the expression or activity of CYP26A. A selective CYP26B inhibitor can have, for example, at least 10-fold selectivity for CYP26A relative to CYP26B, at least 20-fold, at least 40-fold, at least 80-fold, at least 100-fold, at least 500-fold, at least 800-fold, or at least 1000-fold selectivity for CYP26B relative to CYP26A. Exemplary small molecule selective CYP26A inhibitors are disclosed herein as Formulas 1 through 4, 6 through 14, 16, 17 and 18 through 29; exemplary small molecule selective CYP26B inhibitors are disclosed herein as Formulas 5, 15 and 30 through 32. A selective CYP26A or selective CYP26B inhibitor also can be, for example, a protein, peptide, peptidomimetic, ribozyme, nucleic acid molecule or oligonucleotide, oligosaccharide, or small molecule or combination thereof.

A selective CYP26A inhibitor or selective CYP26B inhibitor useful in a method of the invention can act by any mechanism, and can, for example, alter the catalytic action of the specified enzyme and consequently reduce, or in some cases, stop catalysis. A selective CYP26A inhibitor or selective CYP26B inhibitor can therefore be a competitive, noncompetitive, or uncompetitive inhibitor of CYP26A or CYP26B, respectively, and further can function in a reversible or irreversible manner. It is understood that a selective CYP26A inhibitor or selective CYP26B inhibitor also can act indirectly, such as by reducing or down-regulating mRNA or protein expression of CYP26A or CYP26B, respectively.

A selective CYP26A inhibitor or selective CYP26B useful in a method of the invention does not bind to a retinoic acid receptor (RAR), or subunit thereof.

B. Structural Characteristics

As disclosed herein, a variety of structurally unrelated compounds having at least 10-fold selectivity for CYP26A relative to CYP26B can be selective CYP26A inhibitors; and a variety of structures unrelated compounds having at least 10-fold selectivity for CYP26B relative to CYP26A, can be selective CYP26B inhibitors and therefore can be useful in a method of the invention. A selective CYP26A inhibitor can be, for example, an organic molecule represented by any of Formulas 1 through 4, 6 through 14, 16, 17 and 18 through 29 below, or a pharmaceutically acceptable salt, ester, amide, steroisomer or racemic mixture thereof. A selective CYP26B can be, for example, an organic molecule represented by any of Formulas 5, 15 and 30 through 32, below, or a pharmaceutically acceptable salt, ester, amide, steroisomer or racemic mixture thereof.

As disclosed herein in Table 4, identified CYP26A inhibitors have selectivities of about 10-fold, about 40-fold, about 60-fold, about 80-fold, about 200-fold, about 300-fold, and about 900-fold; the identified CYP26B inhibitors have selectivities of about 10 fold, such as about 25-fold, about 50-fold and about 80-fold. It is understood that these and other selective CYP26A inhibitors and selective CYP26B inhibitors can be useful for treating a retinoid responsive disorder according to a method of the invention.

Compounds useful in the methods of the invention are set forth in two sections below. The first section describes Formulas 18 through 32, which are encompassed by generic Formulas 1 through 17. The second section describes Formulas 1 through 17.

I. Formulas 18 through 32

Formula 18:

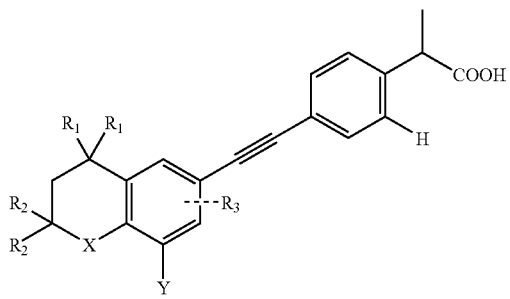

or

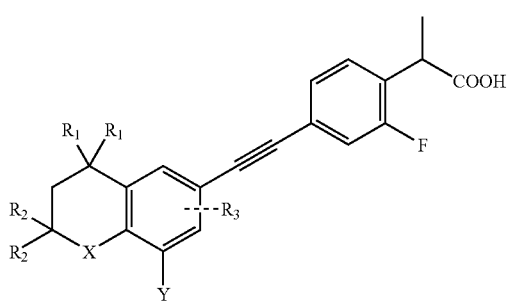

wherein,
$R_3$=H or lower alkyl; and
$R_1$=$R_2$=H, Me or Et;
X=O or S;
Y=$CH_2N(Me)(cyc$-$Pr)$, H, halo, OH, lower alkoxy, lower alkyl, haloalkyl, cycloalkyl, alkenyl, or alkynyl; or
$R_1$=Me;
$R_2$=H;
X=H(C)$CH_2N(Me)(cyc$-$Pr)$;,
Y=H, halo, lower alkoxy, lower alkyl, cycloalkyl or haloalkyl; or
$R_1$=Me,
$R_2$=H;
X=C=O,
Y=H, lower alkyl, haloalkyl, lower alkoxy, cycloalkyl, alkenyl or alkynyl.

Formula 19:

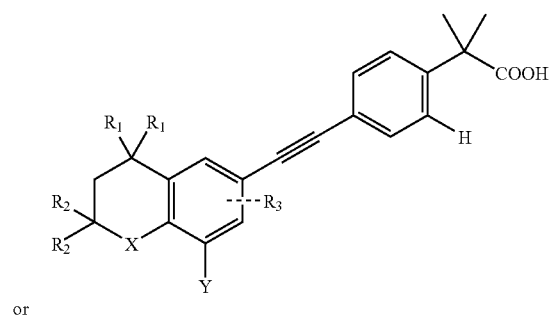

or

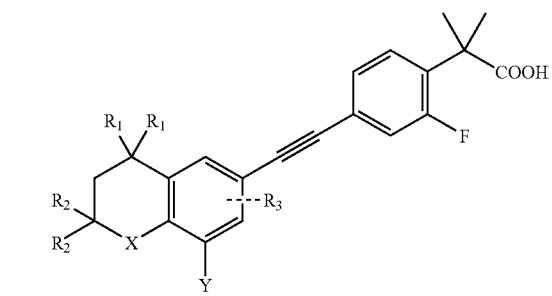

wherein,
$R_3$=H or lower alkyl; and
$R_1$=$R_2$=H, Me or Et;
X=O or S; and
Y=$CH_2N(Me)(cyc$-$Pr)$, H, halo, OH, lower alkoxy, lower alkyl, haloalkyl, cycloalkyl, alkenyl, or alkynyl; or
$R_3$=H or lower alkyl; and
$R_1$=Me;
$R_2$=H;
X=H(C)$CH_2N(Me)(cyc$-$Pr)$; and
Y=H, halo, lower alkoxy, lower alkyl, cycloalkyl or haloalkyl; or
$R_3$=H or lower alkyl; and
$R_1$=Me;
$R_2$=H;
X=C=O; and
Y=H, lower alkyl, haloalkyl, lower alkoxy, cycloalkyl, alkenyl or alkynyl.

Formula 20:

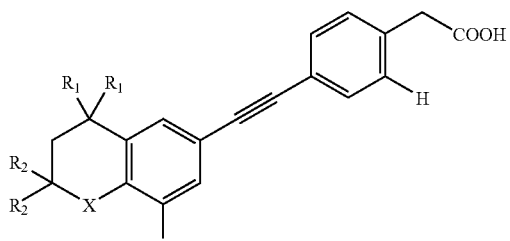

or

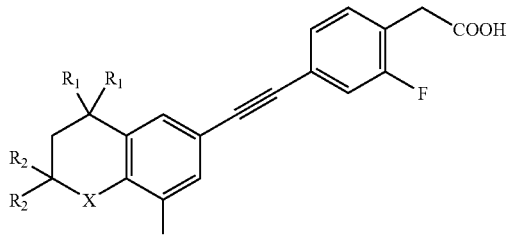

wherein,
R₁=R₂=Me;
X=O or S; and
Y=CH₂N(Me)(cyc-Pr), OR or COOR, wherein R=lower alkyl or cycloalkyl; or
R₁=Me;
R₂=H;
X=H(C)CH₂N(Me)(cyc-Pr); and
Y=OR, COOR wherein R=lower alkyl, or cycloalkyl; or
R₁=Me;
R₂=H;
X=C=O; and
Y=alkenyl.

Formula 21:

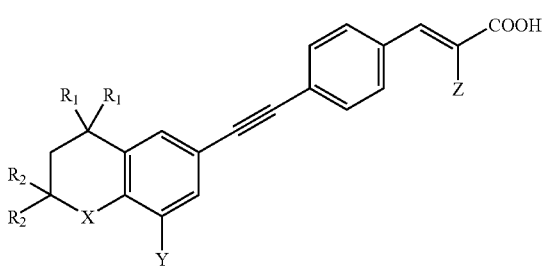

wherein,
R₁=R₂=Me;
X=O or S; and
Y=lower alkyl, haloalkyl, cycloalkyl, CH₂N(Me)(cyc-Pr), OR, COOR, wherein R=lower alkyl, cycloalkyl; or
R₁=Me;
R₂=H;
X=H(C)CH₂N(Me)(cyc-Pr); and
Y=lower alkyl, haloalkyl, cycloalkyl, OR, COOR, wherein R=lower alkyl, or cycloalkyl; or
R₁=Me;
R₂=H;

X=C=O; and
Y=alkenyl, lower alkyl, or cycloalkyl.

Formula 22:

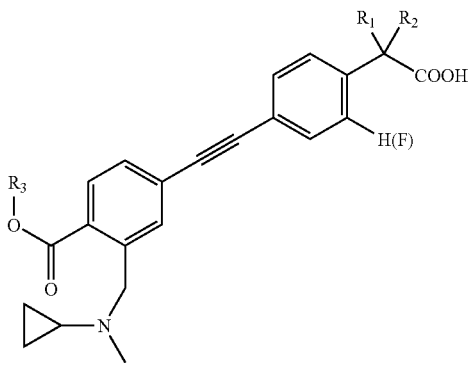

wherein,
R₃=Lower alkyl; and
R₁=R₂=H or Me; or
R₁=Me; and
R₂=H.

Formula 23:

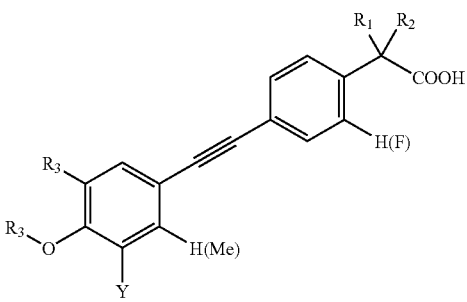

wherein,
R₃=lower alkyl; and
R₁=H and R₂=H; and
Y=alkenyl, or alkynyl; or
R₁=Me and R₂=H or Me; and
Y=lower alkyl, alkenyl, or alkynyl; or
R₁=H or Me and R₂=Me; and
Y=lower alkyl, alkenyl, or alkynyl.

Formula 24:

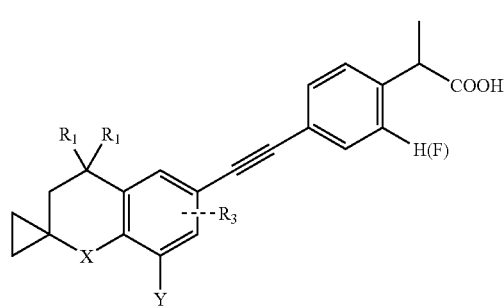

wherein,
R₃=H or lower alkyl; and
R₁=H, Me or Et;
X=O or S; and
Y=CH₂N(Me)(cyc-Pr), H, lower alkoxy, lower alkyl, cycloalkyl, alkenyl, or alkynyl; or
R₁=Me;
X=H(C)CH₂N(Me)(cyc-Pr); and
Y=H, lower alkoxy, lower alkyl, cycloalkyl, alkenyl or alkynyl; or
R₁=Me;
X=C=O; and
Y=H, lower alkyl, lower alkoxy, cycloalkyl, alkenyl or alkynyl.

Formula 25:

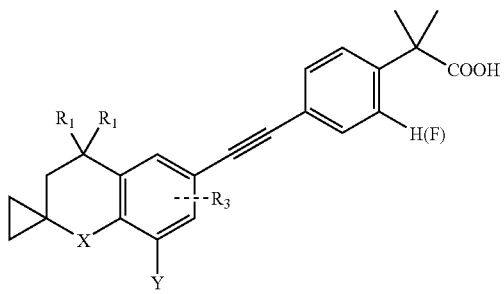

wherein,
R₃=H or lower alkyl; and
R₁=H, Me or Et;
X=O or S; and
Y=CH₂N(Me)(cyc-Pr), H, lower alkoxy, lower alkyl, cycloalkyl, alkenyl or alkynyl; or
R₁=Me;
X=H(C)CH₂N(Me)(cyc-Pr); and
Y=H, lower alkoxy, lower alkyl, cycloalkyl, alkenyl or alkynyl; or
R₁=Me;
X=C=O; and
Y=H, lower alkyl, lower alkoxy, cycloalkyl, alkenyl or alkynyl.

Formula 26:

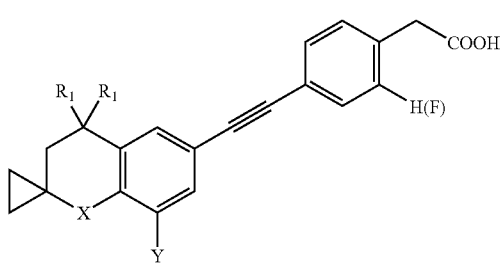

wherein,
R₁=H, Me or Et;
X=O or S; and
Y=CH₂N(Me)(cyc-Pr), OR, or COOR, wherein R=lower alkyl or cycloalkyl; or
R₁=Me,
X=H(C)CH₂N(Me)(cyc-Pr); and
Y=alkenyl, OR, COOR, wherein R=lower alkyl or cycloalkyl; or
R₁=Me;
X=C=O; and
Y=alkenyl.

Formula 27:

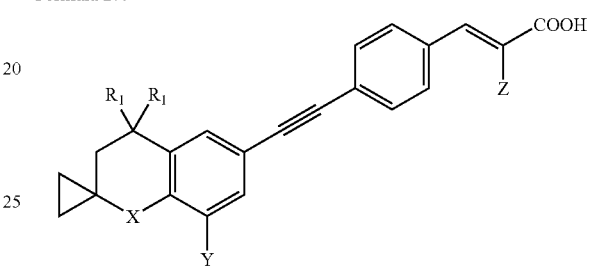

wherein,
Z=H, Me or Cl; and
R₁=H, Me or Et;
X=O or S; and
Y=lower alkyl, cycloalkyl, CH₂N(Me)(cyc-Pr), OR, or COOR, wherein R=lower alkyl or cycloalkyl; or
R₁=Me,
X=H(C)CH₂N(Me)(cyc-Pr); and
Y=lower alkyl, cycloalkyl, OR, or COOR, wherein R=lower alkyl, or cycloalkyl; or
R₁=Me;
X=C=O; and
Y=alkenyl, lower alkyl, or cycloalkyl Formula 28:

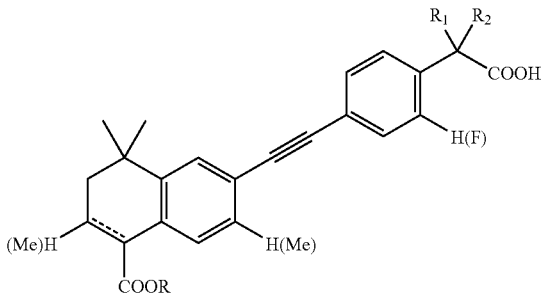

wherein,
R=lower alkyl; and
R₁=H; and
R₂=Me; or
R₁=R₂=Me or H.

Formula 29:

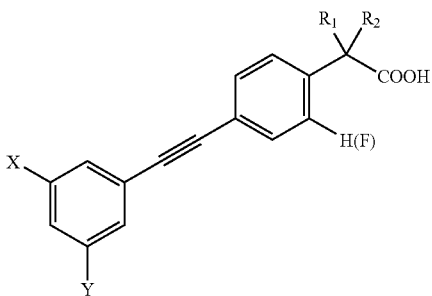

wherein,
X=COOR, C(CH$_3$)$_2$COOR, CH$_2$N(CH$_3$)(cyc-Pr), wherein R lower alkyl;
Y=H, lower alkyl, haloalkyl, alkenyl or alkynyl; and
R$_1$=H and R$_2$=Me; or
R$_1$=R$_2$=Me or H.

A selective CYP26A inhibitor that has at least 10-fold selectivity for CYP26B relative to CYP26A can have a chemical formula shown as any of Formulas 30 through 32 described below.

Formula 30:

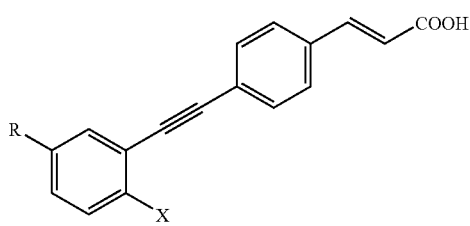

wherein,
R=t-Butyl, CH$_2$N(Me)(cyc-Pr), or N(Me)(cyc-Pr); and
X=H or Me.

Formula 31:

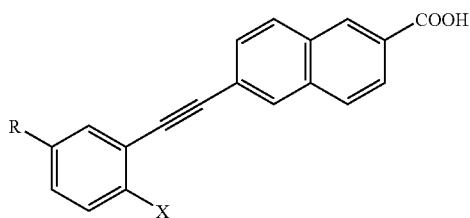

wherein,
R=t-Butyl, CH$_2$N(Me)(cyc-Pr), or N(Me)(cyc-Pr); and
X=H or Me.

Formula 32:

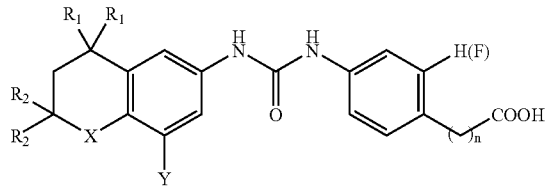

wherein,
n=0 or 1; and
R$_1$=R$_2$=Me;
X=O, S, where R=lower alkyl; and
Y=cycloalkyl, alkenyl, alkynyl, lower alkoxy, halo, or haloalkyl;

or
R$_1$=Me;
R$_2$=—CH$_2$CH$_2$—;
X=O or S; and
Y=cycloalkyl, alkenyl, alkynyl, lower alkoxy, halo, or haloalkyl;

or
R$_1$=Me;
R$_2$=H;
X=—CHCH$_2$N(Me)(cyc-Pr); and
Y=H, lower alkyl, cycloalkyl, alkenyl, lower alkoxy, halo or haloalkyl; or
R$_1$=Me;
R$_2$=H;
X=CMe$_2$; and
Y=H, lower alkyl, cycloalkyl, alkenyl, alkynyl, lower alkoxy, halo or haloalkyl.

II. Formulas 1 through 17
Formula 1

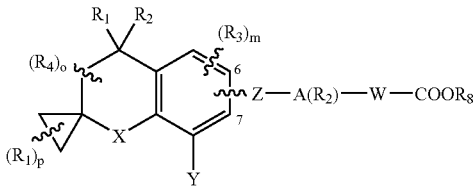

wherein:
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;
X is O, S or NR where R is H, alkyl of 1 to 6 carbons or benzyl;
Y is H, alkyl of 1 to 10 carbons, benzyl, C$_{1-6}$ alkyl or halogen substituted benzyl, fluoro-substituted alkyl of 1 to 10 carbons, cycloalkyl of 3 to 6 carbons, C$_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I or alkoxy of 1 to 6 carbons;
Z is —C≡C—, —(CR$_1$=CR$_1$)$_{n'}$—, where n' is an integer having the value 1-5, —CO—NR$_1$—, NR$_1$—CO—; —CO—O—, —O—CO—, —CS—NR$_1$—, NR$_1$—CS—, —CO—S—, —S—CO—, —N=N—; or —NR$_1$—CO—NR$_1$—;
R$_1$ is independently H or alkyl of 1 to 6 carbons;
p is an integer having the values of 0 to 4;
R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;
R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 2;

$R_4$ is independently H, alkyl of 1 to 6 carbons, or F, fluorosubstituted alkyl of 1 to 6 carbons, or halogen;

o is an integer having the values of 0 to 2;

W is —C($R_5$)$_2$— or —C$R_5$=C$R_5$—;

$R_5$ is independently H, halogen, or alkyl of 1 to 3 carbons with the proviso that when W is —C($R_5$)$_2$— then at least one $R_5$ is alkyl of 1 to 3 carbons, and $R_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 2

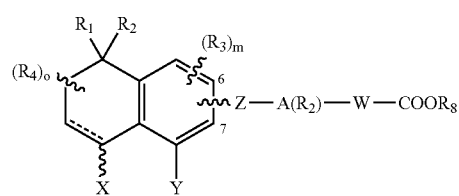

Formula 2 wherein the dashed line represents a bond or absence of a bond;

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is alkyl of 1 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I, OR, SR, NR$R_7$, —CO—OR where R is H, alkyl of 1 to 6 carbons or benzyl;

Y is H, alkyl of 1 to 10 carbons, benzyl, C$_{1-6}$ alkyl or halogen substituted benzyl, fluoro-substituted alkyl of 1 to 10 carbons, cycloalkyl of 3 to 6 carbons, C$_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, COOR$_8$ or alkoxy of 1 to 6 carbons;

Z is —C≡C—, —(CR$_1$=CR$_1$)$_{n'}$—, where n' is an integer having the value 1-5, —CO—NR$_1$—, NR$_1$—CO—; —CO—O—, —O—CO—, —CS—NR$_1$—, NR$_1$—CS—, —CO—S—, —S—CO—, —N=N—; or —NR$_1$—CO—NR$_1$—;

$R_1$ is independently H or alkyl of 1 to 6 carbons;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or fluoro-substituted alkyl of 1 to 6 carbons, or halogen;

o is an integer having the values of O to 4;

W is —C($R_5$)$_2$— or —C$R_5$=C$R_5$—;

$R_5$ is independently H, halogen, or alkyl of 1 to 3 carbons with the proviso that when W is —C($R_5$)$_2$— then at least one $R_5$ is alkyl of 1 to 3 carbons;

$R_7$ is H, lower alkyl, cycloalkyl of 3 to 6 carbons, lower alkyl substituted cycloalkyl of 3 to 6 carbons, and $R_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 3

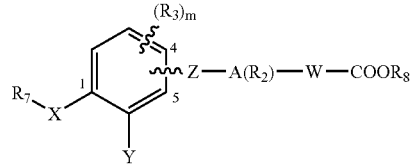

Formula 3 wherein:

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons, C$_{1-6}$-trialkylsilyl or benzyl;

Y is H, alkyl of 1 to 10 carbons, benzyl, C$_{1-6}$ alkyl or halogen substituted benzyl, fluoro-substituted alkyl of 1 to 10 carbons, cycloalkyl of 3 to 6 carbons, C$_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I;

Z is —C≡C—, —(CR$_1$=CR$_1$)$_{n'}$—, where n' is an integer having the value 1-5, —CO—NR$_1$—, NR$_1$—CO—; —CO—O—, —O—CO—, —CS—NR$_1$—, NR$_1$—CS—, —CO—S—, —S—CO—, —N=N—; or —NR$_1$—CO—NR$_1$—;

$R_1$ is independently H or alkyl of 1 to 6 carbons;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

W is —C($R_5$)$_2$— or —C$R_5$=C$R_5$—;

$R_5$ is independently H, halogen, or alkyl of 1 to 3 carbons with the proviso that when W is —C($R_5$)$_2$— then at least one $R_5$ is alkyl of 1 to 3 carbons;

$R_7$ is H, alkyl of 1 to 6 carbons, cycloalkyl of 3 to 6 carbons or C$_{1-6}$ alkyl substituted cycloalkyl of 1 to 6 carbons, and $R_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 4

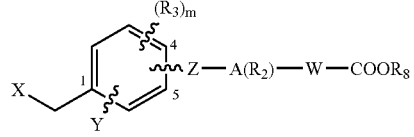

Formula 4 wherein:
- A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
- X is $OR_7$, $SR_7$ or $NRR_7$ where R is H, alkyl of 1 to 6 carbons or benzyl;
- Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, or —$COOR_1$;
- Z is —C≡C—, —$(CR_1=CR_1)_{n'}$—, where n' is an integer having the value 1-5, —CO—$NR_1$—, $NR_1$—CO—; —CO—O—, —O—CO—, —CS—$NR_1$—, $NR_1$—CS—, —CO—S—, —S—CO—, —N=N—; or —$NR_1$—CO—$NR_1$—;
- $R_1$ is independently H or alkyl of 1 to 6 carbons;
- $R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
- $R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
- m is an integer having the values 0 to 3;
- W is —$C(R_5)_2$— or —$CR_5=CR_5$—;
- $R_5$ is independently H, halogen, or alkyl of 1 to 3 carbons with the proviso that when W is —$C(R_5)_2$— then at least one $R_5$ is alkyl of 1 to 3 carbons;
- $R_7$ is H, alkyl of 1 to 6 carbons, cycloalkyl of 3 to 6 carbons or $C_{1-6}$ alkyl substituted cycloalkyl of 1 to 6 carbons, and
- $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

Formula 5

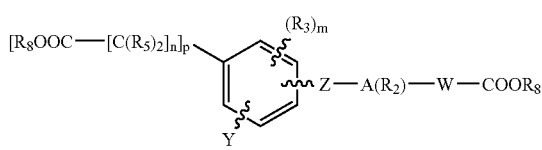

Formula 5 wherein:
- A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
- Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkenyl-alkynyl of 4 to 6 carbons, alkynyl-alkenyl of 4 to 6 carbons, Cl, Br, I, or —$COOR_1$;
- Z is —C≡C—, —$(CR_1=CR_1)_{n'}$—, where n' is an integer having the value 1-5, —CO—$NR_1$—, $NR_1$—CO—; —CO—O—, —O—CO—, —CS—$NR_1$—, $NR_1$—CS—, —CO—S—, —S—CO—, —N=N—; or —$NR_1$—CO—$NR_1$—;
- $R_1$ is independently H or alkyl of 1 to 6 carbons;
- $R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
- $R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
- m is an integer having the values 0 to 3;
- n is an integer having the values of 0 or 1;
- p is an integer having the values of 0 or 1;
- W is —$C(R_5)_2$— or —$CR_5=CR_5$—;
- $R_5$ is independently H, halogen, or alkyl of 1 to 3 carbons with the proviso that when W is —$C(R_5)_2$— then at least one $R_5$ is alkyl of 1 to 3 carbons, and
- $R_8$ independently is H, alkyl of 1 to 6 carbons, —$CH_2O(C_{1-6}$-alkyl), $CH_2OCO(C_{1-6}$-alkyl) or a cation of a pharmaceutically acceptable base.

Formula 6

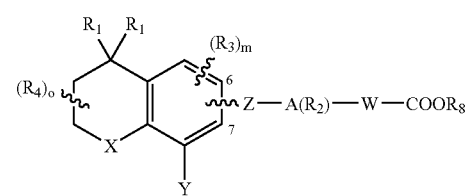

Formula 6 wherein:
- A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
- X is O, S, NR or CO where R is H or alkyl of 1 to 6 carbons;
- Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2$—$NRR_7$ or —$COOR_1$;
- Z is —C≡C—, —$(CR_1=CR_1)_{n'}$—, where n' is an integer having the value 1-5, —CO—$NR_1$—, $NR_1$—CO—; —CO—O—, —O—CO—, —CS—$NR_1$—, $NR_1$—CS—, —CO—S—, —S—CO—, —N=N—; or —$NR_1$—CO—$NR_1$—;
- $R_1$ is independently H or alkyl of 1 to 6 carbons;
- $R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
- $R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
- m is an integer having the values 0 to 3;
- $R_4$ is independently H, alkyl of 1 to 6 carbons, or F; fluorosubstituted alkyl of 1 to 6 carbons, or halogen;
- o is an integer having the values of 0 to 4;

W is —C(R$_5$)$_2$— or —CR$_5$=CR$_5$—;

R$_5$ is independently H, halogen, or alkyl of 1 to 3 carbons with the proviso that when W is —C(R$_5$)$_2$— then at least one R$_5$ is alkyl of 1 to 3 carbons, and R$_7$ is H, alkyl of 1 to 6 carbons, cycloalkyl of 3 to 6 carbons or C$_{1-6}$ alkyl substituted cycloalkyl of 1 to 6 carbons, and R$_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 7

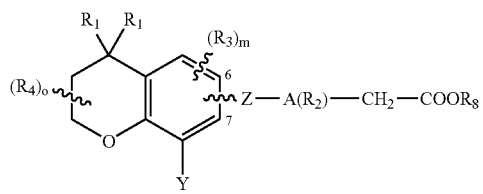

Formula 7 wherein:

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;

Y is alkenyl-alkynyl of 4 to 6 carbons, alkynyl-alkenyl of 4 to 6 carbons, OR$_7$, CH$_2$—NRR$_7$ or —COOR$_1$;

Z is —C≡C—, —CO—O—, or —NR$_1$—CO—NR$_1$—;

R is independently H or alkyl of 1 to 6 carbons;

R$_1$ is independently H or alkyl of 1 to 6 carbons;

R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

R$_4$ is independently H, alkyl of 1 to 6 carbons, or F; fluorosubstituted alkyl of 1 to 6 carbons, or halogen;

o is an integer having the values of 0 to 4;

R$_7$ is H, alkyl of 1 to 6 carbons, cycloalkyl of 3 to 6 carbons or C$_{1-6}$ alkyl substituted cycloalkyl of 1 to 6 carbons, and R$_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 8

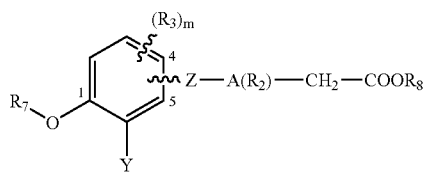

Formula 8 wherein:

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;

Y is alkenyl of 2 to 6 carbons, alkynyl of 2 to 6 carbons, alkenyl-alkynyl of 4 to 6 carbons, alkynyl-alkenyl of 4 to 6 carbons;

Z is —C≡C—, —CO—O—, or —NR$_1$—CO—NR$_1$—;

R$_1$ is independently H or alkyl of 1 to 6 carbons;

R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

R$_7$ is H, alkyl of 1 to 6 carbons, cycloalkyl of 3 to 6 carbons or C$_{1-6}$ alkyl substituted cycloalkyl of 1 to 6 carbons, and R$_8$ is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 9

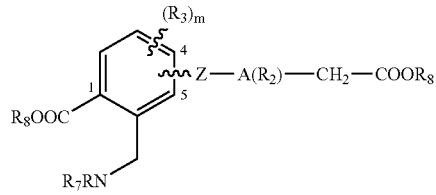

Formula 9 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;

Z is —C≡C—, —CO—O—, or —NR$_1$—CO—NR$_1$—; R is H or alkyl of 1 to 6 carbons;

R$_1$ is independently H or alkyl of 1 to 6 carbons;

R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

R$_7$ is H, alkyl of 1 to 6 carbons, cycloalkyl of 3 to 6 carbons or C$_{1-6}$ alkyl substituted cycloalkyl of 1 to 6 carbons, and R$_8$ independently is H, alkyl of 1 to 6 carbons, —CH$_2$O(C$_{1-6}$-alkyl), CH$_2$OCO(C$_{1-6}$-alkyl) or a cation of a pharmaceutically acceptable base.

Formula 10

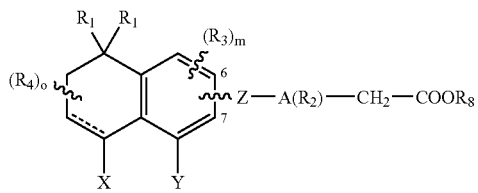

Formula 10 wherein the dashed line represents a bond or absence of a bond;
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
X is $NRR_7$, or $COOR_8$;
Y is H, alkenyl of 2 to 6 carbons, alkenyl-alkynyl of 4 to 6 carbons, alkynyl-alkenyl of 4 to 6 carbons, $OR_7$ or —$COOR_1$;
Z is —C≡C—, —CO—O—, or —$NR_1$—CO—$NR_1$—;
R is independently H or alkyl of 1 to 6 carbons;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3;
$R_4$ is independently H, alkyl of 1 to 6 carbons, or F; fluorosubstituted alkyl of 1 to 6 carbons, or halogen;
o is an integer having the values of 0 to 4;
$R_7$ is H, alkyl of 1 to 6 carbons, cycloalkyl of 3 to 6 carbons or $C_{1-6}$ alkyl substituted cycloalkyl of 1 to 6 carbons, and
$R_8$ independently is H, alkyl of 1 to 6 carbons, —$CH_2O$($C_{1-6}$-alkyl), $CH_2OCO$($C_{1-6}$-alkyl) or a cation of a pharmaceutically acceptable base.

Formula 11

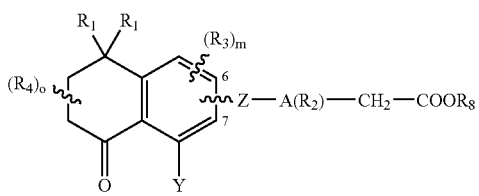

Formula 11 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
Y is, alkenyl of 2 to 6 carbons, alkenyl-alkynyl of 4 to 6 carbons, or alkynyl-alkenyl of 4 to 6 carbons;
Z is —C≡C—, —CO—O—, or —$NR_1$—CO—$NR_1$—;
$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3;
$R_4$ is independently H, alkyl of 1 to 6 carbons, or F; fluorosubstituted alkyl of 1 to 6 carbons, or halogen;
o is an integer having the values of 0 to 4, and
$R_8$ is H, alkyl of 1 to 6 carbons, —$CH_2O$($C_{1-6}$-alkyl), $CH_2OCO$($C_{1-6}$-alkyl) or a cation of a pharmaceutically acceptable base.

Formula 12

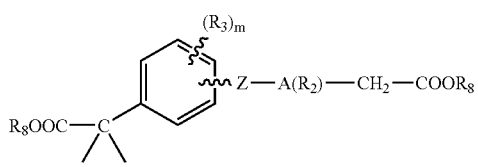

Formula 12 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
Z is —C≡C—, —CO—O—, or —$NR_1$—CO—$NR_1$—;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3, and
$R_8$ independently is H, is alkyl of 1 to 6 carbons, —$CH_2O$($C_{1-6}$-alkyl), $CH_2OCO$($C_{1-6}$-alkyl) or a cation of a pharmaceutically acceptable base.

Formula 13

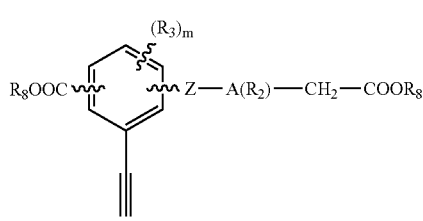

Formula 13 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;
Z is —C≡C—, —CO—O—, or —$NR_1$—CO—$NR_1$—;
$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3, and $R_8$ independently is H, alkyl of 1 to 6 carbons, —$CH_2O$($C_{1-6}$-alkyl), $CH_2OCO(C_{1-6}$-alkyl) or a cation of a pharmaceutically acceptable base.

Formula 14

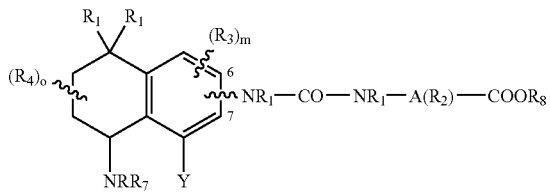

Formula 14 wherein:
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2$—$NRR_7$ or —$COOR_1$;

R is independently H or alkyl of 1 to 6 carbons;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;
$R_4$ is independently H, alkyl of 1 to 6 carbons, or F; fluorosubstituted alkyl of 1 to 6 carbons, or halogen;
o is an integer having the values of 0 to 4;
$R_7$ is H, alkyl of 1 to 6 carbons, cycloalkyl of 3 to 6 carbons or $C_{1-6}$ alkyl substituted cycloalkyl of 1 to 6 carbons, and
$R_8$ is H, alkyl of 1 to 6 carbons, —$CH_2O(C_{1-6}$-alkyl), $CH_2OCO(C_{1-6}$-alkyl) or a cation of a pharmaceutically acceptable base.

Formula 15

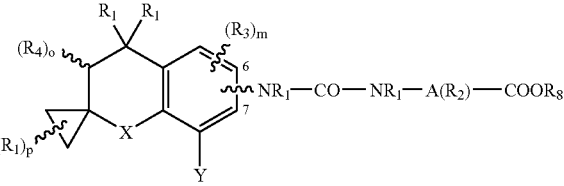

Formula 15 wherein:
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O or S;
Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2$—$NRR_7$ or —$COOR_1$;

$R_1$ is independently H or alkyl of 1 to 6 carbons;
p is an integer having the values of 0 to 4;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;
$R_4$ is independently H, alkyl of 1 to 6 carbons, or F; fluorosubstituted alkyl of 1 to 6 carbons, or halogen;
o is an integer having the values of 0 to 4;
$R_7$ is H, alkyl of 1 to 6 carbons, cycloalkyl of 3 to 6 carbons or $C_{1-6}$ alkyl substituted cycloalkyl of 1 to 6 carbons, and
$R_8$ is H, alkyl of 1 to 6 carbons, —$CH_2O(C_{1-6}$-alkyl), $CH_2OCO(C_{1-6}$-alkyl) or a cation of a pharmaceutically acceptable base.

Formula 16

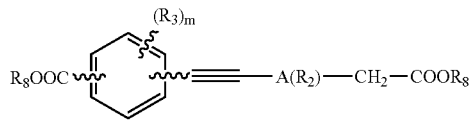

Formula 16 wherein:
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3, and $R_8$ independently is H, alkyl of 1 to 6 carbons, $-CH_2O(C_{1-6}-alkyl)$, $CH_2OCO(C_{1-6}-alkyl)$ or a cation of a pharmaceutically acceptable base.

Formula 17

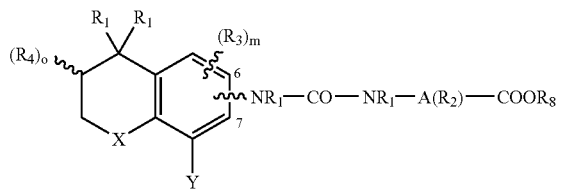

Formula 17 wherein:

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O or S;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2-NRR_7$ or $-COOR_1$;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, $-CH_2O(C_{1-6}-alkyl)$, $CH_2OCO(C_{1-6}-alkyl)$ or a cation of a pharmaceutically acceptable base.

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

The novel compounds used in accordance with the invention are encompassed by the general Formulas 1 through 17 provided above. In each of these formulas a linker or tethering group designated Z covalently connects an aromatic or heteroaromatic moiety designated $A(R_2)-W-COOR_8$, $A(R_2)-CH_2-COOR_8$ or $A(R_2)-COOR_8$ and another cyclic moiety which in accordance with these formulas is a substituted phenyl, substituted tetrahydronaphthalene, substituted dihydronaphthalene, substituted chroman, substituted thiochroman or substituted tetrahydroquinoline moiety.

Generally speaking compounds such as $X_4-A(R_2)-W-COOR_8$, $X_4-A(R_2)-CH_2-COOR_8$ and $X_4-A(R_2)-COOR_8$ are commercially available, or can be made in accordance with the chemical literature, or with such modification of known chemical processes, or of chemical processes disclosed herein which are within the skill of the practicing organic chemist. The group $X_4$ represents a reactive group, which is suitable for coupling the $X_4-A(R_2)-W-COOR_8$, $X_4-A(R_2)-CH_2-COOR_8$ and $X_4-A(R_2)-COOR_8$ compounds to a derivative of the substituted phenyl, substituted tetrahydronaphthalene, substituted dihydronaphthalene, substituted chroman, substituted thiochroman, or substituted tetrahydroquinoline moiety so that as a result of the coupling the linker or tether moiety Z is formed. In many instances the group $X_4$ is a leaving group such as halogen, or trifluoromethanesulfonyloxy, or a group capable of participating in a Wittig or Horner Emmons reaction. In some instances the group $X_4$ is an ethynyl group capable of undergoing a coupling reaction with a leaving group (such as a halogen or a trifluoromethanesulfonyloxy group) attached to the substituted phenyl, substituted tetrahydronaphthalene, substituted dehydronaphthalene, substituted chroman, substituted thiochroman or substituted tetrahydroquinoline moiety. The group $X_4$ can also represent an OH or an $NH_2$ group that forms an ester (COO) or amide (CONH) linker, respectively, when reacted with an activated carboxyl derivative of the substituted phenyl, substituted tetrahydronaphthalene, substituted dihydronaphthalene, substituted chroman, substituted thiochroman, or substituted tetrahydroquinoline moiety. The compounds of the formulas $X_4$-A($R_2$)-W—$COOR_8$, $X_4$-A($R_2$)-$CH_2$—$COOR_8$ and $X_4$-A($R_2$) -$COOR_8$ are generally referred to in this description as "coupling reagents" or just "reagents" and the preparation of several examples of these coupling reagents is described in the specific examples below. Further examples are the pyridyl, thienyl, furyl, pyridazine, pyrazine and other heteroaryl analogs of the coupling reagents described in the specific examples. These reagents can be obtained in accordance with the chemical literature, or with such modification of known chemical processes, or of chemical processes disclosed herein which are within the skill of the practicing organic chemist.

Still further in accordance with the general synthetic methodology to provide the compounds of Formulas 1 through 17 a derivative of the substituted phenyl, substituted tetrahydronaphthalene, substituted dihydronaphthalene, substituted chroman, substituted thiochroman, or substituted tetrahydroquinoline moiety is synthesized first, having a covalently attached $X_5$ group. The $X_5$ group reacts with the $X_4$ group of the reagents $X_4$-A($R_2$)-W—$COOR_8$, $X_4$-A($R_2$)-$CH_2$—$COOR_8$ and $X_4$-A($R_2$)-$COOR_8$ to form the linker designated Z in Formulas 1 through 17. The $X_5$ group is one that is capable of participating in a catalyzed coupling reaction, (such as an ethynyl group when $X_4$ is a leaving group), or a leaving group (such as halogen or trifluoromethanesulfonyloxy when $X_4$ is an ethynyl group), or an activated carboxylic acid function (when $X_4$ is OH or $NH_2$). The $X_5$ group can also be an OH, SH or $NH_2$ group when the $X_4$ group is an activated carboxylic acid function. Specific examples for substituted phenyl, substituted tetrahydronaphthalene, substituted dihydronaphthalene, substituted chroman, substituted thiochroman, or substituted tetrahydroquinoline intermediates having an $X_5$ functionality are provided below, and are also available in the chemical scientific and patent literature. Generally speaking, for reagents and reactions covalently joining a substituted tetrahydronaphthalene, substituted dihydronaphthalene, substituted chroman, substituted thiochroman, or substituted tetrahydroquinoline intermediate with a substituted aryl or heteroaryl group, of the formulas A($R_2$)-W—$COOR_8$, A($R_2$)-$CH_2$—$COOR_8$ and A($R_2$)-$COOR_8$ to form a compound including the linker designated Z, reference is made to U.S. Pat. Nos. 5,648,503; 5,723,666, 5,952,345, 6,252,090 and 6,313,107 the specification of each of which are expressly incorporated herein by reference.

The substituted phenyl, substituted tetrahydronaphthalene, substituted dihydronaphthalene, substituted chroman, substituted thiochroman or substituted tetrahydroquinoline moiety of the novel compounds used in accordance with the invention are derivatized in a manner to include the specific substituents (such as for example the cycloalkyl substituents) encompassed within the scope of the invention, either before or after the A($R_2$)-W—$COOR_8$, A($R_2$)—$CH_2$—$COOR_8$ or A($R_2$)-$COOR_8$ moiety has been attached and the linker Z has formed, as illustrated by the below described specific examples. The W—$COOR_8$, $CH_2$—$COOR_8$ or $COOR_8$ moiety of the compounds of Formulas 1 through 17 can be modified in order to obtain still further novel compounds. One such modification is saponification of compounds where the $R_8$ group is an alkyl, $CH_2O(C_{1-6}$-alkyl) or $CH_2OCO(C_{1-6}$-alkyl) group. Another modification is esterification of the carboxylic acid function when the $R_8$ group is H or a cation. Such saponification and esterification reactions are well known in the art and within the skill of the practicing organic chemist.

With reference to the symbol A in Formulas 1 through 17, the preferred novel compounds used in accordance with the present invention are those where A is phenyl, naphthyl, pyridyl, thienyl or furyl. Even more preferred are compounds where A is phenyl. As far as substitutions on the A (phenyl) and A (pyridyl) groups are concerned, compounds are usually preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred novel compounds used in accordance with the invention either there is no $R_2$ substituent on the A group, or the $R_2$ substituent is preferably a fluoro group that is preferably located on the aromatic carbon adjacent (ortho) to the carbon bearing the W—$COOR_8$, $CH_2$—$COOR_8$ or $COOR_8$ group.

As far as the W—$COOR_8$ moiety is concerned, the variable W preferably represents —CH=CH—, —$CR_5$=CH—, CH=$CR_5$— (cinnamic acid derivatives) C($R_5$)$_2$ or $CHR_5$ where $R_5$ is preferably methyl. For the $R_8$ group H, lower alkyl of 1 to 3 carbons, —$CH_2O(C_{1-3}$-alkyl) and —$CH_2OCO(C_{1-3}$-alkyl) groups are preferred, as well as the pharmaceutically acceptable salts of the free acids when $R_8$ is H. Among the lower alkyl, —$CH_2O(C_{1-3}$-alkyl) and —$CH_2OCO(C_{1-3}$-alkyl) groups methyl, ethyl, $CH_2OCH_3$ and $CH_2OCOCH_3$ respectively, are presently most preferred.

The linker group Z in all of the novel compounds used in accordance with the invention is preferably ethynyl, (—CC—), ester (CO—O), or ureido (NHCONH). Moreover for chroman, thichroman and tetrahydroquinoline derivatives the linker Z is preferably attached to the 6 position (e.g. see Formula 1). For tetrahydronaphthalene and dihydronaphthalene derivatives the linker Z is preferably attached to the to the 6 position as such positions are numbered in Formulas 2 and 11.

The $R_1$ group is preferably methyl when it serves as a substituent attached to a carbon of the chroman, thiochroman, tetrahydroquinoline, tetrahydronaphthalene or dihydronaphthalene nucleus and is preferably hydrogen when it forms part of a linker Z.

The aromatic portion of the chroman, thiochroman, tetrahydroquinoline, tetrahydronaphthalene or dihydronaphthalene nuclei of the compounds of the present invention is either preferably not substituted with an $R_3$ group (the variable m is zero (0)), or $R_3$ is alkyl or halogen. The non-aromatic portion of the chroman, thiochroman, tetrahydroquinoline, tetrahydronaphthalene dihydronaphthalene nuclei of the compounds of the present invention is either preferably not substituted with an $R_4$ group (the variable o is zero (0)), or ($R_4$)$_o$ represents methyl groups, still more prefreably geminal dimethyl or geminal diethyl groups attached to the 2-position of the chroman nucleus.

Structures of the most preferred compounds of the invention are shown in Table 1. Whereas most of the compounds shown in Table 1 are carboxylic acids, it should be understood that the $C_{1-3}$ alkyl esters, $CH_2OCH_3$ and $CH_2OCOCH_3$ esters and the pharmaceutically acceptable salts of these compounds are also preferred.

TABLE 1

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
|---|---|---|---|---|---|---|
| | | α | β | γ | | |
| 2 | 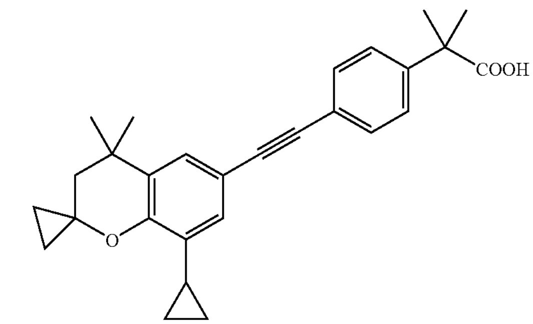 | NA[1] 558 | NA 3439 | NA 5577 | 0.03 | >10 |
| 1 | 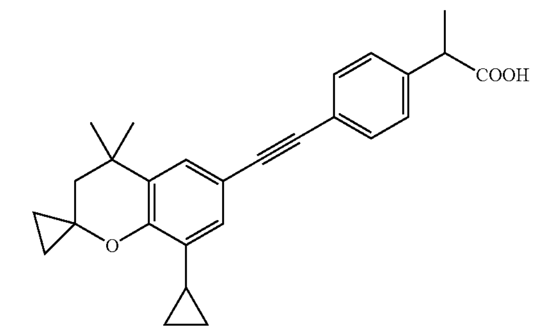 | NA 2090 | NA 3016 | NA 3486 | 0.009 | 8 |
| 3 | 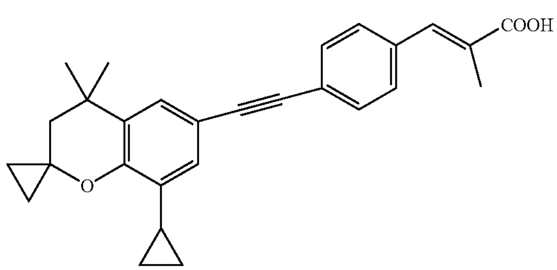 | NA >10K | WA[2] (15) 520 | NA (10) 6040 | 0.25 | >10 |
| 4 | 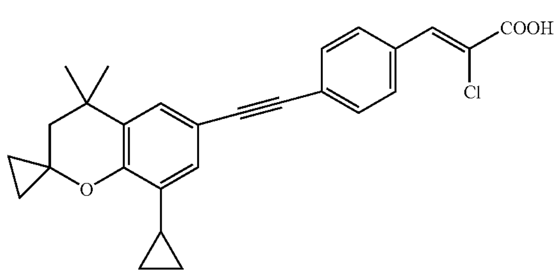 | NA >10K | WA (20) >10K | WA (15) >10K | 0.12 | >10 |
| 13 | 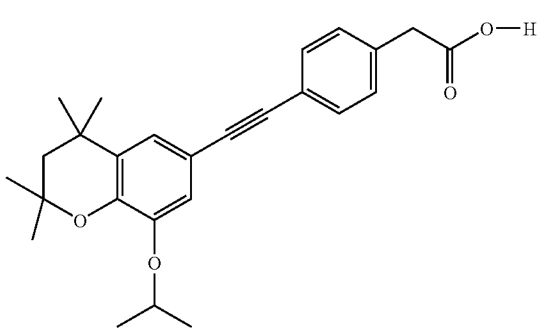 | NA 397 | NA >10K | NA >10K | 0.06 | 8 |

TABLE 1-continued
| Compound # | Structures | RAR EC$_{50}$/(EFFICACY)/K$_d$ nM | | | P450RAI-1 Whole cell IC$_{50}$ µM | P450RAI-2 Whole cell IC$_{50}$ µM |
|---|---|---|---|---|---|---|
| | | α | β | γ | | |
| 12 | 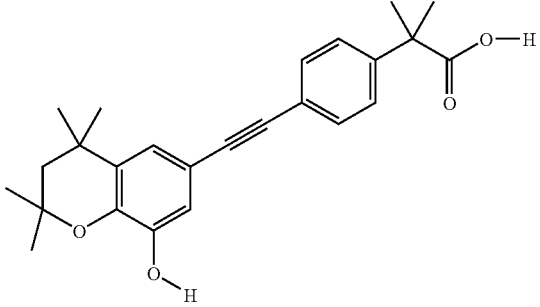 | NA >10K | NA >10K | NA >10K | 0.16 | >10 |
| 11 | 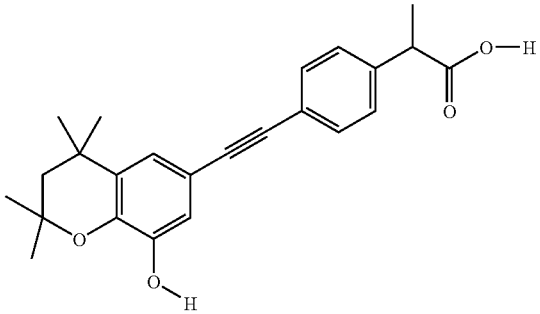 | NA >10K | NA >10K | NA >10K | 0.07 | 3 |
| 10 | 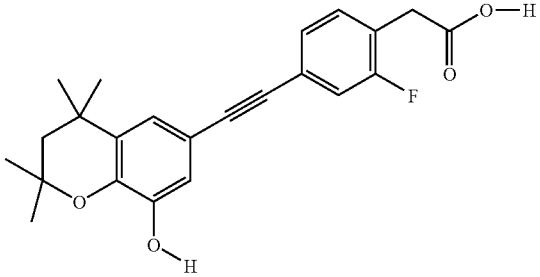 | NA >10K | WA (15) >10K | NA >10K | 0.07 | 0.7 |
| 14 | 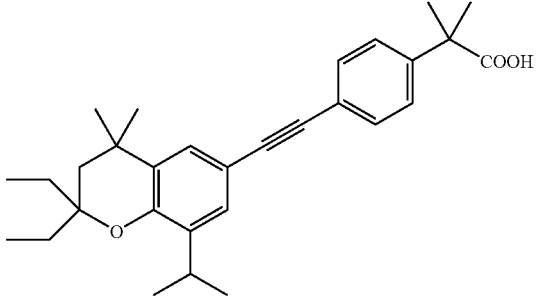 | NA 5170 | WA (10) 7400 | WA (25) >10K | 0.7 | >10 |
| 15 | 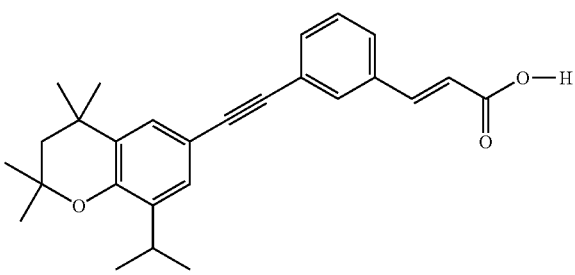 | NA 8896 | NA >10K | NA >10K | 0.6 | >10 |

TABLE 1-continued
| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 9 | 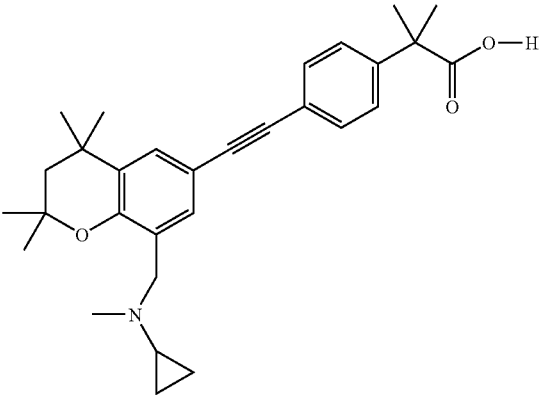 | NA >10K | NA >10K | NA >10K | 0.12 | >10 |
| 8 | 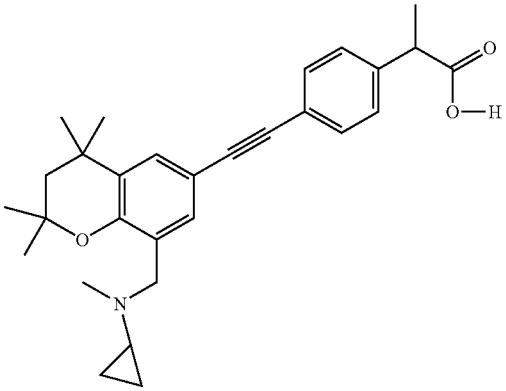 | NA 957 | WA (15) 4805 | NA >10K | 0.05 | >10 |
| 6 | 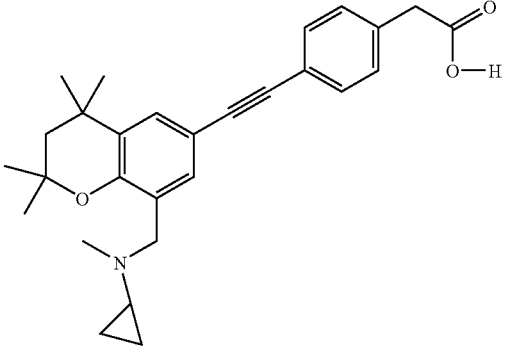 | NA 3412 | NA >10K | NA >10K | 0.06 | 4 |
| 7 | 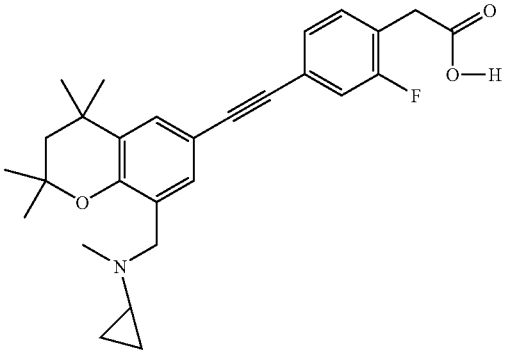 | NA >10K | NA >10K | NA >10K | 0.04 | 2 |

TABLE 1-continued
| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
|---|---|---|---|---|---|---|
| | | α | β | γ | | |
| 18 | 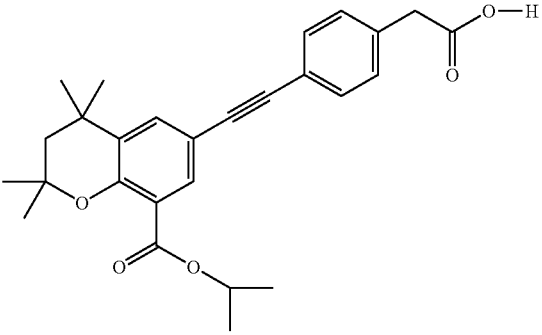 | | | | 0.4 | >10 |
| 20 | 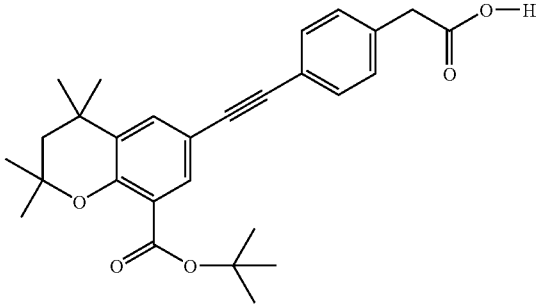 | | | | 2.9 | >10 |
| 19 | 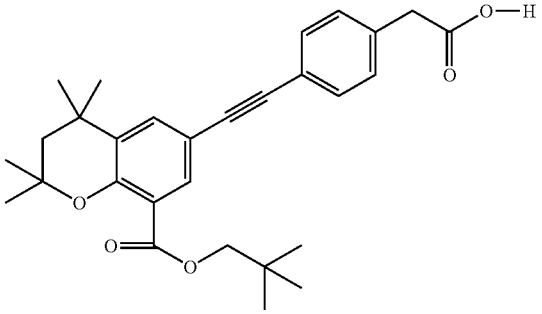 | | | | 7 | >10 |
| 45 | 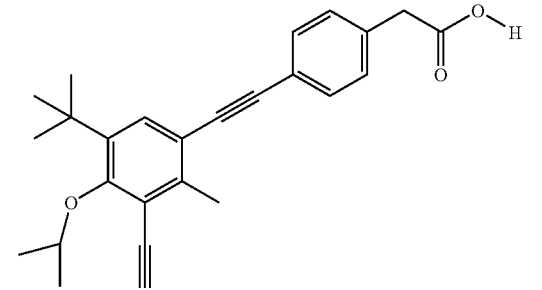 | 118 (52) 9.9 | 18 (55) 76 | 31 (68) 255 | 0.7 | >10 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 46 | 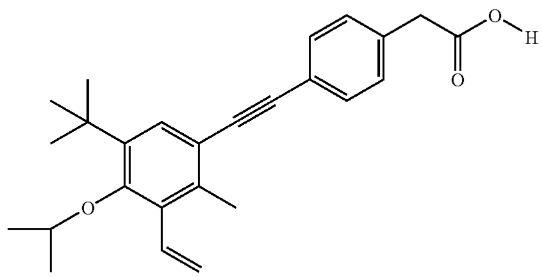 | 65 (67) 85 | 10 (75) 45 | 7 (65) 215 | 0.7 | >10 |
| 47 | 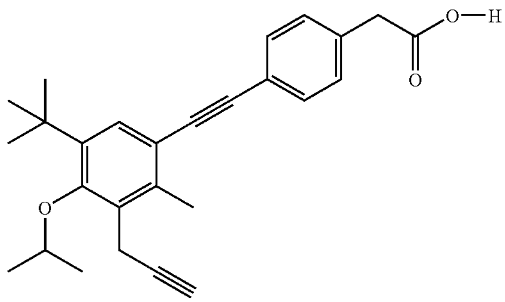 | WA (10) 2242 | 38 (59) 4473 | 125 (66) 1954 | 0.1 | 8.8 |
| 16 | 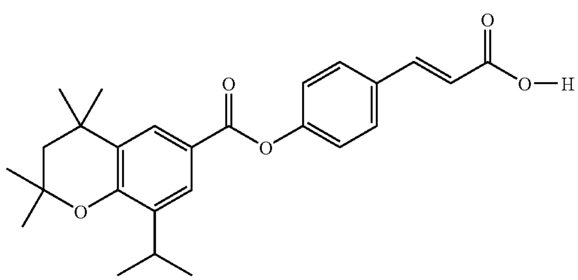 | WA (~5) 3083 | WA (35) 810 | WA (~5) >10K | 0.3 | >10 |
| 17 | 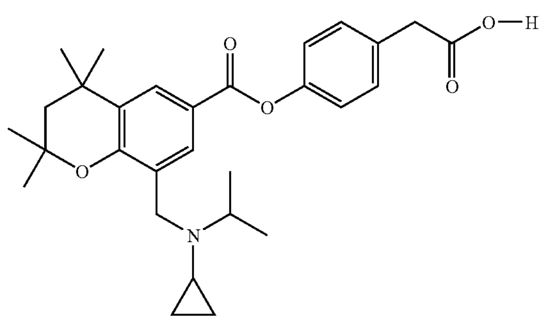 | NA | NA | NA | 2.5 | >10 |
| 23 | 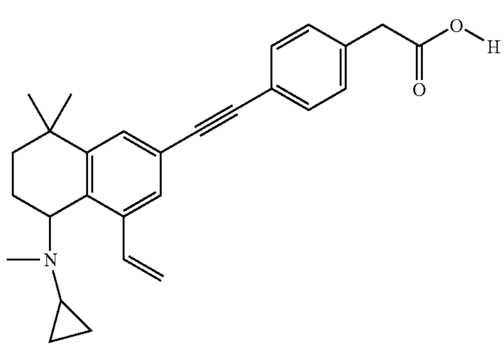 | NA >10K | WA (40) >10K | WA (35) >10K | 0.008 | 0.5 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 49 | 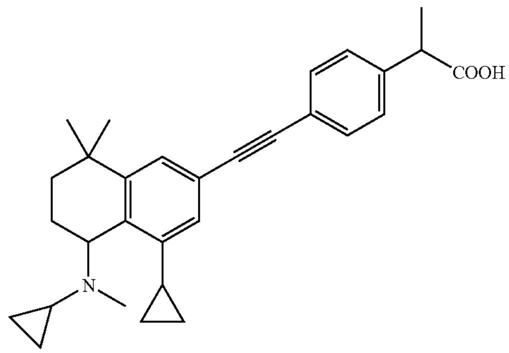 | 5282 | >10K | >10K | 0.05 | >10K |
| 50 | 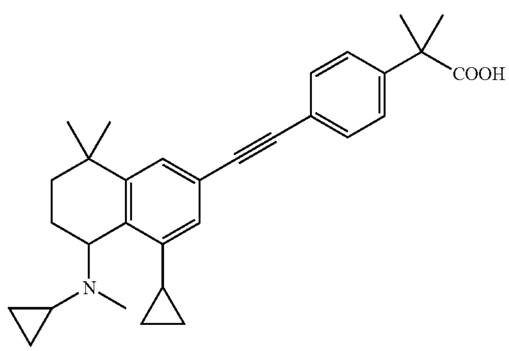 | >10 K | >10 K | >10 K | 0.1 | >10 |
| 48 | 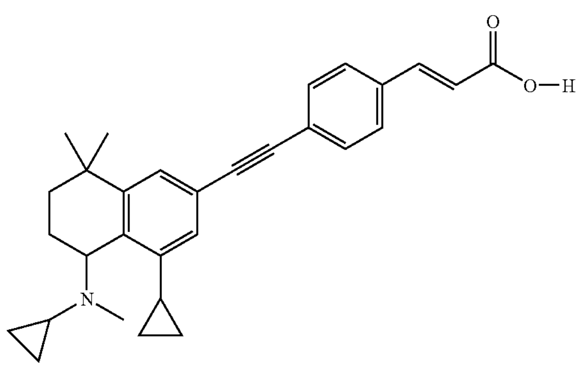 | NA >10K | WA (40) >10K | WA (25) >10K | 0.7 | 10 |
| 52 | 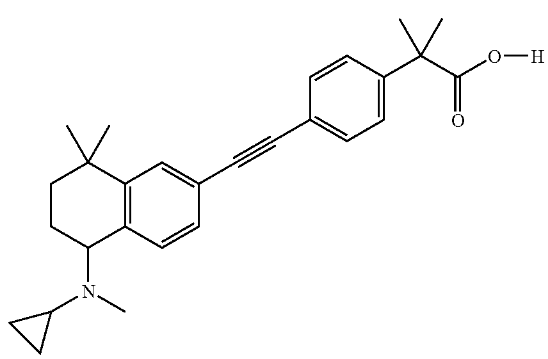 | NA >10K | WA (<5) >10K | NA >10K | 0.4 | >10 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
|---|---|---|---|---|---|---|
| | | α | β | γ | | |
| 51 | 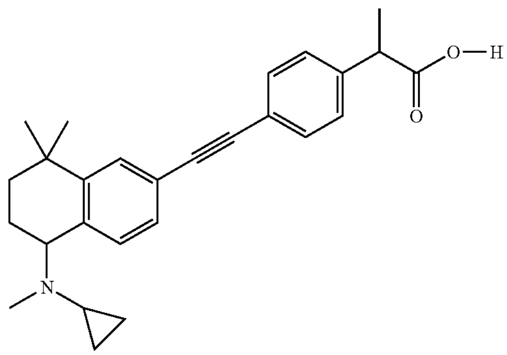 | NA >10K | WA (5) >10K | NA >10K | 0.2 | >10 |
| 53 | 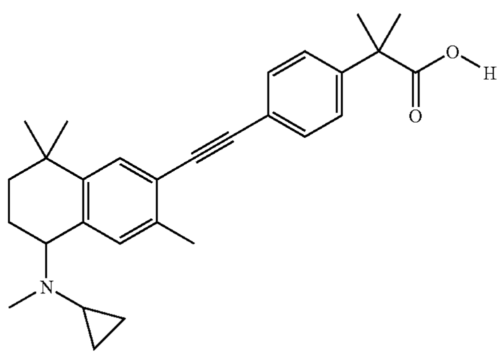 | NA >10K | NA 3906 | NA >10K | 0.5 | 5 |
| 54 | 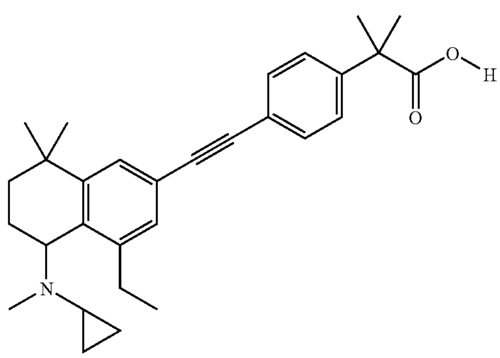 | NA 1808 | NA 5088 | NA >10K | 0.2 | >10 |
| 28 | 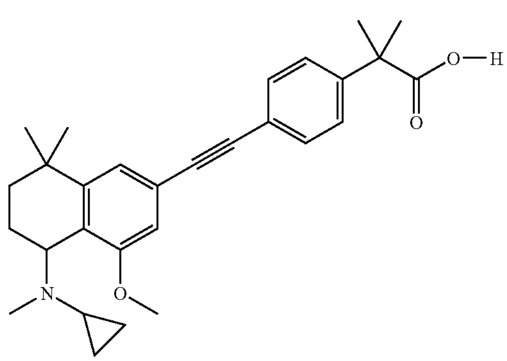 | NA >10K | NA >10K | NA 4200 | 0.25 | >10 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 25 | 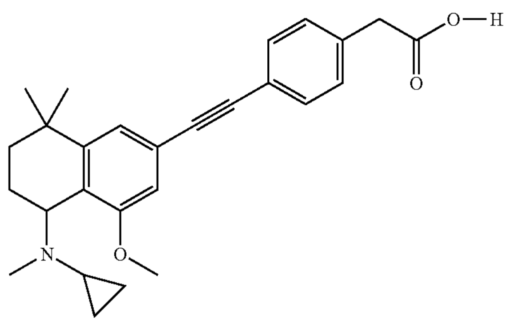 | NA >10K | NA >10K | NA 317 | 0.1 | >10 |
| 26 | 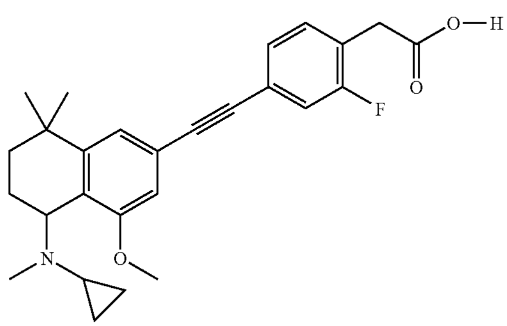 | NA >10K | WA (25) >10K | NA 1123 | 0.018 | 5 |
| 29 | 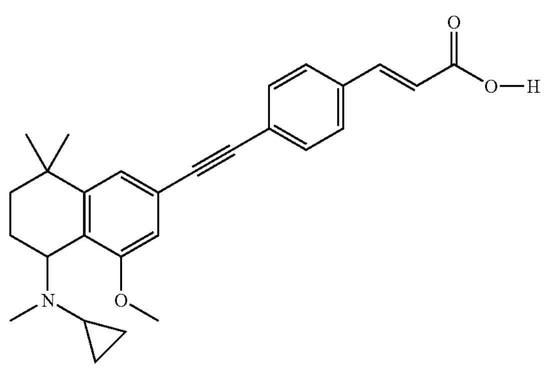 | NA >10K | NA >10K | NA >10K | 0.6 | >10 |
| 27 | 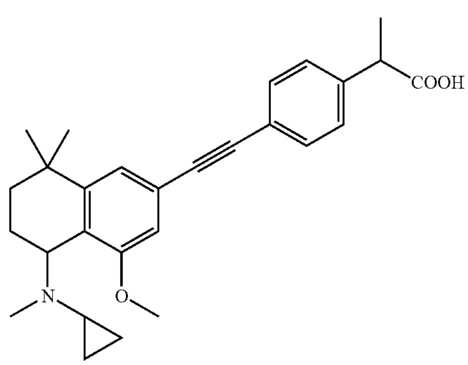 | NA 118 | NA 1275 | NA >10K | 0.028 | >10 |

TABLE 1-continued

| Compound # | Structures | RAR $EC_{50}$/(EFFICACY)/$K_d$ nM | | | P450RAI-1 Whole cell $IC_{50}$ μM | P450RAI-2 Whole cell $IC_{50}$ μM |
|---|---|---|---|---|---|---|
| | | α | β | γ | | |
| 30 | 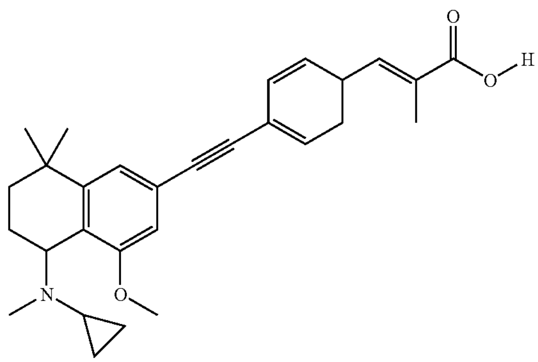 | NA >10K | WA (15) >10K | NA >10K | 0.18 | >10 |
| 41 | 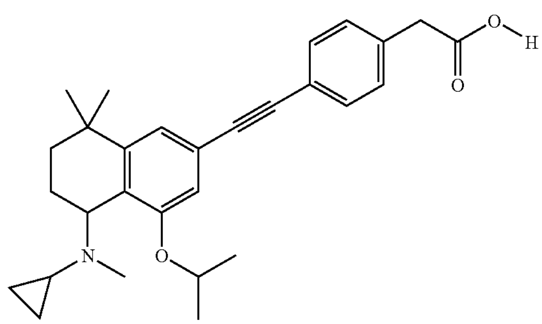 | NA >10K | NA >10K | WA (30) >10K | 0.016 | >10 |
| 22 | 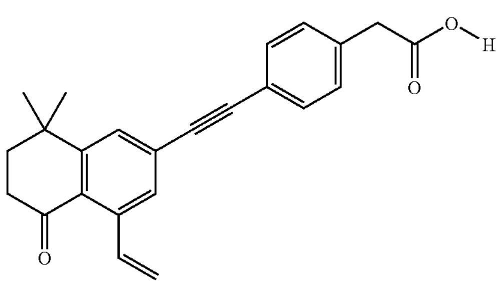 | NA >10K | WA (15) >10K | NA >10K | 0.007 | 0.2 |
| 24 | 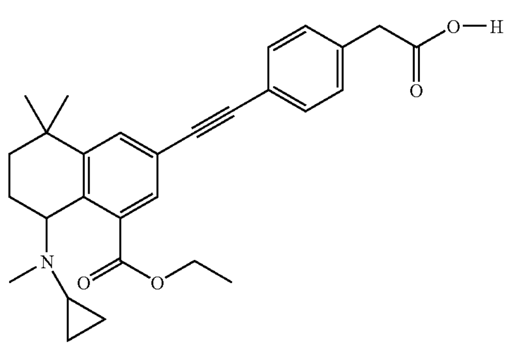 | NA 8570 | WA (30) 7188 | NA 7747 | 0.035 | 5 |

TABLE 1-continued
| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
|---|---|---|---|---|---|---|
| | | α | β | γ | | |
| 32 | 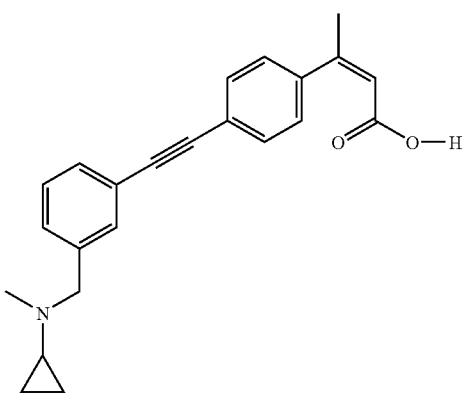 | NA >10K | NA >10K | NA >10K | 0.44 | >10 |
| 33 | 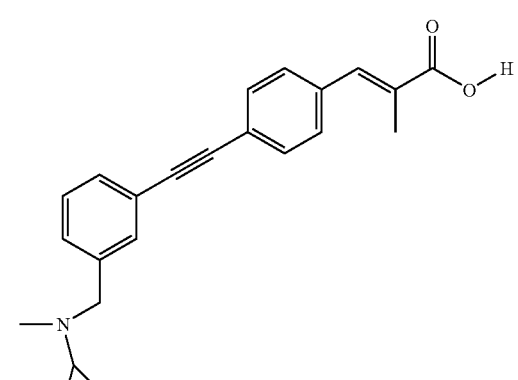 | NA 3252 | WA (30) | WA (10) >10K | >10 | 1 |
| 55 | 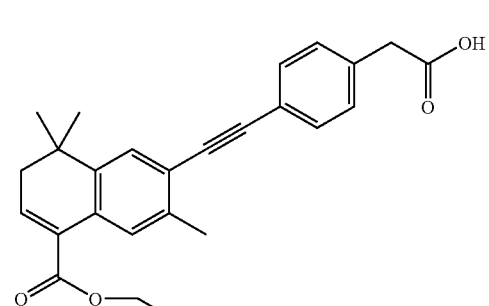 | NA >10K | WA (35) >10K | WA (30) >10K | 1.4 | >10 |
| 56 | 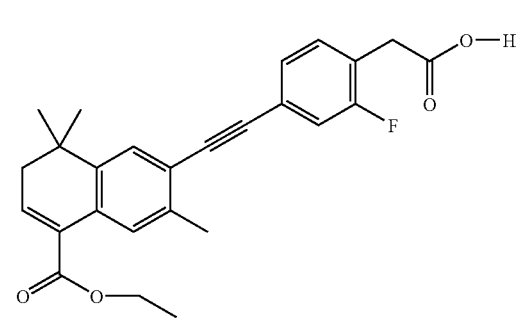 | NA >10K | WA (30) >10K | NA >10K | 0.5 | 10 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 57 | | NA<br>6028 | WA<br>(50)<br>4979 | WA<br>(35)<br>7738 | 0.4 | 10 |
| 60 | | NA<br>6315 | WA<br>(60)<br>3957 | WA<br>(15)<br>8992 | 0.06 | 2.6 |
| 58 | | NA<br>>10K | WA<br>(25)<br>4614 | NA<br>>10K | 3.5 | >10 |
| 59 | | NA<br>>10K | WA<br>(35)<br>2862 | NA<br>>10K | 1.2 | >10 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
|---|---|---|---|---|---|---|
| | | α | β | γ | | |
| 38 | 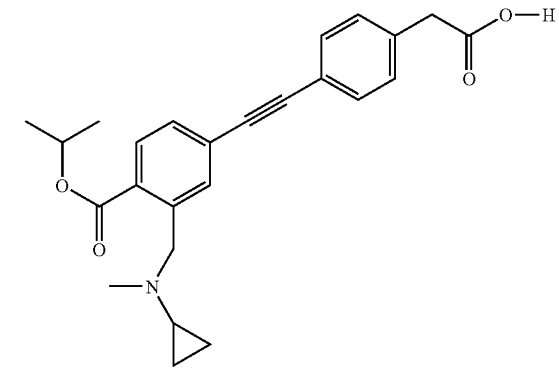 | WA (10) >10K | NA >10K | NA >10K | 4 | >10 |
| 39 | 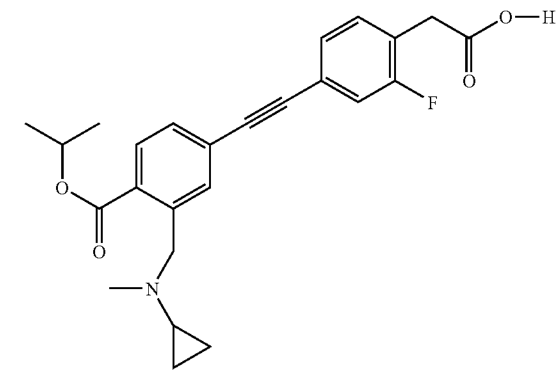 | NA >10K | NA >10K | NA >10K | 2.5 | >10 |
| 40 | 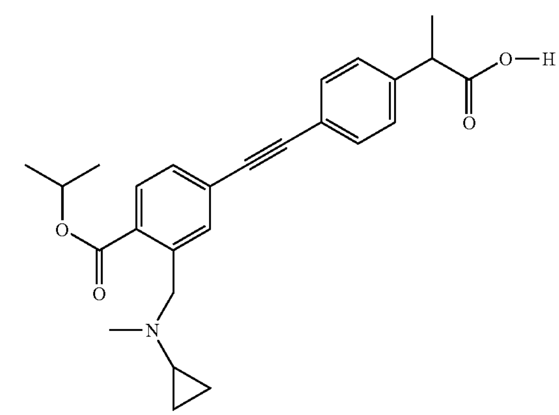 | NA >10K | NA >10K | NA >10K | 1.3 | >10 |
| 42 | 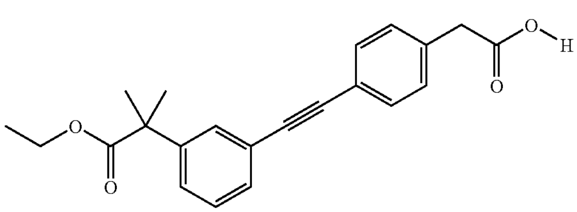 | NA >10K | WA (20) 2765 | NA >10K | 0.06 | 2 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 43 | 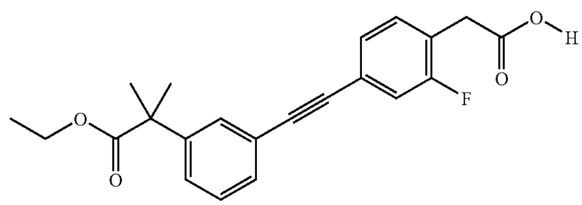 | WA (10) 2661* | WA (60) 1158 | WA (20) 3348* | 0.01 | 0.7 |
| 44 | 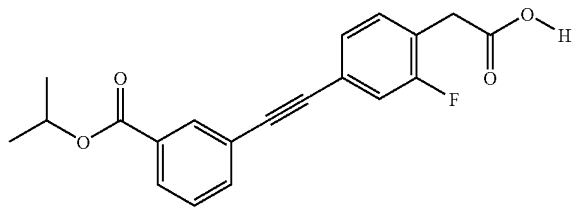 | NA >10K | 8169 | NA >10K | 0.7 | 7.5 |
| 61 | 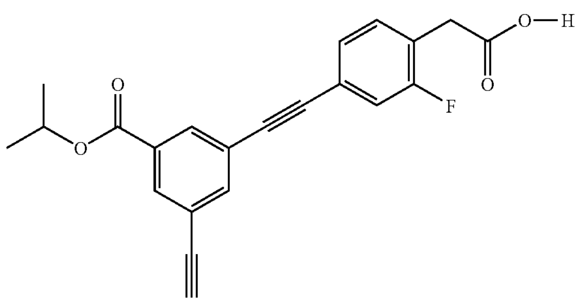 | NA >10K | NA >10K | NA >10K | 0.22 | 8.1 |
| 62 | 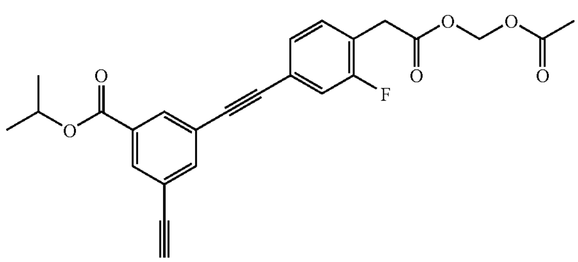 | NA >10K | NA >10K | NA >10K | 0.4 | 6.1 |
| 35 | 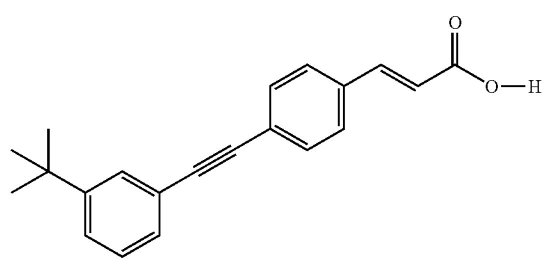 | NA 1931 | 16 (80) 2089 | 126 (48) 2888 | >10 | 0.5 |
| 36 | 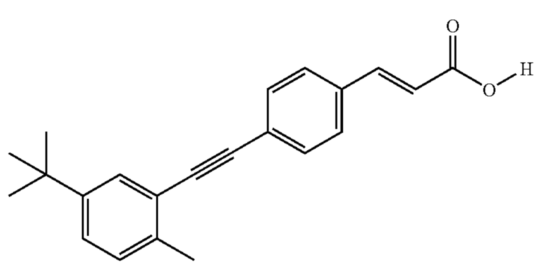 | NA >10K | WA (40) 3518 | WA (15) 2084 | >10 | 0.4 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 21 | 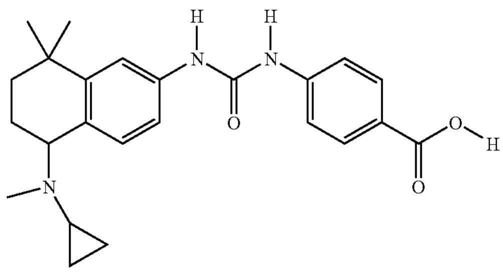 | NA >10K | NA >10K | NA >10K | >10 | 0.7 |
| 5 | 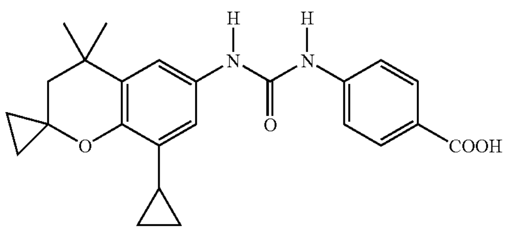 | NA >10K | 320 (55) 4536 | WA (15) >10K | >10 | 0.45 |
| 31 | 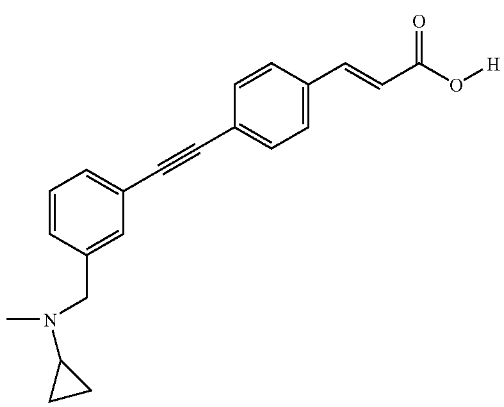 | NA >10K | WA (25) >10K | NA >10K | >10 | 0.6 |
| 34 | 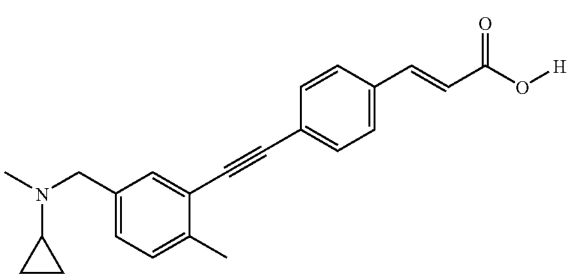 | NA 5648 | WA (20) 3492 | NA 8528 | >10 | 0.12 |

TABLE 1-continued

| Compound # | Structures | RAR EC$_{50}$/(EFFICACY)/K$_d$ nM | | | P450RAI-1 Whole cell IC$_{50}$ μM | P450RAI-2 Whole cell IC$_{50}$ μM |
| --- | --- | --- | --- | --- | --- | --- |
| | | α | β | γ | | |
| 37 | 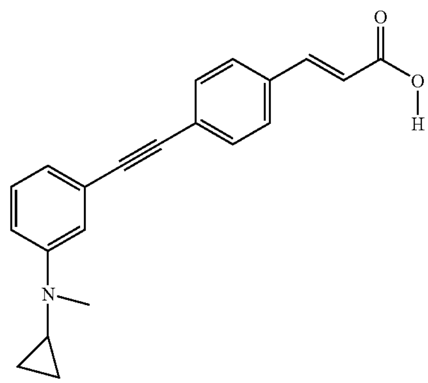 | WA (10) >10K | WA (70) 7015 | WA (15) >10K | >10 | 0.5 |
| 63 | 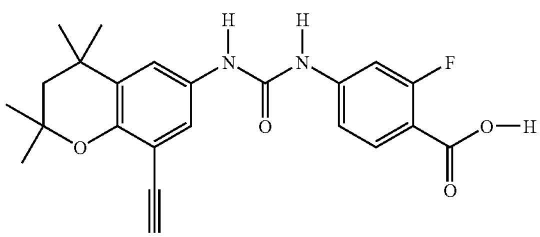 | NA >100K | 853 (37) 11K | NA >100K | >10 | 0.68 |

NA[1] = Not Active;
WA[2] = Weakly Active

The compounds of the invention can be synthesized by applying the general synthetic methodology described above, and by such modifications of the hereinafter described specific synthetic routes which will become readily apparent to the practicing synthetic organic chemist in light of this disclosure and in view of general knowledge available in the art. The hereinafter disclosed specific reaction schemes are directed to the synthesis of exemplary and preferred compounds of the invention. Whereas each of the specific and exemplary synthetic routes shown in these schemes may describe specific compounds of the invention only within the scope of one or two of the general Formulas 1 through 17, the synthetic processes and methods used therein are adaptable within the skill of the practicing organic chemist and can be used with such adaptation for the synthesis of compounds of the invention which are not specifically described herein as examples.

Assays for Confirming Activity

The ability of a compound to selectively inhibit CYP26A or CYP26B can be determined using any of a variety of assays. Such assays can be performed, for example, in a cell or tissue that expresses endogenous or recombinant CYP26A or CYP26B, and generally involve determining CYP26A or CYP26B enzymatic activity or a downstream effect of CYP26A or CYP26 Benzymatic activity prior to and following application of a test compound. A downstream effect of CYP26A or CYP26B enzymatic activity can be, without limitation, a change in the level of a retinoid in a cell.

Methods for measuring CYP26A or CYP26B activity are well known to those skilled in the art, and are described, for example, in U.S. Pat. No. 6,495,552; WO 01/44443; White et al., *Proc. Natl. Acad. Sci. USA* 97:6403-6408 (2000); White et al., *J. Biol. Chem.* 272:18538-18541 (1997), and in Examples I and II. One type of assay useful for assessing CYP26A or CYP26B activity involves determining catabolism of retinoic acid to more polar derivatives including 4-hydroxy retinoic acid and 4-oxo retinoic acid (White et al., supra 1997).

A variety of cell types, including naturally occurring and genetically engineered cells, can be used in an in vitro assay to detect CYP26A or CYP26B activity or a downstream effect of CYP26A or CYP26B enzymatic activity. Naturally occurring cells that express endogenous CYP26A or CYP26B include, for example, cells obtained from an organ that expresses CYP26A or CYP26B, as described above. Cell lines that express CYP26A include, yet are not limited to, HEK293, LC-T, SK-LC6, MCF, NB4, and U937 (White et al., supra 1997). Cell lines that express CYP26B include, yet are not limited to, HPK1a-ras, HeLa and MCF-7 (White et al., supra 2000). Other naturally occurring cells and cell lines that express CYP26A or CYP26B can be identified by those skilled in the art using methods disclosed herein and other methods well known in the art. Cells for use in testing a compound for its ability to selectively inhibit CYP26A or CYP26B can be obtained from a mammal, such as a mouse, rat, pig, goat, primate or human, or a non-mammal.

Cells expressing CYP26A or CYP26B can be prepared using a variety of methods. Recombinant expression can be advantageous in providing a higher level of expression of CYP26A or CYP26B than is found endogenously, and also allows expression in cells or extracts in which expression is not normally found. A recombinant nucleic acid expression construct generally contains a constitutive or inducible promoter of RNA transcription appropriate for the host cell or transcription-translation system, operatively linked to a nucleotide sequence that encodes a polypeptide corresponding to CYP26A or CYP26B or an active fragment thereof. The expression construct can be DNA or RNA, and optionally can be contained in a vector, such as a plasmid or viral vector.

The nucleotide and amino acid sequences of human CYP26A are available to one skilled in the art, for example, under GenBank Accession No. NM_000783 and NM_057157; the nucleotide and amino acid sequences of human CYP26B are available to one skilled in the art, for example, under GenBank Accession No. NM_019885. Other human CYP26A and CYP26B nucleotide and polypeptide sequences are available from GenBank, as are othologous CYP26A and CYP26B sequences from rat, mouse and other species. Any of these CYP26A or CYP26B nucleotide sequences can be used to recombinantly express a CYP26A or CYP26B in an assay for confirming the activity of a selective CYP26A or selective CYP26B inhibitor. One skilled in the art can recombinantly express desired levels of CYP26A or CYP26B using routine laboratory methods, described, for example, in standard molecular biology technical manuals, such as Sambrook et al., supra (1992) and Ausubel et al., supra (1998).

Exemplary host cells that can be used to express recombinant CYP26A and/or CYP26B include isolated mammalian primary cells; established mammalian cell lines, such as COS, CHO, HeLa, NIH3T3, HEK 293-T and PC12; amphibian cells, such as *Xenopus* embryos and oocytes; and other vertebrate cells. Exemplary host cells also include insect cells such as *Drosophila*, yeast cells such as *S. cerevisiae*, *S. pombe*, or *Pichia pastoris* and prokaryotic cells such as *E. coli*.

An exemplary cell-based assay for confirming the ability of a compound to selectively inhibit CYP26A or CYP26B are described in U.S. Pat. No. 6,495,552. In brief, CYP26A or CYP26B can be stably transfected into HeLa cells. Exponentially growing cells are harvested by incubating in trypsin. Cells are then washed and plated in a 48-well plate at $5 \times 10^5$ cells in 0.2 ml MEM medium containing 10% FBS and 0.05 µCi [$^3$H]-RA in the presence or absence of increasing concentrations of the test compounds. The compounds are diluted in 100% DMSO and then added in triplicate wells at either 10, 1 or 0.1 µM final concentration. As a positive control for RA metabolism inhibition, cells are also incubated with ketoconazole at 100, 10 and 1 µM. Cells are incubated for 3 hours at 37 degrees C. The retinoids are then extracted using the procedure of Bligh et al., *Canadian Journal of Biochemistry* 37: 911-917 (1959), modified by using methylenechloride instead of chloroform. This publication by Bligh et al., is specifically incorporated herein by reference. The water soluble radioactivity is quantified using a β scintillation counter, and $IC_{50}$ values are determined.

An exemplary animal model assay for confirming the ability of a compound to selectively inhibit CYP26A or CYP26B also is described in U.S. Pat. No. 6,531,599. Topical application of a selective CYP26A inhibitor or selective CYP26B inhibitor can cause an increase in the endogenous levels of retinoic acid that results in retinoic acid-induced irritation in skin of hairless mice. Thus, a hairless mouse model is an exemplary animal model that can be used to confirm that a particular selective CYP26A inhibitor or selective CYP26B inhibitor has activity in vivo.

Confirming the Efficacy of a Selective CYP26A Inhibitor or Selective CYP26B Inhibitor The efficacy of a selective CYP26A inhibitor or selective CYP26B inhibitor, such as a compound represented by any of Formulas 1 through 4, 6 through 14, 16, 17 and 18 through 29, or a pharmaceutically acceptable salt, ester, amide, sterioisomer or racemic mixture thereof, in treating a retinoid responsive disorder in an individual can be confirmed using any of a variety of well-known methods. For example, well-known animal models can be useful for confirming the efficacy of a selective CYP26A inhibitor or selective CYP26B inhibitor in treating a retinoid responsive disorder such as a skin disorder, inflammatory disorder, autoimmune disorder, neurological disorder, proliferative disorder, ocular disorder or pulmonary disorder. Animal models predictive for such disorders can be used to confirm the efficacy of treatment by measuring appropriate experimental endpoints or clinical or physiological indicators, which will depend on the particular animal model selected. Those skilled in the art will know which animal models can be used for determining the efficacy or effective amount of a selective CYP26A inhibitor or selective CYP26B inhibitor useful in the methods of the invention.

An exemplary animal model for confirming the efficacy of a selective CYP26A inhibitor or selective CYP26B inhibitor in treating acne is disclosed in Example I. A variety of well known animal models for acne can be used to confirm the efficacy of a selective CYP26A inhibitor or selective CYP26B inhibitor.

A variety of exemplary animal models of retinoid responsive inflammatory or autoimmune disorders are well known to those skilled in the art. Several of these models are described, for example, in *Progress in Inflammation Research*, (M. J. Parnham, Ed.) Birkhäuser Verlag, Basel, Switzerland (1998). Those skilled in the art will be able to select an appropriate animal model depending, in part, upon the particular disorder to be treated using a method of the invention.

An exemplary animal model for confirming the efficacy of a selective CYP26A inhibitor or selective CYP26B inhibitor in treating a retinoid responsive proliferative disorder generally involves the inoculation or implantation of a laboratory animal with heterologous tumor cells followed by simultaneous or subsequent administration of a therapeutic treatment. The efficacy of the treatment can be determined, for example, by measuring the extent of cell or tumor growth or tumor metastasis. Measurement of clinical or physiological indicators can alternatively or additional be assessed as an indicator of treatment efficacy. Exemplary animal tumor models are described, for example, in Brugge et al., *Origins of Human Cancer*, Cold Spring Harbor Laboratory Press, Plain View, N.Y., (1991).

Animal models for confirming the efficacy of a selective CYP26A inhibitor or selective CYP26B inhibitor in treating a retinoid responsive neurological disorder include, for example, animal models of trauma due to stroke or neural injury that are known in the art. One experimental model of stroke involves occluding the right middle cerebral artery and both common carotid arteries of rats for a short period, followed by reperfusion (Moore et al., *J. Neurochem.* 80:111-118 (2002)). An experimental model of CNS injury is the fluid percussion injury (FPI) model, in which moderate impact (1.5-2.0 atm) is applied to the parietal cerebral cortex (Akasu et al., *Neurosci. Lett.* 329:305-308 (2002)). Experimental models of spinal cord injury are also used in the art (Scheifer et al., *Neurosci. Lett.* 323:117-120 (2002)). Suitable models for neural damage due to oxidative stress, hypoxia, radiation and toxins are also known in the art and useful for confirming the efficacy of a selective CYP26A inhibitor or selective CYP26B inhibitor.

A variety of animal models of ocular disorders are known to those skilled in the art. An exemplary animal model of retinal degeneration is described, for example, in Lewis et al.,

*Eye* 16: 375-387 (2002). Similarly, a variety of animal models of pulmonary disorders are known to those skilled in the art. An exemplary animal model of emphysema is described, for example, in Chen et al., *J. Invest Surg* 11: 129-137 (1998).

Screening for other Selective CYP26A and CYP26B Inhibitors

A selective CYP26A inhibitor or selective CYP26B inhibitor used in a method of the invention also can be a naturally or non-naturally occurring small molecule, or a naturally or non-naturally occurring macromolecule such as a peptide, peptidomimetic, nucleic acid, carbohydrate or lipid. A selective CYP26A inhibitor or selective CYP26A inhibitor further can be an antibody, or antigen-binding fragment thereof such as a monoclonal antibody, humanized antibody, chimeric antibody, minibody, bifunctional antibody, single chain antibody (scFv), variable region fragment (Fv or Fd), Fab or F(ab)2. A selective CYP26A or CYP26B inhibitor also can be a partially or completely synthetic derivative, analog or mimetic of a naturally occurring macromolecule, or a small organic or inorganic molecule.

A variety of methods can be used for confirming that a selective CYP26 inhibitor has at least 10-fold selectivity for CYP26B relative to CYP26A. Assays for determining activity of CYP26A and CYP26B are described herein and are well known to those skilled in the art. Therefore, by screening known or newly synthesized compounds for their ability to selectively inhibit CYP26B activity, a selective CYP26B inhibitor can be identified and used to treat a retinoid responsive disorder according to a method of the invention.

Therapeutic Administration

The methods of the invention involve administering a selective CYP26A inhibitor or selective CYP26B inhibitor to an individual to treat a retinoid responsive disorder. As used herein, the term "treating" means reducing, delaying or preventing onset of one or more clinical symptoms, physiological indicators or biochemical markers of a retinoid responsive disorder, or reducing the need for a concurrent therapy. Clinical symptoms include perceptible, outward or visible signs of disease. Physiological indicators include detection of the presence or absence of physical and chemical factors associated with a process or function of the body. Biochemical markers include those signs of disease that are observable at the molecular level, such as the presence of a disease marker, such as a tumor marker. One skilled in the art will be able to recognize specific clinical symptoms, physiological indicators and biochemical markers associated with a particular retinoid responsive disorder. The term "treating" encompasses any significant reduction in a symptom of a retinoid responsive disorder such as a reduction of at least 30%, 40%, 60%, 70%, 80%, 90% or 100%.

The skilled clinician will be able to determine appropriate clinical symptoms, physiological indicators or biochemical markers associated with a particular retinoid responsive disorder, such as a particular skin disorder, neurological disorder, autoimmune disorder, inflammatory disorder, ocular disorder or pulmonary disorder. The skilled clinician also will know how to determine if an individual is a candidate for treatment with a selective CYP26A inhibitor or selective CYP26B inhibitor, based in part on the type and severity of the disorder, the degree of responsiveness of the disorder to retinoid therapy, the tissue affected, and the medical history and condition of the individual.

The appropriate effective amount to be administered for a particular application of the methods can be determined by those skilled in the art, using the guidance provided herein. For example, an effective amount can be extrapolated from in vitro and in vivo assays as described herein above. One skilled in the art will recognize that clinical symptoms, physiological indicators and biochemical markers of a disorder in an individual can be monitored throughout the course of therapy and that the effective amount of a selective CYP26A inhibitor or selective CYP26B inhibitor that is administered can be adjusted accordingly.

The invention also can be practiced by administering an effective amount of selective CYP26A inhibitor or selective CYP26B inhibitor together with one or more other agents including, but not limited to, one or more retinoids. In such "combination" therapy, it is understood that a selective CYP26A inhibitor or selective CYP26B inhibitor can be delivered independently or simultaneously, in the same or different pharmaceutical compositions, and by the same or different routes of administration as the one or more other agents. A selective CYP26A inhibitor or selective CYP26B inhibitor can beneficially decrease destruction of therapeutically administered retinoids and thereby allow a reduced amount of retinoid to be administered or a reduced frequency of retinoid administration; and can increase the efficacy of a retinoid or reduce or prevent development of retinoid resistance in individuals treated with a retinoid. Exemplary retinoids which can be useful in combination therapy include, without limitation, tretinoin (all-trans-retinoic acid, vitamin A acid), alitretinoin (9-cis-retinoic acid), bexarotene (Tagretin), isotretinoin (13-cis-retinoic acid), and tazarotene.

Modifications and Pharmaceutical Formulations

Selective CYP26A inhibitors that have at least 10-fold selectivity for CYP26A relative to CYP26B are disclosed herein as Formulas 1 through 4, 6 through 14, 16, 17 and 18 through 29. Exemplary selective CYP26B inhibitors that have at least 10-fold selectivity for CYP26B relative to CYP26A are disclosed herein as Formulas 5, 15 and 30 through 32. Also encompassed by the invention are methods that employ pharmaceutically acceptable salts, esters and amides derived from Formulas 18 to 32. Suitable pharmaceutically acceptable salts of the selective CYP26A inhibitors and selective CYP26B inhibitors useful in the invention include, without limitation, acid addition salts, which can be formed, for example, by mixing a solution of the inhibitor with a solution of an appropriate acid such as hydrochloric acid, sulfuric acid, fumaric acid, maleic acid, succinic acid, acetic acid, benzoic acid, citric acid, tartaric acid, carbonic acid or phosphoric acid.

Where an inhibitor carries an acidic moiety, suitable pharmaceutically acceptable salts thereof can include alkali salts such as sodium or potassium salts; alkaline earth salts such as calcium or magnesium salts; and salts formed with suitable organic ligands, for example, quaternary ammonium salts. Representative pharmaceutically acceptable salts include, yet are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

It is understood that the functional groups of selective CYP26A inhibitors and selective CYP26B inhibitors useful in the invention can be modified to enhance the pharmacological utility of the compounds. Such modifications are well within the knowledge of the skilled chemist and include, without limitation, esters, amides, ethers, N-oxides, and prodrugs of the indicated inhibitor. Examples of modifications that can enhance the activity of an inhibitor include, for example, esterification such as the formation of C1 to C6 alkyl esters, preferably C1 to C4 alkyl esters, wherein the alkyl group is a straight or branched chain. Other acceptable esters include, for example, C5 to C7 cycloalkyl esters and arylalkyl esters such as benzyl esters. Such esters can be prepared from selective CYP26A or CYP26B inhibitors disclosed herein using conventional methods well known in the art of organic chemistry.

Other pharmaceutically acceptable modifications include the formation of amides. Useful amide modifications include, for example, those derived from ammonia; primary C1 to C6 dialkyl amines, where the alkyl groups are straight or branched chain; and arylamines having various substitutions. In the case of secondary amines, the amine also can be in the form of a 5 or 6 membered ring. Methods for preparing these and other amides are well known in the art.

It is understood that, where an inhibitor useful in the invention is a compound having at least one chiral center, the compound can exist as chemically distinct enantiomers. In addition, where a compound has two or more chiral centers, the compound exists as diastereomers. All such isomers and mixtures thereof are encompassed within the scope of the indicated inhibitor. Similarly, where an inhibitor possesses a structural arrangement that permits the structure to exist as tautomers, such tautomers are encompassed within the scope of the indicated inhibitor. Furthermore, in crystalline form, an inhibitor can exist as polymorphs; in the presence of a solvent, an inhibitor can form a solvate, for example, with water or a common organic solvent. Such polymorphs, hydrates and other solvates also are encompassed within the scope of the indicated inhibitor as defined herein.

A selective CYP26A inhibitor or selective CYP26B inhibitor useful in the invention generally is administered in a pharmaceutical composition. Such a pharmaceutical composition includes the active inhibitor and further can include, if desired, an excipient such as a pharmaceutically acceptable carrier or a diluent, which is any carrier or diluent that has substantially no long term or permanent detrimental effect when administered to an individual. Such an excipient generally is mixed with active compound, or permitted to dilute or enclose the active compound. A carrier can be a solid, semi-solid, or liquid agent that acts as an excipient or vehicle for the active compound. Examples of pharmaceutically acceptable carriers and diluents include, without limitation, water, such as distilled or deionized water; saline; and other aqueous media. It is understood that the active ingredients can be soluble or can be delivered as a suspension in the desired carrier or diluent.

A pharmaceutical composition further can include, if desired, one or more agents such as emulsifying agents, wetting agents, sweetening or flavoring agents, tonicity adjusters, preservatives, buffers or anti-oxidants. Tonicity adjustors useful in a pharmaceutical composition include salts such as sodium chloride, potassium chloride, mannitol or glycerin and other pharmaceutically acceptable tonicity adjustors. Preservatives useful in the pharmaceutical compositions of the invention include, without limitation, benzalkonium chloride, chlorobutanol, thimerosal, phenylmercuric acetate, and phenylmercuric nitrate. Various buffers and means for adjusting pH can be used to prepare a pharmaceutical composition, including, but not limited to, acetate buffers, citrate buffers, phosphate buffers and borate buffers. Similarly, anti-oxidants useful in the pharmaceutical compositions of the invention are well known in the art and include, for example, sodium metabisulfite, sodium thiosulfate, acetylcysteine, butylated hydroxyanisole and butylated hydroxytoluene. It is understood that these and other substances known in the art of pharmacology can be included in a pharmaceutical composition useful in the invention.

A selective CYP26A inhibitor or selective CYP26B inhibitor useful in a method of the invention is administered to an individual in an effective amount. Such an effective amount generally is the minimum dose necessary to achieve the desired therapeutic effect, which can be, for example, that amount roughly necessary to reduce a symptom of retinoid responsive disorder to a more comfortable, tolerable, acceptable, or improved level. For example, the term "effective amount" when used with respect to treating a retinoid responsive disorder can be a dose sufficient to reduce a symptom, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the disorder, the age and weight of the individual, the individual's general physical condition, and the route of administration. Where repeated administration is used, the frequency of administration depends, in part, on the half-life of the inhibitor. Suppositories and extended release formulations can be useful in the invention and include, for example, dermal patches, formulations for deposit on or under the skin and formulations for intramuscular injection. It is understood that slow-release formulations also can be useful in the methods of the invention. The individual receiving a selective CYP26A inhibitor or selective CYP26B inhibitor can be any mammal or other vertebrate capable of experiencing a retinoid responsive disorder, for example, a human, primate, horse, cow, pig, dog, cat, hamster, or bird.

Administration of a Selective CYP26A Inhibitor or Selective CYP26B Inhibitor

Various routes of administration can be useful for treating a retinoid responsive disorder according to a method of the invention depending, for example, on the organ or tissue to be treated, the selective inhibitor or other compound to be included in the composition, and the history, risk factors and symptoms of the subject. Routes of administration suitable for the methods of the invention include both systemic and local administration. As non-limiting examples, a pharmaceutical composition useful for treating a retinoid responsive disorder can be administered orally or by subcutaneous pump; by dermal patch; by intravenous, subcutaneous or intramuscular injection; by topical drops, creams, gels or ointments; by suppository; as an implanted or injected extended release formulation; by subcutaneous minipump or other implanted device; by intrathecal pump or injection; or by epidural injection. It is understood that the frequency and duration of dosing will be dependent, in part, on the relief desired and the half-life of the selective CYP26A inhibitor or selective CYP26B inhibitor.

In particular embodiments, a method of the invention is practiced by peripheral administration of a selective CYP26A inhibitor or selective CYP26B inhibitor. As used herein, the term "peripheral administration means introducing an agent into a subject outside of the central nervous system. Peripheral administration encompasses any route of administration other than direct administration to the spine or brain. As such, it is clear that intrathecal and epidural administration as well as cranial injection or implantation is not within the scope of the term "peripheral administration" or "administered peripherally."

Peripheral administration can be local or systemic. Local administration results in significantly more of a pharmaceutical composition being delivered to the site of local administration than to regions distal to the site of administration. Systemic administration results in delivery of a pharmaceutical composition to essentially the entire peripheral nervous system of the subject and can also result in delivery to the central nervous system depending on the properties of the composition.

Routes of peripheral administration useful in the methods of the invention encompass, without limitation, oral administration, topical administration, intraocular administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; by inhalation; and by minipump or other implanted extended release device or formulation.

Topical ophthalmic administration can be useful in the methods of the invention for treating a retinoid responsive ocular disorder. Such administration can be achieved using, without limitation, ocular drops, ocular ointments, ocular gels and ocular creams. Such ophthalmic preparations are easy to apply and deliver the active ingredient effectively and avoid possible systemic side effects.

Topical administration includes administration to the skin or mucosa, including surfaces of the lung. Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Synthetic Methods

SPECIFIC EXAMPLES

The reactions schemes provided below together with the applicable experimental descriptions disclose the presently preferred synthetic routes for preparing the preferred compounds of the invention.

Synthetic Procedures for Preparing Coupling Reagents

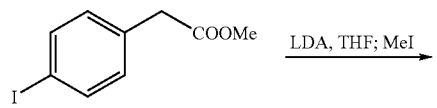

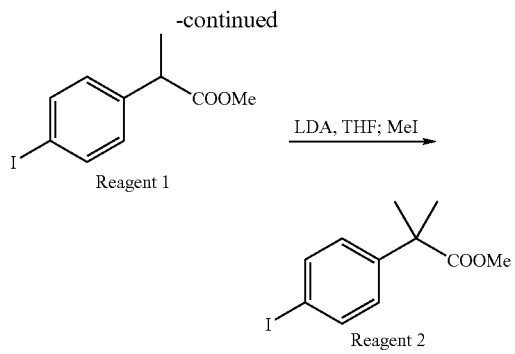

General Procedure A:
Methyl-2-(4-iodophenyl)propionate (Reagent 1)

A stirred, cooled (−78° C.) solution of methyl-4-iodophenyl acetate (described in U.S. Pat. No. 6,252,090, incorporated herein by reference; 2.77 g, 10 mmol) in anhydrous tetrahydrofuran (20 mL) was treated with a 1.5M solution of lithium diisopropyl amide in tetrahydrofuran and cyclohexane (8 mL, 12 mmol). The reaction mixture was allowed to warm to 0° C. over 40 minutes, cooled again to −78° C. and treated with methyl iodide (0.75 mL, 12 mmol). The reaction mixture was allowed to warm to room temperature over 1 h. It was then quenched with saturated aqueous ammonium chloride solution, diluted with water and extracted with diethyl ether. The combined organic phase was washed with brine (×1), dried over anhydrous magnesium sulfate, filtered and evaporated in vacuo to afford the title product as a yellow oil (2.7 g, 92.7%).

$^1$H NMR (300 MHz, CDCl$_3$): δ 7.66 (d, 2H, J=8.5 Hz), 7.06 (d, 2H, J=8.5 Hz), 3.70-3.66 (m, 1H), 3.67 (s, 3H), 1.49 (d, 3H, J=7.0 Hz).

Methyl-2-(4-idophenyl)-2-methyl propionate (Reagent 2)

Following General Procedure A and using methyl-2-(4-iodophenyl)propionate (1.45 g, 5 mmol), lithium diisopropyl amide (1.5M in tetrahydrofuran and cyclohexane, 4 mL, 6 mmol), tetrahydrofuran (15 mL) and methyl iodide (0.5 mL, 8 mmol), the title compound was obtained as an oil (1.5 g, 98%).

$^1$H NMR (300 MHz, CDCl$_3$): δ 7.66 (d, 2H, J=8.7 Hz), 7.11 (d, 2H, J=8.7 Hz), 3.66 (s, 3H), 1.58 (s, 6H).

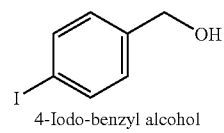
4-Iodo-benzyl alcohol

A stirred, cooled (−78° C.) solution of ethyl-4-iodo-benzoate (available from Lancaster, 12.9 g, 45 mmol) in anhydrous dichloromethane (100 mL) under argon was treated with a 1M solution of di-isobutyl aluminum hydride in dichloromethane (100 mL, 100 mmol). The reaction mixture was allowed to warm to 0° C. in 1.5 h, quenched with saturated aqueous ammonium chloride solution and the resulting emulsion was filtered over a bed of celite. The phases in the filtrate were separated and the aqueous phase was extracted with dichloromethane (×1). The combined organic phase was dried over anhydrous sodium sulfate, filtered and evaporated in vacuo to afford the title product as a white solid (9 g, 85%).

$^1$H NMR (300 MHz, CDCl$_3$): δ 7.65 (d, 2H, J=7.6 Hz), 7.05 (d, 2H, J=7.6 Hz), 4.57 (s, 2H), 2.40 (br s, 1H).

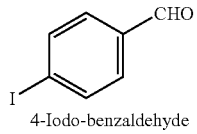

4-Iodo-benzaldehyde

A solution of 4-iodobenzyl alcohol (9 g, 38.29 mmol) in dichloromethane (90 mL) and acetonitrile (10 mL) was treated sequentially with 4 A molecular sieves powder (9 g), tetra-n-propyl ammoniumperruthenate (0.13 g) and N-methyl morpholine-N-oxide (9 g, 76.6 mmol). After stirring at ambient temperature for 2 h, the reaction mixture was diluted with hexane and subjected to flash column chromatography over silica gel (230-400 mesh) using 6-10% ethyl acetate in hexane as the eluent to afford the title compound (2.5 g pure and 4 g ~95% pure, 73%).

$^1$H NMR (300 MHz, CDCl$_3$): δ 9.96 (s, 1H), 7.92 (d, 2H, J=8.5 Hz), 7.59 (d, 2H, J=8.5 Hz).

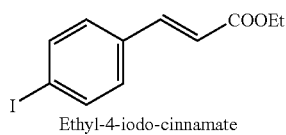

(Reagent 3)

Ethyl-4-iodo-cinnamate

A stirred, cooled (−78° C.) solution of triethylphosphonoacetate (11.1 mL, 56 mmol) in anhydrous tetrahydrofuran (100 mL) was treated with a 1.6M solution of n-butyl lithium in hexanes (27 mL, 43.75 mmol). After 10 min, the reaction mixture was cannulated into a cooled (−78° C.) solution of 4-iodo-benzaldehyde (6.5 g, 28 mmol) in tetrahydrofuran (20 mL). The reaction mixture was allowed to warm to 0° C. over 1 h. It was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230-400 mesh) using 6-8% ethyl acetate in hexane as the eluent to afford the title compound (2.7 g pure, 3.2 g ~95% pure, 69%).

$^1$H NMR (300 MHz, CDCl$_3$): δ 7.70 (d, 2H, J=8.5 Hz), 7.57 (d, 1H, J=15.8 Hz), 7.21 (d, 2H, J=8.5 Hz), 6.43 (d, 1H, J=15.8 Hz), 4.25 (q, 2H, J=7.1 Hz), 1.33 (t, 3H, J=7.1 Hz).

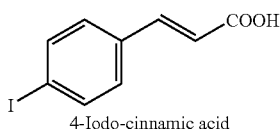

4-Iodo-cinnamic acid

A solution of ethyl-4-iodo-cinnamate (3.2 g, 10.5 mmol) in methanol (25 mL), tetrahydrofuran (25 mL) and water (15 mL) was treated with lithium hydroxide monohydrate (4.2 g, 100 mmol) and the resulting reaction mixture was stirred at ambient temperature over 2 days. The volatiles were evaporated in vacuo and the residue was neutralized with saturated aqueous ammonium chloride solution. The precipitated solid was filtered, washed with water and hexane and dried to afford the title product as a white solid (2.9 g, 91%). It was used as such for the next step.

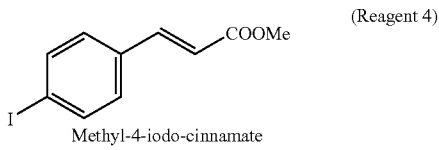

Methyl-4-iodo-cinnamate

A stirred, cooled (ice bath) solution of 4-iodo-cinnamic acid in methanol was treated with a solution of diazomethane in diethyl ether. The reaction mixture was allowed to warm to ambient temperature, the volatiles were evaporated in vacuo to afford the title compound.

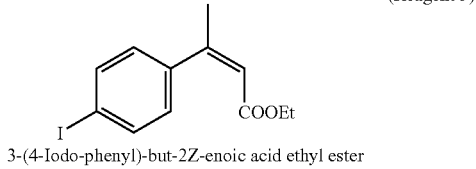

3-(4-Iodo-phenyl)-but-2Z-enoic acid ethyl ester

A stirred, cooled (−78° C.) solution of triethyl-2-phosphonoacetate (4.55 g, 20 mmol) in anhydrous tetrahydrofuran (10 mL) was treated with a 1.6M solution of n-butyl lithium in hexanes (12.8 mL, 20.5 mmol). After 30 min, a solution of 4-iodo-acetophenone (2.5 g, 10 mmol) in tetrahydrofuran (5 mL) was cannulated into the reaction mixture. After 4 h, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230-400 mesh) using 5-10% ethyl acetate in hexane as the eluent, followed by preparative normal phase HPLC to afford the title compound (0.53 g, 15%).

$^1$H NMR (300 MHz, CDCl$_3$): δ 7.67(d, J=8.2 Hz, 2H), 6.94(d, J=8.2 Hz, 2H), 5.91(s, 1H), 4.01(q, J=7.1 Hz, 2H), 2.14 (s, 6H), 1.12(t, J=7.1 Hz, 3H).

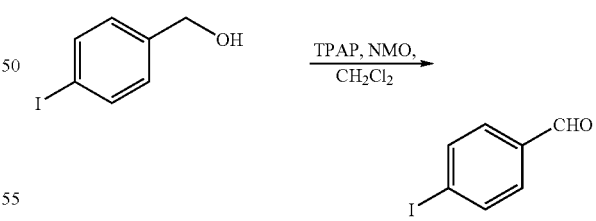

3-Iodo-benzaldehyde

A solution of 3-iodobenzyl alcohol (Aldrich, 4.72 g, 20 mmol) in dichloromethane (50 mL) and acetonitrile (5 mL) was treated sequentially with 4 A molecular sieves powder (5 g), tetra-n-propyl ammoniumperruthenate (0.1 g) and N-methyl morpholine-N-oxide (2.34 g, 40 mmol). After stirring at ambient temperature for 3 h, the reaction mixture was diluted with hexane and subjected to flash column chromatography over silica gel (230-400 mesh) using 6-10% ethyl acetate in hexane as the eluent to afford the title compound (3.7 g, 80%). It was used as such for the next step.

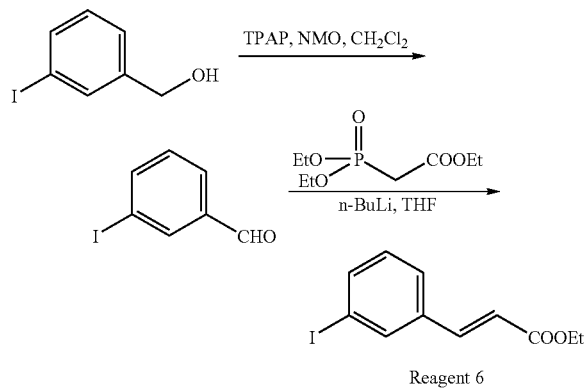

Ethyl-3-iodo-cinnamate (Reagent 6)

A stirred, cooled (−78° C.) solution of triethylphosphonoacetate (11.44 g, 51 mmol) in anhydrous tetrahydrofuran (100 mL) was treated with a 1.6M solution of n-butyl lithium in hexanes (30 mL, 48 mmol). After 10 min, the reaction mixture was cannulated into a cooled (−78° C.) solution of 4-iodo-benzaldehyde (3.7 g, 16 mmol) in tetrahydrofuran (20 mL). The reaction mixture was allowed to warm to 0° C. over 1 h. It was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230-400 mesh) using 8-10% ethyl acetate in hexane as the eluent to afford the title compound (4.6 g, 95%).

$^1$H NMR (300 MHz, CDCl$_3$): δ 7.83 (s, 1H), 7.65 (dd, 1H, J=7.9, 2 Hz), 7.53 (d, 1H, J=15.8 Hz), 7.43 (dd, 1H, J=7.6, 2 Hz), 7.07 (dd, 1H, J=7.6, 7.9 Hz), 6.38 (d, 1H, J=15.8 Hz), 4.24 (q, 2H, J=6.9 Hz), 1.34 (t, 3H, J=6.9 Hz).

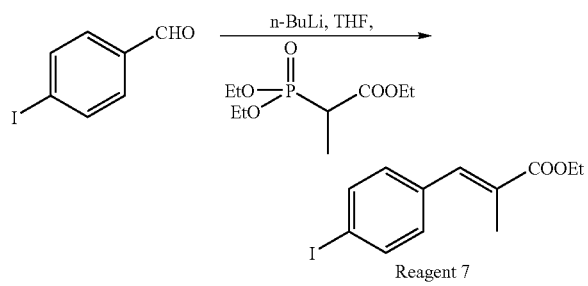

Reagent 7

(E)-3-(4-Iodo-phenyl)-2-methyl-acrylic acid ethyl ester (Reagent 7)

A stirred, cooled (−78° C.) solution of triethyl-2-phosphonopropionate (10 g, 41.9 mmol) in anhydrous tetrahydrofuran (100 mL) was treated with a 1.6M solution of n-butyl lithium in hexanes (25 mL, 40 mmol). After 10 min, the reaction mixture was cannulated into a cooled (−78° C.) solution of 4-iodo-benzaldehyde (4.66 g, 20 mmol) in tetrahydrofuran (25 mL). After 30 minutes, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230-400 mesh) using 9-10% ethyl acetate in hexane as the eluent to afford the title compound (6.3 g, 99%).

$^1$H NMR (300 MHz, CDCl$_3$): δ 7.71 (d, 2H, J=8.4 Hz), 7.58 (s, 1H), 7.12 (d, 2H, J=8.4 Hz), 4.27 (q, 2H, J=7.2 Hz), 2.08 (d, 3H, J=1.5 Hz), 1.35 (t, 3H, J=7.2 Hz).

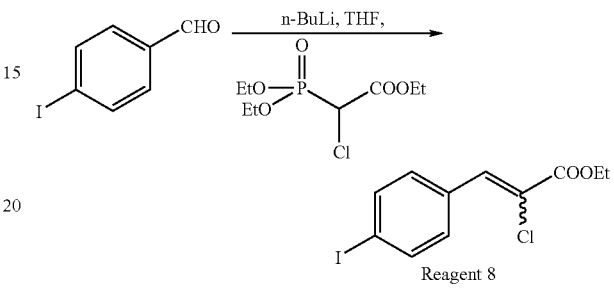

2-Chloro-3-(4-iodo-phenyl)-acrylic acid ethyl ester (Reagent 8)

A stirred, cooled (−78° C.) solution of chloro-(dipropylphosphinoyl)-acetic acid ethyl ester (6.1 g, 23.5 mmol) in anhydrous tetrahydrofuran (70 mL) was treated with a 1.6M solution of n-butyl lithium in hexanes (14 mL, 22 mmol). After 10 min, the reaction mixture was cannulated into a cooled (−78° C.) solution of 4-iodo-benzaldehyde (2.61 g, 11.2 mmol) in tetrahydrofuran (25 mL). After 30 minutes, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230-400 mesh) using 4-5% ethyl acetate in hexane as the eluent to afford the title compound as a 1:1 mixture of E and Z isomers (3.6 g, 95%).

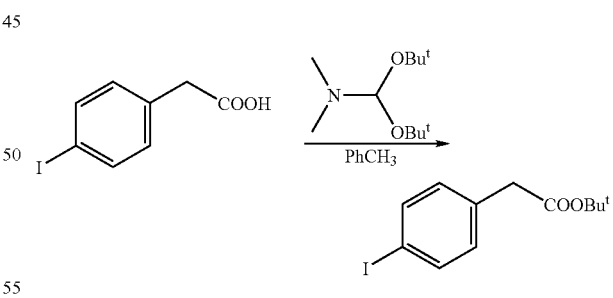

4-Iodo-tert-butyl phenyl acetate (Reagent 10)

A solution of 4-iodo phenyl acetic acid (Lancaster, 1.31 g, 5 mmol) in anhydrous toluene (10 mL) was heated to 80° C. and treated with a solution of N,N-dimethyl formamide di-t-butyl acetal. After 2 h the reaction mixture was cooled to ambient temperature and subjected to flash column chromatography on silica gel (23-400 mesh) using 10% ethyl acetate in hexane as the eluent to afford the title compound (0.7 g, 44%).

$^1$H NMR (300 MHz, CDCl$_3$): δ 7.62 (d, 2H, J=8.2 Hz), 7.01 (d, 2H, J=8.2 Hz), 3.45 (s, 2H), 1.43 (s, 9H).

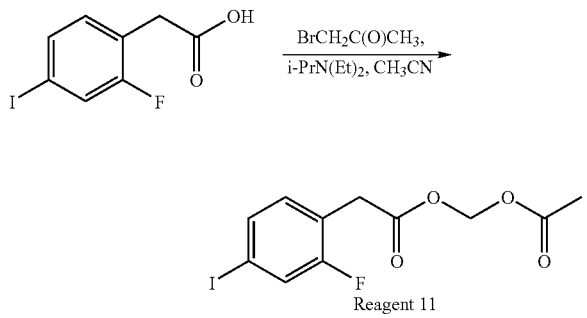

(2-Fluoro-4-iodo-phenyl)-acetic acid acetoxymethyl ester (Reagent 11)

A solution of 2-fluoro-4-iodo phenyl acetic acid (described in U.S. Pat. No. 6,252,090, incorporated herein by reference;, 0.82 g, 2.93 mmol) in anhydrous acetonitrile (10 mL) was treated with N,N-diisopropyl ethyl amine (1.27 mL, 7.32 mmol) followed by acetoxy methyl bromide/bromo methylacetate (0.896 g, 5.86 mmol) and the resulting reaction mixture was stirred overnight at ambient temperature. The volatiles were evaporated in vacuo and the residue was diluted with water and extracted with diethyl ether (×2). The combined organic phase was dried over anhydrous magnesium sulfate, filtered and evaporated in vacuo to an oil that was subjected to flash column chromatography over silica gel (230-400 mesh) using 10-20% ethyl acetate in hexane as the eluent to afford the title compound as an oil (0.75 g, 72%). $^1$H NMR (300 MHz, CDCl$_3$): 7.42(m, 2H), 6.97(dd, J=8.0 & 8.0 Hz, 1H), 5.73(s, 2H), 3.65(s, 2H), 2.08 (s, 3H).

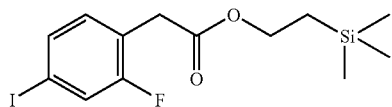

(2-Fluoro-4-iodo-phenyl)-acetic acid 2-trimethylsilanyl-ethyl ester (Reagent 12)

A solution of 2-fluoro-4-iodo phenyl acetic acid (0.3 g, 1.07 mmol) and 2-(trimethylsilyl)ethanol (0.28 mL, 1.95 mmol) in anhydrous dichloromethane (5 mL) was treated with 4-(dimethylamino)pyridine (0.275 g, 2.3 mmol) and 1-(3-dimethylaminopropyl)-3-ethylcarbodiimide hydrochloride (0.37 g, 1.95 mmol) and the resulting reaction mixture was stirred at ambient temperature overnight. The reaction mixture was then subjected to flash column chromatography using 5% ethyl acetate in hexane as the eluent to afford the title compound as a white solid (0.37 g, 91%).

$^1$H NMR (300 MHz, CDCl$_3$): 7.44(m, 2H), 7.02(dd, J=8.0, 8.0 Hz, 1H), 4.20(t, J=8.5 Hz, 2H), 3.59(s, 2H), 0.98(t, J=8.5 Hz, 2H), 0.02(s, 9H).

Synthesis of Preferred Embodiments

Reaction Scheme 1

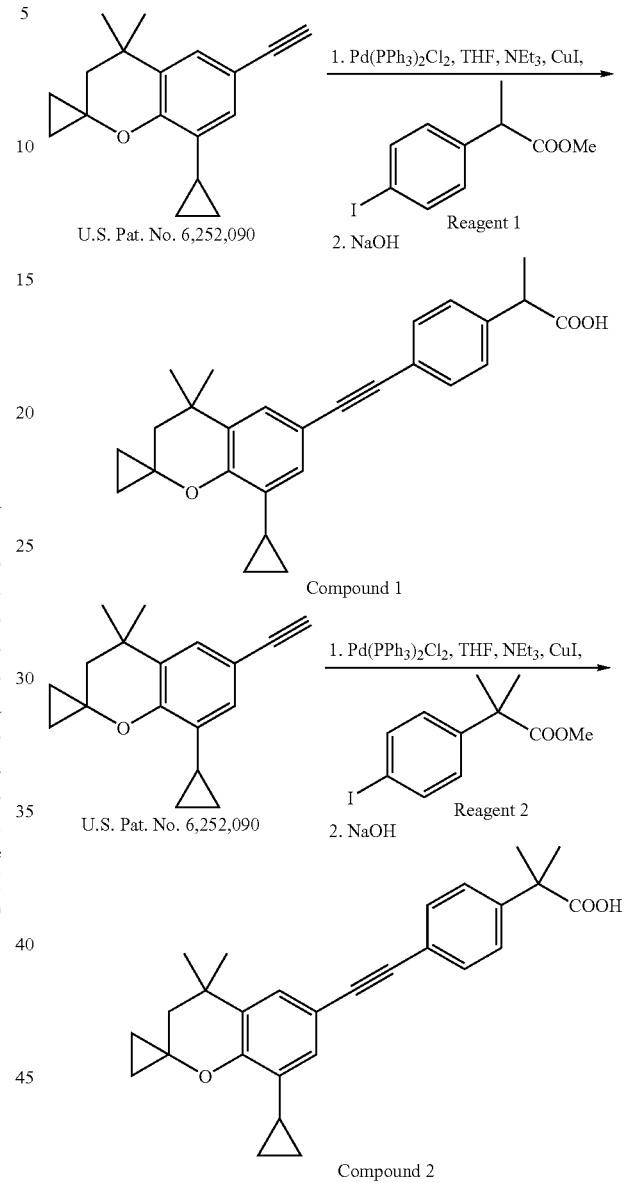

General Procedure B: 2-{4-[(8-Cyclopropyl-3,4-dihydro-4,4-dimethylspiro[2H-1-benzopyran-2,1'-cyclopropane]-6-yl)ethynyl]-phenyl}-propionic acid methyl ester (Intermediate 1)

A solution of 8-cyclopropyl-6-ethynyl-3,4-dihydro-4,4-dimethylspiro[2H-1-benzopyran-2,1'-cyclopropane] (described in U.S. Pat. No. 6,252,090; 0.068 g, 0.27 mmol), and methyl-2-(4-iodo phenyl)propionate (Reagent 1, 0.086 g, 0.3 mmol) in triethyl amine (3 mL), was treated with copper(I) iodide (0.028 g, 0.15 mmol) and sparged with argon for 5 minutes. Dichlorobis(triphenylphosphine)palladium(II) (0.057 g, 0.08 mmol) was added and the reaction mixture was stirred overnight at room temperature. It was diluted with diethyl ether and filtered over a bed of celite. The filtrate was evaporated in vacuo to brown oil that was subjected to flash column chromatography over silica gel (230-400 mesh) to afford the title compound as an oil (0.072 g, 56%).

$^1$H NMR (300 MHz, CDCl$_3$): δ 7.46 (d, 2H, J=8.4 Hz), 7.29 (d, 1H, J=2.1 Hz), 7.25 (d, 2H, J=8.4 Hz), 6.80 (d, 1H, J=2.1 Hz), 3.68 (q, 1H, J=7.2 Hz), 3.66 (s, 3H), 2.02-1.90 (m, 1H), 1.90 (s, 2H), 1.49(d, 3H, J=7.2 Hz), 1.39 (s, 6H), 1.03-0.99 (m, 2H), 0.90-0.83 (m, 2H), 0.68-0.59 (m, 4H).

2-{4-[(8-Cyclopropyl-3,4-dihydro-4,4-dimethylspiro[2H-1-benzopyran-2,1'-cyclopropane]-6-yl)ethynyl]-phenyl}-propionic acid (Compound 1)

A solution of 2-{4-[(8-cyclopropyl-3,4-dihydro-4,4-dimethylspiro[2H-1-benzopyran-2,1'-cyclopropane]-6-yl)ethynyl]-phenyl}-propionic acid methyl ester (Intermediate 1, 0.072 g, 0.174 mmol) in methanol (5 mL) was treated with a 1M solution of sodium hydroxide (1 mL, 1 mmol) and the resulting reaction mixture was heated at 55° C. for 4 h. The reaction mixture was cooled to ambient temperature and the volatiles were evaporated in vacuo to a residue that was diluted with 10% hydrochloric acid till neutral and extracted with ethyl acetate. The organic phase was washed with water and brine, dried over anhydrous magnesium sulfate, filtered and evaporated in vacuo to afford the title product as a white solid after flash column chromatography over silica gel (230-400 mesh) (0.04 g, 57%).

$^1$H NMR (300 MHz, CDCl$_3$): δ 7.46 (d, 2H, J=8.1 Hz), 7.30-7.25 (m, 3H), 6.80 (d, 1H, J=1.8 Hz), 3.74 (q, 1H, J=7.2 Hz), 1.99-1.96 (m, 1H), 1.91 (s, 2H), 1.51(d, 3H, J=7.2 Hz), 1.39 (s, 6H), 1.04-0.99 (m, 2H), 0.90-0.83 (m, 2H), 0.68-0.59 (m, 4H).

2-{4-[(8-Cyclopropyl-3,4-dihydro-4,4-dimethylspiro[2H-1-benzopyran-2,1'-cyclopropane]-6-yl)ethynyl]-phenyl}-2-methyl-propionic acid methyl ester (Intermediate 2)

Following General Procedure B and using 8-cyclopropyl-6-ethynyl-3,4-dihydro-4,4-dimethylspiro[2H-1-benzopyran-2,1'-cyclopropane] (0.096 g, 0.38 mmol), methyl-2-(4-iodo phenyl)-2-methyl-propionate (Reagent 2, 0.127 g, 0.41 mmol), triethyl amine (3 mL), copper(I)iodide (0.040 g, 0.21 mmol) and dichlorobis(triphenylphosphine)palladium(II) (0.080 g, 0.11 mmol) followed by flash column chromatography over silica gel (230-400 mesh), the title compound was obtained as an oil (0.046 g, 47%).

$^1$H NMR (300 MHz, CDCl$_3$): δ 7.39 (d, 2H, J=8.4 Hz), 7.23-7.20 (m, 3H), 6.72 (d, 1H, J=2.1 Hz), 3.58 (s, 3H), 1.92-1.84 (m, 1H), 1.84 (s, 2H), 1.51(s, 6H), 1.33 (s, 6H), 0.97-0.92 (m, 2H), 0.83-0.76 (m, 2H), 0.59-0.52 (m, 4H).

2-{4-[(8-Cyclopropyl-3,4-dihydro-4,4-dimethylspiro[2H-1-benzopyran-2,1'-cyclopropane]-6-yl)ethynyl]-phenyl}-2-methyl-propionic acid (Compound 2)

A solution of 2-{4-[(8-cyclopropyl-3,4-dihydro-4,4-dimethylspiro[2H-1-benzopyran-2,1'-cyclopropane]-6-yl)ethynyl]-phenyl}-2-methyl-propionic acid methyl ester (Intermediate 2, 0.046 g, 0.107 mmol) in methanol (5 mL) was treated with a 1M solution of sodium hydroxide (1.2 mL, 1.2 mmol) and the resulting reaction mixture was heated at 55° C. for 4 h. The reaction mixture was cooled to ambient temperature and the volatiles were evaporated in vacuo to a residue that was neutralized with 10% hydrochloric acid and extracted with ethyl acetate. The organic phase was washed with water and brine, dried over anhydrous magnesium sulfate, filtered and evaporated in vacuo to afford the title product as a white solid after flash column chromatography over silica gel (230-400 mesh) (0.067 g, 89%).

$^1$H NMR (300 MHz, CDCl$_3$): δ 7.47 (d, 2H, J=8.1 Hz), 7.36 (d, 2H, J=8.1 Hz), 7.30 (d, 1H, J=2.1 Hz), 6.80 (d, 1H, J=2.1 Hz), 1.99-1.91 (m, 1H), 1.91 (s, 2H), 1.60(s, 6H), 1.40 (s, 6H), 1.04-0.99 (m, 2H), 0.90-0.84 (m, 2H), 0.69-0.59 (m, 4H).

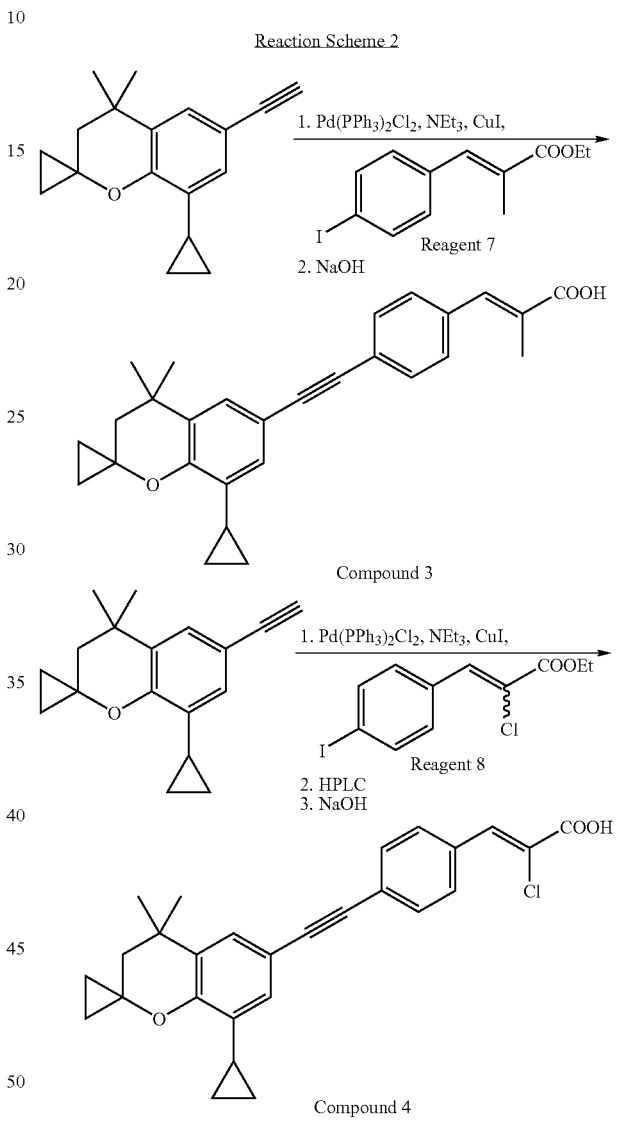

Reaction Scheme 2

Compound 3

Compound 4

(E)-3-{4-[8-Cyclopropyl-3,4-dimethylspiro[2H-1-benzopyran-2,1'-cyclopropane]-6-yl]ethynyl-phenyl}-2-methyl-acrylic acid ethyl ester (Intermediate 3)

Following General Procedure B and using 8-cyclopropyl-6-ethynyl-3,4-dihydro-4,4-dimethylspiro[2H-1-benzopyran-2,1'-cyclopropane] (0.077 g, 0.3 mmol), (E)-3-(4-iodophenyl)-2-methyl-acrylic acid ethyl ester (Reagent 7, 0.106 g, 0.23 mmol), triethyl amine (3 mL), copper(I)iodide (0.029 g, 0.15 mmol) and dichlorobis(triphenylphosphine)palladium (II) (0.064 g, 0.09 mmol) followed by flash column chromatography over silica gel (230-400 mesh), the title compound was obtained (0.06 g, 45%).

$^1$H NMR (300 MHz, CDCl$_3$): δ 7.65 (d, 1H, J=1.5 Hz), 7.52 (d, 2H, J=8.7 Hz), 7.37 (d, 2H, J=8.7 Hz), 7.32 (d, 1H, J=1.8 Hz), 6.82 (d, 1H, J=1.8 Hz), 4.27 (q, 2H, J=7.2 Hz), 2.14 (d, 3H, J=1.5 Hz), 1.99 (m, 1H), 1.91 (s, 2H), 1.40 (s, 12H), 1.35 (t, 3H, J=7.2 Hz), 1.04-1.00 (m, 2H), 0.91-0.84 (m, 2H), 0.69-0.59 (m, 4H).

(E)-3-{4-[8-Cyclopropyl-3,4-dimethylspiro[2H-1-benzopyran-2,1'-cyclopropane]-6-yl]ethynyl-phenyl}-2-methyl-acrylic acid (Compound 3)

A solution of (E)-3-{4-[8-cyclopropyl-3,4-dimethylspiro[2H-1-benzopyran-2,1'-cyclopropane]-6-yl]ethynyl-phenyl}-2-methyl-acrylic acid ethyl ester (Intermediate 3, 0.06 g, 0.13 mmol) in ethanol (2 mL) was treated with a 1M solution of sodium hydroxide (0.5 mL, 0.5 mmol) and the resulting reaction mixture was heated at 55° C. for 4 h. The reaction mixture was cooled to ambient temperature and the volatiles were evaporated in vacuo to a residue that was neutralized with 5% hydrochloric acid and extracted with ethyl acetate. The organic phase was washed with water and brine, dried over anhydrous magnesium sulfate, filtered and evaporated in vacuo to afford the title product as a yellow solid after flash column chromatography over silica gel (230-400 mesh) (0.044 g, 82%).

$^1$H NMR (300 MHz, CDCl$_3$): δ 7.81 (d, 1H, J=1.5 Hz), 7.54 (d, 2H, J=8.4 Hz), 7.41 (d, 2H, J=8.4 Hz), 7.33 (d, 1H, J=2.1 Hz), 6.83 (d, 1H, J=2.1 Hz), 2.17 (d, 3H, J=1.5 Hz), 2.00 (m, 1H), 1.92 (s, 2H), 1.41 (s, 12H), 1.05-1.00 (m, 2H), 0.91-0.84 (m, 2H), 0.69-0.60 (m, 4H).

(Z)-2-Chloro-3-{4-[8-cyclopropyl-3,4-dimethylspiro[2H-1-benzopyran-2,1'-cyclopropane]-6-yl]ethynyl}-acrylic acid ethyl ester (Intermediate 4)

Following General Procedure B and using 8-cyclopropyl-6-ethynyl-3,4-dihydro-4,4-dimethylspiro[2H-1-benzopyran-2,1'-cyclopropane] (0.11 g, 0.436 mmol), (E,Z)-2-chloro-3-(4-iodo-phenyl)-acrylic acid ethyl ester (Reagent 8, 0.162 g, 0.48 mmol), triethyl amine (3 mL), copper(I)iodide (0.041 g, 0.21 mmol) and dichlorobis(triphenylphosphine)palladium(II) (0.092 g, 0.13 mmol) followed by flash column chromatography over silica gel (230-400 mesh), and preparative normal phase HPLC using 5% ethyl acetate in hexane as the mobile phase, the title compound was obtained (0.09 g, 45%).

$^1$H NMR (300 MHz, CDCl$_3$): δ 7.88 (s, 1H), 7.83 (d, 2H, J=8.1 Hz), 7.55 (d, 2H, J=8.1 Hz), 7.33 (d, 1H, J=2.1 Hz), 6.82 (d, 1H, J=2.1 Hz), 4.36 (q, 2H, J=6.9 Hz), 1.99 (m, 1H), 1.92 (s, 2H), 1.41 (s, 12H), 1.39 (t, 3H, J=6.9 Hz), 1.05-1.00 (m, 2H), 0.91-0.84 (m, 2H), 0.70-0.60 (m, 4H).

(Z)-2-Chloro-3-{4-[8-cyclopropyl-3,4-dimethylspiro[2H-1-benzopyran-2,1'-cyclopropane]-6-yl]ethynyl}-acrylic acid (Compound 4)

A solution of (Z)-2-chloro-3-{4-[8-cyclopropyl-3,4-dimethylspiro[2H-1-benzopyran-2,1'-cyclopropane]-6-yl]ethynyl}-acrylic acid ethyl ester (Intermediate 4, 0.09 g, 0.19 mmol) in ethanol (1 mL) and tetrahydrofuran (3 mL) was treated with a 1M solution of sodium hydroxide (0.7 mL, 0.7 mmol) and the resulting reaction mixture was heated at 55° C. overnight. The reaction mixture was cooled to ambient temperature and the volatiles were evaporated in vacuo to a residue that was neutralized with 10% hydrochloric acid and extracted with ethyl acetate. The organic phase was washed with water and brine, dried over anhydrous magnesium sulfate, filtered and evaporated in vacuo to afford the title product as a yellow solid after flash column chromatography over silica gel (230-400 mesh) (0.08 g, 95%).

$^1$H NMR (300 MHz, CDCl$_3$): δ 7.74 (s, 1H), 7.55 (d, 2H, J=8.1 Hz), 7.31 (d, 2H, J=8.1 Hz), 7.20 (d, 1H, J=1.8 Hz), 6.70 (d, 1H, J=1.8 Hz), 1.86 (m, 1H), 1.79 (s, 2H), 1.27 (s, 12H), 0.94-0.81 (m, 2H), 0.77-0.71 (m, 2H), 0.59-0.47 (m, 4H).

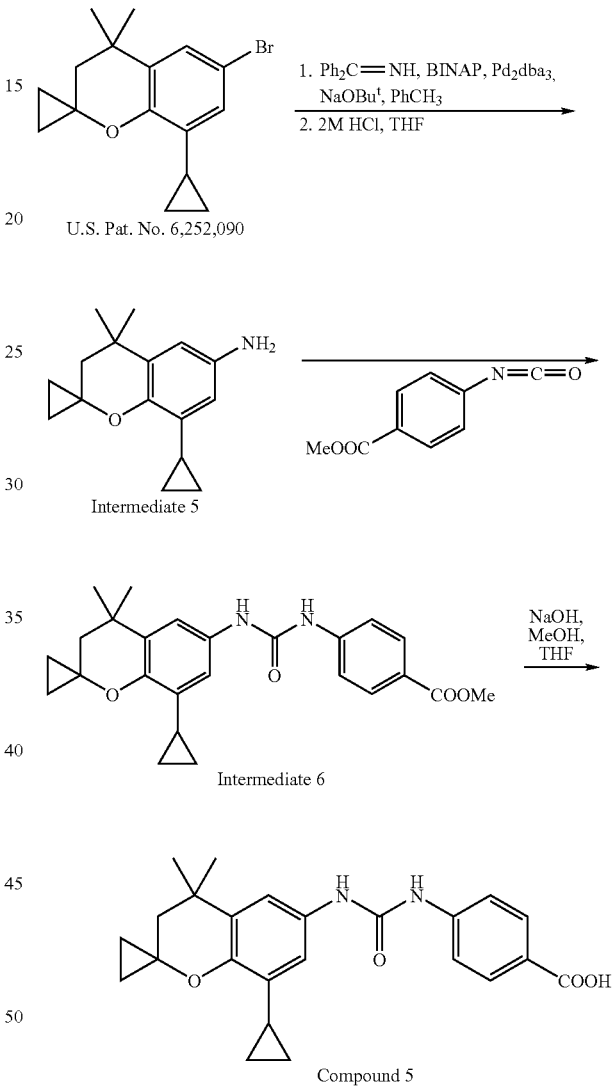

Reaction Scheme 3

6-Amino-8-cyclopropyl-3,4-dihydro-4,4-dimethylspiro[2H-1-benzopyran-2,1'-cyclopropane] (Intermediate 5)

A solution of 6-bromo-8-cyclopropyl-3,4-dihydro-4,4-dimethylspiro[2H-1-benzopyran-2,1'-cyclopropane] (described in U.S. Pat. No. 6,252,090; 0.322 g, 1.049 mmol), benzophenone imine (Fluka 0.093 mL, 1.15 mmol), sodium-tert-butoxide (0.142 g, 1.47 mmol), tris(dibenzylideneacetone)dipalladium(0) (0.023 g, 0.025 mmol) and (S)-(-)-2,2'-bis(diphenylphosphino)-1,1'-binaphthyl (Aldrich, 0.047 g, 0.075 mmol) in 7 mL of anhydrous toluene was sparged with argon and heated at 95° C. for 36 h. The reaction mixture was cooled to ambient temperature, quenched with water and extracted with ethyl acetate. The combined organic phase was washed with water and brine, dried over anhydrous magnesium sulfate, filtered and evaporated in vacuo to afford a thick brown oil (0.73 g). The oil was dissolved in tetrahydrofuran (3.5 mL) and treated with 2M hydrochloric acid (1.7 mL). After stirring at ambient temperature for 20 minutes, 0.5 mL of 2M hydrochloric acid and 40 mL of water were added and the reaction mixture was extracted with hexane:ethyl acetate (2:1, 3×60 mL). The aqueous phase was neutralized with potassium hydroxide and extracted with dichloromethane (3×50 mL). The combined organic phase was dried over anhydrous magnesium sulfate, filtered and evaporated in vacuo to afford an oil that on flash column chromatography over silica gel (230-400 mesh) afforded the title product as a brown solid (0.15 g, 58%).

$^1$H NMR (300 MHz, CDCl$_3$): δ 6.46 (d, 1H, J=2.7 Hz), 6.01 (d, 1H, J=2.7 Hz), 3.28 (br s, 2H), 2.02-1.93 (m, 1H), 1.87 (s, 2H), 1.34 (s, 6H), 0.97-0.93 (m, 2H), 0.85-0.78 (m, 2H), 0.61-0.59 (m, 4H).

4-{3-[8-Cyclopropyl-3,3-dihydro-4,4-dimethylspiro (2H-1-benzopyran-2,2'-cyclopropane)-6-yl]-ureido}-benzoic acid methyl ester (Intermediate 6)

A solution of 4-isocyanato-benzoic acid methyl ester (Aldrich, 0.17 g, 0.97 mmol) in anhydrous toluene (5 mL) was treated with a solution of 6-amino-8-cyclopropyl-3,4-dihydro-4,4-dimethylspiro[2H-1-benzopyran-2,1'-cyclopropane] (Intermediate 5, 0.07 g, 0.28 mmol) in toluene (15 mL). The resulting reaction mixture was stirred at ambient temperature overnight and at 50-60° C. for 5 h. The volatiles were evaporated in vacuo and the residue was subjected to flash column chromatography over silica gel (230-400 mesh) to afford the title compound as a white solid (0.073 g, 62%).

$^1$H NMR (300 MHz, CDCl$_3$): δ 7.93 (d, 2H, J=9.0 Hz), 7.39 (d, 2H, J=9.0 Hz), 7.06 (d, 1H, J=2.4 Hz), 6.62 (br s, 1H), 6.53 (d, 1H, J=2.4 Hz), 3.88 (s, 3H), 2.05-1.97 (m, 1H), 1.89 (s, 2H), 1.35 (s, 6H), 1.01-0.97 (m, 2H), 0.90-0.83 (m, 2H), 0.67-0.54 (m, 4H).

4-{3-[8-Cyclopropyl-3,3-dihydro-4,4-dimethylspiro (2H-1-benzopyran-2,2'-cyclopropane)-6-yl]-ureido}-benzoic acid (Compound 5)

A solution of 4-{3-[8-cyclopropyl-3,3-dihydro-4,4-dimethylspiro(2H-1-benzopyran-2,2'-cyclopropane)-6-yl]-ureido}-benzoic acid methyl ester (Intermediate 6, 0.072 g, 0.17 mmol) in methanol (3.4 mL) and tetrahydrofuran (7 mL) was treated with a 0.5M solution of sodium hydroxide (3.4 mL, 1.7 mmol) and the resulting reaction mixture was stirred at ambient temperature overnight. The volatiles were evaporated in vacuo to a residue that was diluted with water, neutralized with 10% hydrochloric acid and extracted with ethyl acetate. The organic phase was dried over anhydrous magnesium sulfate, filtered and evaporated in vacuo to afford the title product as a white solid (0.066 g, 95%).

$^1$H NMR (300 MHz, CD$_3$COCD$_3$): δ 8.27 (br s, 1H), 7.82 (d, 2H, J=9.0 Hz), 7.52 (d, 2H, J=9.0 Hz), 7.20 (d, 1H, J=2.4 Hz), 6.66 (d, 1H, J=2.4 Hz), 1.93-1.90 (m, 1H), 1.80 (s, 2H), 1.24 (s, 6H), 0.80-0.73 (m, 2H), 0.72-0.67 (m, 2H), 0.57-0.41 (m, 4H).

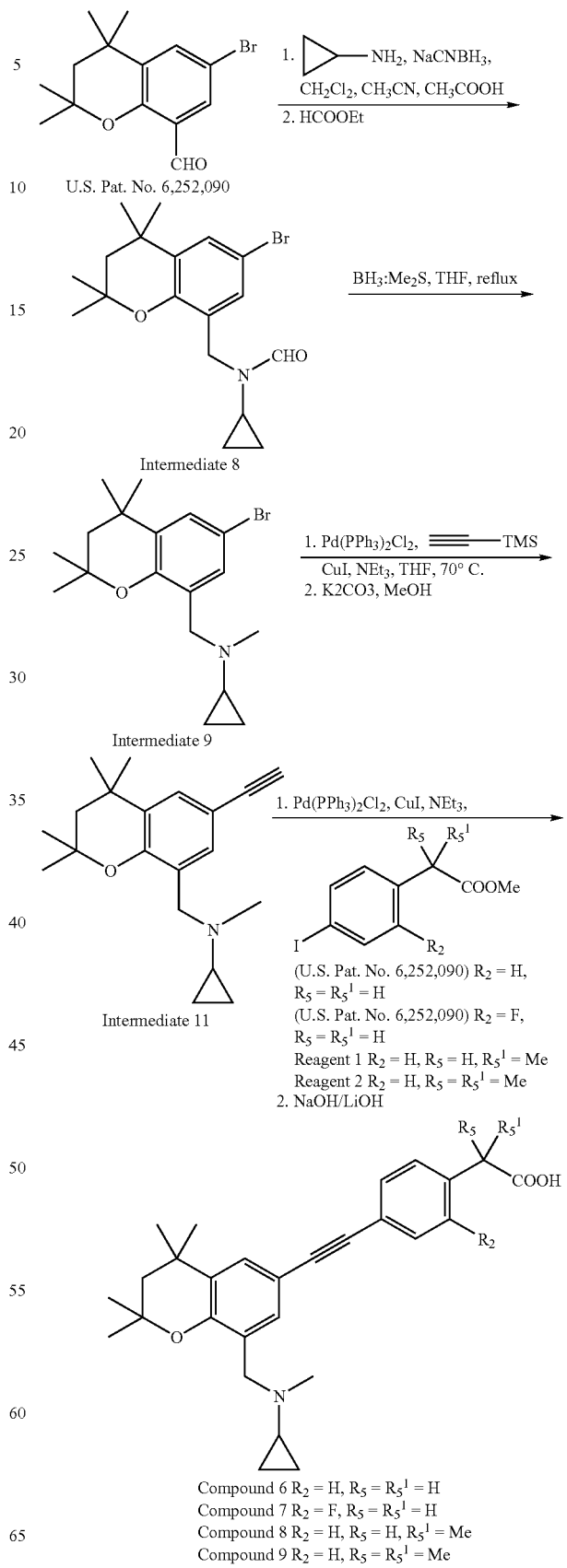

Reaction Scheme 4

General Procedure C: 6-Bromo-8-[(cyclopropyl-amino)-methyl]-2,2,4,4-tetramethyl-chroman (Intermediate 7)

A stirred, cooled (ice bath) solution of 6-bromo-2,2,4,4-tetramethyl chroman-8-carbaldehyde (U.S. Pat. No. 6,252,090, 2.4 g, 8.4 mmol) in dichloromethane (10 mL) and acetonitrile (9 mL) was treated with cyclopropyl amine (1.45 mL, 21 mmol). After 5 minutes, acetic acid (1 mL) was added followed by sodium cyanoborohydride (1.33 g, 21 mmol). The reaction mixture was stirred at ambient temperature for 2 h. The volatiles were distilled off in vacuo, the residue was diluted with water and extracted with ethyl acetate (×2). The combined organic extract was washed with water, saturated aqueous sodium bicarbonate and brine, dried over anhydrous sodium sulfate, filtered and evaporated in vacuo to an oil. Flash column chromatography over silica gel (230-400 mesh) afforded the title compound (1.4 g, 50%) as a clear oil.

$^1$H NMR (300 MHz, CDCl$_3$): δ 7.27 (d, 1H, J=2.1 Hz), 7.16 (d, 1H, J=2.1 Hz), 3.73 (s, 2H), 2.19 (br s, 1H), 2.09-2.04 (m, 1H), 1.82 (s, 2H), 1.35 (s, 6H), 1.32 (s, 6H), 0.43-0.36 (m, 4H).

6-Bromo-8-[(cyclopropyl-formyl-amino)-methyl]-2,2,4,4-tetramethyl-chroman (Intermediate 8)

A solution of 6-bromo-8-[(cyclopropyl-amino)-methyl]-2,2,4,4-tetramethyl-chroman (Intermediate 7, 1.4 g, 4.14 mmol) in ethyl formate was refluxed for 6 h. The solvent was distilled off in vacuo to afford the title compound as a clear oil (1.56 g, 100%).

$^1$H NMR (300 MHz, CDCl$_3$): δ 8.37, 8.27 (2s, 1H), 7.35, 7.29 (2d, 1H, J=2.1 Hz), 7.13, 7.11 (2d, 1H, J=2.1 Hz), 4.48 (s, 2H), 2.60-2.50 (m, 1H), 1.81 (s, 2H), 1.34 (s, 6H), 1.32 (s, 6H), 0.74-0.70 (m, 4H).

6-Bromo-8-[(cyclopropyl-methyl-amino)-methyl]-2,2,4,4-tetramethyl-chroman (Intermediate 9)

A solution of 6-bromo-8-[(cyclopropyl-formyl-amino)-methyl]-2,2,4,4-tetramethyl-chroman (Intermediate 8, 1.46 g, 4.0 mmol) in anhydrous tetrahydrofuran (30 mL) was treated with a 2M solution of borane:methylsulfide complex in tetrahydrofuran (5 mL, 10 mmol) and the resulting reaction mixture was refluxed for 2 h. It was then cooled in an ice bath, quenched cautiously with saturated aqueous sodium carbonate solution and extracted with diethyl ether. The organic phase was washed with water and brine, dried over anhydrous magnesium sulfate, filtered and evaporated in vacuo to afford the title product as a white solid (1.55 g, 100%).

$^1$H NMR (300 MHz, CDCl$_3$): δ 7.26 (d, 1H, J=2.1 Hz), 7.20 (d, 1H, J=2.1 Hz), 3.64 (s, 2H), 2.27 (s, 3H), 1.83 (s, 2H), 1.83-1.78 (m, 1H), 1.34 (s, 6H), 1.33 (s, 6H), 0.48-0.47 (m, 4H).

General Procedure D: 8-[(Cyclopropyl-methyl-amino)-methyl]-2,2,4,4-tetramethyl-6-trimethylsilanylethynyl chroman (Intermediate 10)

A solution of 6-bromo-8-[(cyclopropyl-formyl-amino)-methyl]-2,2,4,4-tetramethyl-chroman (Intermediate 9, 1.5 g, 4.2 mmol) in triethyl amine (5 mL) and anhydrous tetrahydrofuran (10 mL) was treated with copper(I)iodide (0.32 g, 1.68 mmol) and sparged with argon for 5 minutes. Trimethylsilyl acetylene (2.5 mL, 17.6 mmol) was then added followed by dichlorobis(triphenylphosphine)palladium(II) (0.737 g, 1.05 mmol). The resulting reaction mixture was heated at 70° C. for 17 h. It was then cooled to ambient temperature, diluted with diethyl ether and filtered over a bed of celite. The filtrate was evaporated vacuo to an oil which was subjected to flash column chromatography over silica gel (230-400 mesh) to afford the title compound as a brown oil.

$^1$H NMR (300 MHz, CDCl$_3$): δ 7.08 (d, 1H, J=2.1 Hz), 6.97 (d, 1H, J=2.1 Hz), 3.40 (s, 2H), 2.03 (s, 3H), 1.57 (s, 2H), 1.57-1.53 (m, 1H), 1.09 (2s, 12H), 0.25-0.22 (m, 4H), 0.012 (s, 9H).

General Procedure F: 8-[(Cyclopropyl-methyl-amino)-methyl]-6-ethynyl-2,2,4,4-tetramethyl-chroman (Intermediate 11)

A solution of 8-[(cyclopropyl-methyl-amino)-methyl]-2,2,4,4-tetramethyl-6-trimethylsilanylethynyl chroman (Intermediate 10, 0.729 g, 1.97 mmol) in methanol (30 mL) was treated with potassium carbonate (1.4 g, 10.2 mmol) and the resulting reaction mixture was stirred at ambient temperature overnight. The solvent was evaporated in vacuo, the residue was diluted with water and extracted with ethyl acetate. The organic phase dried over anhydrous magnesium sulfate, filtered and evaporated in vacuo to afford the title compound as a brown oil (0.571 g, 98%).

$^1$H NMR (300 MHz, CDCl$_3$): δ 7.35 (d, 1H, J=2.1 Hz), 7.25 (d, 1H, J=2.1 Hz), 3.66 (s, 2H), 2.98 (s, 1H), 2.28 (s, 3H), 1.83 (s, 2H), 1.83-1.77 (m, 1H), 1.35 (s, 6H), 1.34 (s, 6H), 0.50-0.47 (m, 4H).

(4-{8-[(Cyclopropyl-methyl-amino)-methyl]-2,2,4,4-tetramethyl-chroman-6-ylethynyl}phenyl)-acetic acid methyl ester (Intermediate 12)

Following General Procedure B and using 8-[(cyclopropyl-methyl-amino)-methyl]-6-ethynyl-2,2,4,4-tetramethyl-chroman (Intermediate 11, 0.09 g, 0.3 mmol), 4-iodo phenyl acetic acid methyl ester (U.S. Pat. No. 6,252,090, 0.092 g, 0.33 mmol), triethyl amine (3 mL), copper(I)iodide (0.029 g, 0.15 mmol) and dichlorobis(triphenylphosphine)palladium (II) (0.064 g, 0.09 mmol) followed by flash column chromatography over silica gel (230-400 mesh), the title compound was obtained as a yellow oil (0.085 g, 65%).

$^1$H NMR (300 MHz, CDCl$_3$): δ 7.46 (d, 2H, J=8.4 Hz), 7.37 (d, 1H, J=2.1 Hz), 7.27-7.22 (m, 3H), 3.70 (s, 3H), 3.67 (s, 2H), 3.63 (s, 2H), 2.29 (s, 3H), 1.83 (s, 2H), 1.83-1.81 (m, 1H), 1.35 (2s, 12H), 0.50-0.47 (m, 4H).

(4-{8-[(Cyclopropyl-methyl-amino)-methyl]-2,2,4,4-tetramethyl-chroman-6-ylethynyl}phenyl)-acetic acid (Compound 6)

A solution of (4-{8-[(cyclopropyl-methyl-amino)-methyl]-2,2,4,4-tetramethyl-chroman-6-ylethynyl}phenyl)-acetic acid methyl ester (Intermediate 12, 0.057 g, 0.13 mmol) in methanol (1 mL) and tetrahydrofuran (3 mL) was treated with a 1M solution of sodium hydroxide (0.4 mL, 0.4 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow oil (0.046 g, 84%).

$^1$H NMR (300 MHz, CDCl$_3$): δ 7.42-7.26 (m, 6H), 3.94 (s, 2H), 3.57 (s, 2H), 2.48 (s, 3H), 2.04 (m, 1H), 1.82 (s, 2H), 1.35 (s, 6H), 1.33 (s, 6H), 0.55-0.50 (m, 4H).

(4-{8-[(Cyclopropyl-methyl-amino)-methyl]-2,2,4,4-tetramethyl-chroman-6-ylethynyl}-2-fluoro-phenyl)-acetic acid methyl ester (Intermediate 13)

Following General Procedure B and using 8-[(cyclopropyl-methyl-amino)-methyl]-6-ethynyl-2,2,4,4-tetramethyl-chroman (Intermediate 11, 0.084 g, 0.28 mmol), 2-fluoro-4-iodo phenyl acetic acid methyl ester (U.S. Pat. No. 6,252,090, 0.091 g, 0.3 mmol), triethyl amine (3 mL), copper(I)iodide (0.027 g, 0.14 mmol) and dichlorobis(triphenylphosphine)palladium(II) (0.060 g, 0.085 mmol) followed by flash column chromatography over silica gel (230-400 mesh), the title compound was obtained as a yellow oil (0.083 g, 64%).

$^1$H NMR (300 MHz, CDCl$_3$): δ 7.37 (d, 1H, J=2.1 Hz), 7.27-7.24 (m, 4H), 3.72 (s, 3H), 3.67 (s, 4H), 2.29 (s, 3H), 1.83 (s, 2H), 1.83-1.81 (m, 1H), 1.35 (s, 12H), 0.50-0.47 (m, 4H).

(4-{8-[(Cyclopropyl-methyl-amino)-methyl]-2,2,4,4-tetramethyl-chroman-6-ylethynyl}-2-fluoro-phenyl)-acetic acid (Compound 7)

A solution of (4-{8-[(cyclopropyl-methyl-amino)-methyl]-2,2,4,4-tetramethyl-chroman-6-ylethynyl}-2-fluoro-phenyl)-acetic acid methyl ester (Intermediate 13, 0.060 g, 0.13 mmol) in methanol (1 mL) and tetrahydrofuran (3 mL) was treated with a 1M solution of sodium hydroxide (0.4 mL, 0.4 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow oil (0.056 g, 95%).

$^1$H NMR (300 MHz, CDCl$_3$): δ 7.43 (d, 1H, J=2.1 Hz), 7.37-7.13 (m, 4H), 3.99 (s, 2H), 3.61 (s, 2H), 2.52 (s, 3H), 2.10-2.04 (m, 1H), 1.83 (s, 2H), 1.83-1.81 (m, 1H), 1.36 (s, 6H), 1.35 (s, 6H), 0.90-0.82 (m, 2H), 0.59-0.57 (m, 2H).

2-(4-{8-[(Cyclopropyl-methyl-amino)-methyl]-2,2,4,4-tetramethyl-chroman-6-ylethynyl}-phenyl)-propionic acid methyl ester (Intermediate 14)

Following General Procedure B and using 8-[(cyclopropyl-methyl-amino)-methyl]-6-ethynyl-2,2,4,4-tetramethyl-chroman (Intermediate 11, 0.08 g, 0.27 mmol), methyl-2-(4-iodophenyl)propionate (Reagent 1, 0.086 g, 0.29 mmol), triethyl amine (3 mL), copper(I)iodide (0.026 g, 0.14 mmol) and dichlorobis(triphenylphosphine)palladium(II) (0.057 g, 0.08 mmol) followed by flash column chromatography over silica gel (230-400 mesh), the title compound was obtained as a brown oil (0.067 g, 54%).

$^1$H NMR (300 MHz, CDCl$_3$): δ 7.46 (d, 2H, J=8.4 Hz), 7.37 (d, 1H, J=2.1 Hz), 7.27-7.22 (m, 3H), 3.72 (q, 1H, J=7.2 Hz), 3.67 (s, 5H), 2.29 (s, 3H), 1.83 (s, 2H), 1.83-1.79 (m, 1H), 1.50 (d, 3H, J=7.2 Hz), 1.35 (s, 12H), 0.50-0.47 (m, 4H).

2-(4-{8-[(Cyclopropyl-methyl-amino)-methyl]-2,2,4,4-tetramethyl-chroman-6-ylethynyl}-phenyl)-propionic acid (Compound 8)

A solution of 2-(4-{8-[(cyclopropyl-methyl-amino)-methyl]-2,2,4,4-tetramethyl-chroman-6-ylethynyl}-phenyl)-propionic acid methyl ester (Intermediate 14, 0.057 g, 0.12 mmol) in methanol (1 mL) and tetrahydrofuran (3 mL) was treated with a 1M solution of sodium hydroxide (0.3 mL, 0.3 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow solid (0.024 g, 45%).

$^1$H NMR (300 MHz, CDCl$_3$): δ 7.38-7.23 (2m, 6H), 3.85-3.82 (m, 1H), 3.82 (s, 2H), 2.39 (s, 3H), 1.94-1.85 (m, 1H), 1.80 (s, 2H), 1.41 (d, 3H, J=7.2 Hz), 1.33 (s, 12H), 0.70-0.60 (m, 2H), 0.50-0.48 (m, 2H).

2-(4-{8-[(Cyclopropyl-methyl-amino)-methyl]-2,2,4,4-tetramethyl-chroman-6-ylethynyl}-phenyl)-2-methyl-propionic acid methyl ester (Intermediate 15)

Following General Procedure B and using 8-[(cyclopropyl-methyl-amino)-methyl]-6-ethynyl-2,2,4,4-tetramethyl-chroman (Intermediate 11, 0.08 g, 0.27 mol), methyl-2-(4-iodophenyl)-2-methyl-propionate (Reagent 2, 0.082 g, 0.27 mol), diethyl amine (2 mol), copper(I)iodide (0.020 g, 0.1 mol) and dichlorobis(triphenylphosphine)palladium(II) (0.07 g, 0.1 mol) followed by flash column chromatography over silica gel (230-400 mesh) using 10% ethyl acetate in hexane as the eluent, the title compound was obtained as a brown oil (0.040 g, 31%).

$^1$H NMR (300 MHz, CDCl$_3$): δ 7.50-7.28 (m, 6H), 3.68 (s, 3H), 3.66 (s, 2H), 2.30 (s, 3H), 1.85 (s, 2H), 1.85-1.81 (m, 1H), 1.60 (s, 3H), 1.59 (s, 3H), 1.37 (s, 6H), 1.36 (s, 6H), 0.50-0.47 (m, 4H).

2-(4-{8-[(Cyclopropyl-methyl-amino)-methyl]-2,2,4,4-tetramethyl-chroman-6-ylethynyl}-phenyl)-2-methyl-propionic acid (Compound 9)

A solution of 2-(4-{8-[(cyclopropyl-methyl-amino)-methyl]-2,2,4,4-tetramethyl-chroman-6-ylethynyl}-phenyl)-2-methyl-propionic acid methyl ester (Intermediate 15, 0.040 g, 0.084 mol) in methanol (2.5 mol) and tetrahydrofuran (2.5 mol) was treated with a 2M solution of sodium hydroxide (1 mol, 2 mol) and the resulting reaction mixture was refluxed overnight. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to an oil. Preparative reverse phase HPLC on a partisil 10 ODS-3 column using 10% water in acetonitrile as the mobile phase afforded the title compound (0.008 g, 27%).

$^1$H NMR (300 MHz, CDCl$_3$): δ 7.46-7.32 (m, 6H), 6.90-6.50 (br s, 1H), 3.84 (s, 2H), 2.41 (s, 3H), 1.97-1.92 (m, 1H), 1.83 (s, 2H), 1.55 (s, 6H), 1.36 (2s, 12H), 0.73-0.68 (m, 2H), 0.52-0.46 (m, 2H).

Reaction Scheme 5
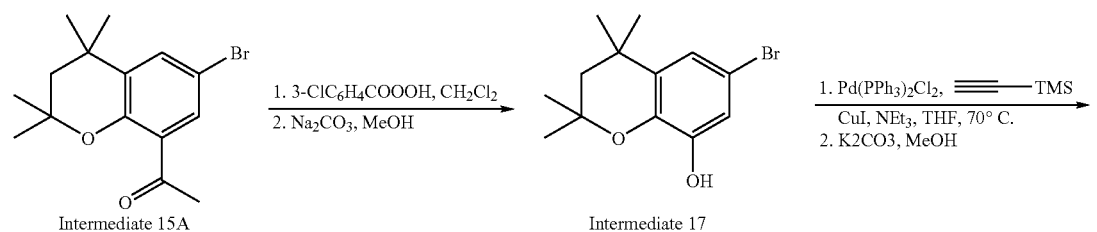
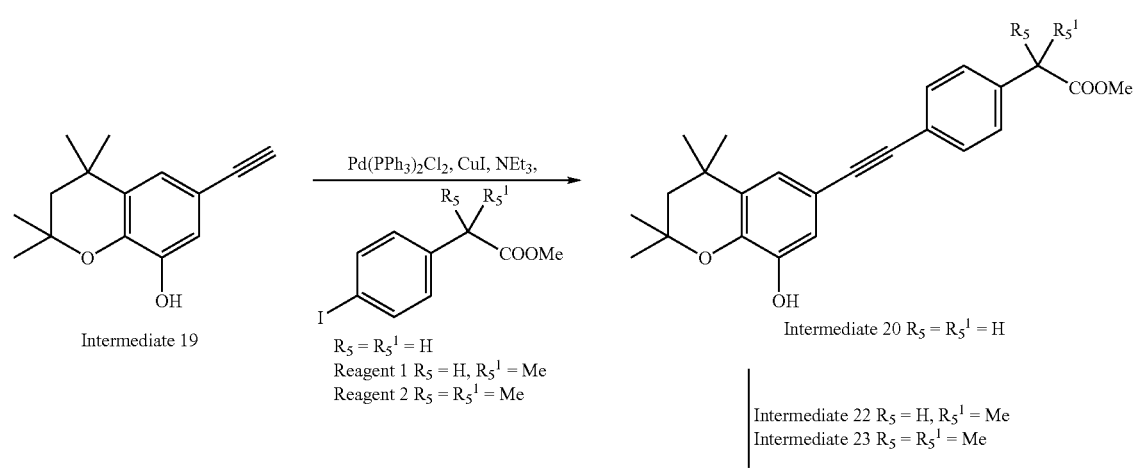
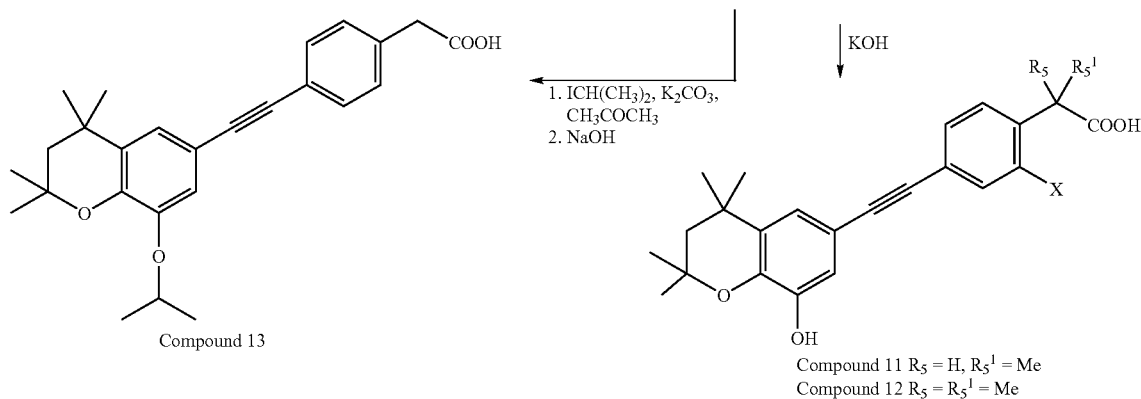
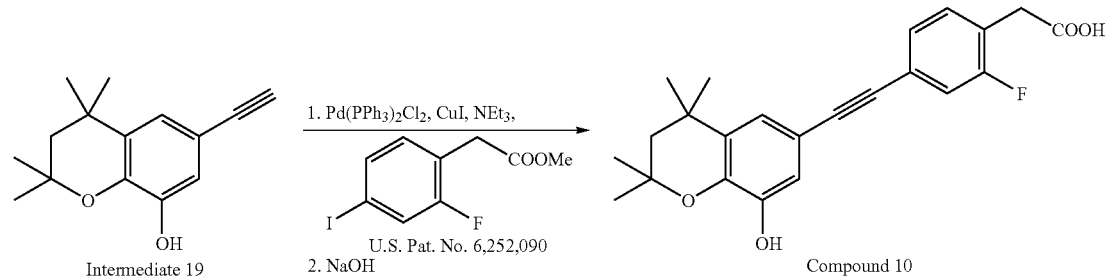

8-acetyl-6-bromo-2,2,4,4-tetramethyl chroman (Intermediate 15A)

A stirred, cooled (−78° C.) solution of 6-bromo-2,2,4,4-tetramethyl chroman (1 g, 3.72 mol) in anhydrous dichloromethane (10 mol) was treated with aluminum chloride (0.8 g, 6.8 mol) followed by acetyl chloride (0.4 mol, 6.08 mol). After 10 minutes, the reaction mixture was diluted with water and extracted with diethyl ether. The organic phase was washed with water, and dried over anhydrous sodium sulfate, filtered and evaporated to a residue that was subjected to flash column chromatography on silica gel (230-400 mesh) using 10% ethyl acetate in hexane as the eluent to afford the title compound as a solid (0.78 g, 67%).

$^1$H NMR (300 MHz, CDCl$_3$): δ 7.64 (d, 1H, J=2.6 Hz), 7.49 (d, 1H, J=2.6 Hz), 2.60 (s, 3H), 1.87 (s, 2H), 1.41 (s, 6H), 1.36 (s, 6H).

8-Acetoxy-6-bromo-2,2,4,4-tetramethyl chroman (Intermediate 16)

A solution of 8-acetyl-6-bromo-2,2,4,4-tetramethyl chroman (Intermediate 15A, 1.3 g, 4.18 mol) in anhydrous dichloromethane (30 mol) was treated with a 77% aqueous solution of 3-chloroperoxybenzoic acid (5.75 g, 33.44 mmol) and the resulting reaction mixture was stirred at ambient temperature for 24 h. The reaction mixture was then cooled in an ice bath and cautiously quenched with saturated sodium thiosulfate solution. The phases were separated and the organic phase was washed with saturated, aqueous sodium bicarbonate solution, water and brine, dried over anhydrous sodium sulfate, filtered and evaporated in vacuo to afford a residue that on flash column chromatography over silica gel (230-400 mesh) using 10% ethyl acetate in hexane as the eluent afforded the title compound as an oil (1.3 g, 92%).

$^1$H NMR (300 MHz, CDCl$_3$): δ 7.27 (s, 1H), 7.00 (s, 1H), 2.29 (s, 3H), 1.83 (s, 2H), 1.34 (s, 6H), 1.32 (s, 6H).

6-Bromo-8-hydroxy-2,2,4,4-tetramethyl chroman (Intermediate 17)

A solution of 8-acetoxy-6-bromo-2,2,4,4-tetramethyl chroman (Intermediate 16, 1.3 g, 3.98 mmol) in methanol was treated with sodium carbonate (0.8 g, 7.95 mmol) and the resulting reaction mixture was stirred at ambient temperature overnight. The volatiles were evaporated in vacuo, the residue was diluted with water and extracted with ethyl acetate. The organic phase was dried over anhydrous magnesium sulfate, filtered and evaporated in vacuo to afford a residue that on flash column chromatography over silica gel (230-400 mesh) using 10% ethyl acetate in hexane as the eluent afforded the title product as an oil (0.95 g, 84%).

$^1$H NMR (300 MHz, CDCl$_3$): δ 6.91 (d, 1H), 6.88 (d, 1H), 5.67 (s, 1H), 1.84 (s, 2H), 1.37 (s, 6H), 1.32 (s, 6H).

6-Bromo-8-trimethylsilanylethynyl-2,2,4,4-tetramethyl chroman (Intermediate 18)

Following General Procedure D and using 6-bromo-8-hydroxy-2,2,4,4-tetramethyl chroman (Intermediate 17, 1.0 g, 3.51 mmol), triethyl amine (5 mL), copper(I)iodide (0.066 g, 0.351 mmol), trimethylsilyl acetylene (2.5 mL, 17.6 mmol) and dichlorobis(triphenylphosphine)palladium(II) (0.246 g, 0.351 mmol) followed by flash column chromatography over silica gel (230-400 mesh) using 0.5% ethyl acetate in hexane as the eluent, the title compound (1.08 g, ~100%) was obtained as a brown oil.

$^1$H NMR (300 MHz, CDCl$_3$): δ 6.97 (d, 1H), 6.86 (d, 1H), 5.61 (s, 1H), 1.84 (s, 2H), 1.37 (s, 6H), 1.33 (s, 6H), 0.24 (s, 9H).

6-Ethynyl-8-hydroxy-2,2,4,4-tetramethyl-chroman (Intermediate 19)

A solution of 6-bromo-8-trimethylsilanylethynyl-2,2,4,4-tetramethyl chroman (Intermediate 18, 0.47 g, 1.56 mmol) in methanol (5 mL) was treated with potassium carbonate (0.2 g, 1.45 mmol) and the resulting reaction mixture was heated at 80° C. for 3 h. The solvent was evaporated in vacuo, the residue was diluted with water and extracted with ethyl acetate. The organic phase dried over anhydrous magnesium sulfate, filtered and evaporated in vacuo to afford the title compound as a brown oil (0.35 g, 99%).

$^1$H NMR (300 MHz, CDCl$_3$): δ 6.97 (d, 1H), 6.86 (d, 1H), 5.70 (br s, 1H), 2.92 (s, 1H), 1.84 (s, 2H), 1.37 (s, 6H), 1.33 (s, 6H).

[4-(8-Hydroxy-2,2,4,4-tetramethyl-chroman-6-ylethynyl)-phenyl]-acetic acid methyl ester (Intermediate 20)

Following General Procedure B and using 6-ethynyl-8-hydroxy-2,2,4,4-tetramethyl-chroman (Intermediate 19, 0.035 g, 0.15 mmol), 4-iodo phenyl acetic acid methyl ester (0.060 g, 0.23 mmol), triethyl amine (3 mL), copper(I)iodide (0.020 g, 0.1 mmol) and dichlorobis(triphenylphosphine)palladium(II) (0.07 g, 0.1 mmol) followed by flash column chromatography over silica gel (230-400 mesh), and preparative normal phase HPLC using 10% ethyl acetate in hexane as the mobile phase, the title compound was obtained (0.015 g, 25%).

$^1$H NMR (300 MHz, CDCl$_3$): δ 7.46 (d, 2H, J=8.1 Hz), 7.24 (d, 2H, J=8.1 Hz), 7.03 (d, 1H, J=2.1 Hz), 6.91 (d, 1H, J=2.1 Hz), 5.72 (s, 1H), 3.69 (s, 3H), 3.63 (s, 2H), 1.86 (s, 2H), 1.38 (s, 6H), 1.35 (s, 6H).

[2-Fluoro-4-(8-hydroxy-2,2,4,4-tetramethyl-chroman-6-ylethynyl)-phenyl]-acetic acid methyl ester (Intermediate 21)

Following General Procedure B and using 6-ethynyl-8-hydroxy-2,2,4,4-tetramethyl-chroman (Intermediate 19, 0.05 g, 0.22 mmol), 2-fluoro-4-iodo phenyl acetic acid methyl ester (0.096 g, 0.33 mmol), triethyl amine (3 mL), copper(I) iodide (0.020 g, 0.1 mmol) and dichlorobis(triphenylphosphine)palladium(II) (0.07 g, 0.1 mmol) followed by flash column chromatography over silica gel (230-400 mesh), and preparative normal phase HPLC using 10% ethyl acetate in hexane as the mobile phase, the title compound was obtained (0.037 g, 43%).

$^1$H NMR (300 MHz, CDCl$_3$): δ 7.27-7.18 (m, 3H), 7.03 (d, 1H, J=1.8 Hz), 6.90 (d, 1H, J=1.8 Hz), 5.68 (s, 1H), 3.72 (s, 3H), 3.67 (s, 2H), 1.87 (s, 2H), 1.39 (s, 6H), 1.36 (s, 6H).

[2-Fluoro-4-(8-hydroxy-2,2,4,4-tetramethyl-chroman-6-ylethynyl)-phenyl]-acetic acid (Compound 10)

A solution of [2-fluoro-4-(8-hydroxy-2,2,4,4-tetramethyl-chroman-6-ylethynyl)-phenyl]-acetic acid methyl ester (Intermediate 21, 0.037 g, 0.0493 mmol) in methanol (2 mL) and tetrahydrofuran (1 mL) was treated with a 2M solution of potassium hydroxide (2 mL, 4 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.024 g, 69%).

$^1$H NMR (300 MHz, CDCl$_3$): δ 7.26-7.24 (m, 3H), 7.03 (d, 1H, J=1.8 Hz), 6.90 (d, 1H, J=1.8 Hz), 3.71 (s, 2H), 1.87 (s, 2H), 1.39 (s, 6H), 1.36 (s, 6H).

2-[4-(8-Hydroxy-2,2,4,4-tetramethyl-chroman-6-ylethynyl)-phenyl]-propionic acid methyl ester (Intermediate 22)87

Following general procedure B and using 6-ethynyl-8-hydroxy-2,2,4,4-tetramethyl-chroman (Intermediate 19, 0.04 g, 0.17 mmol), methyl-2-(4-iodophenyl)propionate (Reagent 1, 0.075 g, 0.26 mmol), triethyl amine (3 mL), copper(I)iodide (0.020 g, 0.1 mmol) and dichlorobis(triphenylphosphine)palladium(II) (0.07 g, 0.1 mmol) followed by flash column chromatography over silica gel (230-400 mesh), and preparative normal phase HPLC using 5% ethyl acetate in hexane as the mobile phase, the title compound was obtained as a brown oil (0.018 g, 26%).

$^1$H NMR (300 MHz, CDCl$_3$): δ 7.46 (d, 2H, J=8.5 Hz), 7.26 (d, 2H, J=8.5 Hz), 7.03 (d, 1H, J=1.8 Hz), 6.91 (d, 1H, J=1.8 Hz), 5.66 (s, 1H), 3.67 (q, 1H, J=7.5 Hz), 1.87 (s, 2H), 1.50 (d, 3H, J=7.5 Hz), 1.39 (s, 6H), 1.36 (s, 6H).

2-[4-(8-Hydroxy-2,2,4,4-tetramethyl-chroman-6-ylethynyl)-phenyl]-propionic acid (Compound 11)

A solution of 2-[4-(8-hydroxy-2,2,4,4-tetramethyl-chroman-6-ylethynyl)-phenyl]-propionic acid methyl ester (Intermediate 22, 0.018 g, 0.046 mmol) in methanol (1 mL) and tetrahydrofuran (0.5 mL) was treated with a 2M solution of potassium hydroxide (1 mL, 2 mmol) and the resulting reaction mixture was stirred at 80° C. for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow solid (0.017 g, 100%).

$^1$H NMR (300 MHz, CDCl$_3$): δ 7.50-7.30 (m, 4H), 7.02 (s, 1H), 6.91 (s, 1H), 3.80-3.70 (m, 1H), 1.86 (s, 2H), 1.52 (d, 3H, J=7.2 Hz), 1.39 (s, 6H), 1.36 (s, 6H).

2-[4-(8-Hydroxy-2,2,4,4-tetramethyl-chroman-6-ylethynyl)-phenyl]-2-methyl-propionic acid methyl ester (Intermediate 23)

Following General Procedure B and using 6-ethynyl-8-hydroxy-2,2,4,4-tetramethyl-chroman (Intermediate 19, 0.057 g, 0.25 mmol), methyl-2-(4-iodophenyl)-2-methyl-propionate (Reagent 2, 0.112 g, 0.37 mmol), triethyl amine (3 mL), copper(I)iodide (0.020 g, 0.1 mmol) and dichlorobis(triphenylphosphine)palladium(II) (0.07 g, 0.1 mmol) followed by flash column chromatography over silica gel (230-400 mesh) and preparative normal phase HPLC using 5% ethyl acetate in hexane as the mobile phase, the title compound was obtained as a brown oil (0.035 g, 35%).

$^1$H NMR (300 MHz, CDCl$_3$): δ 7.46 (d, 2H, J=8.5 Hz), 7.29 (d, 2H, J=8.5 Hz), 7.03(d, 1H, J=1.8 Hz), 6.91 (d, 1H, J=1.8 Hz), 5.67 (s, 1H), 3.66 (s, 3H), 1.86 (s, 2H), 1.58 (s, 6H), 1.39 (s, 6H), 1.36 (s, 6H).

2-[4-(8-Hydroxy-2,2,4,4-tetramethyl-chroman-6-ylethynyl)-phenyl]-2-methyl-propionic acid (Compound 12)

A solution of 2-[4-(8-hydroxy-2,2,4,4-tetramethyl-chroman-6-ylethynyl)-phenyl]-2-methyl-propionic acid methyl ester (Intermediate 23, 0.035 g, 0.087 mmol) in methanol (2 mL) and tetrahydrofuran (1 mL) was treated with a 1M solution of potassium hydroxide (2 mL, 4 mmol) and the resulting reaction mixture was stirred at 80° C. for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow solid (0.034 g, 100%).

$^1$H NMR (300 MHz, CDCl$_3$): δ 7.47 (d, 2H, J=8.7 Hz), 7.35 (d, 2H, J=8.7 Hz), 7.03 (d, 1H, J=1.8 Hz), 6.91 (d, 1H, J=1.8 Hz), 1.86 (s, 2H), 1.60 (s, 6H), 1.39 (s, 6H), 1.36 (s, 6H).

[4-(8-Isopropoxy-2,2,4,4-tetramethyl-chroman-6-ylethynyl)-phenyl]-acetic acid methyl ester (Intermediate 24)

A solution of [4-(8-hydroxy-2,2,4,4-tetramethyl-chroman-6-ylethynyl)-phenyl]-acetic acid methyl ester (Intermediate 20, 0.02 g, 0.076 mmol) in acetone (2 mL) was treated with potassium carbonate (0.026 g, 0.19 mmol) and 2-iodopropane (5 mL, large excess) and the resulting reaction mixture was refluxed for 30 h. The volatiles were evaporated in vacuo, the residue was diluted with water and extracted with ethyl acetate. The organic phase was dried over anhydrous magnesium sulfate, filtered and evaporated in vacuo to afford the title product as an oil (0.02 g, 91%).

$^1$H NMR (300 MHz, CDCl$_3$): δ 7.47 (d, 2H, J=8.4 Hz), 7.24 (d, 2H, J=8.4 Hz), 7.14 (d, 1H, J=2.1 Hz), 6.93 (d, 1H, J=2.1 Hz), 4.40 (heptet, 1H, J=6.3 Hz), 3.70 (s, 3H), 3.63 (s, 2H), 1.83 (s, 2H), 1.38 (s, 6H), 1.35 (s, 6H), 1.33 (d, 3H, J=6.3 Hz).

[4-(8-Isopropoxy-2,2,4,4-tetramethyl-chroman-6-ylethynyl)-phenyl]-acetic acid (Compound 13)

A solution of [4-(8-isopropoxy-2,2,4,4-tetramethyl-chroman-6-ylethynyl)-phenyl]-acetic acid methyl ester (Intermediate 24, 0.02 g, 0.05 mmol) in methanol (1 mL) was treated with a 2M solution of sodium hydroxide (1 mL, 2 mmol) and the resulting reaction mixture was stirred at ambient temperature for 3 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to an oil. Flash column chromatography over silica gel (230-400 mesh) using 5% methanol in ethyl acetate as the eluent followed by preparative reverse phase HPLC using 10% water in acetonitrile as the mobile phase afforded the title product (0.015 g, 78%).

$^1$H NMR (300 MHz, CDCl$_3$): δ 7.47 (d, 2H, J=8.4 Hz), 7.24 (d, 2H, J=8.4 Hz), 7.14 (d, 1H, J=2.1 Hz), 6.92 (d, 1H, J=2.1 Hz), 4.40 (heptet, 1H, J=7.5 Hz), 3.65 (s, 2H), 1.83 (s, 2H), 1.37 (s, 6H), 1.35 (s, 6H), 1.33 (d, 3H, J=7.5 Hz).

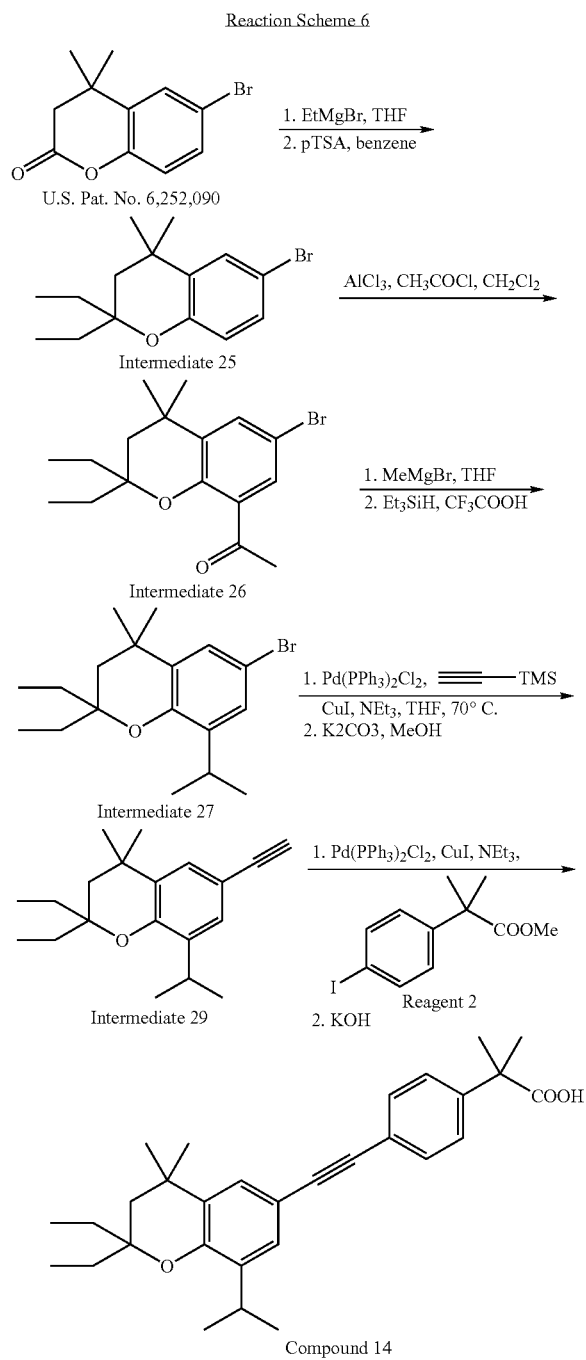

Reaction Scheme 6 with p-toluene sulfonic acid (1 g, 3.92 mmol) and the resulting reaction mixture was refluxed overnight. The reaction mixture cooled to ambient temperature, filtered on silica gel and washed with 10% ethyl acetate in hexane. The filtrate and washings were evaporated in vacuo to an oil which was subjected to flash column chromatography over silica gel (230-400 mesh) using 5% ethyl acetate in hexane as the eluent to afford the title compound as a pale yellow oil (3.9 g, 84%).

$^1$H NMR (300 MHz, CDCl$_3$): δ 7.36 (d, 1H, J=2.4 Hz), 7.35 (dd, 1H, J=2.4, 8.4 Hz), 6.70 (d, 1H, J=8.4 Hz), 1.79 (s, 2H), 1.73-1.55 (m, 4H), 1.34 (s, 6H), 0.90 (t, 6H, J=7.5 Hz).

8-Acetyl-6-bromo-2,2-diethyl-4,4-dimethyl chroman (Intermediate 26)

A stirred, cooled (ice bath) suspension of aluminum chloride (1.1 g, 8.38 mmol) in anhydrous dichloromethane (20 mL) was treated with acetyl chloride (0.6 mL, 8.38 mmol). After 5 minutes, a solution of 6-bromo-2,2-diethyl-4,4-dimethyl chroman (Intermediate 25, 1.66 g, 5.59 mmol) in dichloromethane was added. The reaction mixture was stirred for 1 h. The reaction mixture was then poured into water and extracted with diethyl ether (×2). The combined organic phase was washed with saturated aqueous sodium bicarbonate solution, dried over anhydrous sodium sulfate, filtered and evaporated in vacuo to a residue which was subjected to flash column chromatography over silica gel (230-400 -mesh) using 10% ethyl acetate in hexane as the eluent to afford the title compound as an oil (1.6 g, 84%).

$^1$H NMR (300 MHz, CDCl$_3$): δ 7.64 (d, 1H, J=2.1 Hz), 7.48 (d, 1H, J=2.1 Hz), 2.62(s, 3H), 1.84 (s, 2H), 1.75-1.59 (m, 4H), 1.36 (s, 6H), 0.93 (t, 6H, J=7.5 Hz).

6-Bromo-2,2-diethyl-8-isopropyl-4,4-dimethyl chroman (Intermediate 27)

A stirred, cooled (ice bath) solution of 8-acetyl-6-bromo-2,2-diethyl-4,4-dimethyl chroman (Intermediate 26, 1.57 g, 4.62 mmol) in anhydrous tetrahydrofuran (10 mL) was treated with a 3M solution of methyl magnesium bromide in diethyl ether (3.1 mL, 9.24 mmol). The reaction mixture was allowed to warm to ambient temperature over 2 h. The reaction mixture was poured into cold, dilute aqueous hydrochloric acid and extracted with ethyl acetate. The organic phase was dried over anhydrous magnesium sulfate, filtered and evaporated in vacuo to a residue which on flash column chromatography over silica gel (230-400 mesh) using 5-10% ethyl acetate in hexane as the eluent afforded an oil (1.41 g, 86%). A stirred, cooled (ice bath) solution of the oil (1.4 g, 3.93 mmol) in dichloromethane (10 mL) was treated with triethylsilane (5 mL, 31.46 mmol) followed after 30 minutes by trifluoroacetic acid (2.4 mL, 31.46 mmol) and the resulting reaction mixture was allowed to warm to ambient temperature and stirred for 3 h. The volatiles were distilled off in vacuo and the residue was diluted with water and extracted with ethyl acetate. The combined organic phase was dried over anhydrous sodium sulfate, filtered and evaporated in vacuo to an oil which was subjected to flash column chromatography over silica gel (230-400 mesh) to afford the title compound as a clear oil (0.89 g, 66%) and some recovered starting material (0.23 g, 16.4%).

$^1$H NMR (300 MHz, CDCl$_3$): δ 7.21 (d, 1H, J=2.1 Hz), 7.11 (d, 1H, J=2.1 Hz), 3.40-3.30 (m, 1H), 1.78 (s, 2H), 1.68-1.58 (m, 4H), 1.33 (s, 6H), 1.90 (d, 6H, J=6.6 Hz), 0.92 (t, 6H, J=7.5 Hz).

6-Bromo-2,2-diethyl-4,4-dimethylchroman (Intermediate 25)

A solution of 6-bromo-4,4-dimethyl-chroman-2-one (U.S. Pat. No. 6,252,090, 4 g, 15.7 mmol) in anhydrous tetrahydrofuran (20 mL) was treated with a 3M solution of ethyl magnesium bromide (10.5 mL, 31.5 mmol) and stirred at ambient temperature for 2 h. The reaction mixture was poured into cold dilute hydrochloric acid and extracted with ethyl acetate (×2). The combined organic extract was dried over anhydrous sodium sulfate, filtered and evaporated in vacuo to afford a residue which was dissolved in 50 mL of benzene, treated

2,2-Diethyl-8-isopropyl-6-trimethylsilanylethynyl-4,4-dimethyl chroman (Intermediate 28)

Following General Procedure D and using 6-bromo-2,2-diethyl-8-isopropyl-4,4-dimethyl chroman (Intermediate 27, 0.89 g, 2.62 mmol), triethyl amine (5 mL), tetrahydrofuran (10 mL), copper(I)iodide (0.050 g, 0.26 mmol), trimethylsilyl acetylene (2.5 mL, 17.6 mmol) and dichlorobis(triphenylphosphine)palladium(II) (0.184 g, 0.26 mmol) followed by flash column chromatography over silica gel (230-400 mesh) using hexane to 2% ethyl acetate in hexane as the eluent, the title compound (0.73 g, 79%) was obtained as a brown oil.

$^1$H NMR (300 MHz, CDCl$_3$): δ 7.31 (d, 1H), 7.12 (d, 1H), 3.20-3.10 (m, 1H), 1.70 (s, 2H), 1.70-1.45 (m, 4H), 1.34 (s, 6H), 0.95 (d, 6H), 0.68 (t, 6H), 0.00 (s, 9H).

2,2-Diethyl-6-ethynyl-8-isopropyl-4,4-dimethyl chroman (Intermediate 29)

A solution of 2,2-diethyl-8-isopropyl-6-trimethylsilanyl-ethynyl-4,4-dimethyl chroman (Intermediate 28, 0.73 g, 2.04 mmol) in methanol (40 mL) was treated with potassium carbonate (0.15 g, 1.08 mmol) and the resulting reaction mixture was heated at 80° C. for 3 h. The solvent was evaporated in vacuo, the residue was diluted with water and extracted with ethyl acetate. The organic phase was dried over anhydrous magnesium sulfate, filtered and evaporated in vacuo to afford the title compound as a brown oil (0.56 g, 96%).

$^1$H NMR (300 MHz, CDCl$_3$): δ 7.27 (d, 1H), 7.16 (d, 1H), 3.31-3.06 (m, 1H), 2.96 (s, 1H), 1.81 (s, 2H), 1.81-1.56 (m, 4H), 1.31 (s, 6H), 1.17 (d, 6H), 0.91 (t, 6H).

2-[4-(2,2-Diethyl-8-isopropyl-4,4-dimethyl-chroman-6-ylethynyl)-phenyl]-2-methyl-propionic acid methyl ester (Intermediate 30)

Following General Procedure B and using 2,2-diethyl-6-ethynyl-8-isopropyl-4,4-dimethyl chroman (Intermediate 29, 0.069 g, 0.24 mmol), methyl-2-(4-iodophenyl)-2-methyl-propionate (Reagent 2, 0.146 g, 0.48 mmol), triethyl amine (3 mL), copper(I)iodide (0.025 g, 0.13 mmol) and dichlorobis(triphenylphosphine)palladium(II) (0.075 g, 0.107 mmol) followed by flash column chromatography over silica gel (230-400 mesh) using 5% ethyl acetate in hexane as the eluent, the title compound was obtained as a yellow oil (0.070 g, 62%).

$^1$H NMR (300 MHz, CDCl$_3$): δ 7.47 (d, 2H, J=8.2 Hz), 7.31 (d, 2H, J=8.2 Hz), 7.30(d, 1H, J=2.1 Hz), 7.20 (d, 1H, J=2.1 Hz), 3.65 (s, 3H), 3.40-3.20 (m, 1H), 1.78 (s, 2H), 1.68-1.57 (m, 4H), 1.58 (s, 6H), 1.34 (s, 6H), 1.21 (d, 6H, J=7.0 Hz), 0.91 (t, 6H, J=7.3 Hz).

2-[4-(2,2-Diethyl-8-isopropyl-4,4-dimethyl-chroman-6-ylethynyl)-phenyl]-2-methyl-propionic acid (Compound 14)

A solution of 2-[4-(2,2-diethyl-8-isopropyl-4,4-dimethyl-chroman-6-ylethynyl)-phenyl]-2-methyl-propionic acid methyl ester (Intermediate 30, 0.070 g, 0.15 mmol) in methanol (3 mL) and tetrahydrofuran (0.5 mL) was treated with a 5M solution of potassium hydroxide (2 mL, 10 mmol) and the resulting reaction mixture was stirred at ambient temperature for 2 days. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford a residue that on preparative reverse phase HPLC using 10% water in acetonitrile as the mobile phase afforded the title product as a yellow solid (0.035 g, 51%).

$^1$H NMR (300 MHz, CDCl$_3$): δ 7.48 (d, 2H, J=8.1 Hz), 7.36 (d, 2H, J=8.2 Hz), 7.31 (d, 1H, J=2.1 Hz), 7.20 (d, 1H, J=2.1 Hz), 3.40-3.20 (m, 1H), 1.79 (s, 2H), 1.69-1.60 (m, 4H), 1.61 (s, 6H), 1.35 (s, 6H), 1.21 (d, 6H, J=7.2 Hz), 0.92 (t, 6H, J=7.5 Hz).

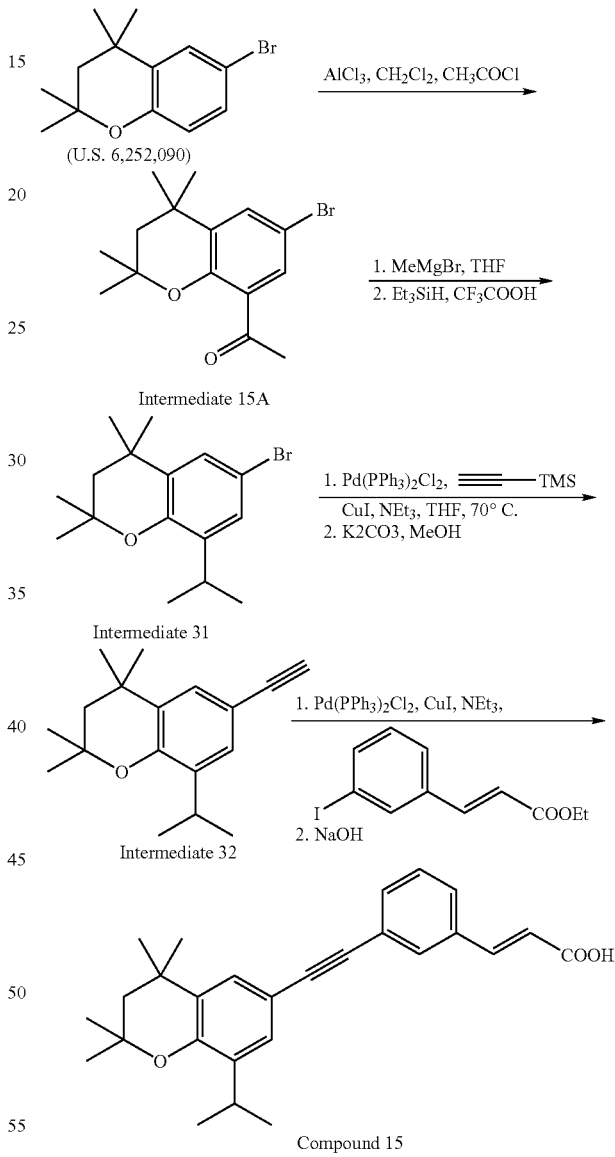

Reaction Scheme 7

6-Bromo-8-isopropyl-2,2,4,4-tetramethyl-chroman (Intermediate 31)

A stirred, cooled (ice bath) solution of 8-acetyl-6-bromo-2,2,4,4-tetramethylchroman (Intermediate 15A, 3.1 g, 10 mmol) in anhydrous tetrahydrofuran (40 mL) was treated with a 3M solution of methyl magnesium bromide in diethyl ether (11 mL, 44 mmol). The reaction mixture was allowed to warm to ambient temperature overnight. The reaction mixture was poured into cold, dilute aqueous hydrochloric acid and extracted with ethyl acetate. The organic phase was dried over anhydrous magnesium sulfate, filtered and evaporated in vacuo to a residue which on flash column chromatography over silica gel (230-400 mesh) using 10% ethyl acetate in hexane as the eluent afforded an oil (2.85 g, 87%). The oil (1.67 g, 5.12 mmol) was cooled (ice bath) and treated with triethylsilane (10 mL, 62 mmol) followed after 30 minutes by trifluoroacetic acid (5 mL, 65 mmol) and the resulting reaction mixture was allowed to warm to ambient temperature overnight. The reaction mixture was diluted with water and extracted with ethyl acetate. The combined organic phase was dried over anhydrous sodium sulfate, filtered and evaporated in vacuo to an oil which was subjected to flash column chromatography over silica gel (230-400 mesh) to afford the title compound as a clear oil (1 g, 63%).

$^1$H NMR (300 MHz, CDCl$_3$): δ 7.20 (d, 1H, J=2.3 Hz), 7.09 (d, 1H, J=2.3 Hz), 3.25 (heptet, 1H, J=7.1 Hz), 1.79 (s, 2H), 1.33 (s, 6H), 1.31 (s, 6H), 1.15 (d, 6H, J=7.1 Hz).

6-Ethynyl-8-isopropyl-2,2,4,4-tetramethyl-chroman (Intermediate 32)

Following General Procedure D and using 6-bromo-8-isopropyl-2,2,4,4-tetramethyl chroman (Intermediate 31, 1 g, 3.2 mmol), triethyl amine (10 mL), copper(I)iodide (0.04 g, 0.21 mmol), trimethylsilyl acetylene (5 mL, 35 mmol) and dichlorobis(triphenylphosphine)palladium(II) (0.12 g, 0.17 mmol) followed by flash column chromatography over silica gel (230-400 mesh), the intermediate trimethylsilylacetylene was obtained, which was dissolved in methanol and treated with potassium carbonate and the resulting reaction mixture was stirred at ambient temperature overnight. The solvent was evaporated in vacuo, the residue was diluted with water and extracted with ethyl acetate. The organic phase was dried over anhydrous magnesium sulfate, filtered and evaporated in vacuo to afford the title compound as a brown oil (0.6 g, 73%). %).

$^1$H NMR (300 MHz, CDCl$_3$): δ 7.34 (d, 1H, J=2.1 Hz), 7.21 (d, 1H, J=2.1 Hz), 3.50 (heptet, 1H, J=6.8 Hz), 3.00 (s, 1H), 1.85 (s, 2H), 1.38 (s, 6H), 1.37 (s, 6H), 1.22 (d, 6H, J=6.8 Hz).

3-[3-(8-Isopropyl-2,2,4,4-tetramethyl-chroman-6-ylethynyl)-phenyl]-acrylic acid ethyl ester (Intermediate 33)

Following General Procedure B and using 6-ethynyl-8-isopropyl-2,2,4,4-tetramethylchroman (Intermediate 32, 0.05 g, 0.2 mmol), ethyl-3-iodo cinnamate (Reagent 6, 0.118 g, 0.39 mmol), triethyl amine (2 mL), copper(I)iodide (0.025 g, 0.13 mmol) and dichlorobis(triphenylphosphine)palladium(II) (0.075 g, 0.107 mmol) followed by flash column chromatography over silica gel (230-400 mesh), the title compound was obtained (0.058 g, 69%).

$^1$H NMR (300 MHz, CDCl$_3$): δ 7.62-7.22 (m, 6H), 7.14 (d, 1H, J=1.8 Hz), 6.39 (d, 1H, J=16.1 Hz), 4.19 (q, 2H, J=7.0 Hz), 3.21(heptet, 1H, J=6.7 Hz), 1.76 (s, 2H), 1.29 (s, 12H), 1.27 (t, 3H, J=7.0 Hz).1.13 (d, 6H, J=6.7 Hz).

3-[3-(8-Isopropyl-2,2,4,4-tetramethyl-chroman-6-ylethynyl)-phenyl]-acrylic acid (Compound 15)

A solution of 3-[3-(8-isopropyl-2,2,4,4-tetramethyl-chroman-6-ylethynyl)-phenyl]-acrylic acid ethyl ester (Intermediate 33, 0.058 g, 0.13 mmol) in ethanol (2 mL) and tetrahydrofuran (2 mL) was treated with a 5N solution of potassium hydroxide (2 mL, 10 mmol) and the reaction mixture was stirred at ambient temperature overnight. The volatiles were evaporated in vacuo, the residue was neutralized with dilute hydrochloric acid and extracted with ethyl acetate. The organic phase was washed with water and brine, dried over anhydrous magnesium sulfate and evaporated to afford the title compound (0.036 g, 66%).

$^1$H NMR (300 MHz, CDCl$_3$): δ 7.69 (d, 1H, J=15.8 Hz), 7.65 (s, 1H), 7.47 (d, 1H, J=7.6 Hz), 7.39 (d, 1H, J=7.9 Hz), 7.32-7.17 (m, 2H), 7.14 (d, 1H, J=1.8 Hz), 6.41 (d, 1H, J=15.8 Hz), 3.21(heptet, 1H, J=6.7 Hz), 1.76 (s, 2H), 1.29 (s, 12H), 1.13 (d, 6H, J=6.7 Hz).

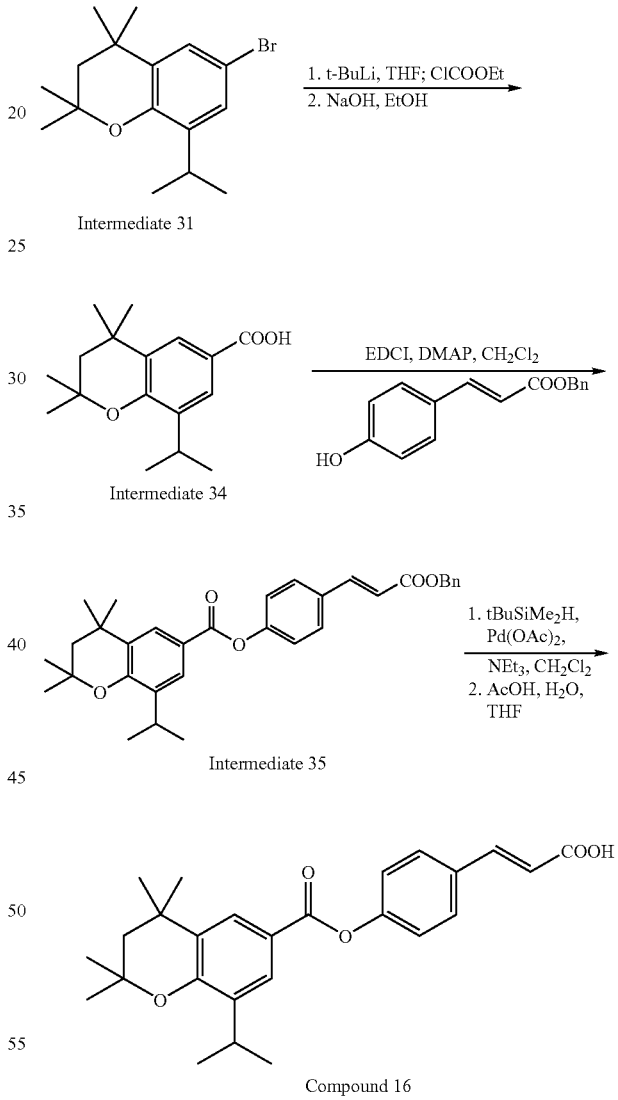

Reaction Scheme 8

8-Isopropyl-2,2,4,4-tetramethyl-chroman-6-carboxylic acid (Intermediate 34)

A stirred, cooled (−78° C.) solution of 6-bromo-8-isopropyl-2,2,4,4-tetramethyl-chroman (Intermediate 31, 0.39 g, 1.26 mmol) in anhydrous diethyl ether (10 mL) was treated with a 1.7M solution of t-butyl lithium in pentane (1.48 mL, 2.516 mmol) and the reaction mixture was stirred for 20 minutes. Carbon dioxide (generated from dry ice) was bubbled into the reaction mixture. The reaction mixture was then quenched with 10% aqueous hydrochloric acid and extracted with ethyl acetate. The organic phase was washed with water and brine, dried over anhydrous sodium sulfate, filtered and evaporated to a residue that was subjected to flash column chromatography to afford the title compound (0.3, 86%).

$^1$H NMR (300 MHz, CDCl$_3$): δ 7.87 (d, 1H, J=2 Hz), 7.72 (d, 1H, J=2 Hz), 3.21 (heptet, 1H, J=7.0 Hz), 1.78 (s, 2H), 1.39 (s, 12H), 1.14 (d, 6H, J=7.0 Hz).

8-Isopropyl-2,2,4,4-tetramethyl-chroman-6-carboxylic acid 4-(2-benzyloxycarbonyl-vinyl)-phenyl ester (Intermediate 35)

A solution of 8-isopropyl-2,2,4,4-tetramethyl-chroman-6-carboxylic acid (Intermediate 34, 0.05 g, 0.18 mmol) and 3-(4-hydroxy-phenyl)-acrylic acid benzyl ester (described in Journal of Natural Products, 1990, 53 (4), p821-824, Bankova V., 0.046 g, 0.18 mmol) in anhydrous dichloromethane (5 mL) was treated with 4-(dimethylamino)pyridine (0.052 g, 0.27 mmol) and 1-(3-dimethylaminopropyl)-3-ethylcarbodiimide hydrochloride (0.044 g, 0.36 mmol) and the resulting reaction mixture was stirred at ambient temperature overnight. The reaction mixture was then subjected to flash column chromatography using 20% ethyl acetate in hexane as the eluent to afford the title compound as a white solid (0.076 g, 83%).

$^1$H NMR (300 MHz, CDCl$_3$): δ 7.93 (d, 1H, J=2 Hz), 7.78 (d, 1H, J=2 Hz), 7.66 (d, 1H, J=16.1 Hz), 7.49 (d, 2H, J=8.5 Hz), 7.35-7.25 (m, 5H), 7.15 (d, 2H, J=8.5 Hz), 6.39 (d, 1H, J=16.1 Hz), 5.18 (s, 2H), 3.24(heptet, 1H, J=7.1 Hz), 1.80 (s, 2H), 1.31 (s, 12H), 1.16 (d, 6H, J=7.1 Hz).

8-Isopropyl-2,2,4,4-tetramethyl-chroman-6-carboxylic acid 4-(2-carboxy-vinyl)-phenyl ester (Compound 16)

A suspension of t-butyldimethyl silane (0.3 mL, 1.85 mmol), palladium(II)acetate (0.013 g, 0.06 mmol) and triethyl amine (0.03 mL, 0.2 mmol) in anhydrous dichloromethane (2 mL) under argon was treated with a solution of 8-isopropyl-2,2,4,4-tetramethyl-chroman-6-carboxylic acid 4-(2-benzyloxycarbonyl-vinyl)-phenyl ester (Intermediate 35, 0.063 g, 0.123 mmol) in dichloromethane (2 mL) and the resulting reaction mixture was stirred overnight at ambient temperature. The reaction mixture was quenched with water and extracted with diethyl ether. The organic extract was dried over anhydrous sodium sulfate, filtered and evaporated to a residue that was subjected to flash column chromatography to yield an intermediate that was treated with acetic acid (1 mL) in water (0.3 mL) and tetrahydrofuran (0.3 mL) at ambient temperature for 1 h. The reaction mixture was diluted with water and extracted with ethyl acetate. The organic extract was dried over anhydrous sodium sulfate, filtered and evaporated to a residue that was subjected to preparative reverse phase HPLC using 10% water in acetonitrile as the mobile phase to afford the title compound (0.007 g).

$^1$H NMR (300 MHz, CDCl$_3$): δ 7.89 (d, 1H, J=2 Hz), 7.74 (d, 1H, J=2 Hz), 7.67 (d, 1H, J=15.8 Hz), 7.49 (d, 2H, J=8.8 Hz), 7.15 (d, 2H, J=8.8 Hz), 6.32 (d, 1H, J=15.8 Hz), 3.20 (heptet, 1H, J=6.8 Hz), 1.77 (s, 2H), 1.29 (s, 6H), 1.28 (s, 6H), 1.12 (d, 6H, J=6.8 Hz).

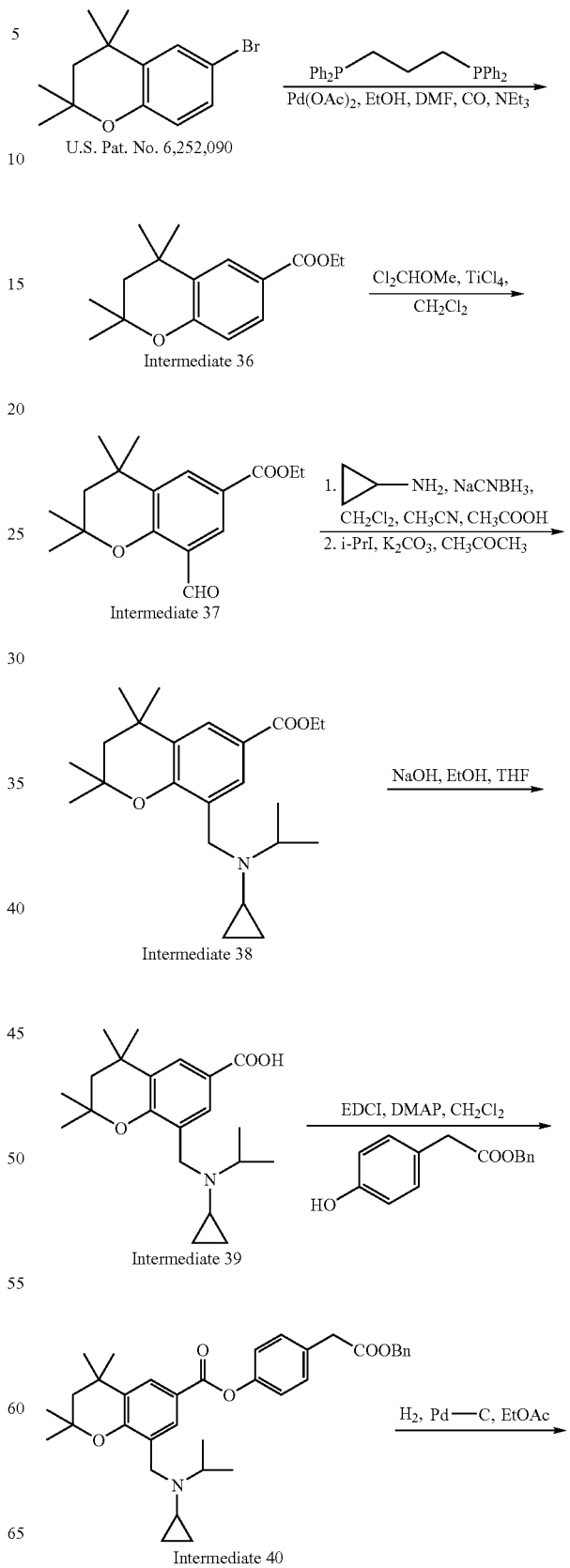

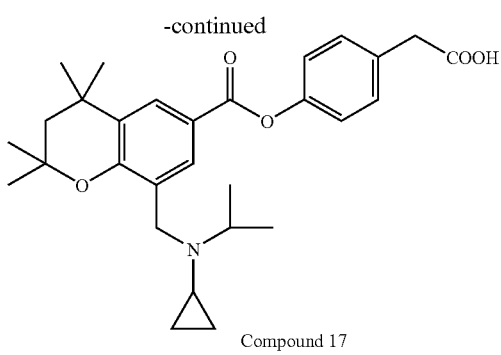

Compound 17

Ethyl-2,2,4,4-tetramethyl chroman-6-carboxylate (Intermediate 36)

A solution of 6-bromo-2,2,4,4-tetramethylchroman (U.S. Pat. No. 6,252,090, 2.2 g, 8.08 mmol), palladium acetate (0.145 g, 0.65 mmol) and 1,3-bis(diphenylphosphino)propane (0.267 g, 0.65 mmol) in a mixture of N,N-dimethylformamide (25 mL), ethanol (20 mL) and triethyl amine (7 mL) was heated at 90° C. under an atmosphere of carbon monoxide overnight. The volatiles were distilled off in vacuo and the residue was diluted with water and extracted with ethyl acetate. The combined organic extract was washed with brine (×1), dried over anhydrous magnesium sulfate, filtered and evaporated in vacuo to an oil which was subjected to flash column chromatography over silica gel (230-400 mesh) using 5-10% ethyl acetate in hexane as the eluent to afford the title compound (1.9 g, 90%).

$^1$H NMR (300 MHz, CDCl$_3$): δ 8.00 (d, 1H, J=2.3 Hz), 7.76 (dd, 1H, J=2.1, 8.5 Hz), 6.79 (d, 1H, J=8.5 Hz), 4.33(q, 2H, J=7.1 Hz), 1.85 (s, 2H), 1.36(s, 6H), 1.37 (s, 6H), 1.39-1.33(m, 3H).

8-Formyl-2,2,4,4-tetramethyl-chroman-6-carboxylic acid ethyl ester (Intermediate 37)

A stirred, cooled (ice bath) solution of of 2,2,4,4-tetramethyl-chroman-6-carboxylic acid ethyl ester (Intermediate 36, 0.5 g, 1.92 mmol) in anhydrous dichloromethane (10 mL) was treated with titanium tetrachloride (0.4 mL, 3.26 mmol) followed by . . . ,-dichloromethyl ether (0.17 mL, 1.92 mmol). The reaction was allowed to warm to ambient temperature over 2 days, quenched cautiously with ice and water and extracted with dichloromethane. The organic extract was washed with water and brine, dried over sodium sulfate, filtered and evaporated in vacuo to a residue that was subjected to flash column chromatography to afford the title compound (0.11 g, 20%).

$^1$H NMR (300 MHz, CDCl$_3$): δ 10.46 (s, 1H), 8.33 (d, 1H, J=2 Hz), 8.20 (d, 1H, J=2 Hz), 4.36 (q, 2H, J=6.7 Hz), 1.93 (s, 2H), 1.45 (s, 6H), 1.42 (s, 6H), 1.39 (t, 3H, J=6.7 Hz).

8-[(Cyclopropyl-isopropyl-amino)-methyl]-2,2,4,4-tetramethyl-chroman-6-carboxylic acid ethyl ester (Intermediate 38)

Following General Procedure C and using 8-formyl-2,2,4,4-tetramethyl-chroman-6-carboxylic acid ethyl ester (Intermediate 37, 0.11 g, 0.23 mmol) in dichloromethane (4 mL) and acetonitrile (2 mL), cyclopropyl amine (0.08 mL, 1.1 mmol), acetic acid (0.8 mL) and sodium cyanoborohydride (0.072 g, 1.1 mmol) followed by work up and flash column chromatography afforded an intermediate. The intermediate (0.122 g, 0.22 mmol) was dissolved in acetone (10 mL) and treated with potassium carbonate (0.153 g, 1.1 mmol) and isopropyl iodide (0.04 mL). The resulting reaction mixture was at 60° C. for 4 h. The volatiles were evaporated in vacuo, the residue was diluted with water and extracted with ethyl acetate. The combined organic phase was dried over anhydrous magnesium sulfate, filtered and evaporated to an oil. Flash column chromatography over silica gel (230-400 mesh) using 15-20% ethyl acetate in hexane as the eluent afforded the title compound (0.09 g, 71%) as a clear oil.

$^1$H NMR (300 MHz, CDCl$_3$): δ 7.87 (d, 1H, J=2.1 Hz), 7.85 (d, 1H, J=2.1 Hz), 4.35 (q, 2H, J=7.0 Hz), 3.72 (s, 2H), 2.97 (heptet, 1H, J=6.7 Hz), 1.97 (m, 1H), 1.83 (s, 2H), 1.37 (t, 3H, J=7.0 Hz), 1.37 (s, 6H), 1.35 (s, 6H), 1.08 (d, 6H, J=6.7 Hz), 0.38-0.30 (m, 4H).

8-[(Cyclopropyl-isopropyl-amino)-methyl]-2,2,4,4-tetramethyl-chroman-6-carboxylic acid (Intermediate 39)

A solution of 8-[(cyclopropyl-isopropyl-amino)-methyl]-2,2,4,4-tetramethyl-chroman-6-carboxylic acid ethyl ester (Intermediate 38, 0.09 g, 0.26 mmol) in ethanol (3 mL) and tetrahydrofuran (1 mL) was treated with a 1M solution of sodium hydroxide (3 mL, 3 mmol) and the resulting reaction mixture was stirred at ambient temperature overnight. The volatiles were evaporated in vacuo, the residue was neutralized with dilute hydrochloric acid and extracted with ethyl acetate. The organic extract was washed with water and brine and dried over anhydrous sodium sulfate, filtered and evaporated to afford the title compound (0.079 g, 96%). It was used as such for the next step.

8-[(Cyclopropyl-isopropyl-amino)-methyl]-2,2,4,4-tetramethyl-chroman-6-carboxylic acid 4-benzyloxycarbonylmethyl-phenyl ester (Intermediate 40)

A solution of 8-[(cyclopropyl-isopropyl-amino)-methyl]-2,2,4,4-tetramethyl-chroman-6-carboxylic acid (Intermediate 39, 0.079 g, 0.25 mmol) and benzyl-4-hydroxy-phenyl acetate (APIN, 0.06 g, 0.25 mmol) in anhydrous dichloromethane (5 mL) was treated with 4-(dimethylamino)pyridine (0.06 g, 0.5 mmol) and 1-(3-dimethylaminopropyl)-3-ethylcarbodiimide hydrochloride (0.072 g, 0.37 mmol) and the resulting reaction mixture was stirred at ambient temperature overnight. The reaction mixture was then subjected to flash column chromatography using 20% ethyl acetate in hexane as the eluent to afford the title compound as an oil (0.093 g, 69%).

$^1$H NMR (300 MHz, CDCl$_3$): δ 7.98 (s, 2H), 7.32-7.21 (m, 7H), 7.13(d, 2H, J=8.5 Hz), 5.11 (s, 2H), 3.73 (s, 2H), 3.66 (s, 2H), 2.93 (heptet, 1H, J=6.5 Hz), 1.93 (m, 1H), 1.84 (s, 2H), 1.07 (s, 12H), 1.07 (d, 6H, J=6.5 Hz).

8-[(Cyclopropyl-isopropyl-amino)-methyl]-2,2,4,4-tetramethyl-chroman-6-carboxylic acid 4-carboxymethyl-phenyl ester (Compound 17)

A solution of 8-[(cyclopropyl-isopropyl-amino)-methyl]-2,2,4,4-tetramethyl-chroman-6-carboxylic acid 4-benzyloxycarbonylmethyl-phenyl ester (Intermediate 40, 0.093 g, 0.17 mmol) in ethyl acetate (3 mL) was treated with a slurry of 10% palladium on carbon (20 mg) in ethyl acetate and the resulting reaction mixture was stirred under an atmosphere of hydrogen at ambient temperature for 2 h. The reaction mixture was filtered over a bed of celite and the filtrate was evaporated to a residue that was purified by flash column chromatography over silica gel to afford the title compound.

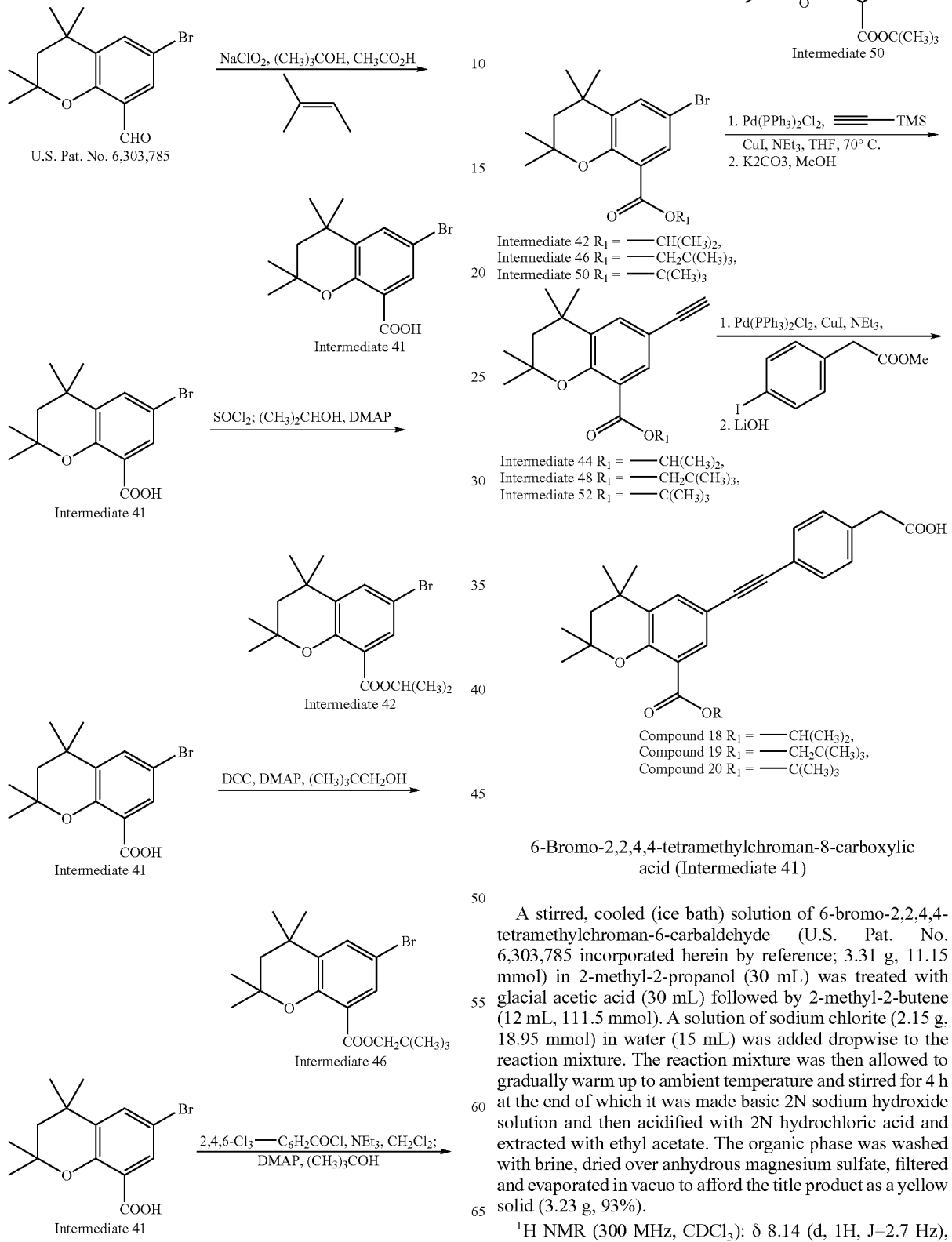

6-Bromo-2,2,4,4-tetramethylchroman-8-carboxylic acid (Intermediate 41)

A stirred, cooled (ice bath) solution of 6-bromo-2,2,4,4-tetramethylchroman-6-carbaldehyde (U.S. Pat. No. 6,303,785 incorporated herein by reference; 3.31 g, 11.15 mmol) in 2-methyl-2-propanol (30 mL) was treated with glacial acetic acid (30 mL) followed by 2-methyl-2-butene (12 mL, 111.5 mmol). A solution of sodium chlorite (2.15 g, 18.95 mmol) in water (15 mL) was added dropwise to the reaction mixture. The reaction mixture was then allowed to gradually warm up to ambient temperature and stirred for 4 h at the end of which it was made basic 2N sodium hydroxide solution and then acidified with 2N hydrochloric acid and extracted with ethyl acetate. The organic phase was washed with brine, dried over anhydrous magnesium sulfate, filtered and evaporated in vacuo to afford the title product as a yellow solid (3.23 g, 93%).

$^1$H NMR (300 MHz, CDCl$_3$): δ 8.14 (d, 1H, J=2.7 Hz), 7.60 (d, 1H, J=2.7 Hz), 1.95 (s, 2H), 1.50 (s, 6H), 1.39 (s, 6H).

6-Bromo-2,2,4,4-tetramethylchroman-8-carboxylic acid isopropyl ester (Intermediate 42)

A solution of 6-bromo-2,2,4,4-tetramethylchroman-8-carboxylic acid (Intermediate 41, 0.3 g, 0.96 mmol) in anhydrous dichloromethane (15 mL) was treated with thionyl chloride (0.7 mL, 9.6 mmol) and the reaction mixture was refluxed for 18 h. It was then cooled to ambient temperature, the volatiles were distilled off in vacuo and the residue was dissolved in isopropanol (15 mL). 4-(Dimethylamino)pyridine (0.35 g, 9.6 mmol) was added and the reaction mixture was stirred at ambient temperature for 5 h. It was diluted with ethyl acetate and washed with 2N hydrochloric acid (×2), 2N sodium hydroxide (×2), and brine, dried over anhydrous magnesium sulfate, filtered and evaporated in vacuo to afford the title product as a brown oil (0.32 g, 93%).

$^1$H NMR (300 MHz, CDCl$_3$): δ 7.60 (d, 1H, J=2.4 Hz), 7.45 (d, 1H, J=2.4 Hz), 5.23 (heptet, 1H, J=6.0 Hz), 1.84 (s, 2H), 1.37 (s, 6H), 1.36 (s, 6H), 1.33 (d, 6H, J=6.0 Hz).

2,2,4,4-Tetramethyl-6-trimethylsilanylethynylchroman-8-carboxylic acid isopropyl ester (Intermediate 43)

Following General Procedure D and using 6-bromo-2,2,4,4-tetramethylchroman-8-carboxylic acid isopropyl ester (Intermediate 42, 0.32 g, 0.89 mmol), triethyl amine (2 mL), copper(I)iodide (0.060 g, 0.33 mmol), trimethylsilyl acetylene (0.5 mL, 3.56 mmol) and dichlorobis(triphenylphosphine)palladium(II) (0.16 g, 0.22 mmol) followed by flash column chromatography over silica gel (230-400 mesh) using 20% ethyl acetate in hexane as the eluent, the title compound (0.23 g, 69%) was obtained as a yellow oil.

$^1$H NMR (300 MHz, CDCl$_3$): δ 7.58 (d, 1H, J=2.4 Hz), 7.44 (d, 1H, J=2.4 Hz), 5.18 (heptet, 1H, J=6.3 Hz), 1.80 (s, 2H), 1.32 (s, 6H), 1.31 (s, 6H), 1.29 (d, 6H, J=6.3 Hz), 0.00 (s, 9H).

6-Ethynyl-2,2,4,4-tetramethylchroman-8-carboxylic acid isopropyl ester (Intermediate 44)

A solution of 2,2,4,4-tetramethyl-6-trimethylsilanylethynylchroman-8-carboxylic acid isopropyl ester (Intermediate 43, 0.23 g, 0.62 mmol) in methanol (5 mL) was treated with potassium carbonate (0.85 g, 6.2 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to a brown oil that was subjected to flash column chromatography over silica gel (230-400 mesh) using 20% ethyl acetate in hexane as the eluent to afford the title compound (0.0246 g, 13%).

$^1$H NMR (300 MHz, CDCl$_3$): δ 7.66 (d, 1H, J=2.1 Hz), 7.53 (d, 1H, J=2.1 Hz), 5.25 (heptet, 1H, J=6.3 Hz), 3.02 (s, 1H), 1.88 (s, 2H), 1.40 (s, 6H), 1.37 (d, 6H, J=6.3 Hz), 1.36 (s, 6H).

6-(4-Methoxycarbonylmethyl-phenylethynyl)-2,2,4,4-tetramethyl-chroman-8-carboxylic acid isopropyl ester (Intermediate 45)

Following General Procedure B and using 6-ethynyl-2,2,4,4-tetramethylchroman-8-carboxylic acid isopropyl ester (Intermediate 44 0.025 g, 0.08 mmol), 4-iodo phenyl acetic acid methyl ester (0.027 g, 0.1 mmol), triethyl amine (2 mL), copper(I)iodide (0.008 g, 0.04 mmol) and dichlorobis(triphenylphosphine)palladium(II) (0.017 g, 0.024 mmol) followed by flash column chromatography over silica gel (230-400 mesh) using 40% ethyl acetate in hexane as the eluent, the title compound was obtained as a yellow oil (0.019 g, 53%).

$^1$H NMR (300 MHz, CDCl$_3$): δ 7.68 (d, 1H, J=2.1 Hz), 7.55 (d, 1H, J=2.1 Hz), 7.49-7.24 (m, 4H), 5.25 (m, 1H), 3.70 (s, 3H), 3.64 (s, 2H), 1.88 (s, 2H), 1.39 (s, 6H), 1.37 (s, 6H), 1.39-1.35 (d, 6H).

6-(4-Carboxymethyl-phenylethynyl)-2,2,4,4-tetramethyl-chroman-8-carboxylic acid isopropyl ester (Compound 18)

A solution of 6-(4-methoxycarbonylmethyl-phenylethynyl)-2,2,4,4-tetramethyl-chroman-8-carboxylic acid isopropyl ester (Intermediate 45, 0.019 g, 0.043 mmol) in ethanol (0.3 mL), tetrahydrofuran (0.3 mL) and water (0.3 mL) was treated with 1N lithium hydroxide (0.086 mL, 0.086 mmol) and the resulting reaction mixture was stirred at ambient temperature for 30 minutes. The volatiles were evaporated in vacuo to a residue that was washed with hexane:ethyl acetate (3:1), neutralized with 2N hydrochloric acid and extracted with ethyl acetate. The organic phase was washed with water and brine, and dried over anhydrous magnesium sulfate, filtered and evaporated in vacuo to afford the title product as a brown oil (0.015 g, 80%). $^1$H NMR (300 MHz, CDCl$_3$): δ 7.69 (d, 1H, J=2.4 Hz), 7.55 (d, 1H, J=2.4 Hz), 7.50-7.26 (m, 4H), 5.25 (heptet, 1H), 3.67 (s, 2H), 1.88 (s, 2H), 1.39 (s, 6H), 1.37 (s, 6H), 1.39-1.35 (d, 6H).

6-Bromo-2,2,4,4-tetramethylchroman-8-carboxylic acid 2,2-dimethylpropyl ester (Intermediate 46)

A stirred cooled (ice bath) solution of 6-bromo-2,2,4,4-tetramethylchroman-8-carboxylic acid (Intermediate 41, 0.5 g, 1.6 mmol), neopentylalcohol (0.35 mL, 3.2 mmol) and 4-(dimethylamino)pyridine (0.03 g, 0.24 mmol) in anhydrous dichloromethane (5 mL) was treated with 1,3-dicyclohexylcarbodiimide (0.36 g, 1.76 mmol) and the reaction mixture was allowed to warm to ambient temperature. After 2 h, the reaction mixture was filtered, the filtrate was diluted with ethyl acetate and washed with 2N hydrochloric acid, 2N sodium hydroxide, and brine, dried over anhydrous magnesium sulfate, filtered and evaporated in vacuo to afford the title product as a yellow solid (0.537 g, 88%).

$^1$H NMR (300 MHz, CDCl$_3$): δ 7.60 (d, 1H, J=2.4 Hz), 7.41 (d, 1H, J=2.4 Hz), 3.91 (s, 2H), 1.78 (s, 2H), 1.30 (s, 6H), 1.27 (s, 6H), 0.95 (s, 9H).

2,2,4,4-Tetramethyl-6-trimethylsilanylethynylchroman-8-carboxylic acid 2,2-dimethylpropyl ester (Intermediate 47)

Following General Procedure D and using 6-bromo-2,2,4,4-tetramethylchroman-8-carboxylic acid 2,2dimethylpropyl ester (Intermediate 46, 0.54 g, 1.4 mmol), triethyl amine (3 mL), copper(I)iodide (0.10 g, 0.52 mmol), trimethylsilyl acetylene (0.8 mL, 5.6 mmol) and dichlorobis(triphenylphosphine)palladium(II) (0.25 g, 0.35 mmol) followed by flash column chromatography over silica gel (230-400 mesh) using 10% ethyl acetate in hexane as the eluent, the title compound (0.396 g, 71%) was obtained as a yellow oil.

$^1$H NMR (300 MHz, CDCl$_3$): δ 7.64 (d, 1H, J=1.8 Hz), 7.46 (d, 1H, J=1.8 Hz), 3.94 (s, 2H), 1.81 (s, 2H), 1.33 (s, 6H), 1.30 (s, 6H), 0.98 (s, 9H), 0.002 (s, 9H).

6-Ethynyl-2,2,4,4-tetramethylchroman-8-carboxylic acid 2,2-dimethylpropyl ester (Intermediate 48)

A solution of 2,2,4,4-tetramethyl-6-trimethylsilanylethynylchroman-8-carboxylic acid 2,2-dimethylpropyl ester (Intermediate 47, 0.396 g, 1 mmol) in methanol (5 mL) was treated with potassium carbonate (1.4 g, 10 mmol) and the resulting reaction mixture was stirred at ambient temperature for 30 minutes. The solvent was evaporated in vacuo, the residue was diluted with water and extracted with ethyl acetate. The organic phase was washed with brine, dried over anhydrous magnesium sulfate, filtered and evaporated in vacuo to afford the title compound as a brown oil (0.227 g, 70%).

$^1$H NMR (300 MHz, CDCl$_3$): δ 7.72 (d, 1H, J=1.5 Hz), 7.55 (d, 1H, J=1.5 Hz), 4.00 (s, 2H), 3.02 (s, 1H), 1.88 (s, 2H), 1.40 (s, 6H), 1.36 (s, 6H), 1.04 (s, 9H).

6-(4-Methoxycarbonylmethyl-phenylethynyl)-2,2,4,4-tetramethyl-chroman-8-carboxylic acid 2,2-dimethylpropyl ester (Intermediate 49)

Following General Procedure B and using 6-ethynyl-2,2,4,4-tetramethylchroman-8-carboxylic acid 2,2-dimethylpropyl ester (Intermediate 48, 0.227 g, 0.70 mmol), 4-iodo phenyl acetic acid methyl ester (0.23 g, 0.83 mmol), triethyl amine (3 mL), copper(I)iodide (0.07 g, 0.39 mmol) and dichlorobis(triphenylphosphine)palladium(II) (0.15 g, 0.21 mmol) followed by flash column chromatography over silica gel (230-400 mesh) using 20% ethyl acetate in hexane as the eluent, the title compound was obtained as a yellow oil (0.198 g, 60%).

$^1$H NMR (300 MHz, CDCl$_3$): δ 7.76 (d, 1H, J=2.4 Hz), 7.58 (d, 1H, J=2.4 Hz), 7.49 (d, 2H, J=8.1 Hz), 7.26 (d, 2H, J=8.1 Hz), 4.01 (s, 2H), 3.70 (s, 3H), 3.64 (s, 2H), 1.88 (s, 2H), 1.40 (s, 6H), 1.38 (s, 6H), 1.05 (s, 9H).

6-(4-Carboxymethyl-phenylethynyl)-2,2,4,4-tetramethyl-chroman-8-carboxylic acid 2,2-dimethylpropyl ester (Compound 19)

A solution of 6-(4-methoxycarbonylmethyl-phenylethynyl)-2,2,4,4-tetramethyl-chroman-8-carboxylic acid 2,2-dimethylpropyl ester (Intermediate 49, 0.198 g, 0.42 mmol) in ethanol (1 mL), tetrahydrofuran (1 mL) and water (1 mL) was treated with 1N lithium hydroxide (1.5 mL, 1.5 mmol) and the resulting reaction mixture was stirred at ambient temperature for 30 minutes. The reaction mixture was neutralized with 2N hydrochloric acid and extracted with ethyl acetate. The organic phase was washed with water and brine, and dried over anhydrous magnesium sulfate, filtered and evaporated in vacuo to afford the title product as a greenish-yellow solid (0.16 g, 84%).

$^1$H NMR (300 MHz, CDCl$_3$): δ 7.76 (d, 1H, J=2.1 Hz), 7.59 (d, 1H, J=2.1 Hz), 7.50 (d, 2H, J=8.1 Hz), 7.28 (d, 2H, J=2.1 Hz), 4.02 (s, 2H), 3.67 (s, 2H), 1.89 (s, 2H), 1.41 (s, 6H), 1.39 (s, 6H), 1.06 (s, 9H).

6-Bromo-2,2,4,4-tetramethylchroman-8-carboxylic acid tert-butyl ester (Intermediate 50)

A solution of 6-bromo-2,2,4,4-tetramethylchroman-8-carboxylic acid (Intermediate 41, 0.3 g, 0.96 mmol) and triethyl amine (0.1 g, 0.96 mmol) in anhydrous tetrahydrofuran (3 mL) was treated with 2,4,6-trichlorobenzoyl chloride (0.23 g, 0.96 mmol) and the reaction mixture was allowed to stir for 20 minutes. The precipitated solid was filtered off and the filtrate was evaporated in vacuo to afford a residue that was dissolved in benzene (3 mL) under argon and treated with 4-(dimethylamino)pyridine (0.47 g, 3.84 mmol) and 2-methyl-2-propanol (0.14 g, 1.92 mmol). After 18 h, the reaction mixture was diluted with ethyl acetate and washed with 2N hydrochloric acid, 2N sodium hydroxide and brine, dried over anhydrous magnesium sulfate, filtered and evaporated in vacuo to afford a residue that was subjected to flash column chromatography over silica gel (230-400 mesh) using 10% ethyl acetate in hexane as the eluent to afford the title product as a white solid (0.14 g, 40%).

$^1$H NMR (300 MHz, CDCl$_3$): δ 7.54 (d, 1H, J=2.4 Hz), 7.43 (d, 1H, J=2.4 Hz), 1.84 (s, 2H), 1.58 (s, 9H), 1.37 (s, 6H), 1.33 (s, 6H).

2,2,4,4-Tetramethyl-6-trimethylsilanylethynylchroman-8-carboxylic acid tert-butyl ester (Intermediate 51)

Following General Procedure D and using 6-bromo-2,2,4,4-tetramethylchroman-8-carboxylic acid tert-butyl ester (Intermediate 50, 0.195 g, 0.53 mmol), triethyl amine (2 mL), copper(I)iodide (0.040 g, 0.2 mmol), trimethylsilyl acetylene (0.3 mL, 2.1 mmol) and dichlorobis(triphenylphosphine)palladium(II) (0.09 g, 0.13 mmol) followed by flash column chromatography over silica gel (230-400 mesh) using 10% ethyl acetate in hexane as the eluent, the title compound (0.064 g, 32%) was obtained as a brown oil.

$^1$H NMR (300 MHz, CDCl$_3$): δ 7.57 (d, 1H, J=2.1 Hz), 7.46 (d, 1H, J=2.1 Hz), 1.84 (s, 2H), 1.57 (s, 9H), 1.37 (s, 6H), 1.34 (s, 6H), 0.045 (s, 9H).

6-Ethynyl-2,2,4,4-tetramethylchroman-8-carboxylic acid tert-butyl ester (Intermediate 52)

A solution of 2,2,4,4-tetramethyl-6-trimethylsilanylethynylchroman-8-carboxylic acid tert-butyl ester (Intermediate 51, 0.064 g, 0.17 mmol) in methanol (5 mL) was treated with potassium carbonate (0.23 g, 1.7 mmol) and the resulting reaction mixture was stirred at ambient temperature for 30 minutes. The solvent was evaporated in vacuo, the residue was diluted with water and extracted with ethyl acetate. The organic phase was washed with brine, dried over anhydrous magnesium sulfate, filtered and evaporated in vacuo to afford the title compound as a brown oil (0.051 g, 97%).

$^1$H NMR (300 MHz, CDCl$_3$): δ 7.52 (d, 1H, J=2.1 Hz), 7.42 (d, 1H, J=1.5 Hz), 2.93 (s, 1H), 1.79 (s, 2H), 1.51 (s, 9H), 1.31 (s, 6H), 1.27 (s, 6H).

6-(4-Methoxycarbonylmethyl-phenylethynyl)-2,2,4,4-tetramethyl-chroman-8-carboxylic acid tert-butyl ester (Intermediate 53)

Following General Procedure B and using 6-ethynyl-2,2,4,4-tetramethylchroman-8-carboxylic acid tert-butyl ester (Intermediate 52, 0.051 g, 0.16 mmol), 4-iodo phenyl acetic acid methyl ester (0.053 g, 0.19 mmol), triethyl amine (3 mL), copper(I)iodide (0.02 g, 0.1 mmol) and dichlorobis(triphenylphosphine)palladium(II) (0.03 g, 0.043 mmol) followed by flash column chromatography over silica gel (230-400 mesh) using 20% ethyl acetate in hexane as the eluent, the title compound was obtained as a yellow oil (0.014 g, 19%).

$^1$H NMR (300 MHz, CDCl$_3$): δ 7.63 (d, 1H, J=2.1 Hz), 7.53 (d, 1H, J=2.1 Hz), 7.48 (d, 2H, J=8.2 Hz), 7.26 (d, 2H, J=8.2 Hz), 3.72 (s, 3H), 3.65 (s, 2H), 1.88 (s, 2H), 1.60 (s, 9H), 1.40 (s, 6H), 1.38 (s, 6H).

6-(4-Carboxymethyl-phenylethynyl)-2,2,4,4-tetramethyl-chroman-8-carboxylic acid tert-butyl ester (Compound 20)

A solution of 6-(4-methoxycarbonylmethyl-phenylethynyl)-2,2,4,4-tetramethyl-chroman-8-carboxylic acid tert-butyl ester (Intermediate 53, 0.014 g, 0.03 mmol) in ethanol (0.3 mL), tetrahydrofuran (0.3 mL) and water (0.3 mL) was treated with 1N lithium hydroxide (0.12 mL, 0.12 mmol) and the resulting reaction mixture was stirred at ambient temperature for 3 h. The reaction mixture was neutralized with 2N hydrochloric acid and extracted with ethyl acetate. The organic phase was washed with water and brine, and dried over anhydrous magnesium sulfate, filtered and evaporated in vacuo to afford the title product as a yellow oil (0.012 g, 88%).

$^1$H NMR (300 MHz, CDCl$_3$): δ 7.63 (d, 1H, J=2.1 Hz), 7.52 (d, 1H, J=2.1 Hz), 7.47 (d, 2H, J=8.2 Hz), 7.26 (d, 2H, J=2.1 Hz), 3.67 (s, 2H), 1.87 (s, 2H), 1.59 (s, 9H), 1.39 (s, 6H), 1.36 (s, 6H).

Reaction Scheme 11

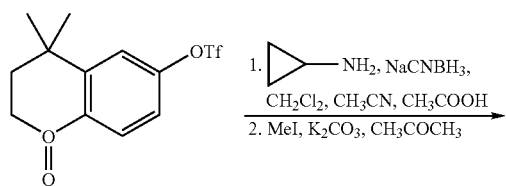

U.S. Pat. No. 6,252,090

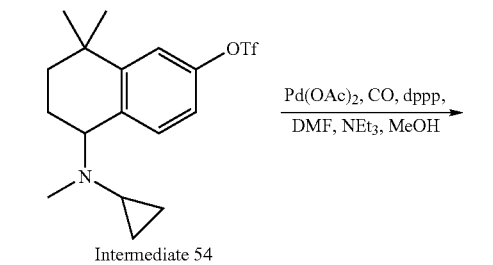

Intermediate 54

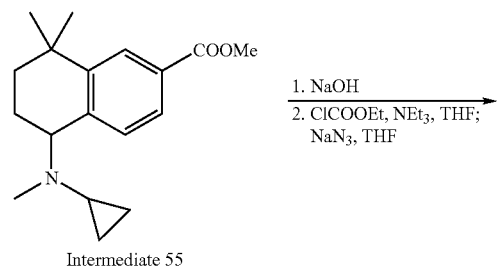

Intermediate 55

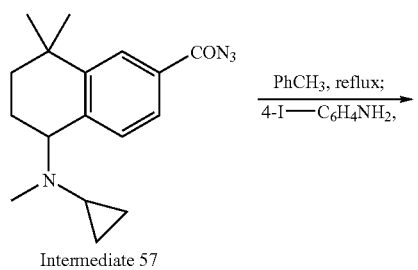

Intermediate 57

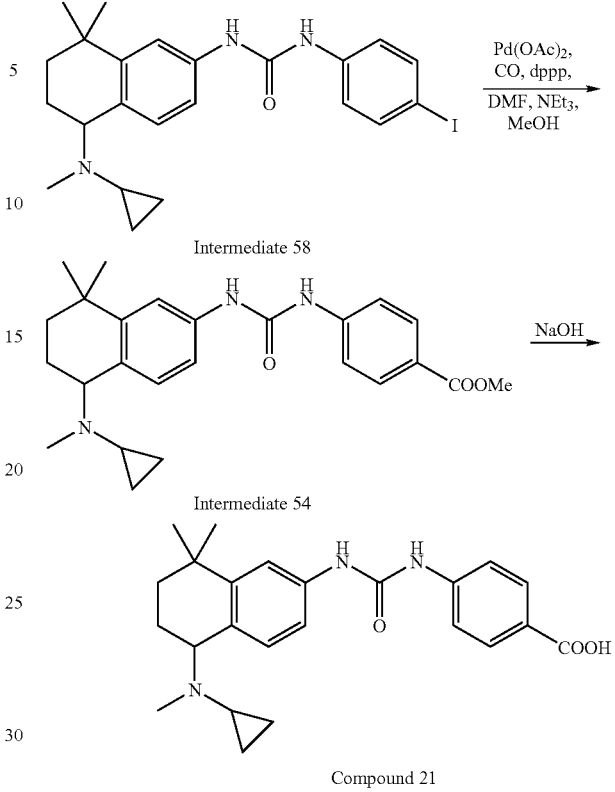

Intermediate 58

Intermediate 54

Compound 21

Trifluoro-methanesulfonic acid 5-(cyclopropyl-methyl-amino)-8,8-dimethyl-5,6,7,8-tetrahydro-naphthalen-2-yl ester (Intermediate 54)

A solution of 4,4-dimethyl-6-trifluoromethylsulfonyloxy-1,2,3,4-tetrahydronaphthalene-1-one (U.S. Pat. No. 6,252,090, 0.85 g, 2.64 mmol) in dichloromethane (6 mL) and acetonitrile (3 mL) was treated with cyclopropyl amine (3 mL, 43.4 mmol). After 5 minutes, acetic acid (3 mL) was added followed by sodium cyanoborohydride (0.66 g, 10.55 mmol). The reaction was stirred overnight at ambient temperature. It was then diluted with water and saturated aqueous sodium carbonate solution and extracted with ethyl acetate. The combined organic extract was washed with water and brine, dried over anhydrous sodium sulfate, filtered and evaporated in vacuo to an oil. The oil was dissolved in acetone (20 mL) and treated with potassium carbonate (1.08 g, 7.8 mmol) and methyl iodide (1.6 mL, 26 mmol). The resulting reaction mixture was stirred at ambient temperature overnight. The solids were filtered off, the filtrate was evaporated in vacuo and the residue was subjected to flash column chromatography over silica gel (230-400 mesh) to afford the title compound (0.85 g, 87%) as a colorless oil.

$^1$H NMR (300 MHz, CDCl$_3$): δ 7.61 (d, 1H, J=9.0 Hz), 7.11 (d, 1H, J=2.4 Hz), 6.97 (dd, 1H, J=2.4, 9.0 Hz), 3.92 (t, 1H, J=8.4 Hz), 2.14-2.10 (m, 1H), 2.12 (s, 3H), 1.96-1.89 (m, 2H), 1.79-1.57 (m, 2H), 1.29(s, 3H), 1.25 (s, 3H), 0.52-0.36 (m, 4H).

General Procedure E: 5-(Cyclopropyl-methyl-amino)-8,8-dimethyl-5,6,7,8-tetrahydro-naphthalene-2-carboxylic acid methyl ester (Intermediate 55)

A solution of trifluoro-methanesulfonic acid 5-(cyclopropyl-methyl-amino)-8,8-dimethyl-5,6,7,8-tetrahydro-naphthalen-2-yl ester (Intermediate 54, 0.37 g, 0.98 mmol), palladium acetate (0.05 g, 0.22 mmol) and 1,3-bis(diphenylphosphino)propane (0.096 g, 0.23 mmol) in a mixture of dimethylformamide (4 mL), methanol (4 mL) and triethyl amine (2 mL) was heated at 70° C. under an atmosphere of carbon monoxide overnight. The volatiles were distilled of in vacuo and the residue was diluted with water and extracted with diethyl ether (×3). The combined organic extract was dried over anhydrous magnesium sulfate, filtered and evaporated in vacuo to an oil which was subjected to flash column chromatography over silica gel (230-400 mesh) using 2-5% ethyl acetate in hexane as the eluent, to afford the title compound (0.236 g, 85%).

$^1$H NMR (300 MHz, CDCl$_3$): δ 7.96 (d, 1H, J=1.8 Hz), 7.73 (dd, 1H, J=1.8, 8.1 Hz), 7.59 (d, 1H, J=8.1 Hz), 3.96 (t, 1H, J=7.5 Hz), 3.89 (s, 3H), 2.17-2.10 (m, 1H), 2.12 (s, 3H), 1.98-1.83 (m, 2H), 1.82-1.60 (m, 2H), 1.34(s, 3H), 1.28 (s, 3H), 0.54-0.39 (m, 4H).

5-(Cyclopropyl-methyl-amino)-8,8-dimethyl-5,6,7,8-tetrahydronaphthalene-2-carboxylic aci d(Intermediate 56)

A solution of 5-(cyclopropyl-methyl-amino)-8,8-dimethyl-5,6,7,8-tetrahydro-naphthalene-2-carboxylic acid methyl ester (Intermediate 55, 0.236 g, 0.83 mmol) in methanol (4 mL) and tetrahydrofuran (4 mL) was treated with a 2M solution of sodium hydroxide (4 mL, 8 mmol) and the resulting reaction mixture was stirred at ambient temperature overnight. The volatiles were evaporated in vacuo to a residue that was neutralized with saturated aqueous ammonium chloride solution and extracted with ethyl acetate. The organic phase was dried over anhydrous magnesium sulfate, filtered and evaporated in vacuo to afford the title compound as a solid (0.22 g, 100%).

$^1$H NMR (300 MHz, CDCl$_3$): δ 7.98 (d, 1H, J=1.8 Hz), 7.72 (dd, 1H, J=1.8, 8.2 Hz), 7.51 (d, 1H, J=8.2 Hz), 3.93 (t, 1H, J=7.8 Hz), 2.15-2.04 (m, 1H), 2.10 (s, 3H), 1.94-1.85 (m, 2H), 1.79-1.62 (m, 2H), 1.27(s, 3H), 1.22 (s, 3H), 0.52-0.40 (m, 4H).

5-(Cyclopropyl-methyl-amino)-8,8-dimethyl-5,6,7,8-tetrahydronaphthalene-2-carboxylic acid azid e(Intermediate 57)

A stirred, cooled (ice bath) solution of 5-(cyclopropyl-methyl-amino)-8,8-dimethyl-5,6,7,8-tetrahydronaphthalene-2-carboxylic acid (Intermediate 56, 0.22 g, 0.83 mmol) in anhydrous tetrahydrofuran (4 mL) was treated with triethyl amine (0.16 mL, 1.1 mmol) followed by ethyl chloroformate (0.10 mL, 1.08 mmol). After 5 h, sodium azide (0.081 g, 1.24 mmol) was added and the reaction mixture was allowed to warm to ambient temperature and stirred overnight. The reaction mixture was diluted with water and extracted with ethyl acetate. The organic phase was washed with water and brine, dried over anhydrous sodium sulfate, filtered and evaporated in vacuo to afford the title product that was used as such for the next reaction (0.24 g, 98%).

1-[5-(Cyclopropyl-methyl-amino)-8,8-dimethyl-5,6,7,8-tetrahydro-naphthalen-2-yl]-3-(4-iodo-phenyl)-urea (Intermediate 58)

A solution of 5-(cyclopropyl-methyl-amino)-8,8-dimethyl-5,6,7,8-tetrahydronaphthalene-2-carboxylic acid azide (Intermediate 57, 0.12 g, 0.4 mmol) in anhydrous toluene (14 mL) was refluxed under argon for 2 h. 4-iodoaniline (0.114 g, 0.52 mmol) was added and the solution was cooled to ambient temperature and stirred overnight. The volatiles were evaporated in vacuo and the residue was subjected to flash column chromatography over silica gel (230-400 mesh) using 20-25% ethyl acetate in hexane as the eluent to afford the title compound (0.13 g, 67%).

$^1$H NMR (300 MHz, CDCl$_3$): δ 7.58 (d, 2H, J=8.7 Hz), 7.51 (d, 1H, J=8.1 Hz), 7.23 (d, 1H, J=1.8 Hz), 7.14 (d, 2H, J=8.7 Hz), 6.99 (dd, 1H, J=1.8, 8.1 Hz), 6.99 (br s, 1H), 6.57 (br s, 1H), 3.92 (t, 1H, J=7.2 Hz), 2.13-2.05 (m, 1H), 2.13 (s, 3H), 1.93-1.88 (m, 2H), 1.78-1.62 (m, 2H), 1.29 (s, 3H), 1.26 (s, 3H), 0.52-0.39 (m, 4H).

4-{3-[5-(Cyclopropyl-methyl-amino)-8,8-dimethyl-5,6,7,8-tetrahydro-naphthalen-2-yl]-ureido}-benzoic acid methyl ester (Intermediate 59)

Following General Procedure E and using 1-[5-(cyclopropyl-methyl-amino)-8,8-dimethyl-5,6,7,8-tetrahydro-naphthalen-2-yl]-3-(4-iodo-phenyl)-urea (Intermediate 58, 0.13 g, 0.267 mmol), palladium acetate (0.02 g, 0.09 mmol), 1,3-bis(diphenylphosphino)propane (0.042 g, 0.101 mmol), N,N-dimethylformamide (3 mL), methanol (3 mL) and triethyl amine (1 mL) followed by flash column chromatography over silica gel (230-400 mesh) using 30-40% ethyl acetate in hexane as the eluent the title compound was obtained (0.045 g, 40%).

$^1$H NMR (300 MHz, CDCl$_3$): δ 7.91 (d, 2H, J=8.4 Hz), 7.51 (d, 1H, J=8.1 Hz), 7.42 (s, 1H), 7.37 (d, 2H, J=8.4 Hz), 7.26 (d, 1H, J=1.8 Hz), 7.09 (s, 1H), 6.97 (dd, 1H, J=2.1, 8.1 Hz), 3.89 (s, 3H), 3.90-3.84 (m, 1H), 2.11-2.06 (m, 1H), 2.09 (s, 3H), 1.89-1.80 (m, 2H), 1.80-1.64 (m, 2H), 1.24 (s, 3H), 1.21 (s, 3H), 0.50-0.36 (m, 4H).

4-{3-[5-(Cyclopropyl-methyl-amino)-8,8-dimethyl-5,6,7,8-tetrahydro-naphthalen-2-yl]-ureido}-benzoic acid (Compound 21)

A solution of 4-{3-[5-(cyclopropyl-methyl-amino)-8,8-dimethyl-5,6,7,8-tetrahydro-naphthalen-2-yl]-ureido}-benzoic acid methyl ester (Intermediate 59, 0.045 g, 0.106 mmol) in methanol (2 mL) and tetrahydrofuran (3 mL) was treated with a 2M solution of sodium hydroxide (1 mL, 2 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to afford a solid that was recrystallized from hot acetonitrile to afford the title product as a white solid (0.012 g, 28%).

$^1$H NMR (300 MHz, CD$_3$OD): δ 7.95 (d, 2H, J=9.0 Hz), 7.53 (d, 2H, J=9.0 Hz), 7.46 (d, 1H, J=2.1 Hz), 7.40 (d, 1H, J=8.7 Hz), 7.09 (s, 1H), 7.19 (dd, 1H, J=2.1, 8.7 Hz), 4.06 (t, 1H, J=6.0 Hz)), 2.30-2.25 (m, 1H), 2.28 (s, 3H), 2.05-1.98 (m, 2H), 1.82-1.68 (m, 2H), 1.32 (s, 3H), 1.30 (s, 3H), 0.60-0.48 (m, 4H).

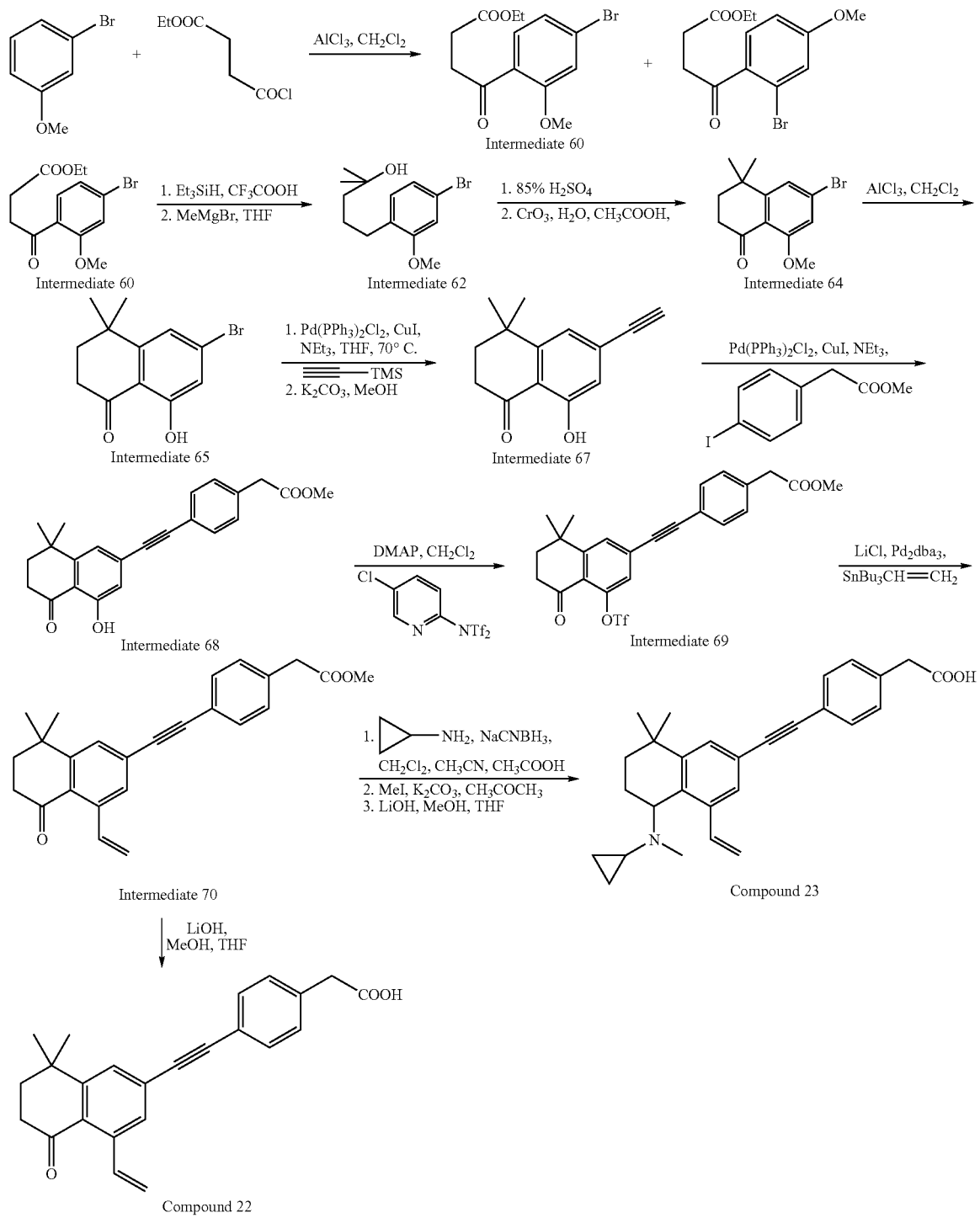

Reaction Scheme 12

4-(4-Bromo-2-methoxy-phenyl)-4-oxo-butyric acid ethyl ester (Intermediate 60)

A stirred, cooled (−30° C.) solution of 3-bromo anisole (Aldrich, 18.7 g, 100 mmol) and ethyl succinyl chloride (21 mL, 150 mmol) in anhydrous dichloromethane (200 mL) was treated with aluminum chloride (26.6 g, 200 mmol) and the reaction mixture was allowed to warm to ambient temperature and stirred overnight. The reaction mixture was poured into water and extracted with dichloromethane (×2). The combined organic phase was washed with brine, dried over anhydrous sodium sulfate, filtered and evaporated in vacuo to a brown oil. A solid separated out on standing. The supernatant liquid was decanted and the solid was washed with 1:3 dichloromethane: hexane and dried to afford the title compound. The combined mother liquor and washings were evaporated to a brown oil that was subjected to flash column chromatography over silica gel (230-400 mesh) using 15% ethyl acetate in hexane as the eluent to afford the title compound (overall 12 g, 38%), and its isomer 4-(2-romo-4-methoxy-phenyl)-4-oxo-butyric acid ethyl ester (11.4 g, 36%) and a 1:1 mixture of both (2 g, 6.3%).

$^1$H NMR (300 MHz, CDCl$_3$): δ 7.56 (d, 1H, J=8.7 Hz), 7.07-7.03 (m, 2H), 4.07 (q, 2H, J=7.2 Hz), 3.84 (s, 3H), 3.20 (t, 2H, J=6.3 Hz), 2.61 (t, 2H, J=6.3 Hz), 1.19 (t, 3H, J=7.2 Hz).

4-(4-Bromo-2-methoxy-phenyl)-butyric acid ethyl ester (Intermediate 61)

A solution of 4-(4-bromo-2-methoxy-phenyl)-4-oxo-butyric acid ethyl ester (Intermediate 60, 14.73 g, 46.8 mmol) in trifluoroacetic acid (72 mL, 935 mmol) was treated with triethylsilane (30 mL, 187 mmol) and the resulting reaction mixture was heated at 55° C. for 4 h. The reaction mixture was then cooled to ambient temperature, neutralized with solid sodium bicarbonate, diluted with water and extracted with diethyl ether. The organic phase was washed with water and brine, dried over anhydrous magnesium sulfate, filtered and evaporated in vacuo to afford a residue that was subjected to flash column chromatography over silica gel (230-400 mesh) using 8% ethyl acetate in hexane as the eluent to afford the title compound (7.4 g, 53%) as a colorless oil.

$^1$H NMR (300 MHz, CDCl$_3$): δ 7.02-6.94 (m, 3H), 4.11 (q, 2H, J=7.2 Hz), 3.79 (s, 3H), 2.60 (t, 2H, J=7.2 Hz), 2.29 (t, 2H, J=7.2 Hz), 1.88 (quintet, 2H, J=7.2 Hz), 1.25 (t, 3H, J=7.2 Hz).

5-(4-Bromo-2-methoxy-phenyl)-2-methyl-pentan-2-ol (Intermediate 62)

A stirred, cooled (−10° C.) solution of 4-(4-bromo-2-methoxy-phenyl)-butyric acid ethyl ester (Intermediate 61, 7.4 g, 24.6 mmol) in anhydrous tetrahydrofuran (50 mL) was treated with a 3M solution of methyl magnesium bromide (20.5 mL, 61.5 mmol) and the resulting reaction mixture was allowed to warm to ambient temperature over 3 h. It was quenched with saturated, aqueous ammonium chloride solution, diluted with water and extracted with diethyl ether. The organic phase was washed with water and brine, dried over anhydrous magnesium sulfate, filtered and evaporated in vacuo to afford the title product (7.3 g, 100%).

$^1$H NMR (300 MHz, CDCl$_3$): δ 6.92-6.87 (m, 3H), 3.71 (s, 3H), 2.48 (t, 2H, J=7.2 Hz), 1.55-1.38 (m, 4H), 1.11 (s, 6H).

7-Bromo-5-methoxy-1,1-dimethyl-12,3,4-tetrahydro-naphthalene (Intermediate 63)

5-(4-Bromo-2-methoxy-phenyl)-2-methyl-pentan-2-ol (Intermediate 62, 7.3 g, 24.6 mmol) was treated with 85% sulfuric acid (25 mL) at ambient temperature. After 30 minutes, the reaction mixture was diluted with cold water and extracted with diethyl ether. The organic phase was washed with water and brine, dried over anhydrous magnesium sulfate, filtered and evaporated in vacuo to afford the title product (5.6 g, 83%).

$^1$H NMR (300 MHz, CDCl$_3$): δ 7.01 (d, 1H, J=1.8 Hz), 6.68 (d, 1H, J=1.8 Hz), 3.71 (s, 3H), 2.49 (t, 2H, J=6.3 Hz), 1.71-1.65 (m, 2H), 1.55-1.51 (m, 2H), 1.18 (s, 6H).

6-Bromo-8-methoxy-4,4-dimethyl-3,4-dihydro-2H-naphthalen-1-one (Intermediate 64)

A solution of 7-bromo-5-methoxy-1,1-dimethyl-1,2,3,4-tetrahydro-naphthalene (Intermediate 63, 5.6 g, 20.81 mmol) in glacial acetic acid (20 mL) was cooled to 0° C. and treated with a solution of chromium trioxide (6.16 g, 61.6 mmol) in acetic acid and water (25 mL). The reaction mixture was then allowed to warm to ambient temperature and stirred for 48 h. It was diluted with water and extracted with diethyl ether (×2). The combined organic phase was washed with water (×3), saturated aqueous sodium bicarbonate (×1) and brine (×1), dried over anhydrous magnesium sulfate, filtered and evaporated in vacuo to afford an oil. Flash column chromatography over silica gel (230-400 mesh) using 10-20-100% ethyl acetate in hexane as the eluent afforded the title compound (2 g, 33%) as a yellow oil and recovered starting material (2.2 g, 39%).

$^1$H NMR (300 MHz, CDCl$_3$): δ 7.12 (d, 1H, J=1.8 Hz), 6.97 (d, 1H, J=1.8 Hz), 3.87 (s, 3H), 2.66 (t, 2H, J=6.6 Hz), 1.92 (t, 2H, J=6.6 Hz), 1.33 (s, 6H).

6-Bromo-8-hydroxy-4,4-dimethyl-3,4-dihydro-2H-naphthalen-1-one (Intermediate 65)

A stirred, cooled (ice bath) solution of 6-bromo-8-methoxy-4,4-dimethyl-3,4-dihydro-2H-naphthalen-1-one (Intermediate 64, 0.24 g, 0.83 mmol) in anhydrous dichloromethane (4 mL) was treated with aluminum chloride (0.4 g, 3 mmol). The reaction mixture was allowed to warm to ambient temperature and stirred overnight. It was poured into water and extracted with dichloromethane and ethyl acetate. The combined organic phase was dried over anhydrous magnesium sulfate, filtered and evaporated in vacuo to a brown oil that was subjected to flash column chromatography over silica gel (230-400 mesh) using 10% ethyl acetate in hexane as the eluent to afford the title product as a pale yellow solid (0.13 g, 56%).

$^1$H NMR (300 MHz, CDCl$_3$): δ 12.85 (s, 1H), 7.00 (d, 1H, J=1.5 Hz), 6.98 (d, 1H, J=1.5 Hz), 2.74 (t, 2H, J=6.9 Hz), 1.96 (t, 2H, J=6.9 Hz), 1.36 (s, 6H).

8-Hydroxy-4,4-dimethyl-6-trimethylsilanylethynyl-3,4-dihydro-2H-naphthalen-1-one (Intermediate 66)

Following General Procedure D and using 6-bromo-8-hydroxy-4,4-dimethyl-3,4-dihydro-2H-naphthalen-1-one (Intermediate 65, 1.56 g, 5.8 mmol), triethyl amine (20 mL), copper(I)iodide (0.088 g, 0.46 mmol), trimethylsilyl acetylene (3 mL, 21.22 mmol) and dichlorobis(triphenylphosphine)palladium(II) (0.325 g, 0.46 mmol) followed by flash column chromatography over silica gel (230-400 mesh) using hexane to 2-5% ethyl acetate in hexane as the eluent, the title compound (1.67 g, 100%) was obtained as an orange solid.

$^1$H NMR (300 MHz, CDCl$_3$): δ 12.72 (s, 1H), 6.93 (d, 1H, J=1.5 Hz), 6.88 (d, 1H, J=1.5 Hz), 2.74 (t, 2H, J=6.6 Hz), 1.96 (t, 2H, J=6.6 Hz), 1.36 (s, 6H), 0.27 (s, 9H).

6-Ethynyl-8-hydroxy-4,4-dimethyl-3,4-dihydro-2H-naphthalen-1-one (Intermediate 67)

A solution of 8-hydroxy-4,4-dimethyl-6-trimethylsilanylethynyl-3,4-dihydro-2H-naphthalen-1-one (Intermediate 66, 2.2 g, 7.4 mmol) in methanol (20 mL) was treated with potassium carbonate (2.04 g, 14.8 mmol) and the resulting reaction mixture was stirred at ambient temperature for 5 h. The solvent was evaporated in vacuo, the residue was diluted with water and extracted with diethyl ether. The organic phase was dried over anhydrous magnesium sulfate, filtered and evaporated in vacuo to afford the title compound as an oil (1.58 g, ~100%).

$^1$H NMR (300 MHz, CDCl$_3$): δ 12.76 (s, 1H), 6.97 (d, 1H, J=1.5 Hz), 6.88 (d, 1H, J=1.5 Hz), 3.28 (s, 1H), 2.73 (t, 2H, J=6.6 Hz), 1.94 (t, 2H, J=6.6 Hz), 1.34 (s, 6H).

{4-[8,8-Dimethyl-4-hydroxy-5-oxo-5,6,7,8-tetrahydro-naphthalen-2-ylethynyl]-phenyl}-acetic acid methyl ester (Intermediate 68)

Following General Procedure B and using 6-ethynyl-8-hydroxy-4,4-dimethyl-3,4-dihydro-2H-naphthalen-1-one (Intermediate 67, 1.58 g, 7.4 mmol), 4-iodo phenyl acetic acid methyl ester (2.2 g, 7.94 mmol), triethyl amine (12 mL), copper(I)iodide (0.38 g, 1.99 mmol) and dichlorobis(triphenylphosphine)palladium(II) (1.2 g, 1.71 mmol) followed by flash column chromatography over silica gel (230-400 mesh) using 16% ethyl acetate in hexane as the eluent, the title compound was obtained as a yellow oil (2.1 g, 78%).

$^1$H NMR (300 MHz, CDCl$_3$): δ 12.79 (s, 1H), 7.52 (d, 2H, J=8.7 Hz), 7.29 (d, 2H, J=8.7 Hz), 7.01 (d, 1H, J=1.5 Hz), 6.94 (d, 1H, J=1.5 Hz), 3.71 (m, 3H), 3.65 (s, 2H), 2.76 (t, 2H, J=6.6 Hz), 1.97 (t, 2H, J=6.6 Hz), 1.38 (s, 6H).

{4-[8,8-Dimethyl-5-oxo-4-trifluoromethanesulfonyloxy-5,6,7,8-tetrahydro-naphthalen-2-ylethynyl]-phenyl}-acetic acid methyl ester (Intermediate 69)

A stirred, cooled (0° C.) solution of {4-[8,8-dimethyl-4-hydroxy-5-oxo-5,6,7,8-tetrahydro-naphthalen-2-ylethynyl]-phenyl}-acetic acid methyl ester (Intermediate 68, 2.1 g, 5.8 mmol) in anhydrous dichloromethane (20 mL) was treated with 4-(dimethylamino)pyridine (1.21 g, 9.9 mmol) followed by N-phenyltrifluoromethanesulfonimide (2.2 g, 6.16 mmol). After stirring at ambient temperature overnight, the reaction mixture was subjected to flash column chromatography over silica gel (230-400 mesh) using 20% ethyl acetate in hexane as the eluent to afford the title compound (2.6 g, 91%).

$^1$H NMR (300 MHz, CDCl$_3$): δ 7.57 (d, 1H, J=1.2 Hz), 7.49 (d, 2H, J=8.4 Hz), 7.27 (d, 2H, J=8.4 Hz), 7.19 (d, 1H, J=1.2 Hz), 3.66 (m, 3H), 3.62 (s, 2H), 2.72 (t, 2H, J=6.9 Hz), 1.99 (t, 2H, J=6.9 Hz), 1.38 (s, 6H).

[4-(8,8-Dimethyl-5-oxo-4-vinyl-5,6,7,8-tetrahydro-naphthalen-2-ylethynyl)-phenyl]-acetic acid methyl ester (Intermediate 70)

A solution of {4-[8,8-dimethyl-5-oxo-4-trifluoromethanesulfonyloxy-5,6,7,8-tetrahydro-naphthalen-2-ylethynyl]-phenyl}-acetic acid methyl ester (Intermediate 69, 0.233 g, 0.47 mmol) in anhydrous 1-methyl 2-pyrrolidinone (3 mL) was sparged with argon, and treated with lithium chloride (0.061 g, 1.45 mmol), tri-2-furylphosphine (0.0071 g, 0.031 mmol) and tris(dibenzylideneacetone)dipalladium(0) (0.007 g, 0.015 mmol). After 5 minutes, tributyl(vinyl)tin (0.175 g, 0.55 mmol) was added and the resulting reaction mixture was stirred at ambient temperature for 2.5 h. The reaction mixture was diluted with water and extracted with ethyl acetate. The organic phase was washed with brine and water, dried over anhydrous sodium sulfate, filtered and evaporated in vacuo to a residue that was subjected to flash column chromatography over silica gel (230-400 mesh) using 10-15% ethyl acetate in hexane as the eluent to afford the title compound (0.15 g, 86%) as a white solid.

$^1$H NMR (300 MHz, CDCl$_3$): δ 7.53 (d, 2H, J=7.8 Hz), 7.51 (d, 1H, J=1.8 Hz), 7.50 (d, 1H, J=1.8 Hz), 7.43 (dd, 1H, J=10.5, 17.1 Hz), 7.29 (d, 2H, J=7.8 Hz), 5.57 (dd, 1H, J=1.5, 17.1 Hz), 5.33 (dd, 1H, J=1.5, 10.5 Hz), 3.71 (s, 3H), 3.66 (s, 2H), 2.74 (t, 2H, J=6.9 Hz), 2.00 (t, 2H, J=6.9 Hz), 1.40 (s, 6H).

[4-(8,8-Dimethyl-5-oxo-4-vinyl-5,6,7,8-tetrahydro-naphthalen-2-ylethynyl)-phenyl]-acetic acid (Compound 22)

A solution of [4-(8,8-dimethyl-5-oxo-4-vinyl-5,6,7,8-tetrahydro-naphthalen-2-ylethynyl)-phenyl]-acetic acid methyl ester (Intermediate 70, 0.082 g, 0.22 mmol) in methanol (3 mL) and tetrahydrofuran (3 mL) was treated with a 2M solution of lithium hydroxide (1.5 mL, 3 mmol) and the resulting reaction mixture was stirred at ambient temperature for 1.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product as a yellow solid (0.065 g, 82%).

$^1$H NMR (300 MHz, CDCl$_3$): δ 7.53 (d, 2H, J=8.1 Hz), 7.50 (s, 2H), 7.43 (dd, 1H, J=10.8, 17.4 Hz), 7.31 (d, 2H, J=8.1 Hz), 5.57 (dd, 1H, J=1.5, 17.4 Hz), 5.33 (dd, 1H, J=1.5, 10.8 Hz), 3.68 (s, 2H), 2.74 (t, 2H, J=6.3 Hz), 1.99 (t, 2H, J=6.3 Hz), 1.39 (s, 6H).

{4-[5-(Cyclopropyl-methyl-amino)-8,8-dimethyl-4-vinyl-5,6,7,8-tetrahydro-naphthalen-2-ylethynyl]-phenyl}-acetic acid methyl ester (Intermediate 71)

A solution of [4-(8,8-dimethyl-5-oxo-4-vinyl-5,6,7,8-tetrahydro-naphthalen-2-ylethynyl)-phenyl]-acetic acid methyl ester (Intermediate 70, 0.205 g, 0.55 mmol) in dichloromethane (4 mL) and acetonitrile (2 mL) was treated with cyclopropyl amine (1 mL, 14.45 mmol). After 5 minutes, acetic acid (1 mL) was added followed by sodium cyanoborohydride (0.138 g, 2.2 mmol). The reaction mixture was stirred overnight at ambient temperature. It was then diluted with water and saturated aqueous sodium bicarbonate solution and extracted with ethyl acetate. The combined organic extract was dried over anhydrous sodium sulfate, filtered and evaporated in vacuo to an oil. The oil was dissolved in acetone (10 mL) and treated with potassium carbonate (0.227 g, 1.65 mmol) followed by methyl iodide (0.54 mL, 8.7 mmol) and the resulting reaction mixture was stirred overnight at ambient temperature. Diethyl ether was added to the reaction mixture and the precipitated solids were filtered off, the filtrate was evaporated in vacuo to a residue. Flash column chromatography over silica gel (230-400 mesh) using 4-5% ethyl acetate in hexane as the eluent afforded the title compound (0.14 g, 60%).

$^1$H NMR (300 MHz, CDCl$_3$): δ 7.50 (d, 2H, J=8.4 Hz), 7.47 (s, 1H), 7.45 (s, 1H), 7.26 (d, 2H, J=8.4 Hz), 7.13 (dd, 1H, J=10.8, 17.7 Hz), 5.47 (dd, 1H, J=1.5, 17.7 Hz), 5.11 (dd, 1H, J=1.5, 10.8 Hz), 4.04 (t, 1H, J=5.4 Hz), 3.69 (s, 3H), 3.63 (s, 2H), 2.18 (s, 3H), 2.18-2.14 (m, 1H), 2.02 (m, 1H), 1.90-1.75 (m, 2H), 1.58-1.51 (m, 1H), 1.35 (s, 3H), 1.24 (s, 3H), 0.39-0.31 (m, 3H), 0.21-0.17 (m, 1H).

{4-[5-(Cyclopropyl-methyl-amino)-8,8-dimethyl-4-vinyl-5,6,7,8-tetrahydro-naphthalen-2-ylethynyl]-phenyl}-acetic acid (Compound 23)

A solution of {4-[5-(cyclopropyl-methyl-amino)-8,8-dimethyl-4-vinyl-5,6,7,8-tetrahydro-naphthalen-2-ylethynyl]-phenyl}-acetic acid methyl ester (Intermediate 71, 0.14 g, 0.327 mmol) in methanol (3 mL) and tetrahydrofuran (3 mL) was treated with a 2M solution of lithium hydroxide (1.5 mL, 3 mmol) and the resulting reaction mixture was stirred at ambient temperature for 2 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product as a white solid (0.135 g, 96%).

$^1$H NMR (300 MHz, CDCl$_3$): δ 9.99 (br s, 1H), 7.47 (d, 2H, J=8.1 Hz), 7.44 (s, 1H), 7.43 (s, 1H), 7.22 (d, 2H, J=8.1 Hz), 7.11 (dd, 1H, J=10.8, 17.1 Hz), 5.47 (dd, 1H, J=0.9, 17.1 Hz), 5.11 (dd, 1H, J=0.9, 10.8 Hz), 4.06 (t, 1H, J=6.0 Hz), 3.55 (s, 2H), 2.18 (s, 3H), 2.18-2.15 (m, 1H), 2.04 (m, 1H), 1.91-1.77 (m, 2H), 1.56-1.50 (m, 1H), 1.34 (s, 3H), 1.22 (s, 3H), 0.42-0.29 (m, 3H), 0.28-0.21 (m, 1H).

Reaction Scheme 13

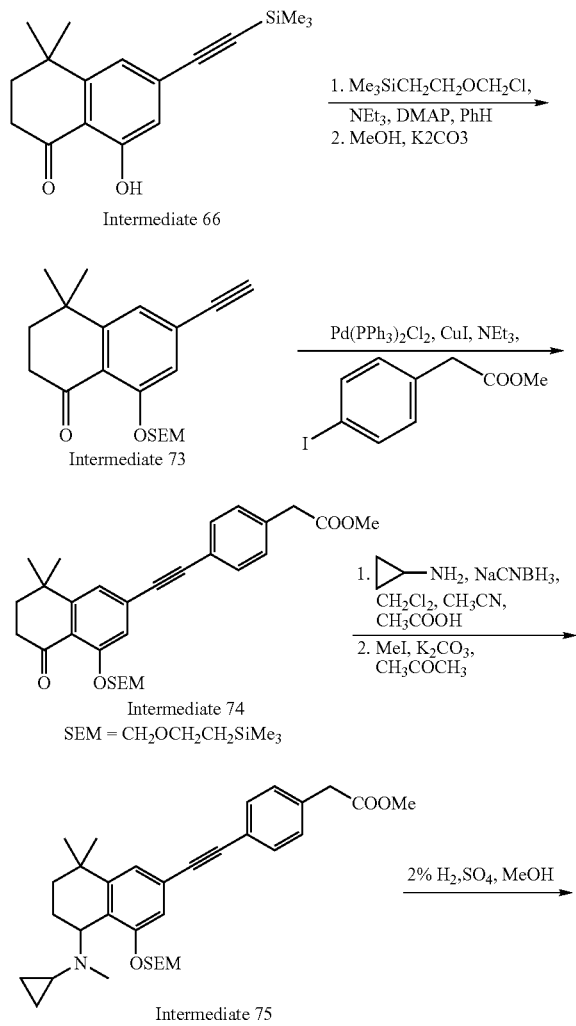

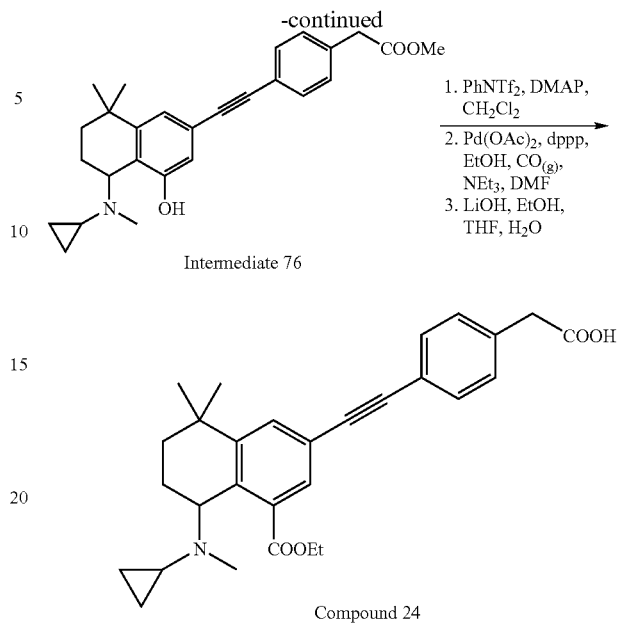

4,4-Dimethyl-8-(2-trimethylsilanyl-ethoxymethoxy)-6-trimethylsilanylethynyl-3,4-dihydro-2H-naphthalen-1-one (Intermediate 72)

A solution of 8-hydroxy-4,4-dimethyl-6-trimethylsilanylethynyl-3,4-dihydro-2H-naphthalen-1-one (Intermediate 66, 1.67 g, 5.8 mmol) in anhydrous benzene was treated with triethyl amine (1.41 g, 11.6 mmol) and catalytic amount of 4-(dimethylamino)pyridine followed by 2-(trimethylsilyl)ethoxymethyl chloride (1.93 g, 11.6 mmol) and the resulting reaction mixture was refluxed for 3 days. It was cooled to ambient temperature, diluted with water and extracted with ethyl acetate. The organic phase was washed with water and brine, dried over anhydrous magnesium sulfate, filtered and evaporated in vacuo to an oil that was subjected to flash column chromatography over silica gel (230-400 mesh) using 2-6% ethyl acetate in hexane as the eluent to afford the title product as a yellow oil (1.58 g, 66%).

$^1$H NMR (300 MHz, CDCl$_3$): δ 7.16 (d, 1H, J=1.2 Hz), 7.12 (d, 1H, J=1.2 Hz), 5.28 (s, 2H), 3.81 (m, 2H), 2.68 (t, 2H, J=6.9 Hz), 1.94 (t, 2H, J=6.9 Hz), 1.34 (s, 6H), 0.96 (m, 2H), 0.27 (s, 9H), 0.00 (s, 9H).

6-Ethynyl-4,4-dimethyl-8-(2-trimethylsilanyl-ethoxymethoxy)-3,4-dihydro-2H-naphthalen-1-one (Intermediate 73)

A solution 4,4-dimethyl-8-(2-trimethylsilanyl-ethoxymethoxy)-6-trimethylsilanylethynyl-3,4-dihydro-2H-naphthalen-1-one (Intermediate 72, 1.58 g, 3.79 mmol) in methanol (20 mL) was treated with potassium carbonate (0.43 g, 3.11 mmol) and the resulting reaction mixture was stirred at ambient temperature overnight. The solvent was evaporated in vacuo, the residue was diluted with water and extracted with ethyl acetate. The organic phase was washed with brine, dried over anhydrous magnesium sulfate, filtered and evaporated in vacuo to afford the title compound (1.28 g, 98%). $^1$H NMR (300 MHz, CDCl$_3$): δ 7.19 (d, 1H, J=1.2 Hz), 7.15 (d, 1H, J=1.2 Hz), 5.26 (s, 2H), 3.79 (m, 2H), 3.19 (s, 1H), 2.67 (t, 2H, J=6.6 Hz), 1.94 (t, 2H, J=6.6 Hz), 1.33 (s, 6H), 0.95 (m, 2H), −0.016 (s, 9H).

{4-[8,8-Dimethyl-5-oxo-4-(2-trimethylsilanyl-ethoxymethoxy)-5,6,7,8-tetrahydro-naphthalen-2-ylethynyl]-phenyl}-acetic acid methyl ester (Intermediate 74)

Following General Procedure B and using 6-ethynyl-4,4-dimethyl-8-(2-trimethylsilanyl-ethoxymethoxy)-3,4-dihydro-2H-naphthalen-1-one (Intermediate 73, 1.28 g, 3.7 mmol), 4-iodo phenyl acetic acid methyl ester (1.02 g, 3.7 mmol), triethyl amine (30 mL), copper(I)iodide (0.095 g, 0.5 mmol) and dichlorobis(triphenylphosphine)palladium(II) (0.35 g, 0.5 mmol) followed by flash column chromatography over silica gel (230-400 mesh) using 5-15% ethyl acetate in hexane as the eluent, the title compound was obtained as a yellow oil (1.61 g, 88%).

$^1$H NMR (300 MHz, CDCl$_3$): δ 7.51 (d, 2H, J=8.1 Hz), 7.28 (d, 2H, J=8.1 Hz), 7.24 (d, 1H, J=1.5 Hz), 7.19 (d, 1H, J=1.5 Hz), 5.31 (s, 2H), 3.82 (m, 2H), 3.70 (s, 3H), 3.65 (s, 2H), 2.69 (t, 2H, J=6.6 Hz), 1.96 (t, 2H, J=6.6 Hz), 1.37 (s, 6H), 0.97 (m, 2H), 0.00 (s, 9H).

{4-[5-(Cyclopropyl-methyl-amino)-8,8-dimethyl-4-(2-trimethylsilanyl-ethoxymethoxy)-5,6,7,8-tetrahydro-naphthalen-2-ylethynyl]-phenyl}-acetic acid methyl ester (Intermediate 75)

A solution of {4-[8,8-dimethyl-5-oxo-4-(2-trimethylsilanyl-ethoxymethoxy)-5,6,7,8-tetrahydro-naphthalen-2-ylethynyl]-phenyl}-acetic acid methyl ester (Intermediate 74, 0.905 g, 1.84 mmol) in dichloromethane (8 mL) and acetonitrile (4 mL) was treated with cyclopropyl amine (4 mL, 57.8 mmol). After 5 minutes, acetic acid (4 mL) was added followed by sodium cyanoborohydride (0.46 g, 7.32 mmol). The reaction mixture was stirred overnight at ambient temperature. It was then diluted with water and saturated aqueous sodium carbonate solution and extracted with dichloromethane (×2). The combined organic extract was dried over anhydrous sodium sulfate, filtered and evaporated in vacuo to an oil. The oil was dissolved in acetone (15 mL) and treated with potassium carbonate (0.745 g, 5.4 mmol) followed by methyl iodide (1.2 mL, 19 mmol) and the resulting reaction mixture was stirred overnight at ambient temperature. The precipitated solids were filtered off, the filtrate was evaporated in vacuo to a residue. Flash column chromatography over silica gel (230-400 mesh) using 2-20% ethyl acetate in hexane as the eluent afforded the title compound (0.6 g, 63%).

$^1$H NMR (300 MHz, CDCl$_3$): δ 7.49 (d, 2H, J=8.4 Hz), 7.23 (d, 2H, J=8.4 Hz), 7.18 (d, 1H, J=1.5 Hz), 7.06 (d, 1H, J=1.5 Hz), 5.21 (s, 2H), 4.03 (m, 1H), 3.76 (m, 2H), 3.68 (s, 3H), 3.62 (s, 2H), 2.30 (s, 3H), 2.04-1.40 (m, 5H), 1.33 (s, 3H), 1.18 (s, 3H), 0.97 (m, 2H), 0.26-0.01 (m, 4H), 0.00 (s, 9H).

4-[5-(Cyclopropyl-methyl-amino)-4-hydroxy-8,8-dimethyl-5,6,7,8-tetrahydro-naphthalen-2-ylethynyl]-phenyl}-acetic acid methyl ester (Intermediate 76)

A solution of {4-[5-(cyclopropyl-methyl-amino)-8,8-dimethyl-4-(2-trimethylsilanyl-ethoxymethoxy)-5,6,7,8-tetrahydro-naphthalen-2-ylethynyl]-phenyl}-acetic acid methyl ester (Intermediate 75, 0.37 g, 0.73 mmol) in tetrahydrofuran (12 mL) was treated with 2% sulfuric acid in methanol (14 mL) and the resulting reaction mixture was stirred at ambient temperature overnight. It was neutralized with saturated sodium bicarbonate solution and extracted with ethyl acetate. The organic phase was dried over anhydrous magnesium sulfate, filtered and evaporated in vacuo to a residue that after flash column chromatography over silica gel (230-400 mesh) using 5-20% ethyl acetate in hexane as the eluent afford the title product as a white solid (0.295 g, 87%).

$^1$H NMR (300 MHz, CDCl$_3$): δ 12.26 (s, 1H), 7.45 (d, 2H, J=8.4 Hz), 7.22 (d, 2H, J=8.4 Hz), 6.96 (d, 1H, J=1.5 Hz), 6.69 (d, 1H, J=1.5 Hz), 4.31 (m, 1H), 3.67 (s, 3H), 3.61 (s, 2H), 2.23 (s, 3H), 2.23-2.17 (m, 1H), 2.05-1.97 (m, 2H), 1.71-1.65 (m, 2H), 1.28 (s, 3H), 1.24 (s, 3H), 0.80-0.45 (m, 4H).

4-[5-(Cyclopropyl-methyl-amino)-8,8-dimethyl-4-trifluoromethanesulfonyloxy-5,6,7,8-tetrahydro-naphthalen-2-ylethynyl]-phenyl}-acetic acid methyl ester (Intermediate 77)

A stirred, cooled (0° C.) solution of 4-[5-(cyclopropyl-methyl-amino)-4-hydroxy-8,8-dimethyl-5,6,7,8-tetrahydro-naphthalen-2-ylethynyl]-phenyl}-acetic acid methyl ester (Intermediate 76, 0.15 g, 0.275 mmol) in anhydrous dichloromethane was treated with 4-(dimethylamino)pyridine (0.067 g, 0.55 mmol) followed by N-phenyltrifluoromethanesulfonimide (0.147 g, 0.413 mmol). After stirring at ambient temperature overnight, the reaction mixture was subjected to flash column chromatography over silica gel (230-400 mesh) using 5-10% ethyl acetate in hexane as the eluent to afford the title compound (0.14 g, 93%).

$^1$H NMR (300 MHz, CDCl$_3$): δ 7.51 (d, 2H, J=8.4 Hz), 7.30-7.26 (m, 3H), 7.17 (d, 1H, J=1.5 Hz), 4.04 (m, 1H), 3.72 (s, 3H), 3.66 (s, 2H), 2.37 (s, 3H), 2.25-2.17 (m, 1H), 2.09-1.74 (m, 3H), 1.59-1.52 (m, 1H), 1.40 (s, 3H), 1.23 (s, 3H), 0.28-0.10 (m, 3H), 0.09-0.005 (m, 1H).

8-(Cyclopropyl-methyl-amino)-3-(4-methoxycarbonylmethyl-phenylethynyl)-5,5-dimethyl-5,6,7,8-tetrahydro-naphthalene-1-carboxylic acid ethyl ester (Intermediate 78)

Following General Procedure E and using 4-[5-(cyclopropyl-methyl-amino)-8,8-dimethyl-4-trifluoromethanesulfonyloxy-5,6,7,8-tetrahydro-naphthalen-2-ylethynyl]-phenyl}-acetic acid methyl ester (Intermediate 77, 0.14 g, 0.26 mmol), palladium acetate (0.013 g, 0.06 mmol), 1,3-bis(diphenylphosphino)propane (0.025 g, 0.061 mmol), N,N-dimethylformamide (4 mL), ethanol (1.5 mL) and triethyl amine (1.5 mL) followed by flash column chromatography over silica gel (230-400 mesh) using 7-10% ethyl acetate in hexane as the eluent, the title compound was obtained (0.09 g, 75%).

$^1$H NMR (300 MHz, CDCl$_3$): δ 7.49 (d, 1H, J=1.8 Hz), 7.47 (d, 2H, J=8.1 Hz), 7.30 (d, 1H, J=1.8 Hz), 7.25 (d, 2H, J=8.1 Hz), 4.33 (m, 1H), 4.28-4.13 (m, 2H), 3.70 (s, 3H), 3.63 (s, 2H), 2.06-1.93 (2m, 6H), 1.72-1.66 (m, 2H), 1.36 (t, 3H, J=7.2 Hz), 1.31 (s, 3H), 1.29 (s, 3H), 0.60-0.40 (m, 1H), 0.40-0.25 (m, 2H), 0.15-0.00 (m, 1H).

3-(4-Carboxymethyl-phenylethynyl)-8-(cyclopropyl-methyl-amino)-5,5-dimethyl-5,6,7,8-tetrahydro-naphthalene-1-carboxylic acid ethyl ester (Compound 24)

A solution of 8-(cyclopropyl-methyl-amino)-3-(4-methoxycarbonylmethyl-phenylethynyl)-5,5-dimethyl-5,6,7,8- tetrahydro-naphthalene-1-carboxylic acid ethyl ester (Intermediate 78, 0.09 g, 0.19 mmol) in ethanol (2 mL), tetrahydrofuran (3 mL) and water (1.5 mL) was treated with lithium hydroxide (0.11 g, 2.62 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as a white solid (0.085 g, 94%).

$^1$H NMR (300 MHz, CDCl$_3$): δ 7.49 (d, 1H, J=1.8 Hz), 7.46 (d, 2H, J=8.1 Hz), 7.30 (d, 1H, J=1.8 Hz), 7.22 (d, 2H, J=8.1 Hz), 4.32 (m, 1H), 4.30-4.10 (m, 2H), 3.58 (s, 2H), 2.06-1.93 (2m, 6H), 1.72-1.65 (m, 2H), 1.35 (t, 3H, J=7.0 Hz), 1.34 (s, 3H), 1.29 (s, 3H), 0.60-0.40 (m, 1H), 0.40-0.25 (m, 2H), 0.15-0.00 (m, 1H).

Reaction Scheme 14

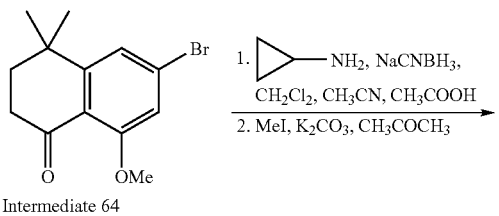

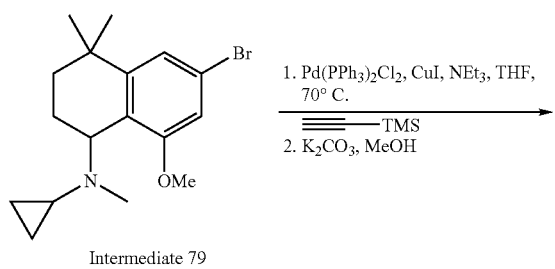

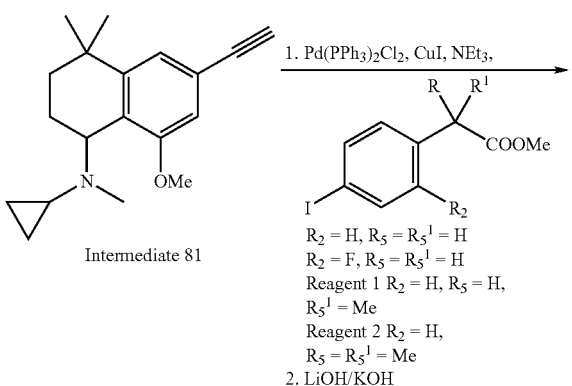

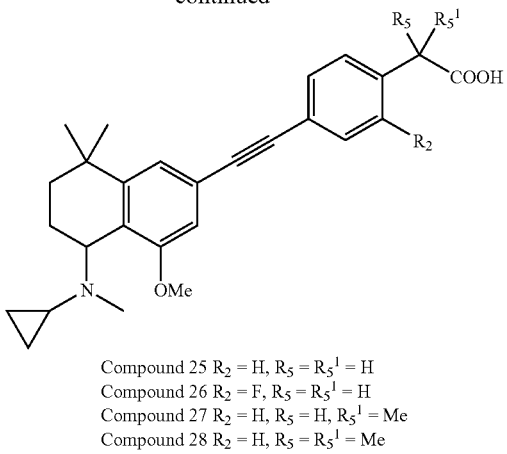

Compound 25 R$_2$ = H, R$_5$ = R$_5^1$ = H
Compound 26 R$_2$ = F, R$_5$ = R$_5^1$ = H
Compound 27 R$_2$ = H, R$_5$ = H, R$_5^1$ = Me
Compound 28 R$_2$ = H, R$_5$ = R$_5^1$ = Me 2-Bromo-5-(cyclopropyl-methyl-amino)-8,8-dimethyl-4-methoxy-5,6,7,8-tetrahydro-naphthalene (Intermediate 79)

A solution of 6-bromo-8-methoxy-4,4-dimethyl-3,4-dihydro-2H-naphthalen-1-one (Intermediate 64, 1.08 g, 3.81 mmol) in dichloromethane (8 mL) and acetonitrile (4 mL) was treated with cyclopropyl amine (5 mL, 72.3 mmol). After 5 minutes, acetic acid (5 mL) was added followed by sodium cyanoborohydride (0.96 g, 15.26 mmol). The reaction mixture was stirred for 2 days at ambient temperature. It was then diluted with water and saturated aqueous sodium carbonate solution and extracted with ethyl acetate. The combined organic extract was dried over anhydrous sodium sulfate, filtered and evaporated in vacuo to an oil. The oil was dissolved in acetone (20 mL) and treated with potassium carbonate (1.58 g, 11.43 mmol) followed by methyl iodide (2.1 mL, 33 mmol) and the resulting reaction mixture was stirred overnight at ambient temperature. Diethyl ether was added and the precipitated solids were filtered off, the filtrate was evaporated in vacuo to a residue. Flash column chromatography over silica gel (230-400 mesh) using 2.5-10% ethyl acetate in hexane as the eluent afforded the title compound (1.08 g, 84%).

$^1$H NMR (300 MHz, CDCl$_3$): δ 7.08 (d, 1H, J=1.8 Hz), 6.78 (d, 1H, J=1.8 Hz), 3.97 (m, 1H), 3.79 (s, 3H), 2.30 (s, 3H), 2.04-1.82 (m, 3H), 1.65-1.27 (m, 2H), 1.30 (s, 3H), 1.16 (s, 3H), 0.30-0.22 (m, 2H), 0.07-0.00 (m, 2H).

5-(Cyclopropyl-methyl-amino)-8,8-dimethyl-4-methoxy-2-trimethylsilanylethynyl-5,6,7,8-tetrahydro-naphthalene (Intermediate 80)

Following General Procedure D and using 2-bromo-5-(cyclopropyl-methyl-amino)-8,8-dimethyl-4-methoxy-5,6,7,8-tetrahydro-naphthalene (Intermediate 79, 1.08 g, 3.2 mmol), triethyl amine (5 mL), copper(I)iodide (0.061 g, 0.32 mmol), trimethylsilyl acetylene (3 mL, 21.1 mmol) and dichlorobis (triphenylphosphine)palladium(II) (0.225 g, 0.32 mmol) followed by flash column chromatography over silica gel (230-400 mesh) using hexane-10% ethyl acetate in hexane as the eluent, the title compound (0.87 g, 80%) was obtained.

$^1$H NMR (300 MHz, CDCl$_3$): δ 7.09 (d, 1H, J=1.5 Hz), 6.73 (d, 1H, J=1.5 Hz), 3.99 (m, 1H), 3.79 (s, 3H), 2.28 (s,

3H), 2.02-1.80 (m, 3H), 1.65-1.26 (2m, 2H), 1.31 (s, 3H), 1.16 (s, 3H), 0.26 (s, 9H), 0.26-0.00 (m, 2H), 0.00- -0.01(m, 2H).

5-(Cyclopropyl-methyl-amino)-2-ethynyl-8,8-dimethyl-4-methoxy-5,6,7,8-tetrahydro-naphthalene (Intermediate 81)

A solution of 5-(cyclopropyl-methyl-amino)-8,8-dimethyl-4-methoxy-2-trimethylsilanylethynyl-5,6,7,8-tetrahydro-naphthalene (Intermediate 80, 0.87 g, 2.45 mmol) in methanol (20 mL) was treated with potassium carbonate (0.4 g, 2.89 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to afford the title compound (0.635 g, 92%).

$^1$H NMR (300 MHz, CDCl$_3$): δ 7.16 (d, 1H, J=1.4 Hz), 6.79 (d, 1H, J=1.4 Hz), 4.04 (m, 1H), 3.82 (s, 3H), 2.32 (s, 3H), 2.03-1.95 (m, 2H), 1.90-1.80 (m, 1H), 1.70-1.55 (m, 1H), 1.45-1.35 (m, 1H), 1.34 (s, 3H), 1.19 (s, 3H), 0.40-0.20 (m, 2H), 0.07-0.00 (m, 2H).

{4-[5-(Cyclopropyl-methyl-amino)-4-methoxy-8,8-dimethyl-5,6,7,8-tetrahydro-naphthalen-2-ylethynyl]-phenyl}-acetic acid methyl ester (Intermediate 82)

Following General Procedure B and using 5-(cyclopropyl-methyl-amino)-2-ethynyl-8,8-dimethyl-4-methoxy-5,6,7,8-tetrahydro-naphthalene (Intermediate 81, 0.065 g, 0.23 mmol), methyl-4-iodophenylacetate (0.063 g, 0.23 mmol), triethyl amine (8 mL), copper(I)iodide (0.018 g, 0.093 mmol) and dichlorobis(triphenylphosphine)palladium(II) (0.065 g, 0.093 mmol) followed by flash column chromatography over silica gel (230-400 mesh) using 5-20% ethyl acetate in hexane as the eluent, the title compound was obtained as a yellow solid (0.09 g, 90%).

$^1$H NMR (300 MHz, CDCl$_3$): 7.50(d, J=8.2 Hz, 2H), 7.26 (d, J=8.2 Hz, 2H), 7.17(d, J=1.2 Hz, 1H), 6.81(d, J=1.2 Hz, 1H), 4.04(bs, 1H), 3.82(s, 3H), 3.70(s, 3H), 3.64(s, 2H), 2.32(s, 3H), 2.05-1.94 (m, 2H), 1.90-1.80(m 1H), 1.70-1.58 (m, 1H), 1.45-1.35(m, 1H), 1.38(s, 3H), 1.20(s, 3H), 0.38-0.20(m, 2H), 0.18-0.02(m, 2H).

{4-[5-(Cyclopropyl-methyl-amino)-4-methoxy-8,8-dimethyl-5,6,7,8-tetrahydro-naphthalen-2-ylethynyl]-phenyl}-acetic acid (Compound 25)

A solution of {4-[5-(cyclopropyl-methyl-amino)-4-methoxy-8,8-dimethyl-5,6,7,8-tetrahydro-naphthalen-2-ylethynyl]-phenyl}-acetic acid methyl ester (Intermediate 82, 0.090 g, 0.208 mmol) in methanol (3 mL) and tetrahydrofuran (2 mL) was treated with a 1.9 M solution of lithium hydroxide (1.5 mL, 2.8 mmol) and the resulting reaction mixture was stirred at ambient temperature for 2 h. The reaction mixture was concentrated, neutralized with ammonium chloride and extracted with ethyl acetate. The organic phase was washed with water and brine, and dried over anhydrous magnesium sulfate, filtered and evaporated in vacuo to a residue that was subjected to flash column chromatography over silica gel (230-400 mesh) using 5-10% methanol in ethyl acetate as the eluent to afford the title product as a white amorphous solid (0.062 g, 60%).

$^1$H NMR (300 MHz, CDCl$_3$): 7.46(d, J=8.2 Hz, 2H), 7.28 (d, J=8.2 Hz, 2H), 7.18(d, J=1.2 Hz, 1H), 6.81(d, J=1.2 Hz, 1H), 4.27(bs, 1H), 3.81(s, 3H), 3.58(s, 2H), 2.42(s, 3H), 2.28-2.18 (m, 1H), 2.15-1.88(m 2H), 1.75-1.65(m, 1H), 1.45-1.38(m, 1H), 1.32 (s, 3H), 1.17(s, 3H), 0.75-0.65(m, 1H), 0.55-0.42(m, 2H), 0.25-0.15(m, 1H).

{4-[5-(Cyclopropyl-methyl-amino)-4-methoxy-8,8-dimethyl-5,6,7,8-tetrahydro-naphthalen-2-ylethynyl]-2-fluoro-phenyl}-acetic acid methyl ester (Intermediate 83)

Following General Procedure B and using 5-(cyclopropyl-methyl-amino)-2-ethynyl-8,8-dimethyl-4-methoxy-5,6,7,8-tetrahydro-naphthalene (Intermediate 81, 0.085 g, 0.3 mmol), methyl-2-fluoro-4-iodophenylacetate (0.088 g, 0.3 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 5-20% ethyl acetate in hexane as the eluent, the title compound was obtained as a yellow solid (0.12 g, 89%).

$^1$H NMR (300 MHz, CDCl$_3$): 7.36-7.17(m, 4H), 6.81(d, J=1.2 Hz, 1H), 4.12(bs, 1H), 3.83(s, 3H), 3.72(s, 3H), 3.69(s, 2H), 2.33(s, 3H), 2.08-1.98(m 2H), 1.98-1.88(m, 1H), 1.75-1.60(m, 1H), 1.45-1.35(m, 1H), 1.35(s, 3H), 1.19(s, 3H), 0.35-0.25(m, 2H), 0.15-0.05(m, 1H).

{4-[5-(Cyclopropyl-methyl-amino)-4-methoxy-8,8-dimethyl-5,6,7,8-tetrahydro-naphthalen-2-ylethynyl]-2-fluoro-phenyl}-acetic acid (Compound 26)

A solution of {4-[5-(cyclopropyl-methyl-amino)-4-methoxy-8,8-dimethyl-5,6,7,8-tetrahydro-naphthalen-2-ylethynyl]-2-fluoro-phenyl}-acetic acid methyl ester (Intermediate 83, 0.12 g, 0.27 mmol) in methanol (4 mL) and tetrahydrofuran (4 mL) was treated with a 2 M solution of lithium hydroxide (2 mL, 4 mmol) and the resulting reaction mixture was stirred at ambient temperature for 2 h. The reaction mixture was concentrated, neutralized with ammonium chloride and extracted with ethyl acetate. The organic phase was washed with water and brine, and dried over anhydrous magnesium sulfate, filtered and evaporated in vacuo to a residue that was subjected to flash column chromatography over silica gel (230-400 mesh) using 5-8% methanol in ethyl acetate as the eluent to afford the title product as a white amorphous solid (0.041 g, 35%).

$^1$H NMR (300 MHz, CDCl$_3$): 7.35-7.15(m, 4H), 6.81(d, J=1.2 Hz, 1H), 4.31(bs, 1H), 3.82(s, 3H), 3.64 (s, 2H), 2.46(s, 3H), 2.32-2.22 (m, 1H), 2.18-1.88(m 2H), 1.78-1.65(m, 1H), 1.50-1.40(m, 1H), 1.32 (s, 3H), 1.17(s, 3H), 0.80-0.70(m, 1H), 0.58-0.40(m, 2H), 0.28-0.18(m, 1H).

2-{4-[5-(Cyclopropyl-methyl-amino)-4-methoxy-8,8-dimethyl-5,6,7,8-tetrahydro-naphthalen-2-ylethynyl]-phenyl}-propionic acid methyl ester (Intermediate 84)

Following General Procedure B and using 5-(cyclopropyl-methyl-amino)-2-ethynyl-8,8-dimethyl-4-methoxy-5,6,7,8-tetrahydro-naphthalene (Intermediate 81, 0.085 g, 0.30 mmol), methyl-2-(4-iodophenyl)propionate (Reagent 1, 0.087 g, 0.3 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 5-20% ethyl acetate in hexane as the eluent, the title compound was obtained as a yellow solid (0.115 g, 86%).

$^1$H NMR (300 MHz, CDCl$_3$): δ 7.50 (d, 2H, J=8.1 Hz), 7.28 (d, 2H, J=8.1 Hz), 7.16 (d, 1H, J=1.2 Hz), 6.81 (d, 1H, J=1.2 Hz), 4.04 (m, 1H), 3.83 (s, 3H), 3.74 (q, 1H, J=6.9 Hz), 3.67 (s, 3H), 2.31 (s, 3H), 2.03-1.98 (m, 2H), 1.89-1.83 (m, 1H), 1.68-1.59 (m, 1H), 1.51 (d, 3H, J=6.9 Hz), 1.42-1.27 (m, 1H), 1.35 (s, 3H), 1.20 (s, 3H), 0.31-0.23 (m, 2H), 0.07-0.008 (m, 2H).

2-{4-[5-(Cyclopropyl-methyl-amino)-4-methoxy-8,8-dimethyl-5,6,7,8-tetrahydro-naphthalen-2-ylethynyl]-phenyl}-propionic acid (Compound 27)

A solution of 2-{4-[5-(cyclopropyl-methyl-amino)-4-methoxy-8,8-dimethyl-5,6,7,8-tetrahydro-naphthalen-2-ylethynyl]-phenyl}-propionic acid methyl ester (Intermediate 84, 0.115 g, 0.26 mmol) in methanol (3 mL) and tetrahydrofuran (2 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was subjected to flash column chromatography over silica gel (230-400 mesh) using 8% methanol in ethyl acetate as the eluent to afford the title product as a yellow solid (0.062 g, 56%).

$^1$H NMR (300 MHz, CDCl$_3$): δ 7.50 (d, 2H, J=8.1 Hz), 7.32 (d, 2H, J=8.1 Hz), 7.17 (s, 1H), 6.80 (s, 1H), 4.23 (m, 1H), 3.80 (s, 3H), 3.68 (q, 1H, J=7.2 Hz), 2.38 (s, 3H), 2.22-2.18 (m, 1H), 2.07-1.87 (m, 2H), 1.70-1.57 (m, 1H), 1.47 (d, 3H, J=7.2 Hz), 1.38-1.27 (m, 1H), 1.31 (s, 3H), 1.16 (s, 3H), 0.65-0.62 (m, 1H), 0.41-0.35 (m, 2H), 0.17-0.00 (m, 1H).

2-{4-[5-(Cyclopropyl-methyl-amino)-4-methoxy-8,8-dimethyl-5,6,7,8-tetrahydro-naphthalen-2-ylethynyl]-phenyl}-2-methyl-propionic acid methyl ester (Intermediate 85)

Following General Procedure B and using 5-(cyclopropyl-methyl-amino)-2-ethynyl-8,8-dimethyl-4-methoxy-5,6,7,8-tetrahydro-naphthalene (Intermediate 81, 0.090 g, 0.32 mmol), methyl-2-(4-iodophenyl)-2-methyl-propionate (Reagent 2, 0.097 g, 0.3 mmol), triethyl amine (8 mL), copper(I) iodide (0.019 g, 0.1 mmol) and dichlorobis(triphenylphosphine)palladium(II) (0.07 g, 0.1 mmol) followed by flash column chromatography over silica gel (230-400 mesh) using 5-20% ethyl acetate in hexane as the eluent, the title compound was obtained as a solid (0.09 g, 78%).

$^1$H NMR (300 MHz, CDCl$_3$): δ 7.50 (d, 2H, J=8.1 Hz), 7.31 (d, 2H, J=8.1 Hz), 7.16 (d, 1H, J=1.2 Hz), 6.80 (d, 1H, J=1.2 Hz), 4.03 (m, 1H), 3.83 (s, 3H), 3.66 (s, 3H), 2.31 (s, 3H), 2.01-1.97 (m, 2H), 1.89-1.83 (m, 1H), 1.68-1.59 (m, 1H), 1.59 (s, 6H), 1.42-1.27 (m, 1H), 1.34 (s, 3H), 1.20 (s, 3H), 0.31-0.22 (m, 2H), 0.07-0.00 (m, 2H).

2-{4-[5-(Cyclopropyl-methyl-amino)-4-methoxy-8,8-dimethyl-5,6,7,8-tetrahydro-naphthalen-2-ylethynyl]-phenyl}-2-methyl-propionic acid (Compound 28)

A solution of 2-{4-[5-(cyclopropyl-methyl-amino)-4-methoxy-8,8-dimethyl-5,6,7,8-tetrahydro-naphthalen-2-ylethynyl]-phenyl}-2-methyl-propionic acid methyl ester (Intermediate 85, 0.09 g, 0.196 mmol) in methanol (3 mL) and tetrahydrofuran (2 mL) was treated with a 3M solution of potassium hydroxide (1.5 mL, 4.5 mmol) and the resulting reaction mixture was stirred at ambient temperature for 3 days. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230-400 mesh) using 5% methanol in ethyl acetate as the eluent to afford the title product as a yellow solid (0.057 g, 65%).

$^1$H NMR (300 MHz, CDCl$_3$): δ 7.46 (d, 2H, J=8.4 Hz), 7.37 (d, 2H, J=8.4 Hz), 7.18 (d, 1H, J=1.2 Hz), 6.81 (d, 1H, J=1.2 Hz), 4.22 (m, 1H), 3.83 (s, 3H), 2.38 (s, 3H), 2.19-1.90 (m, 3H), 1.71-1.56 (m, 1H), 1.56 (s, 6H), 1.45-1.33 (m, 1H), 1.33 (s, 3H), 1.17 (s, 3H), 0.70-0.50 (m, 1H), 0.38-0.25 (m, 2H), 0.16-0.00 (m, 1H).

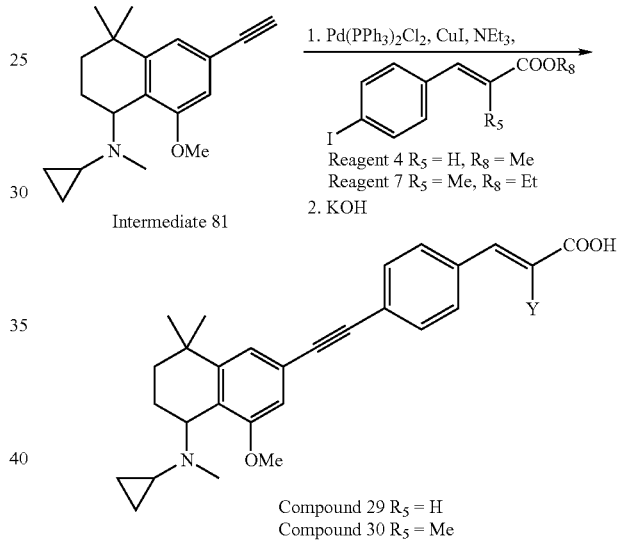

Reaction Scheme 15

Compound 29 R$_5$ = H
Compound 30 R$_5$ = Me

(E)-3-{4-[5-(Cyclopropyl-methyl-amino)-4-methoxy-8,8-dimethyl-5,6,7,8-tetrahydro-naphthalen-2-ylethynyl]-phenyl}-acrylic acid methyl ester (Intermediate 86)

Following General Procedure B and using 5-(cyclopropyl-methyl-amino)-2-ethynyl-8,8-dimethyl-4-methoxy-5,6,7,8-tetrahydro-naphthalene (Intermediate 81, 0.095 g, 0.336 mmol), methyl-4-iodocinnamate (Reagent 4, 0.097 g, 0.336 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 5-15% ethyl acetate in hexane as the eluent, the title compound was obtained as a white solid (0.12 g, 80%).

$^1$H NMR (300 MHz, CDCl$_3$): δ 7.68 (d, 1H, J=15.9 Hz), 7.53 (Abq, 4H, J=8.4 Hz), 7.19 (s, 1H), 6.83 (s, 1H), 7.46 (d, 1H, J=15.9 Hz), 4.04 (m, 1H), 3.84 (s, 3H), 3.82 (s, 3H), 2.32 (s, 3H), 2.04-1.97 (m, 2H), 1.90-1.83 (m, 1H), 1.68-1.60 (m, 1H), 1.43-1.27 (m, 1H), 1.36 (s, 3H), 1.21 (s, 3H), 0.32-0.23 (m, 2H), 0.08-0.00 (m, 2H).

(E)-3-{4-[5-(Cyclopropyl-methyl-amino)-4-methoxy-8,8-dimethyl-5,6,7,8-tetrahydro-naphthalen-2-ylethynyl]-phenyl}-acrylic acid (Compound 29)

A solution of (E)-3-{4-[5-(cyclopropyl-methyl-amino)-4-methoxy-8,8-dimethyl-5,6,7,8-tetrahydro-naphthalen-2-yl-ethynyl]-phenyl}-acrylic acid methyl ester (Intermediate 86, 0.12 g, 0.27 mmol) in methanol (4 mL) and tetrahydrofuran (3 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was subjected to flash column chromatography over silica gel (230-400 mesh) using 5% methanol in ethyl acetate as the eluent to afford the title product as a white solid (0.041 g, 35%).

$^1$H NMR (300 MHz, CDCl$_3$): δ 7.58 (d, 1H, J=16.2 Hz), 7.44 (Abq, 4H), 7.13 (s, 1H), 6.77 (s, 1H), 7.45 (d, 1H, J=16.2 Hz), 4.05 (m, 1H), 3.79 (s, 3H), 2.42 (s, 3H), 2.19-1.97 (m, 2H), 1.67-1.45 (m, 1H), 1.45-1.37 (m, 1H), 1.37-1.20 (m, 1H), 1.30 (s, 3H), 1.12 (s, 3H), 0.80-0.60 (m, 1H), 0.50-0.30 (m, 2H), 0.20-0.00 (m, 1H).

(E)-3-{4-[5-(Cyclopropyl-methyl-amino)-4-methoxy-8,8-dimethyl-5,6,7,8-tetrahydro-naphthalen-2-ylethynyl]-cyclohexa-2,4-dienyl}-2-methyl-acrylic acid ethyl ester (Intermediate 87)

Following General Procedure B and using 5-(cyclopropyl-methyl-amino)-2-ethynyl-8,8-dimethyl-4-methoxy-5,6,7,8-tetrahydro-naphthalene (Intermediate 81 0.08 g, 0.28 mmol), (E)-3-(4-iodo-phenyl)-2-methyl-acrylic acid ethyl ester (Reagent 7, 0.09 g, 0.28 mmol), triethyl amine (8 mL), copper(I) iodide (0.019 g, 0.1 mmol) and dichlorobis(triphenylphosphine)palladium(II) (0.07 g, 0.11 mmol) followed by flash column chromatography over silica gel (230-400 mesh) using 5-10% ethyl acetate in hexane as the eluent, the title compound was obtained as a white solid (0.12 g, 90%).

$^1$H NMR (300 MHz, CDCl$_3$): δ 7.67 (d, 1H, J=1.2 Hz), 7.57 (d, 2H, J=8.4 Hz), 7.40 (d, 2H, J=8.4 Hz), 7.19 (d, 1H, J=1.5 Hz), 6.83 (d, 1H, J=1.5 Hz), 4.28 (q, 2H, J=7.2 Hz), 4.04 (m, 1H), 3.84 (s, 3H), 2.32 (s, 3H), 2.15 (d, 3H, J=1.2 Hz), 2.03-1.83 (m, 3H), 1.68-1.50 (m, 1H), 1.45-1.20 (m, 1H), 1.36 (s, 3H), 1.35 (t, 3H, J=7.2 Hz), 1.20 (s, 3H), 0.32-0.23 (m, 2H), 0.08-0.00 (m, 2H).

(E)-3-{4-[5-(Cyclopropyl-methyl-amino)-4-methoxy-8,8-dimethyl-5,6,7,8-tetrahydro-naphthalen-2-ylethynyl]-cyclohexa-2,4-dienyl}-2-methyl-acrylic acid (Compound 30)

A solution of (E)-3-{4-[5-(cyclopropyl-methyl-amino)-4-methoxy-8,8-dimethyl-5,6,7,8-tetrahydro-naphthalen-2-yl-ethynyl]-cyclohexa-2,4-dienyl}-2-methyl-acrylic acid methyl ester (Intermediate 87, 0.12 g, 0.25 mmol) in methanol (3 mL) and tetrahydrofuran (2 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was recrystallized from hot acetonitrile to afford the title product as a white solid (0.055 g, 49%).

$^1$H NMR (300 MHz, CDCl$_3$): δ 7.78 (d, 1H, J=1.2 Hz), 7.57 (d, 2H, J=8.1 Hz), 7.43 (d, 2H, J=8.1 Hz), 7.29 (d, 1H, J=1.5 Hz), 6.93 (d, 1H, J=1.5 Hz), 4.93 and 4.70 (2m, 1H), 3.97 (s, 3H), 2.54 (s, 3H), 2.40-1.60 (m, 4H), 2.16 (d, 3H, J=1.2 Hz), 1.46-1.23 (m, 1H), 1.46 (s, 3H), 1.23 (s, 3H), 0.90-0.20 (m, 4H).

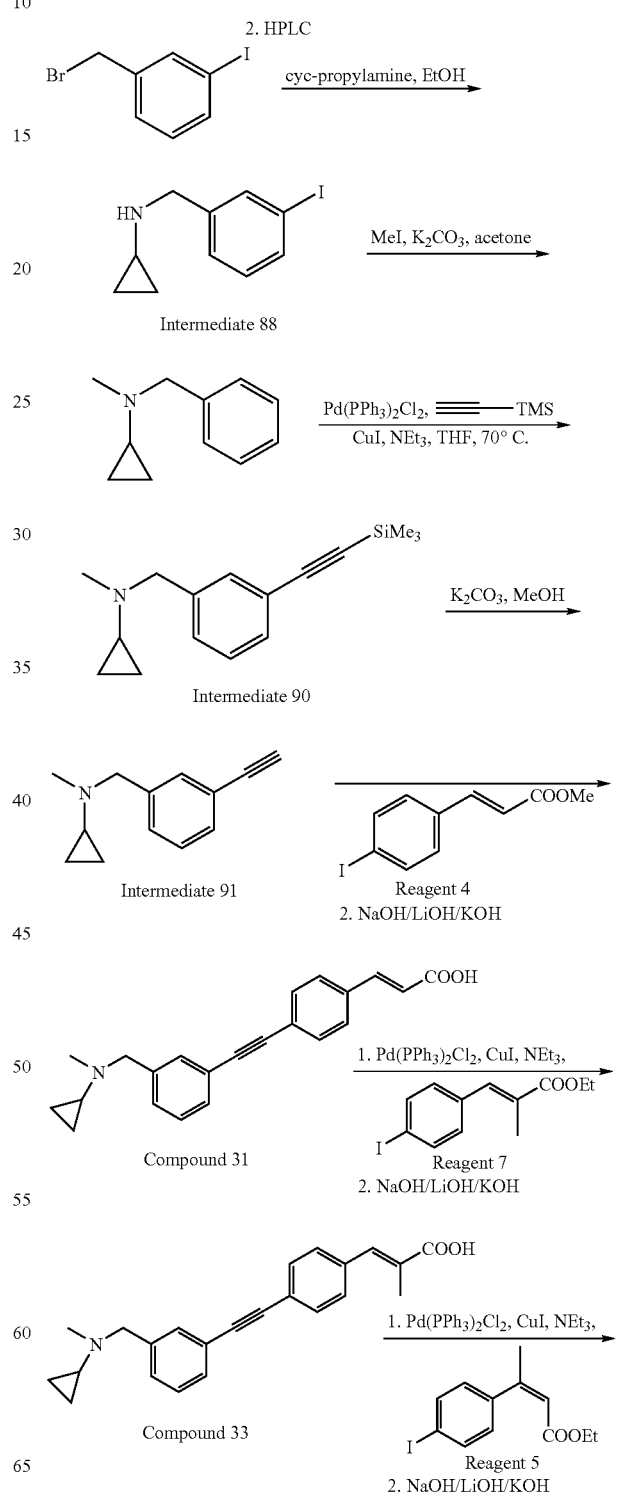

Reaction Scheme 16

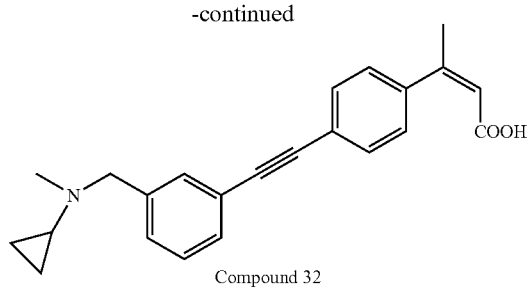

Compound 32

Cyclopropyl-(3-iodo-benzyl)-amine (Intermediate 88)

A solution of 3-iodobenzyl bromide (Aldrich, 3.2 g, 10.77 mmol) in ethanol (20 mL) was treated with cyclopropyl amine (7 mL, 101.5 mmol) and the resulting reaction mixture was stirred over 3 days at ambient temperature. The volatiles were evaporated in vacuo, the residue was diluted with ethyl acetate and washed with saturated, aqueous sodium bicarbonate solution, water and brine, dried over anhydrous sodium sulfate, filtered and evaporated in vacuo to an oil that was subjected to flash column chromatography over silica gel (230-400 mesh) using 10-20% ethyl acetate in hexane as the eluent afford the title product (2.4 g, 81%).

$^1$H NMR (300 MHz, CDCl$_3$): δ 7.67 (s, 1H), 7.58 (d, 1H, J=9.0 Hz), 7.27 (d, 1H, J=6.0 Hz), 7.05 (dd, 1H, J=6.0, 9.0 Hz), 3.78 (s, 2H), 2.13 (m, 1H), 1.76 (br s, 1H), 0.50-0.35 (m, 4H).

Cyclopropyl-(3-iodo-benzyl)-methyl-amine (Intermediate 89)

A solution of cyclopropyl-(3-iodo-benzyl)-amine (Intermediate 88, 4.1 g, 15 mmol) in acetone (20 mL) was treated with potassium carbonate (2.07 g, 15 mmol) and methyl iodide (1.4 mL, 22.5 mmol) and the resulting reaction mixture was stirred at ambient temperature for 1 h. Diethyl ether was added, the solids were filtered off and filtrate was evaporated to a residue that was subjected to flash column chromatography over silica gel (230-400 mesh) using 10% ethyl acetate in hexane as the eluent to afford the title compound (3.3 g, 77%).

$^1$H NMR (300 MHz, CDCl$_3$): δ 7.62 (d, 1H, J=1.5 Hz), 7.55 (dd, 1H, J=1.5, 7.8 Hz), 7.21 (dd, 1H, J=1.5, 7.8 Hz), 7.01 (t, 1H, J=7.8 Hz), 3.61 (s, 2H), 2.22 (s, 3H), 1.69 (m, 1H), 0.50-0.38 (m, 4H).

Cyclopropyl-methyl-(3-trimethylsilanylethynyl-benzyl)-amine (Intermediate 90)

Following General Procedure D and using cyclopropyl-(3-iodo-benzyl)-methyl-amine (Intermediate 89, 0.97 g, 3.4 mmol), triethyl amine (10 mL), copper(I)iodide (0.051 g, 0.27 mmol), trimethylsilyl acetylene (2 mL, 14 mmol) and dichlorobis(triphenylphosphine)palladium(II) (0.19 g, 0.27 mmol) followed by flash column chromatography over silica gel (230-400 mesh) using hexane-5% ethyl acetate in hexane as the eluent, the title compound (0.695 g, 80%) was obtained.

$^1$H NMR (300 MHz, CDCl$_3$): δ 7.37-7.31 (m, 2H), 7.25-7.20 (m, 2H), 3.61 (s, 2H), 2.22 (s, 3H), 1.69 (m, 1H), 0.50-0.32 (m, 4H), 0.25 (s, 9H).

Cyclopropyl-(3-ethynyl-benzyl)-methyl-amine (Intermediate 91)

A solution cyclopropyl-methyl-(3-trimethylsilanylethynyl-benzyl)-amine (Intermediate 90, 0.355 g, 1.38 mmol) in methanol (10 mL) was treated with potassium carbonate (0.13 g, 0.95 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to afford the title compound (0.22 g, 86%).

$^1$H NMR (300 MHz, CDCl$_3$): δ 7.41-7.35 (m, 2H), 7.26-7.23 (m, 2H), 3.63 (s, 2H), 3.05 (s, 1H), 2.23 (s, 3H), 1.70 (m, 1H), 0.48-0.40 (m, 4H).

(E)-3-(4-{3-[(Cyclopropyl-methyl-amino)-methyl]-phenylethynyl}-phenyl)-acrylic acid methyl ester (Intermediate 92)

Following General Procedure B and using cyclopropyl-(3-ethynyl-benzyl)-methyl-amine (Intermediate 91, 0.060 g, 0.32 mmol), methyl-4-iodo-cinnamate (Reagent 4, 0.093 g, 0.32 mmol), triethyl amine (8 mL), copper(I)iodide (0.015 g, 0.08 mmol) and dichlorobis(triphenylphosphine)palladium (II) (0.056 g, 0.08 mmol) followed by flash column chromatography over silica gel (230-400 mesh) using 5-15% ethyl acetate in hexane as the eluent, the title compound was obtained (0.11 g, 100%).

$^1$H NMR (300 MHz, CDCl$_3$): δ 7.66 (d, 2H, J=16.2 Hz), 7.54-7.39 (m, 2H), 7.31-7.25 (m, 2H), 6.43 (d, 2H, J=16.2 Hz), 3.80 (s, 3H), 3.65 (s, 2H), 2.25 (s, 3H), 1.72 (m, 1H), 0.49-0.42 (m, 4H).

(E)-3-(4-{3-[(Cyclopropyl-methyl-amino)-methyl]-phenylethynyl}-phenyl)-acrylic acid (Compound 31)

A solution of (E)-3-(4-{3-[(cyclopropyl-methyl-amino)-methyl]-phenylethynyl}-phenyl)-acrylic acid methyl ester (Intermediate 92, 0.11 g, 0.32 mmol) in methanol (3 mL) and tetrahydrofuran (2 mL) was treated with a 3M solution of potassium hydroxide (1 mL, 3 mmol) and the resulting reaction mixture was stirred at ambient temperature for 2 days. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230-400 mesh) using 10% methanol in ethyl acetate as the eluent to afford the title product as a yellow solid (0.038 g, 36%).

$^1$H NMR (300 MHz, CD$_3$OD): δ 7.61-7.38 (m, 9H), 6.53 (d, 1H, J=15.9 Hz), 3.93 (s, 2H), 2.48 (s, 3H), 2.09 (m, 1H), 0.64-0.61 (m, 4H).

3-(4-{3-[(Cyclopropyl-methyl-amino)-methyl]-phenylethynyl}-phenyl)-but-2-enoic acid ethyl ester (Intermediate 93)

Following General Procedure B and using cyclopropyl-(3-ethynyl-benzyl)-methyl-amine (Intermediate 91, 0.12 g, 0.64 mmol), 3-(4-iodo-phenyl)-but-2Z-enoic acid ethyl ester (Reagent 5, 0.2 g, 0.64 mmol), triethyl amine (8 mL), copper(I) iodide (0.012 g, 0.063 mmol) and dichlorobis(triphenylphosphine)palladium(II) (0.045 g, 0.064 mmol) followed by flash column chromatography over silica gel (230-400 mesh), the title compound was obtained (0.17 g, 70%).

¹H NMR (300 MHz, CDCl₃): δ 7.52-7.40(m, 4H), 7.31-7.18(m, 4H), 5.91(s, 1H), 4.01(q, J=7.1 Hz, 2H), 3.66(s, 2H), 2.26(s, 3H), 2.17 (s, 3H), 1.74-1.70(m, 1H), 1.10(t, J=7.1 Hz, 3H), 0.50-0.43(m, 4H).

3-(4-{3-[(Cyclopropyl-methyl-amino)-methyl]-phenylethynyl}-phenyl)-but-2-enoic acid (Compound 32)

A solution of 3-(4-{3-[(cyclopropyl-methyl-amino)-methyl]-phenylethynyl}-phenyl)-but-2-enoic acid ethyl ester (Intermediate 93, 0.17 g, 0.46 mmol) in ethanol (3 mL) and tetrahydrofuran (3 mL) was treated with a 3.4M solution of potassium hydroxide (1 mL, 3.4 mmol) and the resulting reaction mixture was stirred at ambient temperature for 36 h. The reaction mixture was extracted with diethyl ether, and the aqueous phase was neutralized with 10% aqueous hydrochloric acid and evaporated to a solid. The solid was subjected to flash column chromatography using ethyl acetate as the eluent to afford the title product as a white solid (0.05 g, 32%).
¹H NMR (300 MHz, CDCl₃): δ 7.49-7.43(m, 4H), 7.32-7.20 (m, 4H), 5.93(s, 1H), 3.70(s, 2H), 2.29(s, 3H), 2.17 (s, 3H), 1.76-1.73(m, 1H), 0.50-0.48(m, 4H).

3-(4-{3-[(Cyclopropyl-methyl-amino)-methyl]-phenylethynyl}-phenyl)-2-methyl-acrylic acid ethyl ester (Intermediate 94)

Following General Procedure B and using cyclopropyl-(3-ethynyl-benzyl)-methyl-amine (Intermediate 91, 0.1 g, 0.54 mmol), (E)-3-(4-iodo-phenyl)-2-methyl-acrylic acid ethyl ester (Reagent 7, 0.17 g, 0.54 mmol), triethyl amine (10 mL), copper(I)iodide (0.019 g, 0.1 mmol) and dichlorobis(triphenylphosphine)palladium(II) (0.071 g, 0.1 mmol) followed by flash column chromatography over silica gel (230-400 mesh) using 2-10% ethyl acetate in hexane as the eluent, the title compound was obtained (0.15 g, 75%). ¹H NMR (300 MHz, CDCl₃): δ 7.66-7.25 (m, 9H), 4.27(q, J=7.3 Hz, 2H), 3.65(s, 2H), 2.25(s, 3H), 2.13 (d, J=1.2 Hz, 3H), 1.75-1.65(m, 1H), 1.35(t, J=7.3 Hz, 3H), 0.50-0.40(m, 4H).

3-(4-{3-[(Cyclopropyl-methyl-amino)-methyl]-phenylethynyl}-phenyl)-2-methyl-acrylic acid (Compound 33)

A solution of 3-(4-{3-[(cyclopropyl-methyl-amino)-methyl]-phenylethynyl}-phenyl)-2-methyl-acrylic acid ethyl ester (Intermediate 94, 0.15 g, 0.4 mmol) in ethanol (3 mL) and tetrahydrofuran (3 mL) was treated with a 3M solution of potassium hydroxide (1 mL, 3 mmol) and the resulting reaction mixture was stirred at ambient temperature for overnight. The reaction mixture was concentrated, neutralized with 5% aqueous hydrochloric acid and extracted with ethyl acetate. The organic phase was washed with water and brine, dried over anhydrous sodium sulfate, filtered and evaporated to a solid. The solid was subjected to flash column chromatography using 5% methanol in ethyl acetate as the eluent to afford the title product as an amorphous solid (0.115 g, 83%).

¹H NMR (300 MHz, CDCl₃): 7.71-7.25 (m, 9H), 3.81(s, 2H), 2.44(s, 3H), 2.13 (d, J=1.2 Hz, 3H), 1.92-1.80(m, 1H), 0.76-0.66(m, 2H), 0.58-0.48(m, 2H).

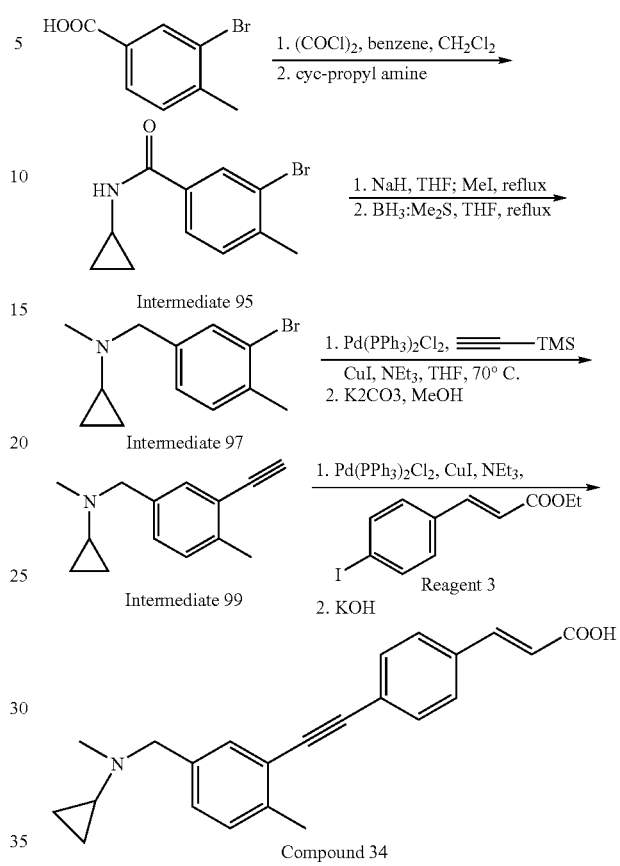

3-Bromo-N-cyclopropyl-4-methyl-benzamide (Intermediate 95)

A stirred, cooled (ice bath) solution of 3-bromo-4-methyl-benzoic acid (Aldrich, 5 g, 23.25 mmol) in benzene (50 mL), dichloromethane (10 mL) and N,N-dimethylformamide (0.5 mL) was treated with oxalyl chloride (4 mL, 46.5 mmol). The reaction mixture was allowed to warm to ambient temperature over 3 h. The volatiles were then distilled off in vacuo, the residue was diluted with anhydrous dichloromethane (50 mL) under argon, cooled (ice bath) and treated with 4-(dimethylamino)pyridine (5.67 g, 46.5 mmol) followed by cyclopropyl amine (1.93 mL, 27.9 mmol). After 3 h, the reaction mixture was diluted with dichloromethane and washed with water. The organic phase was dried over anhydrous sodium sulfate, filtered and evaporated in vacuo to afford the title product that was used as such for the next step (6.0 g, ~100%).

3-Bromo-N-cyclopropyl-4,N-dimethyl-benzamide (Intermediate 96)

A stirred, cooled (ice bath) solution of 3-bromo-N-cyclopropyl-4-methyl-benzamide (Intermediate 95, 6 g, 23.25 mmol) in anhydrous tetrahydrofuran (100 mL) under argon was treated with small portions of sodium hydride (1.6 g, 40 mmol, 60% dispersion in mineral oil). The reaction mixture was allowed to warm to ambient temperature and after 1 h, methyl iodide (3.11 mL, 50 mmol) was added and the reaction mixture was refluxed for 5 h. It was cooled to ambient temperature, poured into cold water and extracted with diethyl ether (×2). The combined organic phase was dried over anhydrous magnesium sulfate, filtered and evaporated in vacuo to afford the title product as a dirty brown solid that was used as such for the next step (6.3 g, 100%).

(3-Bromo-4-methyl-benzyl)-cyclopropyl-methyl-amine (Intermediate 97)

A solution of 3-bromo-N-cyclopropyl-4,N-dimethyl-benzamide (Intermediate 96, 5.3 g, 19.77 mmol) in anhydrous tetrahydrofuran (50 mL) was treated with borane-methyl sulfide complex (10 mL, 100 mmol) and the resulting reaction mixture was refluxed for 2 h. It was cooled to ambient temperature and carefully treated with saturated, aqueous sodium carbonate solution till cessation of effervescence, and extracted with diethyl ether (×2). The combined organic phase was dried over anhydrous magnesium sulfate, filtered and evaporated in vacuo to an oil. Flash column chromatography over silica gel (230-400 mesh) using 10% ethyl acetate in hexane as the eluent afforded the title product as an oil (3.2 g, 63%).

$^1$H NMR (300 MHz, CDCl$_3$): δ 7.47 (s, 1H), 7.17 (d, 1H, J=7.8 Hz), 7.12 (d, 1H, J=7.8 Hz), 3.63 (s, 2H), 2.40 (s, 3H), 2.27 (s, 3H), 1.73 (m, 1H), 0.92-0.43 (m, 4H).

Cyclopropyl-methyl-(4-methyl-3-trimethylsilanyl-ethynyl-benzyl)-amine (Intermediate 98)

Following General Procedure D and using cyclopropyl-(3-bromo-4-methyl-benzyl)-methyl-amine (Intermediate 97, 2.24 g, 8.81 mmol), triethyl amine (10 mL), tetrahydrofuran (5 mL), copper(I)iodide (0.4 g, 2.1 mmol), trimethylsilyl acetylene (5 mL, 35.4 mmol) and dichlorobis(triphenylphosphine)palladium(II) (1.45 g, 2.06 mmol) followed by flash column chromatography over silica gel (230-400 mesh) using 6-10% ethyl acetate in hexane as the eluent, the title compound (2.25 g, 94%) was obtained.

$^1$H NMR (300 MHz, CDCl$_3$): δ 7.08 (s, 1H), 6.84 (2s, 2H), 3.31 (s, 2H), 2.15 (s, 3H), 1.95 (s, 3H), 1.41 (m, 1H), 0.25-0.00 (m, 4H), 0.00 (s, 9H).

Cyclopropyl-(3-ethynyl-4-methyl-benzyl)-methyl-amine (Intermediate 99)

A solution of cyclopropyl-methyl-(4-methyl-3-trimethyl-silanylethynyl-benzyl)-amine (Intermediate 98, 0.95 g, 3.5 mmol) in methanol (10 mL) was treated with potassium carbonate (2.3 g, 16.6 mmol) and the resulting reaction mixture was stirred at ambient temperature for 1 h. The solvent was evaporated in vacuo, the residue was diluted with water and extracted with diethyl ether. The organic phase was washed with brine, dried over anhydrous magnesium sulfate, filtered and evaporated in vacuo to afford the title compound (0.67 g, 96%).

$^1$H NMR (300 MHz, CDCl$_3$): δ 7.12 (s, 1H), 6.87 (2s, 2H), 3.33 (s, 2H), 2.98 (s, 1H), 2.16 (s, 3H), 1.96 (s, 3H), 1.42 (m, 1H), 0.24-0.00 (m, 4H).

(E)-3-(4-{5-[(Cyclopropyl-methyl-amino)-methyl]-2-methyl-phenylethynyl}-phenyl)-acrylic acid ethyl ester (Intermediate 100)

Following General Procedure B and using cyclopropyl-(3-ethynyl-4-methyl-benzyl)-methyl-amine (Intermediate 99, 0.095 g, 0.48 mmol), ethyl-4-iodo-cinnamate (Reagent 3, 0.144 g, 0.47 mmol), triethyl amine (13 mL), copper(I)iodide (0.019 g, 0.1 mmol) and dichlorobis(triphenylphosphine)palladium(II) (0.071 g, 0.1 mmol) followed by flash column chromatography over silica gel (230-400 mesh) using 5-20% ethyl acetate in hexane as the eluent, the title compound was obtained (0.14 g, 82%).

$^1$H NMR (300 MHz, CDCl$_3$): δ 7.66 (d, 1H, J=15.9 Hz), 7.53 (Abq, 4H, J=6.3 Hz), 7.41 (s, 1H), 7.15 (2s, 2H), 6.44 (d, 1H, J=15.9 Hz), 4.26 (q, 2H, J=7.2 Hz), 3.62 (s, 2H), 2.48 (s, 3H), 2.24 (s, 3H), 1.68 (m, 1H), 1.33 (t, 3H, J=7.2 Hz), 0.49-0.41 (m, 4H).

(E)-3-(4-{5-[(Cyclopropyl-methyl-amino)-methyl]-2-methyl-phenylethynyl}-phenyl)-acrylic acid (Compound 34)

A solution of (E)-3-(4-{5-[(cyclopropyl-methyl-amino)-methyl]-2-methyl-phenylethynyl}-phenyl)-acrylic acid ethyl ester (Intermediate 100, 0.14 g, 0.37 mmol) in ethanol (3 mL) and tetrahydrofuran (3 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230-400 mesh) using 5% methanol in ethyl acetate as the eluent to afford the title product as an amorphous solid (0.071 g, 55%).

$^1$H NMR (300 MHz, CDCl$_3$): δ 7.62 (d, 1H, J=15.9 Hz), 7.61 (s, 1H), 7.38 (s, 4H), 7.19 (s, 2H), 6.56 (d, 1H, J=15.9 Hz), 3.87 (s, 2H), 2.50 (s, 3H), 2.49 (s, 3H), 1.94 (m, 1H), 0.89-0.83 (m, 2H), 0.60-0.57 (m, 2H).

Reaction Scheme 18

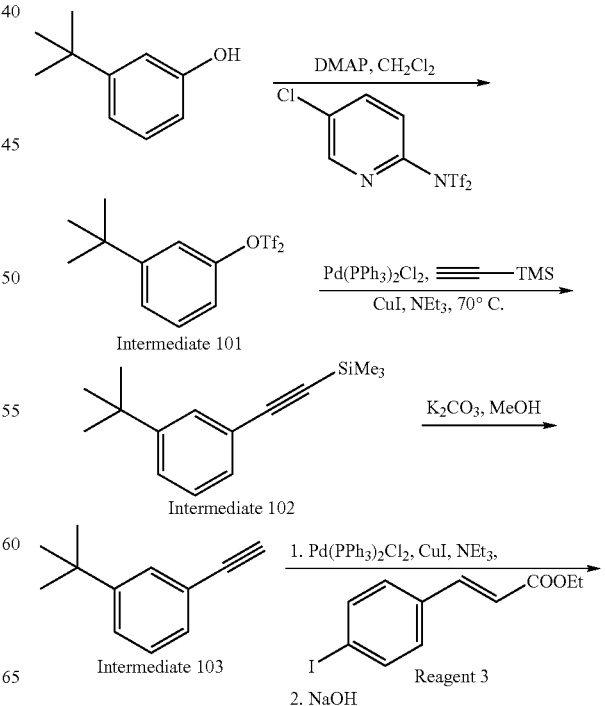

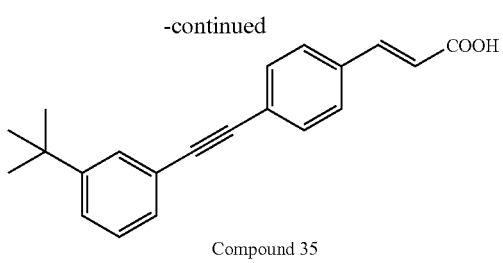

Compound 35

Trifluoro-methanesulfonic acid 3-tert-butyl-phenyl ester (Intermediate 101)

A stirred, cooled (ice bath) solution of 3-tert-butyl phenol (Aldrich, 2 g, 13.3 mmol) in anhydrous dichloromethane (15 mL) was treated with 2-[N,N'-bis(trifluoromethylsulfonyl)amino]-5-chloropyridine (7.8 g, 20 mmol) followed by 4-(dimethylamino)pyridine (3.2 g, 26.6 mmol). The cooling bath was removed and the reaction mixture was stirred at ambient temperature for 18 h. It was diluted with ethyl acetate, washed with 2N hydrochloric acid, 2N sodium hydroxide, and brine, dried over anhydrous magnesium sulfate, filtered and evaporated in vacuo to an oil. Flash column chromatography over silica gel (230-400 mesh) using 10% ethyl acetate in hexane as the eluent afforded the title product as a clear oil (3.06 g, 82%). $^1$H NMR (300 MHz, CDCl$_3$): δ 7.42-7.32 (m, 2H), 7.24 (d, 1H, J=1.8 Hz), 7.10-7.06 (m, 1H), 1.33 (s, 9H).

(3-tert-Butyl-phenylethynyl)-trimethyl-silane (Intermediate 102)

Following General Procedure D and using trifluoromethanesulfonic acid, 3-tert-butyl-phenyl ester (Intermediate 101, 2.54 g, 9.0 mmol), triethyl amine (2 mL), copper(I) iodide (0.63 g, 3.33 mmol), trimethylsilyl acetylene (5 mL, 36 mmol) and dichlorobis(triphenylphosphine)palladium(II) (1.6 g, 2.25 mmol) followed by flash column chromatography over silica gel (230-400 mesh) using 10% ethyl acetate in hexane as the eluent, the title compound was obtained as a brown oil that was used as such for the next step.

1-tert-Butyl-3-ethynyl-benzene (Intermediate 103)

A solution 3-tert-butyl-trimethylsilanylethynyl benzene (Intermediate 102, 0.47 g, 2.04 mmol) in methanol (20 mL) was treated with potassium carbonate (2.8 g, 20.2 mmol) and the resulting reaction mixture was stirred at ambient temperature for 3 days. The reaction mixture was diluted with ethyl acetate, washed with water and brine, dried over anhydrous magnesium sulfate, filtered and evaporated in vacuo to an oil. Flash column chromatography over silica gel (230-400 mesh) using 10% ethyl acetate in hexane as the eluent afforded the title compound as a light yellow oil (0.125 g, 39%).

$^1$H NMR (300 MHz, CDCl$_3$): δ 7.40 (d, 1H, J=1.5 Hz), 7.39-7.10 (m, 3H), 2.91 (s, 1H), 1.18 (s, 9H).

(E)-3-[4-(3-tert-Butyl-phenylethynyl)-phenyl]-acrylic acid (Compound 35)

A solution of (E)-3-[4-(3-tert-Butyl-phenylethynyl)-phenyl]-acrylic acid ethyl ester (Intermediate 103, 0.015 g, 0.047 mmol) in ethanol (2 mL) and tetrahydrofuran (2 mL) was treated with a 2M solution of lithium hydroxide (1 mL, 2 mmol) and the resulting reaction mixture was stirred at ambient temperature overnight. The reaction mixture was neutralized with 10% aqueous hydrochloric acid and evaporated in vacuo to a solid that was washed with water and hexane and dried to afford the title product as a white solid (0.012 g, 85%). $^1$H NMR (300 MHz, CDCl$_3$): δ 7.78 (d, 1H, J=16.2 Hz), 7.59-7.26 (m, 8H), 6.47 (d, 1H, J=16.2 Hz), 1.34 (s, 9H).

Reaction Scheme 19

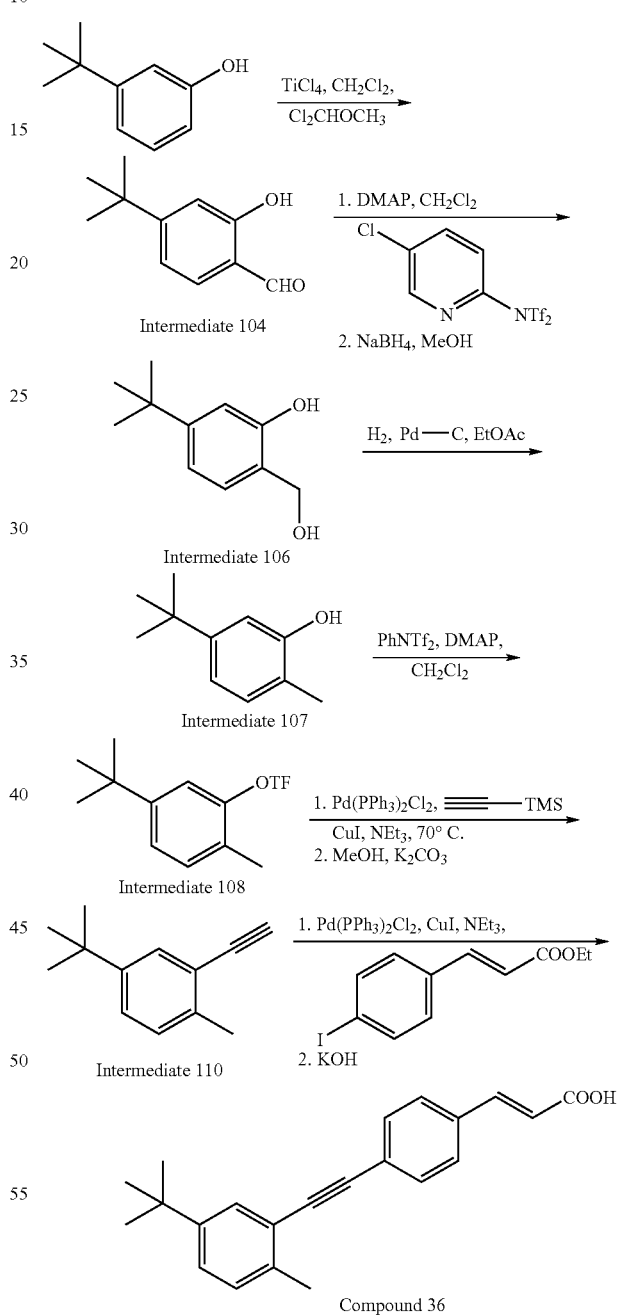

Compound 36

4-tert-Butyl-2-hydroxy-benzaldehyde (Intermediate 104)

A stirred, cooled (ice bath) solution of 3-tert-butyl phenol (1.5 g, 10 mmol) in anhydrous dichloromethane was treated with titanium tetrachloride (1.86 mL, 17 mmol) followed by . . . ,-dichloromethyl ether (0.9 mL, 20 mmol). The reaction was allowed to warm to ambient temperature over 1 h, quenched cautiously with ice and water and extracted with dichloromethane. The organic extract was washed with water and brine, dried over sodium sulfate, filtered and evaporated in vacuo to a residue that was subjected to flash column chromatography using 2-2.5% ethyl acetate in hexane as the eluent to afford the title compound (1.37 g, 77%). $^1$H NMR (300 MHz, CDCl$_3$): δ 11.02(s, 1H), 9.81(s, 1H), 7.45(d, J=8.2 Hz, 1H), 7.03(dd, J=8.2, 1.7 Hz, 1H), 6.99(d, J=1.7 Hz, 1H), 1.31(s, 9H).

Trifluoro-methanesulfonic acid
5-tert-butyl-2-formyl-phenyl ester (Intermediate 105)

A stirred, cooled (ice-bath) solution of 4-tert-butyl-2-hydroxy-benzaldehyde (Intermediate 104, 0.75 g, 4.21 mmol) in anhydrous dichloromethane (10 mL) was treated with triethyl amine (1.76 mL, 12.64 mmol) followed by 2-[N,N-bis (trifluoromethylsulfonyl)amino]pyridine (1.81 g, 4.62 mmol). The reaction mixture was allowed to warm to ambient temperature overnight. The volatiles were evaporated and the residue was subjected to flash column chromatography using 2-2.5% ethyl acetate in hexane as the eluent to afford the title compound (0.16 g) and a 1:1 mixture of product and starting material (0.47 g). The title compound was used as such for the next step.

5-tert-Butyl-2-hydroxymethyl-phenol
(Intermediate 106)

A stirred, cooled (ice-bath) solution of a 1:1 mixture of trifluoro-methanesulfonic acid 5-tert-butyl-2-formyl-phenyl ester and 4-tert-butyl-2-hydroxy-benzaldehyde (Intermediate 105, 0.47 g) in methanol (8 mL) was treated with sodium borohydride (0.1 g, 2.64 mmol). After 1 h, the reaction mixture was diluted with water and extracted with ethyl acetate. The organic phase was washed with water and brine, dried over anhydrous sodium sulfate, filtered and evaporated in vacuo to a residue that was subjected to flash column chromatography on silica gel (230-400 mesh) to afford the title product (0.3 g).
$^1$H NMR (300 MHz, CDCl$_3$): δ 6.94-6.84(m, 3H), 4.72(s, 2H), 1.26(s, 9H).

5-tert-Butyl-2-methyl-phenol (Intermediate 107)

A solution of 5-tert-butyl-2-hydroxymethyl-phenol (Intermediate 106, 0.215 g, 1.19 mmol) in ethyl acetate was treated with 5% palladium on carbon (0.04 g) and the resulting reaction mixture was stirred under an atmosphere of hydrogen at ambient temperature for 2.5 h. The reaction mixture was then filtered over a bed of celite and the filtrate was evaporated in vacuo to afford the title compound as a white solid (0.19 g, 97%).
$^1$H NMR (300 MHz, CDCl$_3$): δ 7.03(d, J=7.9 Hz, 1H), 6.86(dd, J=7.9, 1.7 Hz, 1H), 6.78(d, J=1.7 Hz, 1H), 5.20(s, 1H), 2.20(s, 3H), 1.25(s, 9H).

Trifluoro-methanesulfonic acid
5-tert-butyl-2-methyl-phenyl ester
(Intermediate 108)

A solution of 5-tert-butyl-2-methyl-phenol (Intermediate 107, 0.19 g, 1.15 mmol) and 4-(dimethylamino)pyridine (0.28 g, 2.3 mmol) in anhydrous dichloromethane (8 mL) was treated with N-phenyltrifluoromethanesulfonimide (0.54 g, 1.5 mmol), and the resulting reaction mixture was stirred at ambient temperature overnight. The reaction mixture was concentrated in vacuo and the residue was subjected to flash column chromatography over silica gel (230-400 mesh) to afford the title compound as a colorless oil (0.28 g, 82%).
$^1$H NMR (300 MHz, CDCl$_3$): δ 7.30-7.20(m, 3H), 2.33(s, 3H), 1.30(s, 9H).

(5-tert-Butyl-2-methyl-phenylethynyl)-trimethyl-silane (Intermediate 109)

Following General Procedure D and using trifluoro-methanesulfonic acid 5-tert-butyl-2-methyl-phenyl ester (Intermediate 108, 0.28 g, 0.94 mmol), triethyl amine (3 mL), trimethylsilyl acetylene (1 mL, 7 mmol), N,N-dimethylformamide (6 mL) and dichlorobis(triphenylphosphine)palladium(II) (0.053 g, 0.076 mmol) followed by flash column chromatography over silica gel (230-400 mesh) using hexane as the eluent, the title compound (0.16 g, 69%) was obtained.
$^1$H NMR (300 MHz, CDCl$_3$): δ 7.44(d, J=1.7 Hz, 1H), 7.22 (dd, J=8.2, 1.7 Hz, 1H), 7.10(d, J=8.2 Hz, 1H), 2.39(s, 3H), 1.28(s, 9H), 0.26(s, 9H).

4-tert-Butyl-2-ethynyl-1-methyl-benzene
(Intermediate 110)

Following general procedure F and using (5-tert-butyl-2-methyl-phenylethynyl)-trimethyl-silane (Intermediate 109, 0.16 g, 0.66 mmol), methanol (5 mL) and potassium carbonate (0.05 g, 0.36 mmol), the title compound was obtained (0.08 g, 67%).
$^1$H NMR (300 MHz, CDCl$_3$): δ 7.49(d, J=1.7 Hz, 1H), 7.30(dd, J=8.2, 1.7 Hz, 1H), 7.15(d, J=8.2 Hz, 1H), 3.16(s, 1H), 2.42(s, 3H), 1.32(s, 9H).

3-[4-(5-tert-Butyl-2-methyl-phenylethynyl)-phenyl]-acrylic acid ethyl ester (Intermediate 111)

Following General Procedure B and using 4-tert-butyl-2-ethynyl-1-methyl-benzene (Intermediate 110, 0.08 g, 0.47 mmol), ethyl-4-iodocinnamate (0.12 g, 0.4 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 2-4% ethyl acetate in hexane as the eluent, the title compound was obtained (0.09 g, 55%).
$^1$H NMR (300 MHz, CDCl$_3$): δ 7.67(d, J=16.1 Hz, 1H), 7.56-7.48(m, 5H), 7.28(dd, J=8.2, 1.7 Hz, 1H), 7.16(d, J=8.2 Hz, 1H), 6.44(d, J=16.1 Hz, 1H), 4.27(q, J=7.1 Hz, 2H), 2.48(s, 3H), 1.33(t, J=7.1 Hz, 3H), 1.32(s, 9H).

3-[4-(5-tert-Butyl-2-methyl-phenylethynyl)-phenyl]-acrylic acid (Compound 36)

A solution of 3-[4-(5-tert-butyl-2-methyl-phenylethynyl)-phenyl]-acrylic acid ethyl ester (Intermediate 111, 0.09 g, 0.26 mmol) in ethanol (3 mL) and tetrahydrofuran (3 mL) was treated with 3M potassium hydroxide solution (1 mL, 3 mmol) and the resulting reaction mixture was stirred overnight at ambient temperature. The reaction mixture was concentrated in vacuo slightly, the residue was neutralized with dilute hydrochloric acid, and the solid that was formed was filtered and washed with water and acetonitrile and dried to afford title product (0.064 g, 77%).
$^1$H NMR (300 MHz, CDCl$_3$): δ 7.78(d, J=16.1 Hz, 1H), 7.58-7.53(m, 5H), 7.29(dd, J=7.9, 1.7 Hz, 1H), 7.17(d, J=7.9 Hz, 1H), 6.47(d, J=16.1 Hz, 1H), 2.48(s, 3H), 1.32(s, 9H).

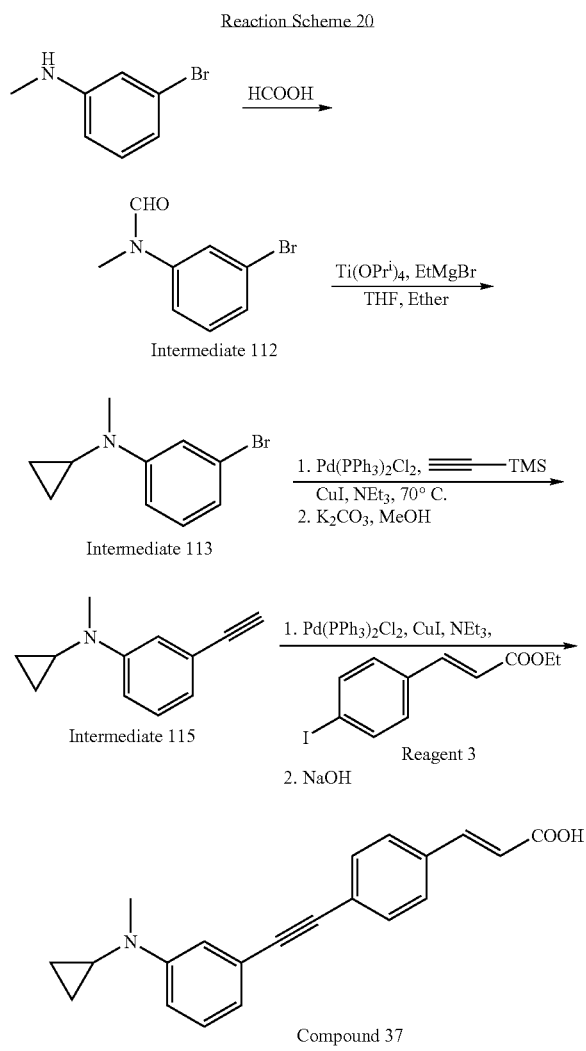

Reaction Scheme 20

Compound 37

N-(3-Bromo-phenyl)-N-methyl-formamide (Intermediate 112)

A solution of 3-bromo-N-methyl aniline (made as described by Lopez et al. in *Tet. Lett.*, 1999, 40, 11, p2071-2074 incorporated herein by reference; 7.4 g, 39.5 mmol) in formic acid (20 mL) was refluxed for 3 h. The reaction mixture was then cooled to ambient temperature, diluted with water and extracted with diethyl ether. The organic phase was washed with saturated, aqueous sodium bicarbonate solution, water and brine, dried over anhydrous magnesium sulfate, filtered and evaporated in vacuo to afford the title product as a dark brown oil.

(3-Bromo-phenyl)-cyclopropyl-methyl-amine (Intermediate 113)

A stirred, cooled (0° C.) solution of N-(3-bromo-phenyl)-N-methyl-formamide (Intermediate 112, 2.6 g, 9.7 mmol) and titanium tetra-iso-propoxide (3.9 mL, 10.67 mmol) in tetrahydrofuran (40 mL) was treated with a 3M solution of ethyl magnesium bromide in ether (8.08 mL, 24.25 mmol) under argon and the resulting reaction mixture was allowed to warm to ambient temperature gradually and refluxed at 55° C. overnight. It was then cooled in an ice-bath, quenched with saturated aqueous ammonium chloride solution, filtered over celite and the aqueous phase was extracted with diethyl ether. The organic phase was dried over anhydrous magnesium sulfate, filtered and evaporated in vacuo to afford an oil. Flash column chromatography over silica gel (230-400 mesh) using 1.5% ethyl acetate in hexane as the eluent afforded the title compound (0.321 g, 15%).

Cyclopropyl-methyl-(3-trimethylsilanylethynyl-phenyl)-amine (Intermediate 114)

Following General Procedure D and using (3-bromo-phenyl)-cyclopropyl-methyl-amine (Intermediate 113, 0.056 g, 0.25 mmol), triethyl amine (3 mL), copper(I)iodide (0.025 g, 0.13 mmol), trimethylsilyl acetylene (2.5 mL, 17.6 mmol) and dichlorobis(triphenylphosphine)palladium(II) (0.065 g, 0.09 mmol) followed by flash column chromatography over silica gel (230-400 mesh) using 1.5% ethyl acetate in hexane as the eluent, the title compound (0.051 g, 84%) was obtained.

Cyclopropyl-(3-ethynyl-phenyl)-methyl-amine (Intermediate 115)

A solution of cyclopropyl-methyl-(3-trimethylsilanylethynyl-phenyl)-amine (Intermediate 114, 0.05 g, 0.2 mmol) in methanol (5 mL) was treated with potassium carbonate (0.063 g, 0.46 mmol) and the resulting reaction mixture was heated at 80° C. for 3 h. The solvent was evaporated in vacuo, the residue was diluted with water and extracted with diethyl ether. The organic phase was dried over anhydrous magnesium sulfate, filtered and evaporated in vacuo to afford the title compound (0.035 g, 100%).

(E)-3-{4-[3-(Cyclopropyl-methyl-amino)-phenylethynyl}-acrylic acid ethyl ester (Intermediate 116)

Following General Procedure B and using cyclopropyl-(3-ethynyl-phenyl)-methyl-amine (Intermediate 115, 0.035 g, 0.2 mmol), ethyl-4-iodo-cinnamate (0.082 g, 0.27 mmol), triethyl amine (3 mL), copper(I)iodide (0.025 g, 0.13 mmol) and dichlorobis(triphenylphosphine)palladium(II) (0.033 g, 0.047 mmol) followed by flash column chromatography over silica gel (230-400 mesh), and preparative normal phase HPLC using 10% ethyl acetate in hexane as the mobile phase, the title compound was obtained (0.020 g, 29%).

(E)-3-{4-[3-(Cyclopropyl-methyl-amino)-phenylethynyl]-phenyl}-acrylic acid (Compound 37)

A solution of (E)-3-{4-[3-(cyclopropyl-methyl-amino)-phenylethynyl}-acrylic acid ethyl ester (Intermediate 116, 0.020 g, 0.057 mmol) in ethanol (1 mL) was treated with a 1M solution of sodium hydroxide (1 mL, 1 mmol) and the resulting reaction mixture was heated at 80° C. for 30 minutes. The volatiles were evaporated in vacuo to a residue that was neutralized with saturated aqueous ammonium chloride solution and extracted with ethyl acetate. The organic phase was dried over anhydrous magnesium sulfate, filtered and evaporated in vacuo to afford a residue that on preparative reverse phase HPLC using 10% water in acetonitrile as the mobile phase afforded the title product as a yellow solid (0.006 g, 33%).

Reaction Scheme 21

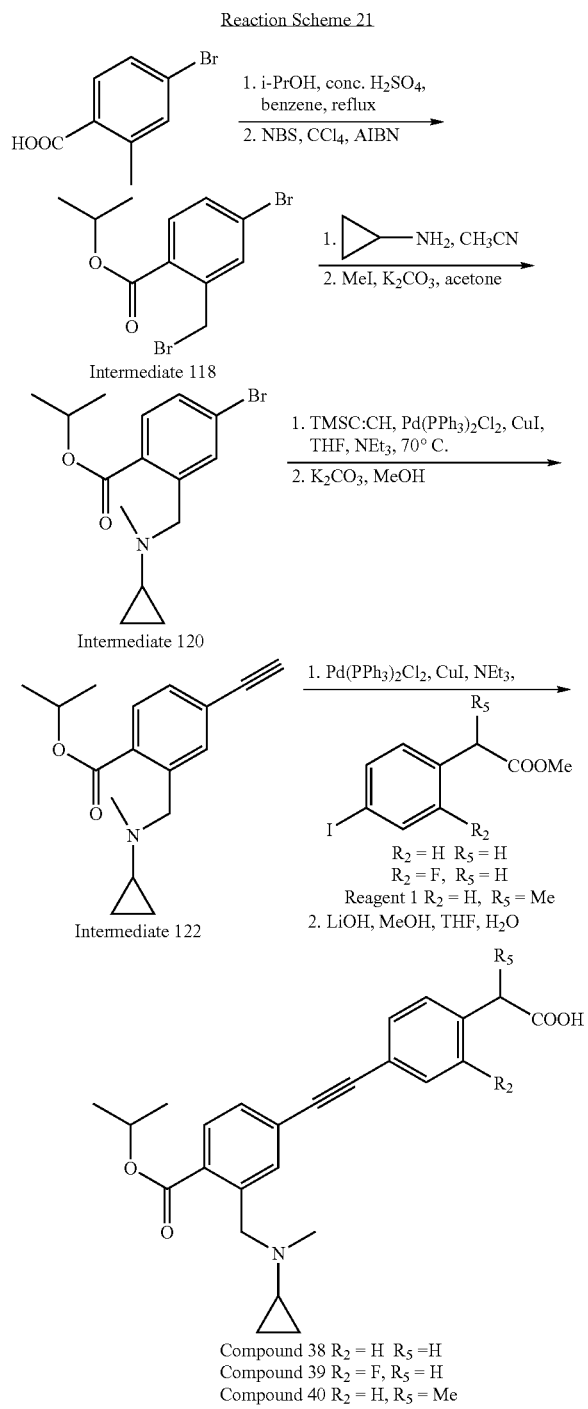

Compound 38 R$_2$ = H R$_5$ =H
Compound 39 R$_2$ = F, R$_5$ = H
Compound 40 R$_2$ = H, R$_5$ = Me

4-Bromo-2-methyl-benzoic acid isopropyl ester (Intermediate 117)

A solution of 4-bromo-2-methyl-benzoic acid (Aldrich, 5.4 g, 25 mmol) in benzene (75 mL) and isopropanol (75 mL) was treated with concentrated sulfuric acid (1.5 mL) and heated to reflux over 4 days using a Dean-Stark water trap. The volatiles were evaporated in vacuo, the residue was diluted with water and extracted with diethyl ether. The organic phase was washed with water and saturated, aqueous sodium bicarbonate solution, dried over anhydrous magnesium sulfate, filtered and evaporated in vacuo to afford the title product as a clear oil that was used as such for the next step (6.12 g, 95%).

4-Bromo-2-bromomethyl-benzoic acid isopropyl ester (Intermediate 118)

A solution of 4-bromo-2-methyl-benzoic acid isopropyl ester (Intermediate 117, 6.12 g, 23.8 mmol) in carbon tetrachloride (120 mL) was treated with N-bromosuccinimide (4.6 g, 26.18 mmol) and 2,2'-azobisisobutyronitrile (0.6 g) and the resulting reaction mixture was refluxed overnight. It was cooled to ambient temperature, the solids were filtered off and washed with 1:1 hexane:diethyl ether, and the filtrate and washings were evaporated in vacuo to afford an oil (5.1 g, 64%) that was used as such for the next step.

4-Bromo-2-cyclopropylaminomethyl-benzoic acid isopropyl ester (Intermediate 119)

A stirred, cooled (ice bath) solution of 4-bromo-2-bromomethyl-benzoic acid isopropyl ester (Intermediate 118, 5.1 g, 15.17 mmol) in acetonitrile (25 mL) was treated with cyclopropyl amine (2 mL, 28.9 mmol). The reaction mixture was allowed to warm to ambient temperature. After 2 h, the volatiles were evaporated in vacuo, the residue was diluted with water and extracted with diethyl ether (×2). The combined organic phase was dried over anhydrous magnesium sulfate, filtered and evaporated in vacuo to an oil. Flash column chromatography over silica gel (230-400 mesh) using 4-20% ethyl acetate in hexane as the eluent to afforded the title product (1.33 g, 28%).
$^1$H NMR (300 MHz, CDCl$_3$): δ 7.73 (d, 1H, J=8.4 Hz), 7.56 (d, 1H, J=2.1 Hz), 7.41 (dd, 1H, J=2.1, 8.4 Hz), 5.21 (heptet, 1H, J=6.3 Hz), 4.00 (s, 2H), 2.39 (br s, 1H), 2.06 (m, 1H), 1.35 (d, 6H, J=6.3 Hz), 0.42-0.34 (m, 4H).

4-Bromo-2-[(cyclopropyl-methyl-amino)-methyl]-benzoic acid isopropyl ester (Intermediate 120)

A solution of 4-bromo-2-cyclopropylaminomethyl-benzoic acid isopropyl ester (Intermediate 119, 1.33 g, 4.26 mmol) in acetone (8 mL) was treated with potassium carbonate (2.36 g, 17.05 mmol) and methyl iodide (0.53 mL, 8.52 mmol) and the resulting reaction mixture was stirred at ambient temperature for 3 h. The volatiles were evaporated in vacuo, the residue was diluted with water and extracted with diethyl ether (×2). The combined organic phase was dried over anhydrous magnesium sulfate, filtered over a short bed of silica gel (230-400 mesh) and evaporated in vacuo to afford the title product (1.23 g, 70%).
$^1$H NMR (300 MHz, CDCl$_3$): δ 7.64 (d, 1H, J=2.1 Hz), 7.58 (d, 1H, J=8.4 Hz), 7.39 (dd, 1H, J=2.1, 8.4 Hz), 5.20 (heptet, 1H, J=6.0 Hz), 3.97 (s, 2H), 2.22 (s, 3H), 1.77 (m, 1H), 1.35 (d, 6H, J=6.0 Hz), 0.46-0.38 (m, 4H).

2-[(Cyclopropyl-methyl-amino)-methyl]-4-trimethylsilanylethynyl-benzoic acid isopropyl ester (Intermediate 121)

Following General Procedure D and using 4-bromo-2-[(cyclopropyl-methyl-amino)-methyl]-benzoic acid isopropyl ester (Intermediate 120, 1.23 g, 3.68 mmol), triethyl amine (10 mL), tetrahydrofuran (5 mL), copper(I)iodide (0.21 g, 1.1 mmol), trimethylsilyl acetylene (2.1 mL, 14.7 mmol) and dichlorobis(triphenylphosphine)palladium(II)

(0.77 g, 1.1 mmol) followed by flash column chromatography over silica gel (230-400 mesh) using 7% ethyl acetate in hexane as the eluent, the title compound was obtained as an oil (1.2 g, ~100%).

$^1$H NMR (300 MHz, CDCl$_3$): δ 7.62 (d, 1H, J=8.1 Hz), 7.53 (s, 1H), 7.35 (d, 1H, J=8.4 Hz), 5.20 (heptet, 1H, J=6.3 Hz), 3.95 (s, 2H), 2.22 (s, 3H), 1.74 (m, 1H), 1.36 (d, 6H, J=6.3 Hz), 0.37-0.28 (m, 4H), 0.27 (s, 9H).

2-[(Cyclopropyl-methyl-amino)-methyl]-4-ethynyl-benzoic acid isopropyl ester (Intermediate 122)

A solution 2-[(cyclopropyl-methyl-amino)-methyl]-4-trimethylsilanylethynyl-benzoic acid isopropyl ester (Intermediate 121, 0.34 g, 1 mmol) in methanol (2 mL) was treated with potassium carbonate (0.207 g, 1.5 mmol) and the resulting reaction mixture was stirred at ambient temperature for 4 h. The volatiles were evaporated in vacuo, the residue was diluted with water and extracted with diethyl ether, dried over anhydrous magnesium sulfate, filtered and evaporated in vacuo to afford the title compound as an oil (0.21 g, 78%).

$^1$H NMR (300 MHz, CDCl$_3$): δ 7.67 (d, 1H, J=7.8 Hz), 7.64 (d, 1H, J=1.8 Hz), 7.38 (dd, 1H, J=1.8, 7.8 Hz), 5.21 (heptet, 1H, J=6.0 Hz), 3.96 (s, 2H), 3.16 (s, 1H), 2.22 (s, 3H), 1.74 (m, 1H), 1.36 (d, 6H, J=6.0 Hz), 0.44-0.33 (m, 4H).

2-[(Cyclopropyl-methyl-amino)-methyl]-4-(4-methoxycarbonylmethyl-phenylethynyl)-benzoic acid isopropyl ester (Intermediate 123)

Following General Procedure B and using 2-[(cyclopropyl-methyl-amino)-methyl]-4-ethynyl-benzoic acid isopropyl ester (Intermediate 122, 0.09 g, 0.33 mmol), 4-iodophenyl acetic acid methyl ester (0.09 g, 0.33 mmol), triethyl amine (2 mL), copper(I)iodide (0.04 g, 0.21 mmol) and dichlorobis(triphenylphosphine)palladium(II) (0.1 g, 0.14 mmol) followed by flash column chromatography over silica gel (230-400 mesh) using 10-15% ethyl acetate in hexane as the eluent, the title compound was obtained as an oil. (0.1 g, 72%).

$^1$H NMR (300 MHz, CDCl$_3$): δ 7.70 (d, 1H, J=7.8 Hz), 7.62 (d, 1H, J=1.8 Hz), 7.52 (d, 2H, J=8.1 Hz), 7.43 (dd, 1H, J=1.8, 7.8 Hz), 7.28 (d, 2H, J=8.1 Hz), 5.25 (heptet, 1H, J=6.0 Hz), 4.00 (s, 2H), 3.71 (s, 3H), 3.65 (s, 2H), 2.26 (s, 3H), 1.78 (m, 1H), 1.38 (d, 6H, J=6.0 Hz), 0.44-0.40 (m, 4H).

4-(4-Carboxymethyl-phenylethynyl)-2-[(cyclopropyl-methyl-amino)-methyl]-benzoic acid isopropyl ester (Compound 38)

A solution of 2-[(cyclopropyl-methyl-amino)-methyl]-4-(4-methoxycarbonylmethyl-phenylethynyl)-benzoic acid isopropyl ester (Intermediate 123, 0.1 g, 0.23 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 2 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to a solid. Preparative reverse phase HPLC using 10% water in acetonitrile as the mobile phase afforded the title product as a white solid (0.068 g, 72%). $^1$H NMR (300 MHz, CDCl$_3$): δ 9.05 (br s, 1H), 7.73 (d, 1H, J=8.4 Hz), 7.66 (s, 1H), 7.44-7.37 (m, 3H), 7.23-7.21 (m, 2H), 5.20 (heptet, 1H, J=6.0 Hz), 4.21 (s, 2H), 3.52 (s, 2H), 2.36 (s, 3H), 1.94 (m, 1H), 1.36 (d, 6H, J=6.0 Hz), 0.55-0.43 (m, 4H).

2-[(Cyclopropyl-methyl-amino)-methyl]-4-(3-fluoro-4-methoxycarbonylmethyl-phenylethynyl)-benzoic acid isopropyl ester (Intermediate 124)

Following General Procedure B and using 2-[(cyclopropyl-methyl-amino)-methyl]-4-ethynyl-benzoic acid isopropyl ester (Intermediate 122, 0.05 g, 0.18 mmol), 2-fluoro-4-iodo phenylacetic acid methyl ester (0.07 g, 0.24 mmol), triethyl amine (2 mL), copper(I)iodide (0.04 g, 0.21 mmol) and dichlorobis(triphenylphosphine)palladium(II) (0.07 g, 0.1 mmol) followed by flash column chromatography over silica gel (230-400 mesh) using 15-16% ethyl acetate in hexane as the eluent, the title compound was obtained as an oil (0.04 g, 50%).

$^1$H NMR (300 MHz, CDCl$_3$): δ 7.63 (d, 1H, J=7.8 Hz), 7.55 (d, 1H, J=1.2 Hz), 7.35 (dd, 1H, J=1.2, 7.8 Hz), 7.26-7.17 (m, 3H), 5.16 (heptet, 1H, J=6.3 Hz), 3.93 (s, 2H), 3.66 (s, 3H), 3.64 (s, 2H), 2.20 (s, 3H), 1.71 (m, 1H), 1.31 (d, 6H, J=6.3 Hz), 0.40-0.33 (m, 4H).

4-(4-Carboxymethyl-3-fluoro-phenylethynyl)-2-[(cyclopropyl-methyl-amino)-methyl]-benzoic acid isopropyl ester (Compound 39)

A solution of 2-[(cyclopropyl-methyl-amino)-methyl]-4-(3-fluoro-4-methoxycarbonylmethyl-phenylethynyl)-benzoic acid isopropyl ester (Intermediate 124, 0.04 g, 0.09 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 2 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to a solid. Preparative reverse phase HPLC using 10% water in acetonitrile as the mobile phase afforded the title product as a white solid (0.026 g, 54%). $^1$H NMR (300 MHz, CDCl$_3$): δ 7.71 (d, 1H, J=8.1 Hz), 7.64 (s, 1H), 7.41 (d, 1H, J=8.1 Hz), 7.17-7.09 (m, 3H), 5.20 (heptet, 1H, J=6.3 Hz), 4.16 (s, 2H), 3.54 (s, 2H), 2.34 (s, 3H), 1.91 (m, 1H), 1.36 (d, 6H, J=6.3 Hz), 0.50-0.41 (m, 4H).

2-[(Cyclopropyl-methyl-amino)-methyl]-4-(4-methoxycarbonylmethyl-phenylethynyl)-benzoic acid isopropyl ester (Intermediate 125)

Following General Procedure B and using 2-[(cyclopropyl-methyl-amino)-methyl]-4-ethynyl-benzoic acid isopropyl ester (Intermediate 122, 0.07 g, 0.26 mmol), methyl-2-(4-iodophenyl)-propionate (Reagent 1, 0.081 g, 0.29 mmol), triethyl amine (2 mL), copper(I)iodide (0.03 g, 0.158 mmol) and dichlorobis(triphenylphosphine)palladium(II) (0.07 g, 0.1 mmol) followed by flash column chromatography over silica gel (230-400 mesh) using 10-15% ethyl acetate in hexane as the eluent, the title compound was obtained as an oil (0.09 g, 81%).

$^1$H NMR (300 MHz, CDCl$_3$): δ 7.57 (d, 1H, J=8.1 Hz), 7.49 (d, 1H, J=1.8 Hz), 7.39 (d, 2H, J=8.4 Hz), 7.30 (dd, 1H, J=1.8, 8.1 Hz), 7.18 (d, 2H, J=8.4 Hz), 5.10 (heptet, 1H, J=6.0 Hz), 3.88 (s, 2H), 3.63 (q, 1H, J=7.2 Hz), 3.56 (s, 3H), 2.13 (s, 3H), 1.65 (m, 1H), 1.40 (d, 3H, J=7.2 Hz), 1.25 (d, 6H, J=6.0 Hz), 0.35-0.27 (m, 4H).

4-[4-(1-Carboxy-ethyl)-phenylethynyl]-2-[(cyclopropyl-methyl-amino)-methyl]-benzoic acid isopropyl ester (Compound 40)

A solution of 2-[(cyclopropyl-methyl-amino)-methyl]-4-(4-methoxycarbonylmethyl-phenylethynyl)-benzoic acid isopropyl ester (Intermediate 125, 0.09 g, 0.21 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 4 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to afford the title product as a white solid foam (0.053 g, 61%).

$^1$H NMR (300 MHz, CDCl$_3$): δ 7.68 (d, 1H, J=8.1 Hz), 7.58 (d, 1H, J=1.8 Hz), 7.44-7.25 (m, 5H), 5.13 (heptet, 1H, J=6.0 Hz), 4.18 (s, 2H), 3.79 (m, 1H), 2.32 (s, 3H), 1.89 (m, 1H), 1.39 (d, 3H, J=6.6 Hz), 1.28 (d, 6H, J=6.3 Hz), 0.52-0.21 (m, 4H).

Reaction Scheme 22

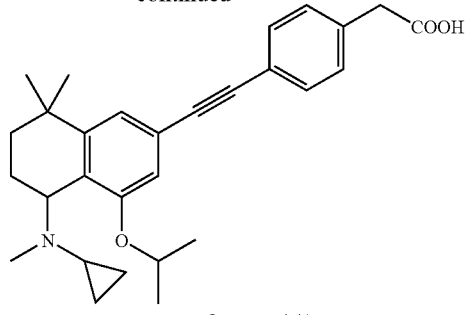

Compound 41

4,4-Dimethyl-8-(2-propoxy)-6-trimethylsilanylethynyl-3,4-dihydro-2H-naphthalen-1-one (Intermediate 126)

A solution of 8-hydroxy-4,4-dimethyl-6-trimethylsilanylethynyl-3,4-dihydro-2H-naphthalen-1-one (Intermediate 66, 0.32 g, 1.12 mmol) in acetone (20 mL) was treated with potassium carbonate (0.773 g, 5.6 mmol) and 2-iodopropane (2 g, 11.76 mmol) and the resulting reaction mixture was refluxed for 3 days. It was cooled to ambient temperature, the solids were filtered off and the filtrate was evaporated in vacuo to an oil that was subjected to flash column chromatography over silica gel (230-400 mesh) using 2-6% ethyl acetate in hexane as the eluent to afford the title product as (0.055 g, 15%).

$^1$H NMR (300 MHz, CDCl$_3$): δ 7.04 (d, 1H, J=1.2 Hz), 6.89 (d, 1H, J=1.2 Hz), 4.57 (heptet, 1H, J=6.3 Hz), 2.66 (t, 2H, J=7.2 Hz), 1.92 (t, 2H, J=7.2 Hz), 1.38 (d, 6H, J=6.3 Hz), 1.33 (s, 6H), 0.27 (s, 9H).

4,4-Dimethyl-6-ethynyl-8-(2-propoxy)-3,4-dihydro-2H-naphthalen-1-one (Intermediate 127)

A solution 4,4-dimethyl-8-(2-propoxy)-6-trimethylsilanylethynyl-3,4-dihydro-2H-naphthalen-1-one (Intermediate 126, 0.055 g, 0.167 mmol) in methanol (5 mL) was treated with potassium carbonate (0.03 g, 0.22 mmol) and the resulting reaction mixture was stirred at ambient temperature overnight. The solvent was evaporated in vacuo, the residue was diluted with water and extracted with ethyl acetate. The organic phase was washed with brine, dried over anhydrous magnesium sulfate, filtered and evaporated in vacuo to afford the title compound (0.042 g, 98%).

$^1$H NMR (300 MHz, CDCl$_3$): δ 7.08 (d, 1H, J=1.2 Hz), 6.93 (d, 1H, J=1.2 Hz), 4.56 (heptet, 1H, J=6.0 Hz), 3.19 (s, 1H), 2.67 (t, 2H, J=6.9 Hz), 1.93 (t, 2H, J=6.9 Hz), 1.39 (d, 6H, J=6.0 Hz), 1.34 (s, 6H).

{4-[8,8-Dimethyl-5-oxo-4-(2-propoxy)-5,6,7,8-tetrahydro-naphthalen-2-ylethynyl]-phenyl}-acetic acid methyl ester (Intermediate 128)

Following General Procedure B and using 4,4-dimethyl-6-ethynyl-8-(2-propoxy)-3,4-dihydro-2H-naphthalen-1-one (Intermediate 127, 0.075 g, 0.29 mmol), 4-iodo phenyl acetic acid methyl ester (0.081 g, 0.29 mmol), triethyl amine (8 mL), tetrahydrofuran (3 mL), copper(I)iodide (0.019 g, 0.1 mmol) and dichlorobis(triphenylphosphine)palladium(II) (0.07 g, 0.11 mmol) followed by flash column chromatography over silica gel (230-400 mesh) using 5-15% ethyl acetate in hexane as the eluent, the title compound was obtained as a yellow oil (0.07 g, 64%).

$^1$H NMR (300 MHz, CDCl$_3$): δ 7.52 (d, 2H, J=8.4 Hz), 7.29 (d, 2H, J=8.4 Hz), 7.12 (d, 1H, J=1.5 Hz), 6.97 (d, 1H, J=1.5 Hz), 4.60 (heptet, 1H, J=5.8 Hz), 3.71 (s, 3H), 3.66 (s, 2H), 2.68 (t, 2H, J=6.6 Hz), 1.95 (t, 2H, J=6.6 Hz), 1.41 (d, 6H, J=5.8 Hz), 1.36 (s, 6H).

{4-[5-(Cyclopropyl-methyl-amino)-4-isopropoxy-8, 8-dimethyl-5,6,7,8-tetrahydro-naphthalen-2-ylethynyl]-phenyl}-acetic acid methyl ester (Intermediate 129)

A solution of {4-[8,8-dimethyl-5-oxo-4-(2-propoxy)-5,6, 7,8-tetrahydro-naphthalen-2-ylethynyl]-phenyl}-acetic acid methyl ester (Intermediate 128, 0.07 g, 0.187 mmol) in dichloromethane (3 mL) and acetonitrile (1.5 mL) was treated with cyclopropyl amine (1 mL, 14.45 mmol). After 5 minutes, acetic acid (1 mL) was added followed by sodium cyanoborohydride (0.12 g, 1.91 mmol). The reaction mixture was stirred overnight at ambient temperature. It was then diluted with water and saturated aqueous sodium carbonate solution and extracted with dichloromethane (×2). The combined organic extract was dried over anhydrous sodium sulfate, filtered and evaporated in vacuo to an oil. The oil was dissolved in acetone (15 mL) and treated with potassium carbonate (0.2 g, 1.45 mmol) followed by methyl iodide (1 mL, 15.8 mmol) and the resulting reaction mixture was stirred overnight at ambient temperature. The precipitated solids were filtered off, the filtrate was evaporated in vacuo to a residue. Flash column chromatography over silica gel (230-400 mesh) using 2.5-6% ethyl acetate in hexane as the eluent afforded the title compound (0.045 g, 53%).

$^1$H NMR (300 MHz, CDCl$_3$): δ 7.50 (d, 2H, J=8.4 Hz), 7.26 (d, 2H, J=8.4 Hz), 7.12 (d, 1H, J=1.5 Hz), 6.77 (d, 1H, J=1.5 Hz), 4.58 (heptet, 1H, J=6.3 Hz), 4.04 (m, 1H), 3.70 (s, 3H), 3.64 (s, 2H), 2.32 (s, 3H), 2.10-1.95 (m, 2H), 1.84-1.78 (m, 1H), 1.66-1.60 (m, 1H), 1.40-1.26 (m, 1H), 1.39 and 1.35 (2d, 6H, J=6.3 Hz), 1.34 (s, 3H), 1.19 (s, 3H), 0.29-0.22 (m, 2H), 0.083-0.00 (m, 2H).

{4-[5-(Cyclopropyl-methyl-amino)-4-isopropoxy-8, 8-dimethyl-5,6,7,8-tetrahydro-naphthalen-2-ylethynyl]-phenyl}-acetic acid (Compound 41)

A solution of {4-[5-(cyclopropyl-methyl-amino)-4-isopropoxy-8,8-dimethyl-5,6,7,8-tetrahydro-naphthalen-2-ylethynyl]-phenyl}-acetic acid methyl ester (Intermediate 129, 0.045 g, 0.098 mmol) in methanol (2 mL) and tetrahydrofuran (2 mL) was treated with 2M lithium hydroxide (1 mL, 2 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to a residue that was subjected to flash column chromatography over silica gel (230-400 mesh) using 5% methanol in ethyl acetate as the eluent to afford the title product as a white solid (0.027 g, 61%).

$^1$H NMR (300 MHz, CDCl$_3$): δ 7.46 (d, 2H, J=8.1 Hz), 7.29 (d, 2H, J=8.1 Hz), 7.14 (d, 1H, J=1.2 Hz), 6.80 (d, 1H, J=1.2 Hz), 4.62 (heptet, 1H, J=6.0 Hz), 4.31 (m, 1H), 3.58 (s, 2H), 2.46 (s, 3H), 2.46-2.39 (m, 1H), 2.14-1.87 (m, 2H), 1.72-1.67 (m, 1H), 1.42-1.23 (m, 1H), 1.40 and 1.34 (2d, 6H, J=6.0 Hz), 1.31 (s, 3H), 1.16 (s, 3H), 0.80-0.70 (m, 1H), 0.53-0.38 (m, 2H), 0.23-0.18 (m, 1H).

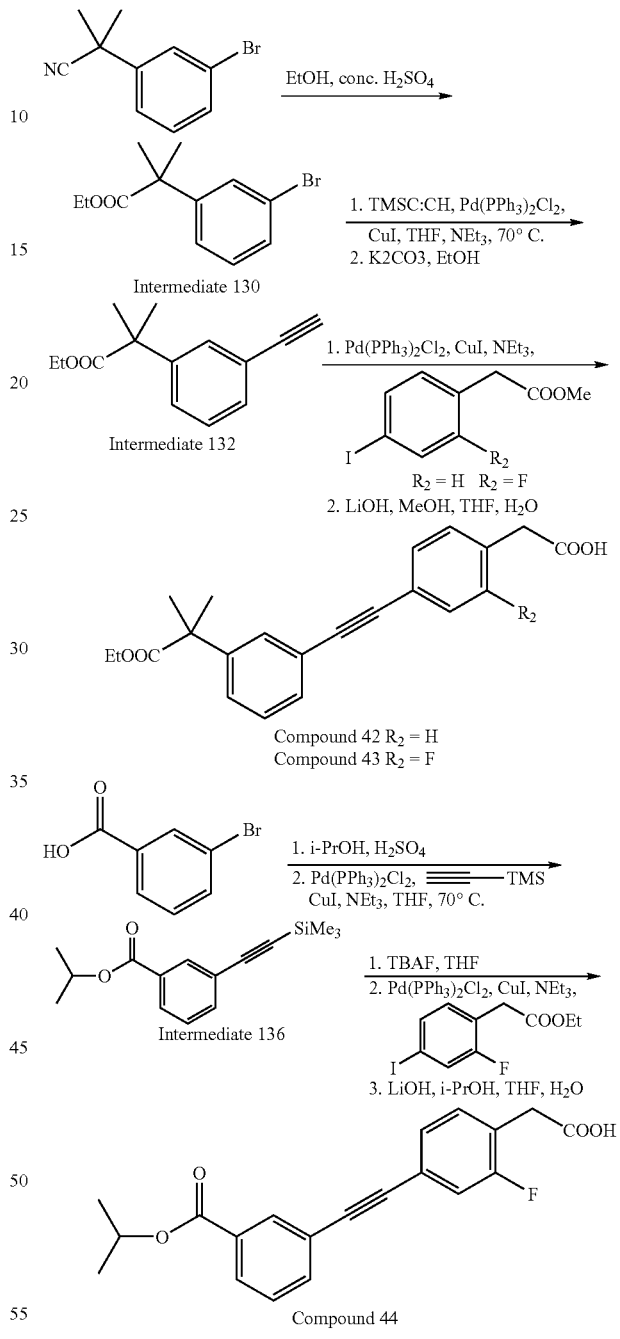

Reaction Scheme 23

2-(3-Bromo-phenyl)-2-methyl-propionic acid ethyl ester (Intermediate 130)

A solution of 2-(3-bromo-phenyl)-2-methyl-propionitrile (prepared as described by Barlaam et al. *J. Med. Chem.*, 1999, 42, 23, 4890-4908 incorporated herein by reference; 1.4 g, 6.24 mmol) was dissolved in ethanol (40 mL), treated with concentrated sulfuric acid (1 mL) and the resulting reaction mixture was refluxed for 36 h. The reaction mixture was cooled to ambient temperature, diluted with water and extracted with ethyl acetate. The organic phase was washed with water and brine, dried over anhydrous magnesium sulfate, filtered and evaporated in vacuo to a residue that was subjected to flash column chromatography over silica gel (230-400 mesh) using 5% ethyl acetate in hexane as the eluent to afford the title product as an orange oil (0.77 g, 46%).

$^1$H NMR (300 MHz, CDCl$_3$): δ 7.48 (s, 1H), 7.36 (dd, 1H, J=2.8, 7.7 Hz), 7.26 (dd, 1H, J=2.8, 8.3 Hz), 7.20 (dd, 1H, J=7.8, 8.3 Hz), 4.12 (q, 2H, J=7.0 Hz), 1.55 (s, 6H), 1.18 (t, 3H, J=7.0 Hz).

2-Methyl-2-(3-trimethylsilanylethynyl-phenyl)-propionic acid ethyl ester (Intermediate 131)

Following General Procedure D and using 2-(3-bromophenyl)-2-methyl-propionic acid ethyl ester (Intermediate 130, 0.77 g, 2.84 mmol), triethyl amine (5 mL), copper(I) iodide (0.044 g, 0.23 mmol), trimethylsilyl acetylene (2 mL, 14.1 mmol) and dichlorobis(triphenylphosphine)palladium (II) (0.159 g, 0.23 mmol) followed by flash column chromatography over silica gel (230-400 mesh) using hexane to 5% ethyl acetate in hexane as the eluent, the title compound (0.74 g, 90%) was obtained as an orange oil.

$^1$H NMR (300 MHz, CDCl$_3$): δ 7.45 (s, 1H), 7.33-7.24 (m, 3H), 4.12 (q, 2H, J=7.0 Hz), 1.56 (s, 6H), 1.17 (t, 3H, J=7.0 Hz), 0.25 (s, 9H).

2-(3-Ethynyl-phenyl)-2-methyl-propionic acid ethyl ester (Intermediate 132)

A solution of 2-methyl-2-(3-trimethylsilanylethynyl-phenyl)-propionic acid ethyl ester (Intermediate 131, 0.74 g, 2.56 mmol) in ethanol (10 mL) was treated with potassium carbonate (0.2 g, 1.45 mmol). The resulting reaction mixture was stirred at ambient temperature overnight. The volatiles were evaporated in vacuo and the residue was diluted with water and extracted with diethyl ether. The organic phase was washed with water and brine, dried over anhydrous magnesium sulfate, filtered and evaporated in vacuo to a residue that was subjected to flash column chromatography over silica gel (230-400 mesh) using 1-5% ethyl acetate in hexane as the eluent to afford the title product (0.4 g, 72%).

$^1$H NMR (300 MHz, CDCl$_3$): δ 7.56 (s, 1H), 7.45-7.33 (m, 3H), 4.18 (q, 2H, J=7.0 Hz), 3.14 (s, 1H), 1.63 (s, 6H), 1.24 (t, 3H, J=7.0 Hz).

2-[3-(4-Methoxycarbonylmethyl-phenylethynyl)-phenyl]-2-methyl-propionic acid ethyl ester (Intermediate 133)

Following General Procedure B and using 2-(3-ethynyl-phenyl)-2-methyl-propionic acid ethyl ester (Intermediate 132, 0.101 g, 0.47 mmol), 4-iodo phenyl acetic acid methyl ester (0.129 g, 0.47 mmol), triethyl amine (8 mL), copper(I) iodide (0.01 g, 0.05 mmol) and dichlorobis(triphenylphosphine)palladium(II) (0.035 g, 0.05 mmol) followed by flash column chromatography over silica gel (230-400 mesh) using 10-15% ethyl acetate in hexane as the eluent, the title compound was obtained as an oil (0.14 g, 82%).

$^1$H NMR (300 MHz, CDCl$_3$): δ 7.52-7.25 (m, 8H), 4.13 (q, 2H, J=7.0 Hz), 3.70 (s, 3H), 3.64 (s, 2H), 1.58 (s, 6H), 1.18 (t, 3H, J=7.0 Hz).

2-[3-(4-Methoxycarbonylmethyl-phenylethynyl)-phenyl]-2-methyl-propionic acid (Compound 42)

A solution of 2-[3-(4-methoxycarbonylmethyl-phenylethynyl)-phenyl]-2-methyl-propionic acid ethyl ester (Intermediate 133, 0.12 g, 0.33 mmol) in ethanol (2 mL) and tetrahydrofuran (2 mL) was treated with 2M lithium hydroxide (1 mL, 2 mmol) and the resulting reaction mixture was stirred at ambient temperature for 1 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as an oil (0.11 g, 95%).

$^1$H NMR (300 MHz, CDCl$_3$): δ 7.48 (s, 1H), 7.35-7.04 (m, 7H), 4.11 (q, 2H, J=7.0 Hz), 3.32 (s, 2H), 1.50 (s, 6H), 1.11 (t, 3H, J=7.0 Hz).

2-[3-(3-Fluoro-4-methoxycarbonylmethyl-phenylethynyl)-phenyl]-2-methyl-propionic acid ethyl ester (Intermediate 134)

Following General Procedure B and using 2-(3-ethynyl-phenyl)-2-methyl-propionic acid ethyl ester (Intermediate 132, 0.10 g, 0.46 mmol), 2-fluoro-4-iodo phenyl acetic acid methyl ester (0.136 g, 0.46 mmol), triethyl amine (8 mL), copper(I)iodide (0.01 g, 0.05 mmol) and dichlorobis(triphenylphosphine)palladium(II) (0.035 g, 0.05 mmol) followed by flash column chromatography over silica gel (230-400 mesh) using 10-15% ethyl acetate in hexane as the eluent, the title compound was obtained as an oil (0.15 g, 85%).

$^1$H NMR (300 MHz, CDCl$_3$): δ 7.52 (s, 1H) 7.39-7.21 (m, 6H), 4.13 (q, 2H, J=7.0 Hz), 3.71 (s, 3H), 3.68 (s, 2H), 1.58 (s, 6H), 1.18 (t, 3H, J=7.0 Hz).

2-[3-(3-Fluoro-4-methoxycarbonylmethyl-phenylethynyl)-phenyl]-2-methyl-propionic acid (Compound 43)

A solution of 2-[3-(3-fluoro-4-methoxycarbonylmethyl-phenylethynyl)-phenyl]-2-methyl-propionic acid ethyl ester (Intermediate 134, 0.13 g, 0.34 mmol) in ethanol (2 mL) and tetrahydrofuran (2 mL) was treated with 2M lithium hydroxide (1 mL, 2 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.125 g, ~100%).

$^1$H NMR (300 MHz, CDCl$_3$): δ 7.48 (s, 1H) 7.34-7.06 (m, 6H), 4.10 (q, 2H, J=7.0 Hz), 3.41 (s, 2H), 1.52 (s, 6H), 1.13 (t, 3H, J=7.0 Hz).

3-Bromo-benzoic acid isopropyl ester (Intermediate 135)

A solution of 3-bromo benzoic acid (Aldrich, 2.4 g, 11.9 mmol) in isopropanol (20 mL) was treated with 1 mL of concentrated sulfuric acid and the resulting reaction mixture was refluxed overnight. The reaction mixture was then cooled to ambient temperature and diluted with water and extracted with diethyl ether. The organic phase was dried over anhydrous sodium sulfate, filtered and evaporated to an oil that was subjected to flash column chromatography over silica gel (230-400 mesh) using 10% ethyl acetate in hexane as the eluent to afford the title compound as an oil (2.54 g, 88%).

¹H NMR (300 MHz, CDCl₃): δ 8.14(s, 1H), 7.95(d, J=7.6 Hz, 1H), 7.64(d, J=7.6 Hz, 1H), 7.29(t, J=7.6 Hz, 1H), 5.24 (hept, J=6.1 Hz, 1H), 1.35(d, J=6.1 Hz, 6H).

3-Trimethylsilanylethynyl-benzoic acid isopropyl ester (Intermediate 136)

Following General Procedure D and using 3-bromo-benzoic acid isopropyl ester (Intermediate 135, 1.25 g, 5.14 mmol), triethyl amine (12 mL), copper(I)iodide (0.078 g, 0.41 mmol), trimethylsilyl acetylene (4 mL, 28.16 mmol) and dichlorobis(triphenylphosphine)palladium(II) (0.288 g, 0.41 mmol) followed by flash column chromatography over silica gel (230-400 mesh) using 3% ethyl acetate in hexane as the eluent, the title compound (1.25 g, 94%) was obtained as an orange oil.

¹H NMR (300 MHz, CDCl₃): δ 8.09(s, 1H), 7.96(d, J=7.6 Hz, 1H), 7.59 (d, J=7.6 Hz, 1H), 7.35(t, J=7.6 Hz, 1H), 5.24(hept, J=6.1 Hz, 1H), 1.35(d, J=6.1 Hz, 6H), 0.25(s, 9H).

3-Ethynyl-benzoic acid isopropyl ester (Intermediate 137)

A solution of 3-trimethylsilanylethynyl-benzoic acid isopropyl ester (Intermediate 136, 0.6 g, 2.3 mmol) in anhydrous tetrahydrofuran (3 mL) was treated with a 1M solution of tetra-n-butyl ammonium fluoride in tetrahydrofuran (4.6 mL, 4.6 mmol) and the resulting reaction mixture was stirred in an ice bath for 5 min. Water was added and the reaction mixture was extracted with ethyl acetate. The organic phase was washed with water and brine, dried over anhydrous sodium sulfate, filtered and evaporated to an oil that was purified by flash column chromatography using 5%-30% ethyl acetate in hexane as the eluent to afford the title compound as a solid (0.33 g, 76%).

¹H NMR (300 MHz, CDCl₃): δ 8.15(s, 1H), 8.01(d, J=7.6 Hz, 1H), 7.64 (d, J=7.6 Hz, 1H), 7.39(t, J=7.6 Hz, 1H), 5.25(hept, J=6.1 Hz, 1H), 3.13(s, 1H), 1.37(d, J=6.1 Hz, 6H).

3-(4-Ethoxycarbonylmethyl-3-fluoro-phenylethynyl)-benzoic acid isopropyl ester (Intermediate 138)

Following General Procedure B and using 3-ethynyl-benzoic acid isopropyl ester (Intermediate 137, 0.099 g, 0.53 mmol), 2-fluoro-4-iodo phenyl acetic acid ethyl ester (0.164 g, 0.53 mmol), triethyl amine (3 mL), copper(I)iodide (0.01 g, 0.05 mmol) and dichlorobis(triphenylphosphine)palladium (II) (0.035 g, 0.5 mmol) followed by flash column chromatography over silica gel (230-400 -mesh) using 7-10% ethyl acetate in hexane as the eluent, the title compound was obtained as a light orange oil (0.08 g, 92%).

¹H NMR (300 MHz, CDCl₃): δ 8.17(s, 1H), 8.01(d, J=7.6 Hz, 1H), 7.67 (d, J=7.6 Hz, 1H), 7.42(t, J=7.6 Hz, 1H), 7.29-7.22(m, 3H), 5.21(hept, J=6.1 Hz, 1H), 4.18(q, J=7.1 Hz, 2H), 3.68(s, 2H), 1.38(d, J=6.1 Hz, 6H), 1.26(t, J=7.1 Hz, 3H).

3-(4-Carboxymethyl-3-fluoro-phenylethynyl)-benzoic acid isopropyl ester (Compound 44)

A solution of 3-(4-ethoxycarbonylmethyl-3-fluoro-phenylethynyl)-benzoic acid isopropyl ester (Intermediate 138, 0.1 g, 0.27 mmol) in isopropanol (2 mL) and tetrahydrofuran (2 mL) was treated with a 2M solution of lithium hydroxide (1 mL, 2 mmol). After 40 min. at ambient temperature, the reaction mixture was concentrated in vacuo a bit, neutralized with 10% hydrochloric acid and the solid formed was filtered, washed with water and dried to afford the title compound (0.09 g, 97%).

¹H NMR (300 MHz, CDCl₃): δ 8.18(s, 1H), 8.02(d, J=7.6 Hz, 1H), 7.68(d, J=7.6 Hz, 1H), 7.44(t, J=7.6 Hz, 1H), 7.31-7.24(m, 3H), 5.27(hept, J=6.1 Hz, 1H), 3.74(s, 2H), 1.39(d, J=6.1 Hz, 6H).

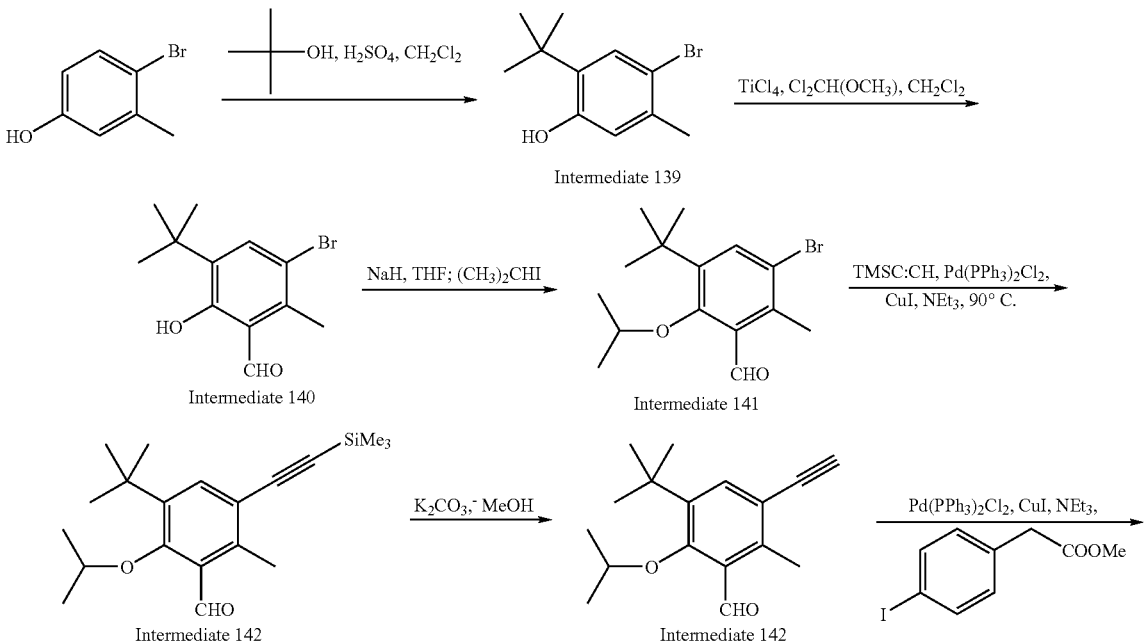

Reaction Scheme 24

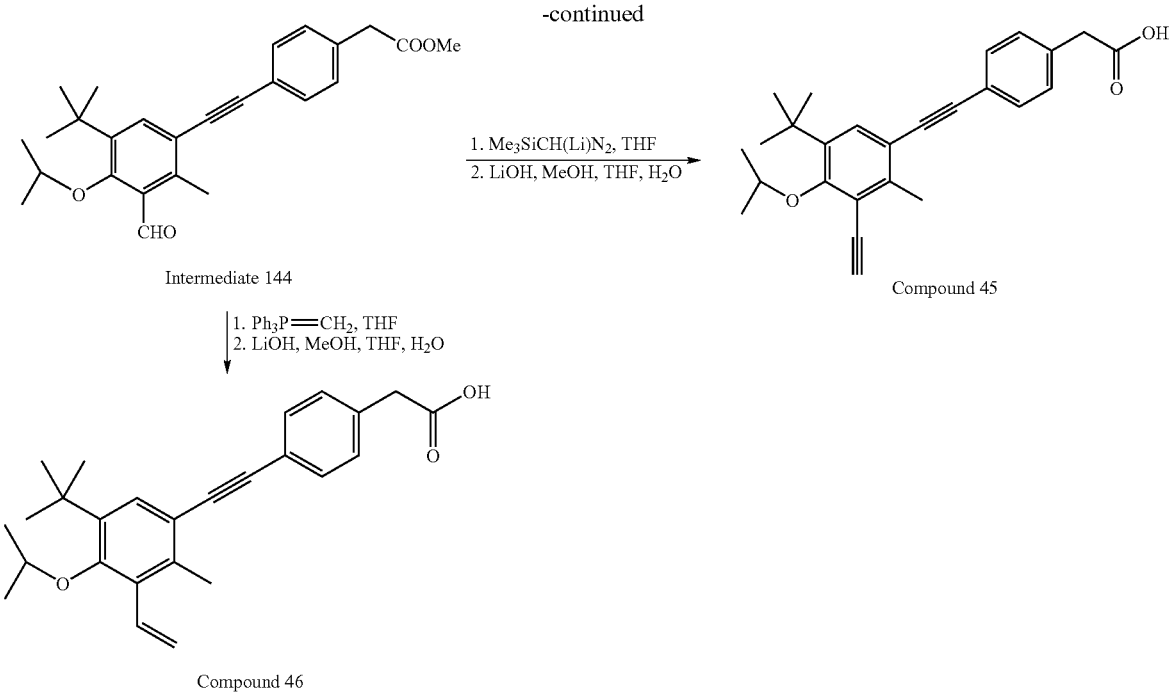

Intermediate 144

Compound 45

Compound 46

4-Bromo-2-tert-butyl-5-methyl-phenol (Intermediate 139)

A solution of 4-bromo-3-methylphenol (Aldrich, 5.1 g, 27.3 mmol) in anhydrous dichloromethane (50 mL) was treated with 2-methyl-2-propanol (15 mL) and concentrated sulfuric acid (3 mL) and stirred at ambient temperature for 3 months. The volatiles were evaporated in vacuo, the residue was diluted with water and extracted with diethyl ether. The combined organic phase was dried over anhydrous magnesium sulfate, filtered and evaporated in vacuo to an oil. Flash column chromatography using 3-5% ethyl acetate in hexane as the eluent afforded the title compound as a deep yellow oil (3.42 g, 51%). It was used as such for the next step.

$^1$H NMR (300 MHz, CDCl$_3$): δ 7.40 (s, 1H), 6.56 (s, 1H), 5.23 (s, 1H), 2.30 (s, 3H), 1.41 (s, 9H).

3-Bromo-5-tert-butyl-6-hydroxy-2-methyl-benzaldehyde (Intermediate 140)

A stirred, cooled (ice bath) solution of 4-bromo-2-tert-butyl-5-methyl-phenol (Intermediate 139, 0.85 g, 3.5 mmol) in anhydrous dichloromethane (7 mL) was treated with titanium tetrachloride (0.64 mL, 5.8 mmol) followed by ☐☐-dichloro methyl ether (0.3 g, 3.5 mmol). The reaction mixture was allowed to warm to ambient temperature for 4 h. The reaction mixture was diluted with diethyl ether, washed with brine (×1) and dried over anhydrous sodium sulfate, filtered and evaporated in vacuo to a residue which was subjected to flash column chromatography over silica gel (230-400 mesh) using 1% ethyl acetate in hexane to afford the title compound as a yellow solid (0.58 g, 61%).

$^1$H NMR (300 MHz, CDCl$_3$): δ 12.89 (s, 1H), 10.32 (s, 1H), 7.60 (s, 1H), 2.63 (s, 3H), 1.38 (s, 9H).

3-Bromo-5-tert-butyl-6-isopropoxy-2-methyl-benzaldehyde (Intermediate 141)

A stirred, cooled (ice bath) solution of 3-bromo-5-tert-butyl-6-hydroxy-2-methyl-benzaldehyde (Intermediate 140, 0.58 g, 2.14 mmol) in anhydrous N,N-dimethylformamide (10 mL) was treated with sodium hydride (0.34 g of 60% suspension in mineral oil, 8.56 mmol). After 30 minutes, 2-iodopropane (1.3 mL, 12.84 mmol) was added and the reaction mixture was heated at 75° C. overnight. The reaction mixture was then cooled and poured into iced water and extracted with diethyl ether. The organic extract was then washed with water and brine, dried over anhydrous magnesium sulfate, filtered and evaporated in vacuo to an oil. Flash column chromatography using 2-4% ethyl acetate in hexane as the eluent afforded the title product (0.43 g, 64%).

$^1$H NMR (300 MHz, CDCl$_3$): δ 10.23 (s, 1H), 7.68 (s, 1H), 4.34 (heptet, 1H, J=6.2 Hz), 2.57 (s, 3H), 1.40 (s, 9H), 1.28 (d, 6H, J=6.2 Hz).

3-tert-Butyl-2-isopropoxy-6-methyl-5-trimethylsilanylethynyl-benzaldehyde (Intermediate 142)

Following General Procedure D and using 3-bromo-5-tert-butyl-6-isopropoxy-2-methyl-benzaldehyde (Intermediate 141, 0.43 g, 1.37 mmol), triethyl amine, copper(I)iodide (0.021 g, 0.11 mmol), trimethylsilyl acetylene (1 mL), and dichlorobis(triphenylphosphine)palladium(II) (0.077 g, 0.11 mmol) followed by flash column chromatography over silica gel (230-400 mesh) using 2% ethyl acetate in hexane as the eluent, the title compound was obtained (0.45 g, ~100%).

$^1$H NMR (300 MHz, CDCl$_3$): δ 10.10 (s, 1H), 7.41 (s, 1H), 4.19 (heptet, 1H, J=6.1 Hz), 2.44 (s, 3H), 1.21 (s, 9H), 1.09 (d, 6H, J=6.1 Hz), 0.08 (s, 9H).

3-tert-Butyl-5-ethynyl-2-isopropoxy-6-methyl-benzaldehyde (Intermediate 143)

A solution of 3-tert-butyl-2-isopropoxy-6-methyl-5-trimethylsilanylethynyl-benzaldehyde (Intermediate 142, 0.45 g, 1.37 mmol) in methanol (5 mL) and tetrahydrofuran was treated with potassium carbonate (0.2 g, 1.45 mmol) and the resulting reaction mixture was stirred at ambient temperature for 3 h. The reaction mixture was evaporated in vacuo and the residue was extracted with diethyl ether and washed with water and brine. The organic phase was dried, filtered and evaporated in vacuo to afford the title compound (0.35 g, 90%).

$^1$H NMR (300 MHz, CDCl$_3$): δ 10.28 (s, 1H), 7.63 (s, 1H), 4.38 (heptet, 1H, J=6.2 Hz), 3.49 (s, 1H), 2.63 (s, 3H), 1.39 (s, 9H), 1.29 (d, 6H, J=6.2 Hz).

[4-(5-tert-Butyl-3-formyl-4-isopropoxy-2-methyl-phenylethynyl)-phenyl]-acetic acid methyl ester (Intermediate 144)

Following General Procedure B and using 3-tert-butyl-5-ethynyl-2-isopropoxy-6-methyl-benzaldehyde (Intermediate 143, 0.35 g, 1.35 mmol), 4-iodo phenyl acetic acid methyl ester (0.374 g, 1.35 mmol), triethyl amine (8 mL), copper(I) iodide (0.02 g, 0.1 mmol) and dichlorobis(triphenylphosphine)palladium(II) (0.072 g, 0.1 mmol) followed by flash column chromatography over silica gel (230-400 mesh) using 3-5% ethyl acetate in hexane as the eluent, the title compound was obtained as a white solid (0.37 g, 75%).

$^1$H NMR (300 MHz, CDCl$_3$): δ 10.29 (s, 1H), 7.65 (s, 1H), 7.48 (d, 2H, J=8.2 Hz), 7.53 (d, 2H, J=8.2 Hz), 4.38 (heptet, 11H, J=6.1 Hz), 3.68 (s, 3H), 3.62 (s, 2H), 2.68 (s, 3H), 1.41 (s, 9H), 1.27 (d, 6H, J=6.1 Hz).

[4-(5-tert-Butyl-3-ethynyl-4-isopropoxy-2-methyl-phenylethynyl)-phenyl]-acetic acid methyl ester (Intermediate 145)

Anhydrous tetrahydrofuran (3 mL) was added to a 2M solution of trimethylsilyl diazomethane in hexanes (0.37 mL, 0.74 mmol) and the resulting reaction mixture was cooled to −78° C. A solution of 1.6M n-butyl lithium in hexanes (0.5 mL, 0.8 mmol) was added followed, after 30 minutes, by a solution of [4-(5-tert-butyl-3-formyl-4-isopropoxy-2-methyl-phenylethynyl)-phenyl]-acetic acid methyl ester (Intermediate 144, 0.2 g, 0.49 mmol) in anhydrous tetrahydrofuran and the resulting reaction mixture was stirred at −78° C. for 1 h and at 0° C. for 40 minutes. The reaction mixture was then quenched with saturated aqueous ammonium chloride solution and extracted with diethyl ether. The organic phase was washed with brine, dried over anhydrous magnesium sulfate, filtered and evaporated in vacuo to a residue that was subjected to flash column chromatography over silica gel (230-400 mesh) using 2.5-4% ethyl acetate in hexane as the eluent followed by preparative normal phase HPLC using 5% ethyl acetate in hexane as the mobile phase to afford the title product as a colorless oil (0.023 g, 11.6%). $^1$H NMR (300 MHz, CDCl$_3$): δ 7.49 (d, 2H, J=8.0 Hz), 7.44 (s, 1H), 7.26 (d, 2H, J=8.0 Hz), 5.76 (heptet, 1H, J=6.1 Hz), 3.70 (s, 3H), 3.64 (s, 2H), 3.58 (s, 1H), 2.58 (s, 3H), 1.39 (s, 9H), 1.31 (d, 6H, J=6.1 Hz).

[4-(5-tert-Butyl-3-ethynyl-4-isopropoxy-2-methyl-phenylethynyl)-phenyl]-acetic acid (Compound 45)

A solution of [4-(5-tert-butyl-3-ethynyl-4-isopropoxy-2-methyl-phenylethynyl)-phenyl]-acetic acid methyl ester (Intermediate 145, 0.023 g, 0.057 mmol) in methanol (1.5 mL) and tetrahydrofuran (1.5 mL) was treated with 1M lithium hydroxide (0.5 mL, 1 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.020 g, 91%).

$^1$H NMR (300 MHz, CDCl$_3$): δ 7.47 (d, 2H, J=8.0 Hz), 7.43 (s, 1H), 7.24 (d, 2H, J=8.0 Hz), 5.75 (heptet, 1H, J=6.1 Hz), 3.62 (s, 2H), 3.57 (s, 1H), 2.57 (s, 3H), 1.38 (s, 9H), 1.30 (d, 6H, J=6.1 Hz).

[4-(5-tert-Butyl-4-isopropoxy-2-methyl-3-vinyl-phenyl ethynyl)-phenyl]-acetic acid methyl ester (Intermediate 146)

A solution of methylidene triphenyl phosphorane [5 mL of 0.1M solution, 0.5 mmol, generated from methyl triphenylphosphonium bromide (2.5 g, 7 mmol) and 1.6M n-butyllithium solution in hexanes (2.9 mL, 4.7 mmol) in 50 mL of tetrahydrofuran] was added to a solution of [4-(5-tert-butyl-3-formyl-4-isopropoxy-2-methyl-phenylethynyl)-phenyl]-acetic acid methyl ester (Intermediate 144, 0.052 g, 0.13 mmol) in tetrahydrofuran (1 mL). After 1 h the reaction mixture was quenched with water and extracted with ethyl acetate. The organic phase was washed with water and brine, dried over anhydrous sodium sulfate, filtered and evaporated in vacuo to a clear oil that after flash column chromatography over silica gel (230-400 mesh) using 5% ethyl acetate in hexane as the eluent afforded the title compound (0.02 g, 39%).

$^1$H NMR (300 MHz, CDCl$_3$): δ 7.48 (d, 2H, J=7.9 Hz), 7.39 (s, 1H), 7.25 (d, 2H, =7.9 Hz), 6.73 (dd, 1H, J=11.4, 17.9 Hz), 5.49 (dd, 1H, J=2.0, 11.4 Hz), 5.37 (dd, 1H, J=2.1, 17.9 Hz), 4.93 (heptet, 1H, J=6.4 Hz), 3.70 (s, 3H), 3.63 (s, 2H), 2.44 (s, 3H), 1.40 (s, 9H), 1.17 (d, 6H, J=6.4 Hz).

[4-(5-tert-Butyl-4-isopropoxy-2-methyl-3-vinyl-phenylethynyl)-phenyl]-acetic acid (Compound 46)

A solution of [4-(5-tert-butyl-4-isopropoxy-2-methyl-3-vinyl-phenylethynyl)-phenyl]-acetic acid methyl ester (Intermediate 146, 0.02 g, 0.049 mmol) in methanol (1.5 mL) and tetrahydrofuran (1.5 mL) was treated with 1M lithium hydroxide (0.5 mL, 1 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.020 g, 100%).

$^1$H NMR (300 MHz, CDCl$_3$): δ 7.48 (d, 2H, J=8.2 Hz), 7.39 (s, 1H), 7.24 (d, 2H, J=8.2 Hz), 6.72 (dd, 1H, J=11.4, 17.9 Hz), 5.49 (dd, 1H, J=2.0, 11.4 Hz), 5.37 (dd, 1H, J=2.1, 17.9 Hz), 4.92 (heptet, 1H, J=6.2 Hz), 3.64 (s, 2H), 2.43 (s, 3H), 1.40 (s, 9H), 1.17 (d, 6H, J=6.2 Hz).

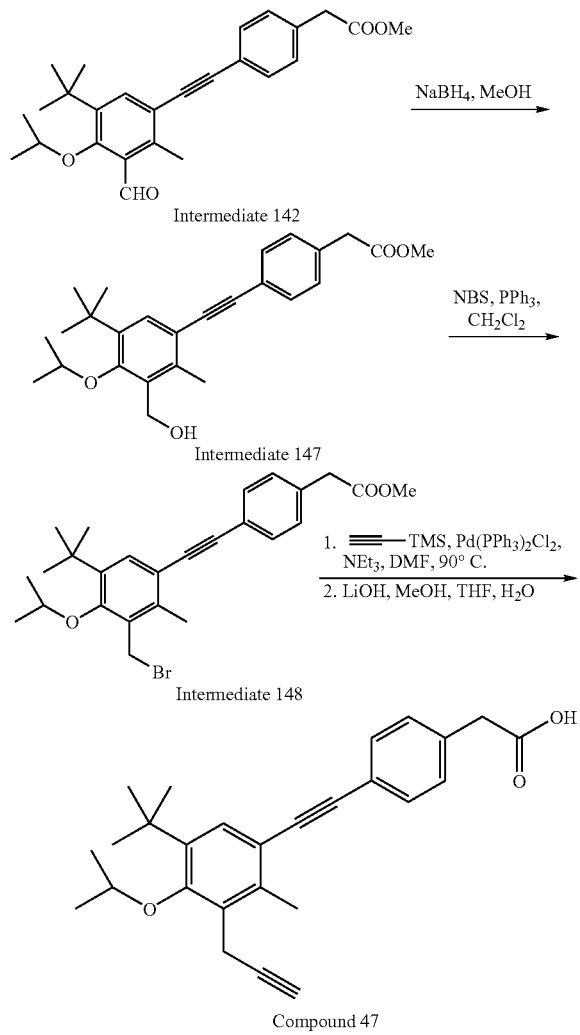

Reaction Scheme 25

Intermediate 142

Intermediate 147

Intermediate 148

Compound 47

[4-(5-tert-Butyl-3-hydroxymethyl-4-isopropoxy-2-methyl-phenylethynyl)-phenyl]-acetic acid methyl ester (Intermediate 147)

A stirred, cooled (ice bath) solution of [4-(5-tert-butyl-3-formyl-4-isopropoxy-2-methyl-phenylethynyl)-phenyl]-acetic acid methyl ester (Intermediate 142, 0.172 g, 0.42 mmol) in methanol (4 mL) was treated with sodium borohydride (0.02 g, 0.51 mmol) and the resulting reaction mixture was stirred for 1.5 h. The reaction mixture was quenched with water and extracted with diethyl ether. The organic phase was washed with water (×1) and brine (×1), dried over anhydrous sodium sulfate, filtered and evaporated in vacuo to a residue that was subjected to flash column chromatography over silica gel (230-400 mesh) using 15-20% ethyl acetate in hexane as the eluent to afford the title product as a white solid (0.15 g, 88%).

$^1$H NMR (300 MHz, CDCl$_3$): δ 7.48 (d, 2H, J=8.5 Hz), 7.47 (s, 1H), 7.25 (d, 2H, J=8.5 Hz), 4.74 (br s, 2H), 4.74-4.60 (m, 1H), 3.69 (s, 3H), 3.63 (s, 2H), 2.60 (s, 3H), 1.40 (s, 9H), 1.27 (d, 6H, J=6.2 Hz).

[4-(3-Bromomethyl-5-tert-butyl-4-isopropoxy-2-methyl-phenylethynyl)-phenyl]-acetic acid methyl ester (Intermediate 148)

A stirred, cooled (ice bath) solution of [4-(5-tert-butyl-3-hydroxymethyl-4-isopropoxy-2-methyl-phenylethynyl)-phenyl]-acetic acid methyl ester (Intermediate 147, 0.15 g, 0.37 mmol) and triphenylphosphine (0.125 g, 0.48 mmol) in anhydrous dichloromethane (5 mL) was treated with N-bromo succinimide (0.085 g, 0.48 mmol) under argon and the resulting reaction mixture was allowed to warm to ambient temperature and stirred overnight. The reaction mixture was quenched with dilute, aqueous sodium bicarbonate solution and extracted with diethyl ether. The organic phase was washed with water (×1) and brine (×1), dried over anhydrous magnesium sulfate, filtered and evaporated in vacuo to a residue that on flash column chromatography over silica gel (230-400 mesh) using 4-5% ethyl acetate in hexane as the eluent afforded the title compound (0.12 g, 69%) as a colorless oil. It was used as such for the next step.

{4-[5-tert-Butyl-4-isopropoxy-2-methyl-3-(3-trimethylsilanyl-prop-2-ynyl)-phenylethynyl]-phenyl}-acetic acid methyl ester (Intermediate 149)

A solution of [4-(3-bromomethyl-5-tert-butyl-4-isopropoxy-2-methyl-phenylethynyl)-phenyl]-acetic acid methyl ester (Intermediate 148, 0.12 g, 0.25 mmol) in triethyl amine (1 mL) and N,N-dimethylformamide (4 mL) was sparged with argon and treated with trimethylsilylacetylene (0.5 mL, 3.5 mmol) and dichlorobis(triphenylphosphine)palladium (II) (0.025 g, 0.036 mmol). The resulting reaction mixture was heated at 85° C. overnight at the end of which it was cooled to ambient temperature and subjected to flash column chromatography over silica gel (230-400 mesh) using 4% ethyl acetate in hexane as the eluent followed by preparative normal phase HPLC using 3% ethyl acetate in hexane as the mobile phase to afford the title compound as an oil (0.038 g, 31%).

$^1$H NMR (300 MHz, CDCl$_3$): δ 7.50 (d, 2H, J=7.9 Hz), 7.48 (s, 1H), 7.26 (d, 2H, J=7.9 Hz), 4.89 (heptet, 1H, J=6.5 Hz), 3.70 (s, 3H), 3.64 (s, 2H), 3.50 (s, 2H), 2.57 (s, 3H), 1.40 (s, 9H), 1.27 (d, 6H, J=6.5 Hz), 0.12 (s, 9H).

[4-(5-tert-Butyl-4-isopropoxy-2-methyl-3-prop-2-ynyl-phenylethynyl)-phenyl]-acetic acid (Compound 47)

A solution of {4-[5-tert-butyl-4-isopropoxy-2-methyl-3-(3-trimethylsilanyl-prop-2-ynyl)-phenylethynyl]-phenyl}-acetic acid methyl ester (Intermediate 149, 0.038 g, 0.078 mmol) in methanol (1.5 mL) and tetrahydrofuran (1.5 mL) was treated with 2M lithium hydroxide (1 mL, 2 mmol) and the resulting reaction mixture was stirred at ambient temperature for 1.5 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.032 g, 98%). $^1$H NMR (300 MHz, CDCl$_3$): δ 7.50 (d, 2H, J=8.1 Hz), 7.43 (s, 1H), 7.27 (d, 2H, J=8.1 Hz), 4.82 (heptet, 1H, J=6.4 Hz), 3.67 (s, 2H), 3.48 (d, 2H, J=2.5 Hz), 2.58 (s, 3H), 1.39 (s, 9H), 1.28 (d, 6H, J=6.4 Hz).

Reaction Scheme 26

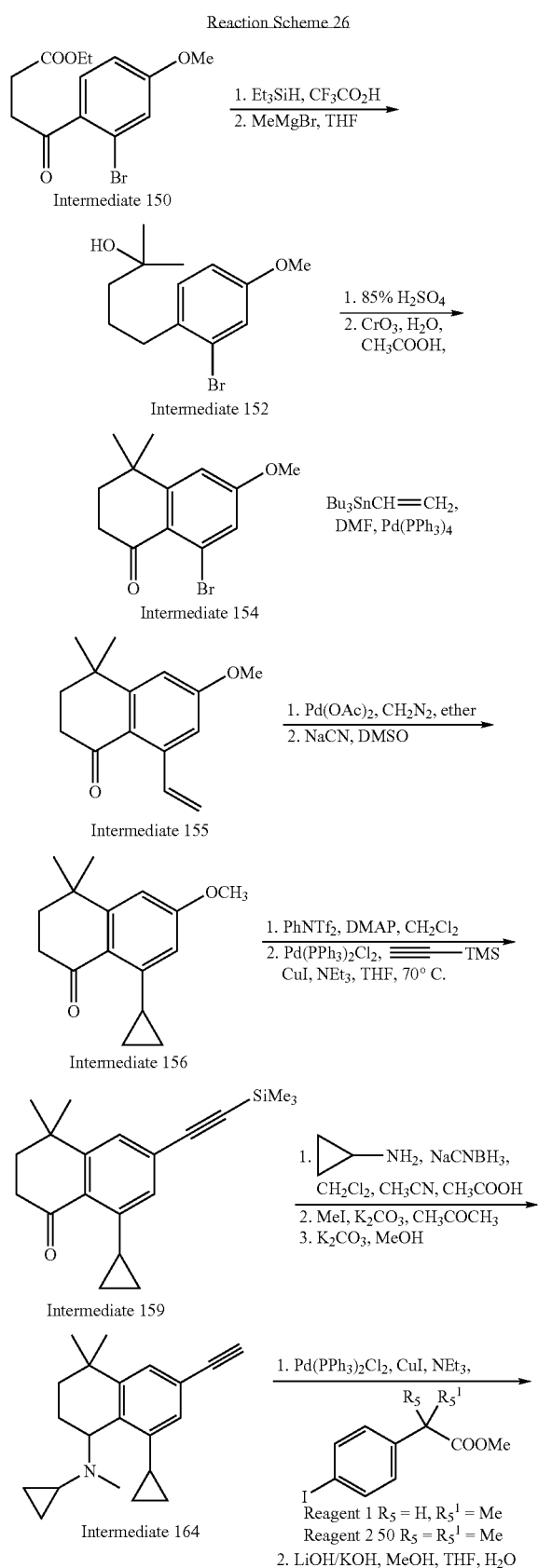

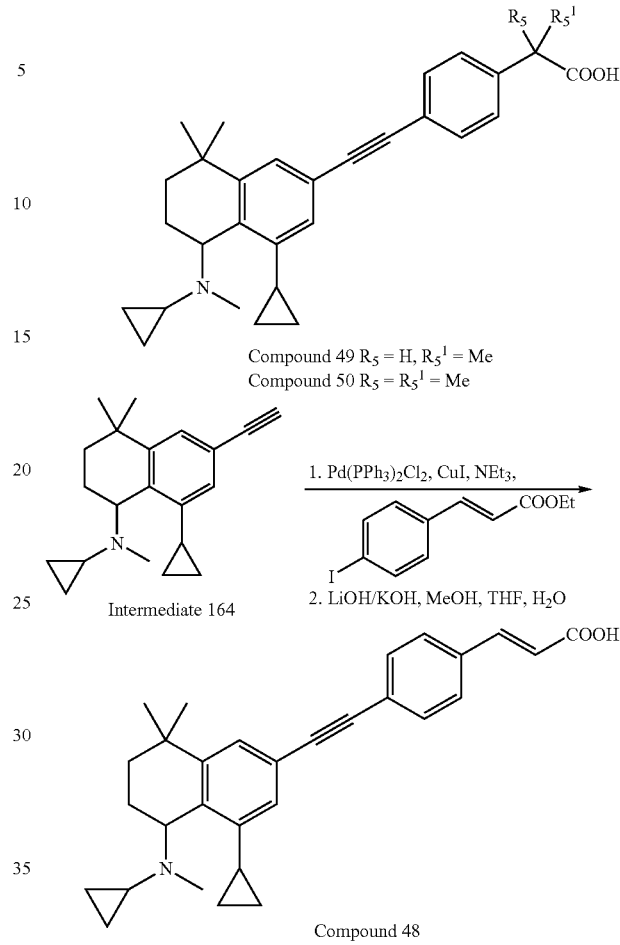

4-(2-Bromo-4-methoxy-phenyl)-4-oxo-butyric acid ethyl ester (Intermediate 150)

A stirred, cooled (−30° C.) solution of 3-bromo anisole (18.7 g, 100 mmol) and ethyl succinyl chloride (21 mL, 150 mmol) in anhydrous dichloromethane (200 mL) was treated with aluminum chloride (26.6 g, 200 mmol) and the reaction mixture was allowed to warm to ambient temperature and stirred overnight. The reaction mixture was poured into water and extracted with dichloromethane (×2). The combined organic phase was washed with brine, dried over anhydrous sodium sulfate, filtered and evaporated in vacuo to a brown oil. A solid separated out on standing. The supernatant liquid was decanted and the solid was washed with 1:3 dichloromethane: hexane and dried to afford the isomer 4-(4-bromo-2-methoxy-phenyl)-4-oxo-butyric acid ethyl ester. The combined mother liquor and washings was evaporated to a brown oil that was subjected to flash column chromatography over silica gel (230-400 mesh) using 15% ethyl acetate in hexane as the eluent to afford the isomer 4-(4-bromo-2-methoxy-phenyl)-4-oxo-butyric acid ethyl ester (overall 12 g, 38%), and the title compound (11.4 g, 36%) and a 1:1 mixture of both (2 g, 6.3%).

$^1$H NMR (300 MHz, CDCl$_3$): δ 7.59 (d, 1H, J=8.8 Hz), 7.14 (d, 1H, J=2.6 Hz), 6.87 (dd, 1H, J=2.6, 8.8 Hz), 4.14 (q,

2H, J=7.0 Hz), 3.83 (s, 3H), 3.23 (t, 2H, J=6.4 Hz), 2.74 (t, 2H, J=6.4 Hz), 1.25 (t, 3H, J=7.0 Hz).

4-(2-Bromo-4-methoxy-phenyl)-butyric acid ethyl ester (Intermediate 151)

A solution of 4-(2-bromo-4-methoxy-phenyl)-4-oxo-butyric acid ethyl ester (Intermediate 150, 6.45 g, 20.5 mmol) in trifluoroacetic acid (32 mL, 409 mmol) was treated with triethylsilane (14.4 mL, 90 mmol) and the resulting reaction mixture was heated at 55° C. for 3 h. The reaction mixture was then cooled to ambient temperature, neutralized with solid sodium bicarbonate, diluted with water and extracted with diethyl ether. The organic phase was washed with water and brine, dried over anhydrous magnesium sulfate, filtered and evaporated in vacuo to afford the title compound (5.4 g, 88%) as a colorless oil.

$^1$H NMR (300 MHz, CDCl$_3$): δ 7.11 (d, 1H, J=8.2 Hz), 7.08 (d, 1H, J=2.6 Hz), 6.79 (dd, 1H, J=2.6, 8.2 Hz), 4.13 (q, 2H, J=7.3 Hz), 3.76 (s, 3H), 2.71 (t, 2H, J=7.6 Hz), 2.34 (t, 2H, J=7.6 Hz), 1.92 (quintet, 2H, J=7.6 Hz), 1.26 (t, 3H, J=7.3 Hz).

5-(2-Bromo-4-methoxy-phenyl)-2-methyl-pentan-2-ol (Intermediate 152)

A stirred, cooled (−10° C.) solution of 4-(2-bromo-4-methoxy-phenyl)-butyric acid ethyl ester (Intermediate 151, 5.4 g, 18 mmol) in anhydrous tetrahydrofuran (100 mL) was treated with a 3M solution of methyl magnesium bromide (16 mL, 48 mmol) and the resulting reaction mixture was allowed to warm to ambient temperature over 3 h. It was quenched with saturated, aqueous ammonium chloride solution, diluted with water and extracted with diethyl ether. The organic phase was washed with water and brine, dried over anhydrous magnesium sulfate, filtered and evaporated in vacuo to afford the title product as a viscous oil (5.16 g, ~100%).

$^1$H NMR (300 MHz, CDCl$_3$): δ 7.11 (d, 1H, J=8.5 Hz), 7.08 (d, 1H, J=2.6 Hz), 6.78 (dd, 1H, J=2.6, 8.5 Hz), 3.77 (s, 3H), 2.67 (t, 2H, J=7.3 Hz), 1.69-1.43 (m, 4H), 1.21 (s, 6H).

5-Bromo-2-methoxy-1,1-dimethyl-1,2,3,4-tetrahydro-naphthalene (Intermediate 153)

5-(2-Bromo-4-methoxy-phenyl)-2-methyl-pentan-2-ol (Intermediate 152, 5.16 g, 17.9 mmol) was treated with 85% sulfuric acid (50 mL) at ambient temperature. After 30 minutes, the reaction mixture was diluted with cold water and extracted with diethyl ether. The organic phase was washed with water and brine, dried over anhydrous magnesium sulfate, filtered and evaporated in vacuo to afford the title product (4.63 g, 96%) as a pale yellow oil.

$^1$H NMR (300 MHz, CDCl$_3$): δ 6.96 (d, 1H, J=2.6 Hz), 6.86 (d, 1H, J=2.6 Hz), 3.76 (s, 3H), 2.68 (t, 2H, J=6.7 Hz), 1.83-1.75 (m, 2H), 1.62-1.58 (m, 2H), 1.26 (s, 6H).

8-Bromo-6-methoxy-4,4-dimethyl-3,4-dihydro-2H-naphthalen-1-one (Intermediate 154)

A solution of 5-bromo-2-methoxy-1,1-dimethyl-1,2,3,4-tetrahydro-naphthalene (Intermediate 153, 4.6 g, 17.1 mmol) in glacial acetic acid (20 mL) was cooled to 0° C. and treated with a solution of chromium trioxide (5.5 g, 55 mmol) in acetic acid and water (20 mL each). The reaction mixture was then allowed to warm to ambient temperature and stirred for 24 h. It was diluted with water and extracted with diethyl ether (×2). The combined organic phase was washed with water (×3), saturated aqueous sodium bicarbonate (×1) and brine (×1), dried over anhydrous magnesium sulfate, filtered and evaporated in vacuo to afford the title compound (3.9 g, 81%) as a yellow oil.

$^1$H NMR (300 MHz, CDCl$_3$): δ 7.09 (d, 1H, J=2.6 Hz), 6.87 (d, 1H, J=2.6 Hz), 3.85 (s, 3H), 2.71 (t, 2H, J=7.0 Hz), 1.96 (t, 2H, J=7.0 Hz), 1.35 (s, 6H).

6-Methoxy-4,4-dimethyl-8-vinyl-3,4-dihydro-2H-naphthalen-1-one (Intermediate 155)

A solution of 8-bromo-6-methoxy-4,4-dimethyl-3,4-dihydro-2H-naphthalen-1-one (Intermediate 154, 2.83 g, 10 mmol) and tributyl(vinyl)tin (3 mL, 10 mmol) in anhydrous N,N-dimethyl formamide (30 mL) was sparged with argon and treated with tetrakis(triphenylphosphine)palladium (0) (0.3 g, 0.26 mmol). The resulting reaction mixture was heated to 91° C. for two days at the end of which it was cooled to ambient temperature, diluted with water and extracted with diethyl ether (×2). The combined organic phase was washed with water (×1), and brine (×1), dried over anhydrous magnesium sulfate, filtered and evaporated to a pale yellow oil. Flash chromatography using 15% ethyl acetate in hexane as the eluent afforded the title product (1.7 g, 73%) as a pale yellow oil.

$^1$H NMR (300 MHz, CDCl$_3$): δ 7.50 (dd, 1H, J=10.8, 17.3 Hz), 6.85 (s, 2H), 5.50 (dd, 1H, J=1.4, 17.3 Hz), 5.28 (dd, 1H, J=1.4, 10.8 Hz), 3.88 (s, 3H), 2.68 (t, 2H, J=6.7 Hz), 1.95 (t, 2H, J=6.7 Hz), 1.35 (s, 6H).

8-Cyclopropyl-6-methoxy-4,4-dimethyl-3,4-dihydro-2H-naphthalen-1-one (Intermediate 156)

A stirred, cooled (−40° C.) solution of 6-methoxy-4,4-dimethyl-8-vinyl-3,4-dihydro-2H-naphthalen-1-one (Intermediate 155, 51.7 g, 7.4 mmol) in diethyl ether (10 mL) was treated with a solution of diazomethane in ether (40 mmol in 50 mL of ether) followed by palladium(II)acetate (0.08 g) and the resulting reaction mixture was warmed to −25° C. when effervescence was observed. The reaction mixture was then filtered through a plug of silica and the filtrate was evaporated to afford a dark brown residue that was subjected to flash column chromatography over silica gel (23-400 mesh) using 20% ethyl acetate in hexane as the eluent to afford the title product as a pale yellow solid (1.5 g, 83%).

$^1$H NMR (300 MHz, CDCl$_3$): δ 6.71 (d, 1H, J=2.6 Hz), 6.44 (d, 1H, J=2.6 Hz), 3.82 (s, 3H), 2.98 (m, 1H), 2.69 (t, 2H, J=6.7 Hz), 1.94 (t, 2H, J=6.7 Hz), 1.34 (s, 6H), 1.02-0.88 (m, 2H), 0.65-0.59 (m, 2H).

8-Cyclopropyl-6-hydroxy-3,4-dihydro-2H-naphthalen-1-one (Intermediate 157)

A solution of 8-cyclopropyl-6-methoxy-4,4-dimethyl-3,4-dihydro-2H-naphthalen-1-one (Intermediate 156, 1.5 g, 6.14 mmol) and sodium cyanide (2 g, 40.8 mmol) in anhydrous dimethylsulfoxide (25 mL) was heated at 230° C. overnight under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford a dark brown oil. Flash column chromatography on silica gel (230-400 mesh) using 25% ethyl acetate in hexane as the eluent afforded the title compound as a solid (1.1 g, 78%).

¹H NMR (300 MHz, CD₃COCD₃): δ 8.14 (s, 1H), 6.75 (d, 1H, J=2.4 Hz), 6.40 (d, 1H, J=2.4 Hz), 3.02 (m, 1H), 2.62 (t, 2H, J=6.8 Hz), 1.94 (t, 2H, J=6.8 Hz), 1.33 (s, 6H), 0.93-0.89 (m, 2H), 0.59-0.55 (m, 2H).

Trifluoro-methanesulfonic acid 4-cyclopropyl-8,8-dimethyl-5-oxo-5,6,7,8-tetrahydro-naphthalen-2yl ester (Intermediate 158)

A solution of 8-cyclopropyl-6-hydroxy-4,4-dimethyl-3,4-dihydro-2H-naphthalen-1-one (Intermediate 157, 1.1 g, 4.78 mmol) and 4-dimethylaminopyridine (1.22 g, 10 mmol) in anhydrous dichloromethane (20 mL) was treated 2-[N,N-bis(trifluoromethylsulfonyl)amino]-5-chloro-pyridine (2.07 g, 5.26 mmol) under argon at ambient temperature. After 3.5 h, the reaction mixture was subjected to flash column chromatography on silica gel (230-400 mesh) using 10% ethyl acetate in hexane as the eluent to afford the title compound as solid (1.76 g, 100%).

¹H NMR (300 MHz, CDCl₃): δ 7.10 (d, 1H, J=2.3 Hz), 6.78 (d, 1H, J=2.3 Hz), 2.90 (m, 1H), 2.78 (t, 2H, J=7.0 Hz), 2.01 (t, 2H, J=7.0 Hz), 1.38 (s, 6H), 1.10-1.04 (m, 2H), 0.67-0.62 (m, 2H).

8-Cyclopropyl-4,4-dimethyl-6-(trimethylsilanyl) ethynyl-3,4-dihydro-2H-naphthalen-1-one (Intermediate 159)

Following General Procedure B and using trifluoro-methanesulfonic acid 4-cyclopropyl-8,8-dimethyl-5-oxo-5,6,7,8-tetrahydro-naphthalen-2yl ester (Intermediate 158, 1.09 g, 3 mmol), triethyl amine (5 mL), tetrahydrofuran (5 mL), copper (I)iodide (0.12 g, 0.6 mmol), dichlorobis(triphenylphosphine)palladium(II) (0.42 g, 0.6 mmol) and (trimethylsilyl)acetylene (2.2 mL, 15 mmol) followed by flash column chromatography over silica gel (230-400 mesh) using 7% ethyl acetate in hexane as the eluent, the title compound was obtained as an orange oil (1.05 g, quantitative).

¹H NMR (300 MHz, CDCl₃): δ 7.29 (d, 1H, J=1.2 Hz), 6.98 (d, 1H, J=1.2 Hz), 2.81 (m, 1H), 2.72 (t, 2H, J=6.7 Hz), 1.95 (t, 2H, J=6.7 Hz), 1.34 (s, 6H), 1.01-0.95 (m, 2H), 0.66-0.61 (m, 2H), 0.26 (s, 9H).

8-Cyclopropyl-4,4-dimethyl-6-ethynyl-1-tetralone (Intermediate 160)

Following General Procedure F and using 8-cyclopropyl-4,4-dimethyl-6-(trimethylsilanyl)ethynyl-1-tetralone (Intermediate 159, 1.05 g, 3.38 mmol), methanol (20 mL) and potassium carbonate (1 g, 14.5 mmol) followed by flash column chromatography using 7% ethyl acetate in hexane as the eluent, the title compound was obtained (0.57 g, 80%) as a pale yellow solid.

¹H NMR (300 MHz, CDCl₃): δ 7.34 (d, 1H, J=2.5 Hz), 7.02 (d, 1H, J=2.5 Hz), 3.19 (s, 1H), 2.83 (m, 1H), 2.74 (t, 2H, J=6.7 Hz), 1.97 (t, 2H, J=6.7 Hz), 1.35 (s, 6H), 1.03-0.86 (m, 2H), 0.66-0.61 (m, 2H).

3-[4-(4-Cyclopropyl-8,8-dimethyl-5-oxo-5,6,7,8-tetrahydro-naphthalen-2-ylethynyl)-phenyl]-acrylic acid ethyl ester (Intermediate 161)

Following General Procedure B and using 8-cyclopropyl-4,4-dimethyl-6-ethynyl-1-tetralone (Intermediate 160, 0.1 g, 0.42 mmol), (E)-3-(4-iodo-phenyl)-acrylic acid ethyl ester (0.13 g, 0.42 mmol), triethyl amine (1 mL), copper(I)iodide (0.02 g, 0.1 mmol) and dichlorobis(triphenylphosphine)palladium(II) (0.070 g, 0.1 mmol) followed by flash column chromatography over silica gel (230-400 mesh), the title compound was obtained (0.12 g, 69%).

¹H NMR (300 MHz, CDCl₃): δ 7.65 (d, 1H, J=15.8 Hz), 7.52 (ABq, 4H, J=8.1 Hz), 7.37 (d, 2H, J=1.5 Hz), 7.05 (d, 1H, J=1.5 Hz), 6.45 (d, 1H, J=15.8 Hz), 4.26 (q, 2H, J=7.2 Hz), 2.88-2.79 (m, 1H), 2.77-2.71 (m, 2H), 2.00-1.92 (m, 2H), 1.36-1.21 (m, 9H), 1.04-0.97 (m, 2H), 0.69-0.59 (m, 2H).

3-{4-[4-Cyclopropyl-5-(cyclopropyl-methyl-amino)-8,8-dimethyl-5,6,7,8-tetrahydro-naphthalen-2-yl-ethynyl]-phenyl}-acrylic acid ethyl ester (Intermediate 162)

Following General Procedure C and using 3-[4-(4-cyclopropyl-8,8-dimethyl-5-oxo-5,6,7,8-tetrahydro-naphthalen-2-ylethynyl)-phenyl]-acrylic acid ethyl ester (Intermediate 161, 0.12 g, 0.29 mmol) in dichloromethane (4 mL) and acetonitrile (2 mL), cyclopropyl amine (1 mL, 14.5 mmol), acetic acid (1 mL) and sodium cyanoborohydride (0.16 g, 2.4 mmol) followed by work up afforded an intermediate as an oil, that was used as such for the next step. The residue (crude 0.18 g) was dissolved in acetone (6 mL) and treated with potassium carbonate (0.28 g, 2 mmol) and methyl iodide (1 mL, 16 mmol). The resulting reaction mixture was stirred at ambient temperature overnight. The volatiles were evaporated in vacuo, the residue was diluted with water and extracted with diethyl ether (×2). The combined organic phase was dried over anhydrous magnesium sulfate, filtered and evaporated to an oil. Flash column chromatography over silica gel (230-400 mesh) followed by preparative normal phase HPLC using 5% ethyl acetate in hexane as the mobile phase afforded the title compound (0.08 g) as a clear oil, which was used as such for the next step.

3-{4-[4-Cyclopropyl-5-(cyclopropyl-methyl-amino)-8,8-dimethyl-5,6,7,8-tetrahydro-naphthalen-2-yl-ethynyl]-phenyl}-acrylic acid (Compound 48)

A solution of 3-{4-[4-cyclopropyl-5-(cyclopropyl-methyl-amino)-8,8-dimethyl-5,6,7,8-tetrahydro-naphthalen-2-yl-ethynyl]-phenyl}-acrylic acid ethyl ester (Intermediate 164, 0.08 g, 0.17 mmol) in methanol (3 mL) and tetrahydrofuran (3 mL) was treated with 2M sodium hydroxide solution (2 mL, 4 mmol) and the resulting reaction mixture was refluxed overnight. The reaction mixture was cooled to ambient temperature, the volatiles were evaporated in vacuo, the residue was diluted with saturated aqueous ammonium chloride solution, and extracted with ethyl acetate (×2). The combined organic extract was dried over anhydrous sodium sulfate, filtered and evaporated in vacuo to a solid. Preparative reverse phase HPLC using 10% water in acetonitrile as the mobile phase afforded the title product as a solid (0.04 g, 50%).

¹H NMR (300 MHz, CDCl₃): δ 7.76 (d, 1H, J=15.8 Hz), 7.54 (Abq, 4H, J=8.8 Hz), 7.38 (d, 1H, J=1.5 Hz), 6.96 (d, 1H, J=1.5 Hz), 6.47 (d, 1H, J=15.8 Hz), 4.31(t, 1H, J=4.7 Hz) 2.27 (s, 3H), 2.40-1.43 (m, 6H), 1.38 (s, 3H), 1.23 (s, 3H), 0.98-0.78 (m, 4H), 0.39-0.13 (m, 4H).

8-Cyclopropyl-5-(cyclopropyl-methyl-amino)-4,4-dimethyl-(2-trimethylsilanyl)ethynyl-1,2,3,4-tetrahydronaphthalene (Intermediate 163)

Following General Procedure C and using 8-cyclopropyl-4,4-dimethyl-6-(trimethylsilanyl)ethynyl-3,4-dihydro-2H-naphthalen-1-one (Intermediate 159, 0.77 g, 2.5 mmol) in dichloromethane (6 mL) and acetonitrile (3 mL), cyclopropyl amine (3 mL, 45 mmol), acetic acid (1 mL) and sodium cyanoborohydride (0.63 g, 9.5 mmol) followed by work up afforded an intermediate as an oil, that was used as such for the next step. Th residue (crude 2.5 mmol) was dissolved in acetone (20 mL) and treated with potassium carbonate (1.03 g, 7.5 mmol) and methyl iodide (1.55 mL, 25 mmol). The resulting reaction mixture was stirred at ambient temperature over 2 days. The solids were filtered off, thr filtrate and washings were evaporated in vacuo to an oil. Flash column chromatography over silica gel (230-400 mesh) using 2-4% ethyl acetate in hexane as the mobile phase afforded the title compound (0.58 g, 75%).

$^1$H NMR (300 MHz, CDCl$_3$): δ 7.31(d, J=1.6 Hz, 1H), 6.89(d, J=1.6 Hz, 1H), 4.27(br s, 1H), 2.40-2.30 (m, 1H), 2.30-2.20(m, 1H), 2.24(s, 3H), 2.10-2.00 (m, 1H), 2.00-1.80 (m, 2H), 1.60-1.50(m, 1H), 1.35 (s, 3H), 1.20(s, 3H), 0.90-0.75(m, 4H), 0.40-0.25 (m, 3H), 0.26(s, 9H), 0.20-0.10(m, 1H).

8-Cyclopropyl-5-(cyclopropyl-methyl-amino)-2-ethynyl-4,4-dimethyl-1,2,3,4-tetrahydronaphthalene (Intermediate 164)

A solution of 8-cyclopropyl-5-(cyclopropyl-methyl-amino)-4,4-dimethyl-(2-trimethylsilanyl)ethynyl-1,2,3,4-tetrahydronaphthalene (Intermediate 163, 0.3 g, 0.82 mmol) in methanol (10 mL) was treated with potassium carbonate (0.2 g, 1.44 mmol) and the resulting reaction mixture was stirred at ambient temperature overnight. The solids were filtered off, the residue was diluted with water and extracted with diethyl ether. The organic phase was dried over anhydrous magnesium sulfate, fltered and evaporated to aford the title compound (0.22 g, 92%).

$^1$H NMR (300 MHz, CDCl$_3$): δ 7.44 (d, J=1.6 Hz, 1H), 7.01(d, J=1.6 Hz, 1H), 4.38(br s, 1H), 3.11(s, 1H), 2.48-2.38 (m, 1H), 2.38-2.28(m, 1H), 2.34(s, 3H), 2.18-2.08 (m, 1H), 2.05-1.85(m, 2H), 1.70-1.60(m, 1H), 1.44 (s, 3H), 1.30(s, 3H), 1.00-0.85(m, 4H), 0.50-0.35 (m, 3H), 0.30-0.18(m, 1H).

2-{4-[4-Cyclopropyl-5-(cyclopropyl-methyl-amino)-8,8-dimethyl-5,6,7,8-tetrahydro-naphthalen-2-yl-ethynyl]-phenyl}-propionic acid methyl ester (Intermediate 165)

Following General Procedure B and using 8-cyclopropyl-5-(cyclopropyl-methyl-amino)-2-ethynyl-4,4-dimethyl-1,2,3,4-tetrahydronaphthalene (Intermediate 164, 0.11 g, 0.37 mmol), methyl-2-(4-iodo phenyl)propionate (Reagent 1, 0.108 g, 0.37 mmol), triethyl amine (10 mL), copper(I)iodide (0.019 g, 0.1 mmol) and dichlorobis(triphenylphosphine)palladium(II) (0.07 g, 0.1 mmol) followed by work up and flash column chromatography over silica gel (230-400 -mesh) using 1%-4% ethyl acetate in hexane as the eluent, the title compound was obtained as a pale yellow amorphous solid (0.148 g, 87%).

$^1$H NMR (300 MHz, CDCl$_3$): δ 7.51(d, J=8.5 Hz, 2H), 7.39 (d, J=1.6 Hz, 1H), 7.29(d, J=8.5 Hz, 2H), 6.97(d, J=1.6 Hz, 1H), 4.32(bs, 1H), 3.75(q, J=7.0 Hz, 1H), 3.70(s, 3H), 2.40-2.30 (m, 1H), 2.30-2.20(m,1H), 2.28(s, 3H), 2.18-2.08 (m, 1H), 2.02-1.82(m, 2H), 1.62-1.52(m, 1H), 1.52(d, J=7.0 Hz, 3H), 1.39 (s, 3H), 1.25(s, 3H), 0.98-0.80(m, 4H), 0.45-0.25 (m, 3H), 0.20-0.15(m, 1H).

2-{4-[4-Cyclopropyl-5-(cyclopropyl-methyl-amino)-8,8-dimethyl-5,6,7,8-tetrahydro-naphthalen-2-yl-ethynyl]-phenyl}-propionic acid (Compound 49)

A solution of 2-{4-[4-cyclopropyl-5-(cyclopropyl-methyl-amino)-8,8-dimethyl-5,6,7,8-tetrahydro-naphthalen-2-yl-ethynyl]-phenyl}-propionic acid methyl ester (Intermediate 165, 0.075 g, 0.16 mmol) in methanol (2 mL) and tetrahydrofuran (2 mL) was treated with 2M lithium hydroxide (1 mL, 2 mmol) and the resulting reaction mixture was stirred at ambient temperature for 5 h. The reaction mixture was neutralized with ammonium chloride and extracted with ethyl acetate. The organic phase was washed with water and brine, and dried over anhydrous sodium sulfate, filtered and evaporated in vacuo to afford the title product as a yellow solid (0.07 g, 96%).

$^1$H NMR (300 MHz, CDCl$_3$): δ 7.50(d, J=8.5 Hz, 2H), 7.39 (d, J=1.6 Hz, 1H), 7.31(d, J=8.5 Hz, 2H), 6.97(d, J=1.6 Hz, 1H), 4.34(bs, 1H), 3.74(q, J=7.0 Hz, 1H), 2.40-2.30(m, 1H), 2.30-2.20(m, 1H), 2.29(s, 3H), 2.18-2.08 (m, 1H), 2.02-1.82 (m, 2H), 1.62-1.52(m, 1H), 1.52(d, J=7.0 Hz, 3H), 1.39 (s, 3H), 1.24(s, 3H), 0.98-0.80(m, 4H), 0.40-0.30 (m, 3H), 0.20-0.15(m, 1H).

2-{4-[4-Cyclopropyl-5-(cyclopropyl-methyl-amino)-8,8-dimethyl-5,6,7,8-tetrahydro-naphthalen-2-yl-ethynyl]-phenyl}-2-methyl-propionic acid methyl ester (Intermediate 166)

Following General Procedure B and using 8-cyclopropyl-5-(cyclopropyl-methyl-amino)-2-ethynyl-4,4-dimethyl-1,2,3,4-tetrahydronaphthalene (Intermediate 164, 0.11 g, 0.37 mmol), methyl-2-(4-iodo phenyl)-2-methyl-propionate (Reagent 2, 0.118 g, 0.39 mmol), triethyl amine (10 mL), copper (I)iodide (0.019 g, 0.1 mmol) and dichlorobis(triphenylphosphine)palladium(II) (0.07 g, 0.1 mmol) followed by work up and flash column chromatography over silica gel (230-400 mesh) using 1%-4% ethyl acetate in hexane as the eluent, the title compound was obtained as a pale yellow amorphous solid (0.125 g, 70%).

$^1$H NMR (300 MHz, CDCl$_3$): δ 7.51(d, J=8.5 Hz, 2H), 7.39(d, J=1.6 Hz, 1H), 7.33 (d, J=8.5 Hz, 2H), 6.97(d, J=1.6 Hz, 1H), 4.32(bs, 1H), 3.68(s, 3H), 2.40-2.30(m, 1H), 2.30-2.20(m, 1H), 2.28(s, 3H), 2.15-2.05 (m, 1H), 2.00-1.80(m, 2H), 1.61(s, 6H), 1.62-1.52(m, 1H), 1.39 (s, 3H), 1.25(s, 3H), 0.95-0.80(m, 4H), 0.45-0.30 (m, 3H), 0.20-0.10(m, 1H).

2-{4-[4-Cyclopropyl-5-(cyclopropyl-methyl-amino)-8,8-dimethyl-5,6,7,8-tetrahydro-naphthalen-2-yl-ethynyl]-phenyl}-2-methyl-propionic acid (Compound 50)

A solution of 2-{4-[4-cyclopropyl-5-(cyclopropyl-methyl-amino)-8,8-dimethyl-5,6,7,8-tetrahydro-naphthalen-2-yl-ethynyl]-phenyl}-2-methyl-propionic acid methyl ester (Intermediate 166, 0.125 g, 0.266 mmol) in methanol (2.5 mL) and tetrahydrofuran (2.5 mL) was treated with 3M potassium hydroxide (1 mL, 3 mmol) and the resulting reaction mixture was stirred at ambient temperature overnight. The reaction mixture was neutralized with ammonium chloride and extracted with ethyl acetate. The organic phase was washed with water and brine, and dried over anhydrous sodium sulfate, filtered and evaporated in vacuo to afford the title product as an amorphous pale yellow solid (0.12 g, 98%).

$^1$H NMR (300 MHz, CDCl$_3$): δ 7.51(d, J=8.5 Hz, 2H), 7.40-7.38 (m, 3H), 6.97(d, J=1.6 Hz, 1H), 4.33(bs, 1H), 2.40-2.30(m, 1H), 2.30-2.20(m, 1H), 2.28(s, 3H), 2.10-2.00 (m,

1H), 2.00-1.80(m, 2H), 1.62(s, 6H), 1.60-1.50(m, 1H), 1.39 (s, 3H), 1.24(s, 3H), 0.95-0.80(m, 4H), 0.45-0.30 (m, 3H), 0.20-0.10(m, 1H).

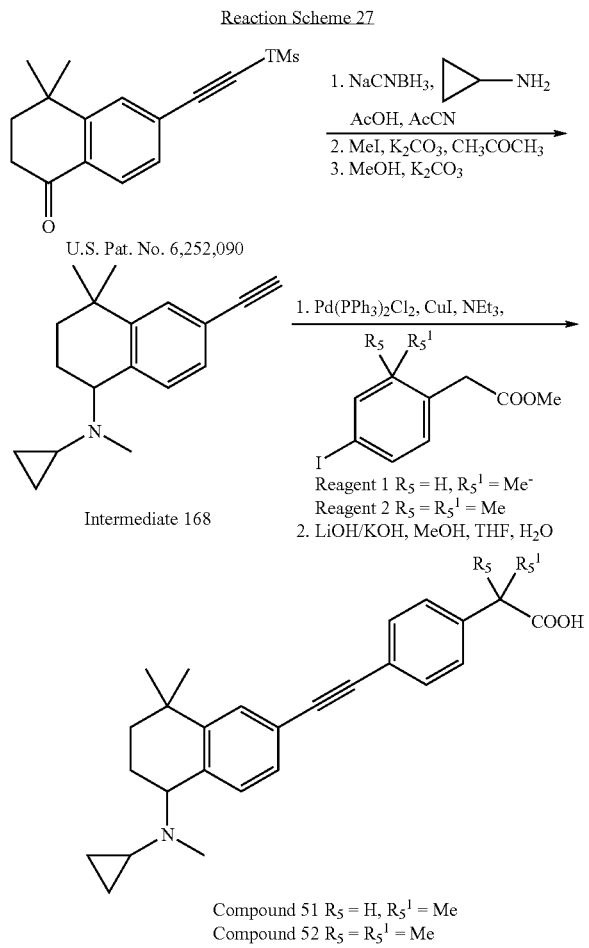

Cyclopropyl-(4,4-dimethyl-6-trimethylsilanylethynyl-1,2,3,4-tetrahydro-naphthalen-1-yl)-methyl-amine (Intermediate 167)

Following General Procedure C and using 4,4-dimethyl-6-trimethylsilanylethynyl-3,4-dihydro-2H-naphthalen-1-one (described in U.S. Pat. No. 6,252,090, 1.23 g, 4.6 mmol) in dichloromethane (7 mL) and acetonitrile (3 mL), cyclopropyl amine (2.5 mL, 36 mmol), acetic acid (2.5 mL) and sodium cyanoborohydride (0.58 g, 8.6 mmol) followed by work up and flash column chromatography over silica gel (230-400 mesh) using 8% ethyl acetate in hexane as the eluent afforded an intermediate as a golden yellow solid (1.07 g, 76%). The intermediate (0.67 g, 2.62 mmol) was dissolved in acetone (10 mL) and treated with potassium carbonate (2.2 g, 16 mmol) and methyl iodide (0.75 mL, 12 mmol). The resulting reaction mixture was stirred at ambient temperature overnight. The volatiles were evaporated in vacuo, the residue was diluted with water and extracted with diethyl ether. The organic phase was dried over anhydrous magnesium sulfate, filtered and evaporated to an oil which was used as such for the next step.

Cyclopropyl-(6-ethynyl-4,4-dimethyl-1,2,3,4-tetrahydro-naphthalen-1-yl)-methyl-amine (Intermediate 168)

A solution of cyclopropyl-(4,4-dimethyl-6-trimethylsilanylethynyl-1,2,3,4-tetrahydro-naphthalen-1-yl)-methyl-amine (Intermediate 167, 0.67 g, 2.62 mmol) in methanol (10 mL) was treated with potassium carbonate (1 g, 7.23 mmol) and the resulting reaction mixture was stirred at ambient temperature overnight. The volatiles were evaporated in vacuo and the residue was diluted with water and extracted with diethyl ether. The organic extract was dried over anhydrous magnesium sulfate, filtered and evaporated in vacuo to afford the title product as a light yellow oil (0.5 g, 75%).

$^1$H NMR (300 MHz, CDCl$_3$): δ 7.47 (d, 1H, J=8.2 Hz), 7.41 (d, 1H, J=1.4 Hz), 6.79 (dd, 1H, J=8.2, 1.4 Hz), 3.92 (t, 1H, J=8.2 Hz), 3.01 (s, 3H), 2.11 (s, 3H), 2.15-2.07 (m, 1H), 1.95-1.57 (m, 4H), 1.29 (s, 3H), 1.24 (s, 3H), 0.53-0.37 (m, 4H).

2-{4-[5-(Cyclopropyl-methyl-amino)-8,8-dimethyl-5,6,7,8-tetrahydro-naphthalen-2-ylethynyl]-phenyl}-propionic acid methyl ester (Intermediate 169)

Following General Procedure B and using 5-(cyclopropyl-methyl-amino)-2-ethynyl-8,8-dimethyl-5,6,7,8-tetrahydro-naphthalene (Intermediate 168, 0.116 g, 0.46 mmol), methyl-2-(4-iodophenyl)propionate (Reagent 1, 0.17 g, 0.59 mmol), triethyl amine (0.75 mL), copper(I)iodide (0.07 g, 0.37 mmol) and tetrakis(triphenylphosphine)palladium(0) (0.022 g, 0.019 mmol) followed by flash column chromatography over silica gel (230-400 mesh) and preparative normal phase HPLC using 5% ethyl acetate in hexane as the eluent, the title compound was obtained (0.08 g, 42%).

$^1$H NMR (300 MHz, CDCl$_3$): δ7.51-7.43 (m, 3H), 7.29-7.22 (m, 4H), 3.94 (t, 1H, J=7.9 Hz), 3.76-3.62 (m, 1H), 3.65 (s, 3H), 2.12 (s, 3H), 2.15-2.08 (m, 1H), 2.00-1.54 (2m, 4H), 1.52-1.46 (2d, 3H, J=7.4 Hz), 1.31 (s, 3H), 1.27 (s, 3H), 0.53-0.38 (m, 4H).

2-{4-[5-(Cyclopropyl-methyl-amino)-8,8-dimethyl-5,6,7,8-tetrahydro-naphthalen-2-ylethynyl]-phenyl}-propionic acid (Compound 51)

A solution of 2-{4-[5-(cyclopropyl-methyl-amino)-8,8-dimethyl-5,6,7,8-tetrahydro-naphthalen-2-ylethynyl]-phenyl}-propionic acid methyl ester (Intermediate 169, 0.022 g, 0.05 mmol) in methanol (2 mL) and tetrahydrofuran (2 mL) was treated with a 2M solution of sodium hydroxide (1 mL, 2 mmol) and the resulting reaction mixture was stirred at ambient temperature overnight. The reaction mixture was neutralized with saturated aqueous ammonium chloride solution and extracted with ethyl acetate. The organic phase was washed with water and brine, and dried over anhydrous magnesium sulfate, filtered and evaporated in vacuo to a residue that was subjected to preparative reverse phase HPLC using 10% water in acetonitrile as the mobile phase to afford the title product (0.008 g, 40%).

$^1$H NMR (300 MHz, CDCl$_3$): δ 7.50-7.44 (m, 3H), 7.31-7.27 (m, 3H), 7.20 (dd, 1H, J=8.2, 1.5 Hz), 4.00 (t, 1H, J=8.2 Hz), 3.74 (q, 1H, J=7.1 Hz), 1H), 2.15 (s, 3H), 2.15-2.10 (m, 1H), 1.98-1.81 (m, 2H), 1.80-1.63 (m, 2H), 1.51(d, 3H, J=7.1 Hz), 1.31 (s, 3H), 1.27 (s, 3H), 0.52-0.49 (m, 4H).

2-{4-[5-(Cyclopropyl-methyl-amino)-8,8-dimethyl-
5,6,7,8-tetrahydro-naphthalen-2-ylethynyl]-phenyl}-
2-methyl-propionic acid methyl ester
(Intermediate 170)

Following General Procedure B and using S-(cyclopropyl-methyl-amino)-2-ethynyl-8,8-dimethyl-5,6,7,8-tetrahydro-naphthalene (Intermediate 168, 0.16 g, 0.63 mmol), methyl-2-(4-iodophenyl)-2-methyl-propionate (Reagent 2, 0.18 g, 0.58 mmol), triethyl amine (3 mL), copper(I)iodide (0.048 g, 0.25 mmol) and tetrakis(triphenylphosphine)palladium(0) (0.032 g, 0.027 mmol) followed by flash column chromatography over silica gel (230-400 mesh) and preparative normal phase HPLC using 6% ethyl acetate in hexane as the mobile phase, the title compound was obtained (0.14 g, 56%).

$^1$H NMR (300 MHz, CDCl$_3$): δ 7.54-7.47 (m, 4H), 7.34-7.26 (m, 3H), 3.97 (t, 1H, J=7.9 Hz), 3.68 (s, 3H), 2.16 (s, 3H), 2.16-2.00 (m, 1H), 2.00-1.61 (2m, 4H), 1.61 (s, 6H), 1.35 (s, 3H), 1.30 (s, 3H), 0.56-0.44 (m, 4H).

2-{4-[5-(Cyclopropyl-methyl-amino)-8,8-dimethyl-
5,6,7,8-tetrahydro-naphthalen-2-ylethynyl]-phenyl}-
2-methyl-propionic acid (Compound 52)

A solution of 2-{4-[5-(cyclopropyl-methyl-amino)-8,8-dimethyl-5,6,7,8-tetrahydro-naphthalen-2-ylethynyl]-phenyl}-2-methyl-propionic acid methyl ester (Intermediate 170, 0.08 g, 0.19 mmol) in methanol (3 mL) and tetrahydrofuran (3 mL) was treated with a 2M solution of sodium hydroxide (2 mL, 4 mmol) and the resulting reaction mixture was refluxed overnight. The volatiles were evaporated in vacuo and the residue was diluted with saturated aqueous ammonium chloride solution and extracted with ethyl acetate. The organic phase was dried over anhydrous magnesium sulfate, filtered and evaporated in vacuo to afford the title product (0.07 g, ~100%).

$^1$H NMR (300 MHz, CDCl$_3$): δ 9.47 (br s, 1H), 7.53-7.49 (m, 4H), 7.39 (d, 2H, J=8.5 Hz), 7.26 (dd, 1H, J=7.9, 1.5 Hz), 3.97 (t, 1H, J=7.9 Hz), 2.16 (s, 3H), 2.16-2.00 (m, 1H), 2.00-1.61 (2m, 4H), 1.61 (s, 6H), 1.35 (s, 3H), 1.30 (s, 3H), 0.56-0.44 (m, 4H).

Reaction Scheme 28

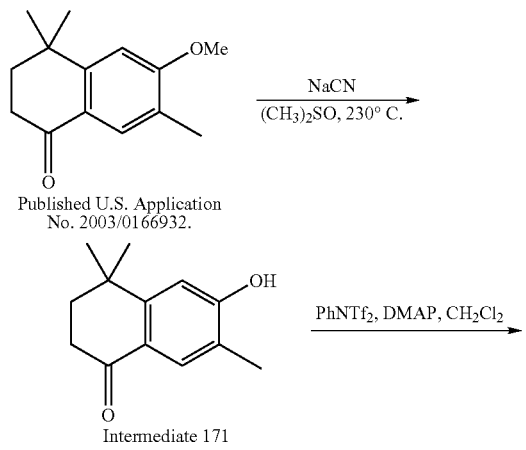

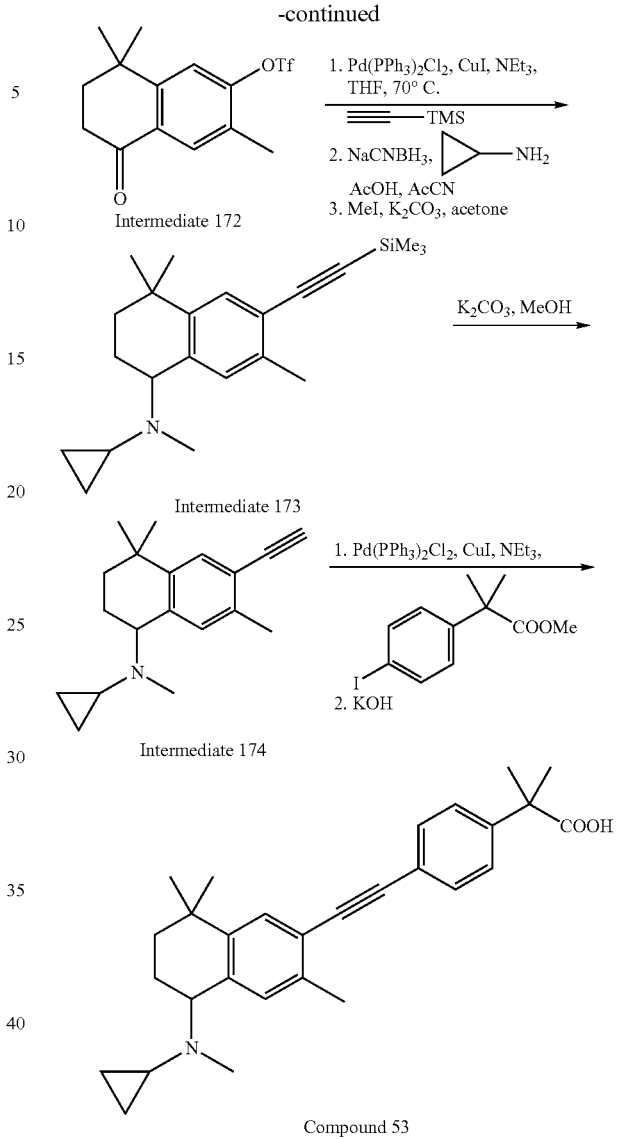

6-Hydroxy-4,4,7-trimethyl-3,4-dihydro-2H-naphthalen-1-one (Intermediate 171)

A solution of 6-methoxy-4,4,7-trimethyl-3,4-dihydro-2H-naphthalen-1-one (described in U.S. 2003/0166932, published Sep. 4, 2003, incorporated herein by reference; 5.5 g, 25.6 mmol) and sodium cyanide (6.25 g, 127 mmol) in anhydrous dimethylsulfoxide (100 mL) was heated at 230° C. for 48 h under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford the title compound, which was used as such for the next step (5.2 g, 100%).

$^1$H NMR (300 MHz, CDCl$_3$): δ 7.86 (s, 1H), 6.87 (s, 1H), 2.70 (t, 2H, J=7.0 Hz), 2.24 (s, 3H), 1.97 (t, 2H, J=7.0 Hz), 1.32 (s, 6H).

Trifluoro-methanesulfonic acid 3,8,8-trimethyl-5-oxo-5,6,7,8-tetrahydro-naphthalen-2-yl ester (Intermediate 172)

A solution of 6-hydroxy-4,4,7-trimethyl-3,4-dihydro-2H-naphthalen-1-one (Intermediate 171, 5.2 g, 25.6 mmol) and 4-dimethylaminopyridine (6.1 g, 50 mmol) in anhydrous dichloromethane (50 mL) was treated with N-phenyltrifluoromethanesulfonimide (9.54 g, 26.7 mmol) under argon and stirred at ambient temperature for 1 h. The reaction mixture was subjected to flash column chromatography on silica gel (230-400 mesh) using 6-7% ethyl acetate in hexane as the eluent to afford the title compound (6.4 g, 75%).

$^1$H NMR (300 MHz, CDCl$_3$): δ 7.96(s, 1H), 7.28 (s, 1H), 2.74 (t, 2H, J=7.0 Hz), 2.37 (s, 3H), 2.04 (t, 2H, J=7.0 Hz), 1.39 (s, 6H).

4,4,7-Trimethyl-6-trimethylsilanylethynyl-3,4-dihydro-2H-naphthalen-1-one (Intermediate 173)

Following General Procedure D and using trifluoro-methanesulfonic acid 3,8,8-trimethyl-5-oxo-5,6,7,8-tetrahydro-naphthalen-2-yl ester (Intermediate 172, 5.04 g, 15 mmol), triethyl amine (20 mL), copper(I)iodide (0.6 g, 3 mmol), trimethylsilyl acetylene (5.3 mL, 37.5 mmol) and dichlorobis(triphenylphosphine)palladium(II) (2.2 g, 3 mmol) followed by flash column chromatography over silica gel (230-400 mesh) using 6% ethyl acetate in hexane as the eluent, the title compound (4 g, 93%) was obtained as a pale yellow solid.

$^1$H NMR (300 MHz, CDCl$_3$): δ 7.54(s, 1H), 7.19 (s, 1H), 2.42 (t, 2H, J=7.0 Hz), 2.14 (s, 3H), 1.70 (t, 2H, J=7.0 Hz), 1.08 (s, 6H), 0.00 (s, 9H).

Cyclopropyl-(6-ethynyl-4,4,7-trimethyl-1,2,3,4-tetrahydro-naphthalen-1-yl)-methyl-amine (Intermediate 174)

Following General Procedure C and using 4,4,7-trimethyl-6-trimethylsilanylethynyl-3,4-dihydro-2H-naphthalen-1-one (Intermediate 173, 4 g, 14 mmol) in dichloromethane (30 mL) and acetonitrile (10 mL), cyclopropyl amine (3.11 mL, 45 mmol), acetic acid (3.2 mL) and sodium cyanoborohydride (2 g, 30 mmol) followed by work up and flash column chromatography over silica gel (230-400 mesh) using 10% ethyl acetate in hexane as the eluent afforded an intermediate as a pale yellow solid, that was used as such for the next step (4.1 g, 90%). The intermediate (4.1 g, 13 mmol) was dissolved in acetone (40 mL) and treated with potassium carbonate (10 g, 72 mmol) and methyl iodide (2.5 mL, 40 mmol). The resulting reaction mixture was stirred at ambient temperature overnight. The volatiles were evaporated in vacuo, the residue was dissolved in methanol (100 mL) and treated with potassium carbonate (10 g, 72 mmol) and the resulting reaction mixture was stirred at ambient temperature for 1.5 h. The volatiles were evaporated in vacuo, the residue was diluted with water and extracted with diethyl ether (×2). The combined organic phase was dried over anhydrous magnesium sulfate, filtered and evaporated to an oil that was filtered over a short plug of silica gel (230-400 mesh) to afford the title compound (3.2 g, 92%) as a clear oil.

$^1$H NMR (300 MHz, CDCl$_3$): δ 7.42(s, 1H), 7.38 (s, 1H), 3.49 (t, 1H, J=7.0 Hz), 3.23 (s, 1H), 2.40 (s, 3H), 2.15 (s, 3H), 2.15-2.10 (m, 1H), 1.97-1.62 (2m, 4H), 1.30 (s, 3H), 1.26 (s, 3H), 0.56-0.28 (m, 4H).

2-{4-[5-(Cyclopropyl-methyl-amino)-3,8,8-trimethyl-5,6,7,8-tetrahydro-naphthalen-2-ylethynyl]-phenyl}-2-methyl-propionic acid methyl ester (Intermediate 175)

Following General Procedure B and using cyclopropyl-(6-ethynyl-4,4,7-trimethyl-1,2,3,4-tetrahydro-naphthalen-1-yl)-methyl-amine (Intermediate 174, 0.1 g, 0.29 mmol), methyl-2-(4-iodophenyl)-2-methyl-propionate (Reagent 2, 0.09 g, 0.29 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 1-2% ethyl acetate in hexane as the eluent, the title compound was obtained (0.035 g, 26%).

$^1$H NMR (300 MHz, CDCl$_3$): δ 7.49(d, J=8.5 Hz, 2H), 7.41 (s, 1H), 7.38(d, J=8.5 Hz, 2H), 7.32 (s, 1H), 3.92 (m, 1H), 3.67(s, 3H), 2.43(s, 3H), 2.18-2.10 (m, 1H), 2.14(s, 3H), 1.98-1.85(m, 2H), 1.80-1.64(m, 2H), 1.60(s, 6H), 1.31(s, 3H), 1.26(s, 3H), 0.58-0.42(m, 4H).

2-{4-[5-(Cyclopropyl-methyl-amino)-3,8,8-trimethyl-5,6,7,8-tetrahydro-naphthalen-2-ylethynyl]-phenyl}-2-methyl-propionic acid (Compound 53)

A solution of 2-{4-[5-(cyclopropyl-methyl-amino)-3,8,8-trimethyl-5,6,7,8-tetrahydro-naphthalen-2-ylethynyl]-phenyl}-2-methyl-propionic acid methyl ester (Intermediate 175, 0.035 g, 0.08 mmol) in methanol (2 mL) and tetrahydrofuran (2 mL) was treated with a 2M solution of sodium hydroxide (2 mL, 4 mmol) and the resulting reaction mixture was refluxed for 2 days. The volatiles were evaporated in vacuo and the residue was neutralized with 5% aqueous hydrochloric acid and extracted with ethyl acetate. The organic phase was washed with water and brine, dried over anhydrous sodium sulfate, filtered and evaporated in vacuo to a residue that was purified by preparative reverse phjase HPLC using 10% water in acetonitrile as the mobile phase to afford the title product (0.022 g, 64%).

$^1$H NMR (300 MHz, CDCl$_3$): δ 7.48(d, J=8.5 Hz, 2H), 7.41 (s, 1H), 7.37-7.34(m, 3H), 3.95 (m, 1H), 2.40(s, 3H), 2.18-2.10 (m, 1H), 2.14(s, 3H), 1.98-1.85(m, 2H), 1.80-1.64(m, 2H), 1.57(s, 6H), 1.29 (s, 3H), 1.25(s, 3H), 0.56-0.42(m, 4H).

Reaction Scheme 29

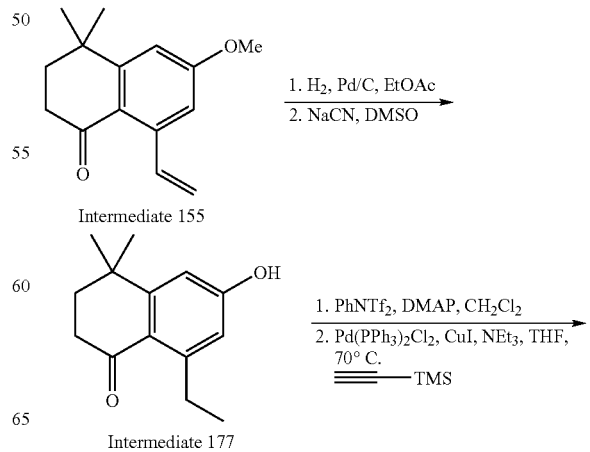

Intermediate 155

Intermediate 177

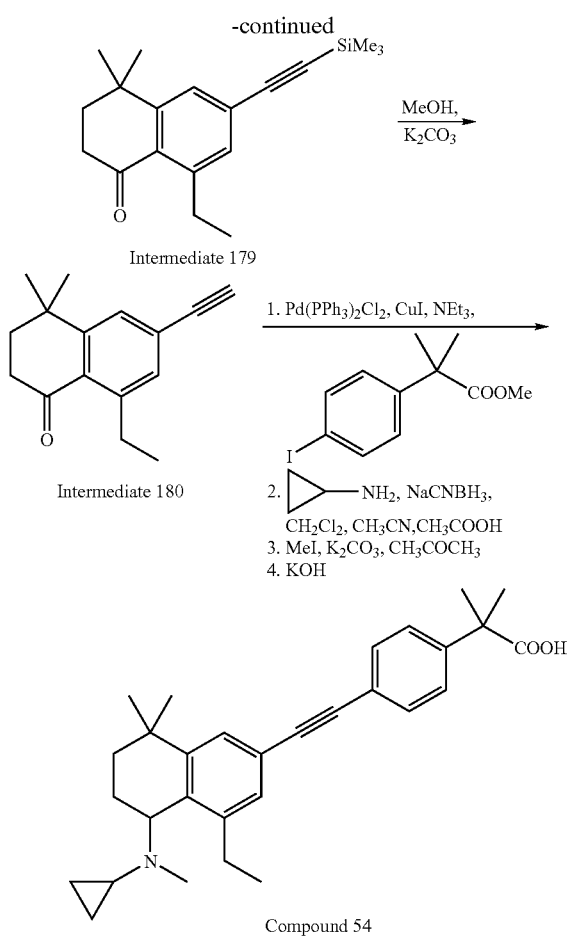

8-Ethyl-4,4-dimethyl-6-methoxy-3,4-dihydro-2H-naphthalen-1-one (Intermediate 176)

A solution of 8-vinyl-6-methoxy-4,4-dimethyl-3,4-dihydro-2H-naphthalen-1-one (Intermediate 155, 1.12 g, 4.86 mmol) in ethyl acetate (10 mL) was treated with 10% palladium on carbon (100 mg) and the resulting reaction mixture was stirred under an atmosphere of hydrogen overnight. The reaction mixture was filtered over a bed of celite and the filtrate was evaporated to afford the title product (1.1 g, 98%).

$^1$H NMR (300 MHz, CDCl$_3$): δ 6.77 (d, 1H, J=2.6 Hz), 6.54 (d, 1H, J=2.6 Hz), 3.87 (s, 3H), 3.05 (q, 2H, J=7.3 Hz), 2.67 (t, 2H, J=6.7 Hz), 1.95 (t, 2H, J=6.7 Hz), 1.36 (s, 6H), 1.23 (t, 3H, J=7.3 Hz).

8-Ethyl-6-hydroxy-4,4-dimethyl-3,4-dihydro-2H-naphthalen-1-one (Intermediate 177)

A solution of 8-ethyl-4,4-dimethyl-6-methoxy-3,4-dihydro-2H-naphthalen-1-one (Intermediate 176, 1.1 g, 4.73 mmol) and sodium cyanide (1.6 g, 33 mmol) in anhydrous dimethylsulfoxide (20 mL) was heated at 210° C. overnight under argon. The reaction mixture was then cooled to ambient temperature, poured into ice and acidified (Caution! Hydrogen cyanide evolution!) using 10% hydrochloric acid and extracted with ethyl acetate. The combined organic extract was washed with brine (×1), dried over anhydrous sodium sulfate, filtered and evaporated to afford a dark orange solid. Flash column chromatography on silica gel (230-400 mesh) using 10-20% ethyl acetate in hexane as the eluent afforded the title compound as a yellow solid (0.82 g, 82%).

$^1$H NMR (300 MHz, CD$_3$COCD$_3$): δ 8.99 (s, 1H), 6.81 (d, 1H, J=2.6 Hz), 6.64 (d, 1H, J=2.6 Hz), 2.99 (q, 2H, J=7.3 Hz), 2.60 (t, 2H, J=6.7 Hz), 1.93 (t, 2H, J=6.7 Hz), 1.34 (s, 6H), 1.17 (t, 3H, J=7.3 Hz).

Trifluoro-methanesulfonic acid 4-ethyl-8,8-dimethyl-5-oxo-5,6,7,8-tetrahydro-naphthalen-2yl ester (Intermediate 178)

A solution of 8-ethyl-6-hydroxy-4,4-dimethyl-3,4-dihydro-2H-naphthalen-1-one (Intermediate 177, 0.27 g, 1.24 mmol) and 4-dimethylaminopyridine (0.242 g, 1.98 mmol) in anhydrous dichloromethane (10mL) was treated with 2-[N,N-bis(trifluoromethylsulfonyl)amino]-5-chloro-pyridine (0.58 g, 1.48 mmol) under argon at ambient temperature for 5 h. The reaction mixture was subjected to flash column chromatography on silica gel (230-400 mesh) using 5% ethyl acetate in hexane as the eluent to afford the title compound (0.43 g, 98%).

$^1$H NMR (300 MHz, CDCl$_3$): δ 7.15 (d, 1H, J=2.6 Hz), 7.04 (d, 1H, J=2.6 Hz), 3.05 (q, 2H, J=7.3 Hz), 2.74 (t, 2H, J=6.7 Hz), 2.00 (t, 2H, J=6.7 Hz), 1.38 (s, 6H), 1.24 (t, 3H, J=7.3 Hz).

8-Ethyl-4,4-dimethyl-6-(trimethylsilanyl)ethynyl-3,4-dihydro-2H-naphthalen-1-one (Intermediate 179)

Following General Procedure D and using trifluoro-methanesulfonic acid 4-ethyl-8,8-dimethyl-5-oxo-5,6,7,8-tetrahydro-naphthalen-2yl ester (Intermediate 178, 0.9 g, 2.57 mmol), triethyl amine (6 mL), anhydrous N,N-dimethylformamide (5 mL), dichlorobis(triphenylphosphine)palladium (II) (0.144 g, 0.2 mmol) and (trimethylsilyl)acetylene (2 mL, 13.64 mmol), the reaction was conducted overnight in a sealed tube at 90° C. Work-up followed by flash column chromatography over silica gel (230-400 mesh) using 2-3% ethyl acetate in hexane as the eluent to afforded the title compound as an orange oil (0.82 g, quantitative).

$^1$H NMR (300 MHz, CDCl$_3$): δ 7.34 (d, 1H, J=1.5 Hz), 7.21 (d, 1H, J=1.5 Hz), 2.97 (q, 2H, J=7.6 Hz), 2.69 (t, 2H, J=6.7 Hz), 1.95 (t, 2H, J=6.7 Hz), 1.35 (s, 6H), 1.20 (t, 3H, J=7.6 Hz), 0.27 (s, 9H).

8-Ethyl-6-ethynyl-4,4-dimethyl-3,4-dihydro-2H-naphthalen-1-one (Intermediate 180)

Following General Procedure F and using 8-ethyl-4,4-dimethyl-6-(trimethylsilanyl)ethynyl-3,4-dihydro-2H-naphthalen-1-one (Intermediate 179, 0.66 g, 2.2 mmol), methanol (10 mL) and potassium carbonate (0.4 g, 2.9 mmol) the title compound was obtained as an orange oil (0.59 g, 100%). $^1$H NMR (300 MHz, CDCl$_3$): δ 7.51 (d, 1H, J=1.5 Hz), 7.37 (d, 1H, J=1.5 Hz), 3.32 (s, 1H), 3.10 (q, 2H, J=7.3 Hz), 2.84 (t, 2H, J=6.7 Hz), 2.08 (t, 2H, J=6.7 Hz), 1.48 (s, 6H), 1.33 (t, 3H, J=7.3 Hz).

2-[4-(4-Ethyl-8,8-dimethyl-5-oxo-5,6,7,8-tetrahydro-naphthalen-2-ylethynyl) phenyl]-2-methyl-propionic acid methyl ester (Intermediate 181)

Following General Procedure B and using 8-ethyl-6-ethynyl-4,4-dimethyl-3,4-dihydro-2H-naphthalen-1-one (Intermediate 180, 0.09 g, 0.39 mmol), methyl-2-(4-iodo phenyl)-2-methyl-propionate (Reagent 2, 0.152 g, 0.5 mmol), triethyl amine (8 mL), copper(I)iodide (0.024 g, 0.12 mmol) and dichlorobis(triphenylphosphine)palladium(II) (0.087 g, 0.12 mmol) followed by flash column chromatography over silica gel (230-400 mesh) using 2-10% ethyl acetate in hexane as the eluent, the title compound was obtained as an oil (0.095 g, 59%).

$^{1}$H NMR (300 MHz, CDCl$_3$): δ 7.53(d, J=8.8 Hz, 2H), 7.43(d, J=1.8 Hz, 1H), 7.35 (d, J=8.8 Hz, 2H), 7.30(d, J=1.8 Hz, 1H), 3.68(s, 3H), 3.03(q, J=7.3 Hz, 2H), 2.73(t, J=6.9 Hz, 2H), 1.99(t, J=6.9 Hz, 2H), 1.61(s, 6H), 1.40(s, 6H), 1.25(t, J=7.3 Hz, 3H).

2-{4-[5-(Cyclopropyl-methyl-amino)-4-ethyl-8,8-dimethyl-5,6,7,8-tetrahydro-naphthalen-2-ylethynyl]-phenyl}-2-methyl-propionic acid methyl ester (Intermediate 182)

Following General Procedure C and using 2-[4-(4-ethyl-8,8-dimethyl-5-oxo-5,6,7,8-tetrahydro-naphthalen-2-ylethynyl)-phenyl]-2-methyl-propionic acid methyl ester (Intermediate 181, 0.095 g, 0.23 mmol) in dichloromethane (3 mL) and acetonitrile (1.5 mL), cyclopropyl amine (1 mL, 14.5 mmol), acetic acid (1 mL) and sodium cyanoborohydride (0.12 g, 1.91 mmol) followed by work up afforded an intermediate as an oil, that was used as such for the next step. The intermediate (crude 0.23 mmol, 0.13 g) Was dissolved in acetone (6 mL) and treated with potassium carbonate (0.23 g, 1.66 mmol) and methyl iodide (1.5 mL, 25 mmol). The resulting reaction mixture was stirred at ambient temperature overnight. The solids were filtered off, the filtrate and washings were evaporated in vacuo to an oil. Flash column chromatography over silica gel (230-400 mesh) using 5-10% ethyl acetate in hexane as the eluent afforded the title compound (0.07, 65%).

$^{1}$H NMR (300 MHz, CDCl$_3$): δ 7.55(d, J=8.8 Hz, 2H), 7.43(d, J=1.7 Hz, 1H), 7.37(d, J=8.8 Hz, 2H), 7.22(d, J=1.7 Hz, 1H), 4.13 (m, 1H), 3.72(s, 3H), 2.78-2.68(m, 2H), 2.32-2.24 (m, 1H), 2.25(s, 3H), 2.18-2.08(m, 1H), 1.99-1.79(m, 2H), 1.65(s, 6H), 1.63-1.53(m, 1H), 1.42 (s, 3H), 1.29(s, 3H), 1.23(t, J=7.3 Hz, 3H), 0.50-0.40(m, 3H), 0.30-0.20(m, 1H).

2-{4-[5-(Cyclopropyl-methyl-amino)-4-ethyl-8,8-dimethyl-5,6,7,8-tetrahydro-naphthalen-2-ylethynyl]-phenyl}-2-methyl-propionic acid (Compound 54)

A solution of 2-{4-[5-(cyclopropyl-methyl-amino)-4-ethyl-8,8-dimethyl-5,6,7,8-tetrahydro-naphthalen-2-ylethynyl]-phenyl}-2-methyl-propionic acid methyl ester (Intermediate 182, 0.035 g, 0.076 mmol) in methanol (3 mL) and tetrahydrofuran (2 mL) was treated with 3M potassium hydroxide (2 mL, 4 mmol) and the resulting reaction mixture was heated at 80° C. for 2 days. The reaction mixture was neutralized with ammonium chloride and extracted with ethyl acetate. The organic phase was washed with water and brine, and dried over anhydrous sodium sulfate, filtered and evaporated in vacuo to afford a residue that was purified by preparative reverse phase HPLC to afford the title product (0.023 g, 69%).

$^{1}$H NMR (300 MHz, CDCl$_3$): δ 7.49(d, J=8.4 Hz, 2H), 7.36-7.26(m, 3H), 7.16(d, J=1.7 Hz, 1H), 4.06 (m, 1H), 2.71-2.63(m, 2H), 2.25-2.17 (m, 1H), 2.18(s, 3H), 2.05-2.00(m, 1H), 1.95-1.78(m, 2H), 1.60-1.50(m, 1H), 1.58(s, 6H), 1.35 (s, 3H), 1.22(s, 3H), 1.16(t, J=7.3 Hz, 3H), 0.4-0.3(m, 3H), 0.2-0.1 (m, 1H).

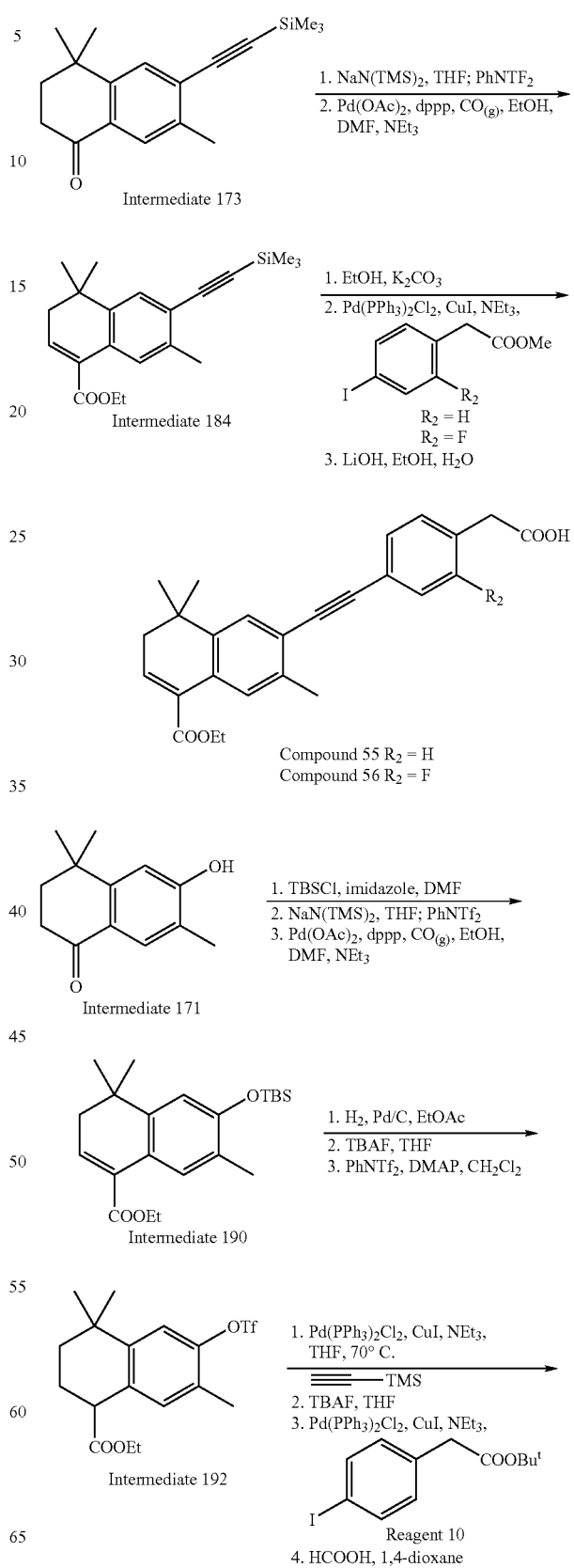

Reaction Scheme 30

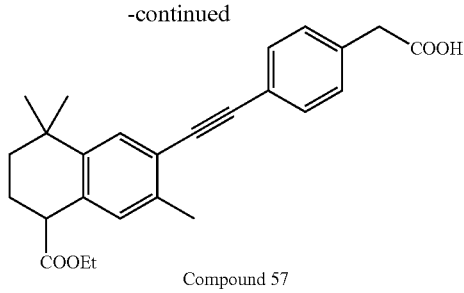

Compound 57

Trifluoro-methanesulfonic acid 4,4,7-trimethyl-6-trimethylsilanylethynyl-3,4-dihydro-naphthalen-1-yl ester (Intermediate 183)

A stirred, cooled (−78° C.) solution of 4,4,7-trimethyl-6-trimethylsilanylethynyl-3,4-dihydro-2H-naphthalen-1-one (Intermediate 173, 0.95 g, 3.33 mmol) in anhydrous tetrahydrofuran (10 mL) under argon was treated with a 1M solution of sodium bis(trimethylsilyl)amide in tetrahydrofuran (5 mL, 5 mmol). After 1 h, N-phenyltrifluoromethanesulfonimide (1.08 g, 3.33 mmol) was added and the reaction mixture was stirred at ambient temperature for 1 h. The reaction was quenched with saturated aqueous ammonium chloride solution, diluted with water and extracted with diethyl ether (×2). The combined organic extract was dried over anhydrous magnesium sulfate, filtered and evaporated in vacuo to a residue that was subjected to flash column chromatography on silica gel using 2-4% ethyl acetate in hexane as the eluent to afford the title compound (0.73 g, 52%).

$^1$H NMR (300 MHz, CDCl$_3$): δ 7.08 (s, 1H), 6.92 (s, 1H), 5.67 (t, 2H, J=5.0 Hz), 2.15 (s, 3H), 2.08 (d, 2H, J=5.0 Hz), 1.00(s, 6H), 0.00 (s, 9H).

4,4,7-Trimethyl-6-trimethylsilanylethynyl-3,4-dihydro-naphthalene-1-carboxylic acid ethyl ester (Intermediate 184)

Following General Procedure E and using trifluoro-methanesulfonic acid 4,4,7-trimethyl-6-trimethylsilanylethynyl-3,4-dihydro-naphthalen-1-yl ester (Intermediate 183, 0.73 g, 1.75 mmol), palladium acetate (0.1 g, 0.45 mmol), 1,3-bis(diphenylphosphino)propane (0.1 g, 0.24 mmol), N,N-dimethylformamide (3.5 mL), ethanol (3.5 mL) and triethyl amine (3.5 mL) followed by flash column chromatography over silica gel (230-400 mesh) using 5-10% ethyl acetate in hexane as the eluent the title compound was obtained (0.435 g, 73%).

$^1$H NMR (300 MHz, CDCl$_3$): δ 7.42 (s, 1H), 7.10 (s, 1H), 6.76 (t, 2H, J=5.0 Hz), 4.04 (q, 2H, J=7.0 Hz), 2.15 (s, 3H), 2.02 (d, 2H, J=5.0 Hz), 1.09 (t, 3H, J=7.0 Hz), 0.97(s, 6H), 0.00 (s, 9H).

6-Ethynyl-4,4,7-trimethyl-3,4-dihydro-naphthalene-1-carboxylic acid ethyl ester (Intermediate 185)

Following General Procedure F and using 4,4,7-trimethyl-6-trimethylsilanylethynyl-3,4-dihydro-naphthalene-1-carboxylic acid ethyl ester (Intermediate 184, 0.43 g, 1.3 mmol), ethanol (4 mL) and potassium carbonate (0.84 g, 6.06 mmol), the title compound was obtained (0.33 g, 95%).

$^1$H NMR (300 MHz, CDCl$_3$): δ 7.70 (s, 1H), 7.40 (s, 1H), 7.05 (t, 2H, J=5.0 Hz), 4.30 (q, 2H, J=7.0 Hz), 2.43 (s, 3H), 2.30 (d, 2H, J=5.0 Hz), 1.36 (t, 3H, J=7.0 Hz), 1.23(s, 6H).

6-(4-Methoxycarbonylmethyl-phenylethynyl)-4,4,7-trimethyl-3,4-dihydro-naphthalene-1-carboxylic acid ethyl ester (Intermediate 186)

Following General Procedure B and using 6-ethynyl-4,4,7-trimethyl-3,4-dihydro-naphthalene-1-carboxylic acid ethyl ester (Intermediate 185, 0.126 g, 0.47 mmol), 4-iodo phenyl acetic acid methyl ester (0.13 g, 0.47 mmol), triethyl amine (2 mL), copper(I)iodide (0.029 g, 0.15 mmol) and dichlorobis(triphenylphosphine)palladium(II) (0.07 g, 0.1 mmol) followed by flash column chromatography over silica gel (230-400 mesh) using 10-12% ethyl acetate in hexane as the eluent, the title compound was obtained as a viscous oil (0.144 g, 74%).

$^1$H NMR (300 MHz, CDCl$_3$): δ 7.72 (s, 1H), 7.47(d, 2H, J=8.1 Hz), 7.35 (s, 1H), 7.27 (d, 2H, J=8.1 Hz), 7.05 (t, 2H, J=5.0 Hz), 4.34 (q, 2H, J=7.0 Hz), 3.70 (s, 3H), 3.64(s, 2H), 2.48 (s, 3H), 2.32 (d, 2H, J=5.0 Hz), 1.38 (t, 3H, J=7.0 Hz), 1.27(s, 6H).

6-(4-Carboxymethyl-phenylethynyl)-4,4,7-trimethyl-3,4-dihydro-naphthalene-1-carboxylic acid ethyl ester (Compound 55)

A solution of 6-(4-carboxymethyl-phenylethynyl)-4,4,7-trimethyl-3,4-dihydro-naphthalene-1-carboxylic acid ethyl ester (Intermediate 186, 0.144 g, 0.35 mmol) in ethanol (2 mL) was treated with a 1M solution of lithium hydroxide (1 mL, 1 mmol) and the resulting reaction mixture was stirred at ambient temperature for 3 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 10% water in acetonitrile as the mobile phase to afford the title product (0.071 g, 50%).

$^1$H NMR (300 MHz, CDCl$_3$): δ 7.68 (s, 1H), 7.47 (br d, 2H, J=8.1 Hz), 7.41 (s, 1H), 7.21 (br d, 2H), 7.04 (t, 2H, J=5.0 Hz), 4.31 (q, 2H, J=7.0 Hz), 3.65 (br s, 2H), 2.46 (s, 3H), 2.30 (d, 2H, J=5.0 Hz), 1.37 (t, 3H, J=7.0 Hz), 1.24(s, 6H).

6-(3-Fluoro-4-methoxycarbonylmethyl-phenylethynyl)-4,4,7-trimethyl-3,4-dihydro-naphthalene-1-carboxylic acid ethyl ester (Intermediate 187)

Following General Procedure B and using 6-ethynyl-4,4,7-trimethyl-3,4-dihydro-naphthalene-1-carboxylic acid ethyl ester (Intermediate 185, 0.2 g, 0.75 mmol), 2-fluoro-4-iodo phenyl acetic acid methyl ester (0.22 g, 0.75 mmol), triethyl amine (2 mL), copper(I)iodide (0.03 g, 0.16 mmol) and dichlorobis(triphenylphosphine)palladium(II) (0.1 g, 0.14 mmol) followed by flash column chromatography over silica gel (230-400 mesh) using 10-12% ethyl acetate in hexane as the eluent, the title compound was obtained as a viscous oil (0.23 g, 73%).

$^1$H NMR (300 MHz, CDCl$_3$): δ 7.73 (s, 1H), 7.42 (s, 1H), 7.30-7.20 (m, 3H), 7.06 (t, 2H, J=5.0 Hz), 4.32 (q, 2H, J=7.0 Hz), 3.71 (s, 3H), 3.68(s, 2H), 2.47 (s, 3H), 2.32 (d, 2H, J=5.0 Hz), 1.37 (t, 3H, J=7.0 Hz), 1.26(s, 6H).

6-(4-Carboxymethyl-3-fluoro-phenylethynyl)-4,4,7-trimethyl-3,4-dihydro-naphthalene-1-carboxylic acid ethyl ester (Compound 56)

A solution of 6-(4-carboxymethyl-3-fluoro-phenylethynyl)-4,4,7-trimethyl-3,4-dihydro-naphthalene-1-carboxylic acid ethyl ester (Intermediate 187, 0.24 g, 0.54 mmol) in ethanol (2 mL) was treated with a 2M solution of lithium hydroxide (1 mL, 2 mmol) and the resulting reaction mixture was stirred at ambient temperature for 3 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 10% water in acetonitrile as the mobile phase to afford the title product (0.05 g, 22%).

$^{1}$H NMR (300 MHz, CDCl$_3$): δ 7.69 (s, 1H), 7.41 (s, 1H), 7.27-7.19 (m, 3H), 7.05 (t, 2H, J=4.7 Hz), 4.32 (q, 2H, J=7.0 Hz), 3.64 (br s, 2H), 2.45 (s, 3H), 2.31 (d, 2H, J=4.7 Hz), 1.37 (t, 3H, J=7.0 Hz), 1.25(s, 6H).

6-(tert-Butyl-dimethyl-silanyloxy)-4,4,7-trimethyl-3, 4-dihydro-2H-naphthalen-1-one (Intermediate 188)

A solution of 6-hydroxy-4,4,7-trimethyl-3,4-dihydro-2H-naphthalen-1-one (Intermediate 171, 2.04 g, 10 mmol) in anhydrous N,N-dimethyl formamide (10 mL) under argon was treated with imidazole (1 g, 14.7 mmol) followed by tert-butyldimethylsilyl chloride (1.5 g, 10 mmol). After stirring the reaction mixture at ambient temperature overnight, it was poured into water and extracted with diethyl ether (×2). The combined organic phase was dried over anhydrous sodium sulfate, filtered and evaporated to a residue that was purified by flash column chromatography on silica gel (230-400 mesh) usng 8-14% ethyl acetate in hexane as the eluent to afford the title compound (2.5 g, 79%).

$^{1}$H NMR (300 MHz, CDCl$_3$): δ 7.74 (s, 1H), 6.65 (s, 1H), 2.56 (t, 2H, J=6.8 Hz), 2.09 (s, 3H), 1.88 (t, 2H, J=6.8 Hz), 1.24 (s, 6H), 0.93(s, 9H), 0.17 (s, 6H).

Trifluoro-methanesulfonic acid 6-(tert-butyl-dimethyl-silanyloxy)-4,4,7-trimethyl-3,4-dihydro-naphthalen-1-yl ester (Intermediate 189)

A stirred, cooled (−78° C.) solution of trifluoro-methanesulfonic acid 6-(tert-butyl-dimethyl-silanyloxy)-4,4,7-trimethyl-3,4-dihydro-naphthalen-1-yl ester (Intermediate 188, 2.53 g, 8 mmol) in anhydrous tetrahydrofuran (25 mL) under argon was treated with a 1M solution of sodium bis(trimethylsilyl)amide in tetrahydrofuran (12 mL, 12 mmol). After 1 h, N-phenyltrifluoromethanesulfonimide (4.28 g, 12 mmol) was added and the reaction mixture was stirred at ambient temperature for 1 h. The reaction was quenched with saturated aqueous ammonium chloride solution, diluted with water and extracted with diethyl ether (×2). The combined organic extract was dried over anhydrous magnesium sulfate, filtered and evaporated in vacuo to a residue that was subjected to flash column chromatography on silica gel using 4% ethyl acetate in hexane as the eluent to afford the title compound (1.4 g, 39%).

$^{1}$H NMR (300 MHz, CDCl$_3$): δ 6.90 (s, 1H), 6.49 (s, 1H), 5.53 (t, 2H, J=5.0 Hz), 2.09 (d, 2H, J=5.0 Hz), 1.95 (s, 3H), 1.01 (s, 6H), 0.78(s, 9H), 0.00 (s, 6H).

6-(tert-Butyl-dimethyl-silanyloxy)-4,4,7-trimethyl-3, 4-dihydro-naphthalene-1-carboxylic acid ethyl ester (Intermediate 190)

Following General Procedure E and using trifluoro-methanesulfonic acid 6-(tert-butyl-dimethyl-silanyloxy)-4,4,7-trimethyl-3,4-dihydro-naphthalen-1-yl ester (Intermediate 189, 3.4 g, 7.55 mmol), palladium acetate (0.36 g, 1.62 mmol), 1,3-bis(diphenylphosphino)propane (0.36 g, 0.86 mmol), N,N-dimethylformamide (7 mL), ethanol (7 mL) and triethyl amine (7 mL) followed by flash column chromatography over silica gel (230-400 mesh) using 7% ethyl acetate in hexane as the eluent the title compound was obtained (1.35 g, 48%).

$^{1}$H NMR (300 MHz, CDCl$_3$): δ 7.40 (s, 1H), 6.65 (t, 2H, J=5.0 Hz), 6.65 (s, 1H), 4.08 (q, 2H, J=7.0 Hz), 2.04 (d, 2H, J=5.0 Hz), 1.96 (s, 3H), 1.13 (t, 3H, J=7.0 Hz), 0.99 (s, 6H), 0.79(s, 9H), 0.00 (s, 6H).

6-(tert-Butyl-dimethyl-silanyloxy)-4,4,7-trimethyl-1, 2,3,4-tetrahydro-naphthalene-1-carboxylic acid ethyl ester (Intermediate 191)

A solution of 6-(tert-butyl-dimethyl-silanyloxy)-4,4,7-trimethyl-3,4-dihydro-naphthalene-1-carboxylic acid ethyl ester (Intermediate 190, 0.95 g, 2.54 mmol) in ethanol was treated with a slurry of 5% palladium on carbon (0.3 g) in ethyl acetate (0.5 mL) and the resulting reaction mixture was stirred under an atmosphere of hydrogen overnight. The solids were filtered over a bed of celite and the filtrate was evaporated in vacuo to aford the title compound as a viscous oil (0.95 g, ~100%).

$^{1}$H NMR (300 MHz, CDCl$_3$): δ 6.66 (s, 1H), 6.51 (s, 1H), 3.95 (q, 2H, J=7.0 Hz), 3.46 (m, 1H), 1.92 (s, 3H), 1.93-1.75 (m, 2H), 1.64-1.55 (m, 1H), 1.38-1.30 (m, 1H), 1.06 (s, 3H), 1.01 (t, 3H, J=7.0 Hz), 1.01 (s, 3H), 0.80(s, 9H), 0.00 (s, 6H).

4,4,7-Trimethyl-6-trifluoromethanesulfonyloxy-1,2, 3,4-tetrahydro-naphthalene-1-carboxylic acid ethyl ester (Intermediate 192)

6-(Tert-butyl-dimethyl-silanyloxy)-4,4,7-trimethyl-1,2,3, 4-tetrahydro-naphthalene-1-carboxylic acid ethyl ester (Intermediate 191, 0.95 g, 2.54 mmol) was treated with a 1M solution of tetra-n-butyl ammonium fluoride in tetrahydrofuran (4 mL, 2 mmol) under argon and the resulting reaction mixture was stirred at ambient temperature for 45 min. Water was added and the reaction mixture was extracted with 10% ethyl acetate in diethyl ether. The organic phase was washed with water and brine, dried over anhydrous sodium sulfate, filtered and evaporated to an oil that was used for the next step. The oil was dissolved in anhydrous dichloromethane under argon and treated with 4-(dimethylamino)pyridine (0.62 g, 5.1 mmol) and N-phenyltrifluoromethanesulfonimide (0.91 g, 2.54 mmol). After 1 h at ambient temperature, the reaction mixture was subjected to flash column chromatography using 8% ethyl acetate in hexane as the eluent to afford the title compound as an oil (0.86 g, 86%).

$^{1}$H NMR (300 MHz, CDCl$_3$): δ7.19 (s, 1H), 7.07 (s, 1H), 4.17 (q, 2H, J=7.0 Hz), 3.73 (t, 1H, J=5.9 Hz), 2.30 (s, 3H), 2.18-1.97 (m, 2H), 1.87-1.78 (m, 1H), 1.70-1.56 (m, 1H), 1.31-1.25 (2s, 3H and 1t, 3H, overlapping).

4,4,7-Trimethyl-6-trimethylsilanylethynyl-1,2,3,4-tetrahydro-naphthalene-1-carboxylic acid ethyl ester (Intermediate 193)

Following General Procedure D in a sealed tube and using 4,4,7-trimethyl-6-trifluoromethanesulfonyloxy-1,2,3,4-tetrahydro-naphthalene-1-carboxylic acid ethyl ester (Intermediate 192, 0.86 g, 2.2 mmol), triethyl amine (2 mL), copper (I)iodide (0.083 g, 0.44 mmol), trimethylsilyl acetylene (2 mL, 14 mmol) and dichlorobis(triphenylphosphine)palladium(II) (0.306 g, 0.44 mmol) followed by flash column chromatography over silica gel (230-400 mesh) using 5% ethyl acetate in hexane as the eluent, and preaprative normal phase HPLC using 5% ethyl acetate in hexane as the mobile phase in order to separate recovered starting material from the product, the title compound (0.26 g) was obtained.

$^1$H NMR (300 MHz, CDCl$_3$): δ 7.21 (s, 1H), 6.72 (s, 1H), 3.95 (q, 2H, J=7.0 Hz), 3.49 (t, 1H, J=5.8 Hz), 2.13 (s, 3H), 1.95-1.62 (m, 2H), 1.60-1.48 (m, 1H), 1.42-1.31 (m, 1H), 1.10-1.00 (2s, 3H and 1t, 3H, overlapping), 0.04 (s, 9H).

6-(4-tert-Butoxycarbonylmethyl-phenylethynyl)-4,4,7-trimethyl-1,2,3,4-tetrahydro-naphthalene-1-carboxylic acid ethyl ester (Intermediate 194)

4,4,7-Trimethyl-6-trimethylsilanylethynyl-1,2,3,4-tetrahydro-naphthalene-1-carboxylic acid ethyl ester (Intermediate 193, 0.26 g, 0.76 mmol) was treated with a 1M solution of tetra-n-butyl ammonium fluoride in tetrahydrofuran (3 mL, 3 mmol) under argon and the resulting reaction mixture was stirred at ambient temperature for 1 h. Water was added and the reaction mixture was extracted with diethyl ether. The organic phase was washed with water and brine, dried over anhydrous sodium sulfate, filtered and evaporated to an oil that was used as such for the next step. Following General Procedure B and using the oil (0.76 mmol), 4-iodo-tert-butyl phenyl acetate (Reagent 10, 0.23 g, 0.72 mmol), triethyl amine (2 mL), copper(I)iodide (0.06 g, 0.32 mmol) and dichlorobis(triphenylphosphine)palladium(II) (0.14 g, 0.2 mmol) followed by flash column chromatography over silica gel (230-400 mesh) using 12% ethyl acetate in hexane as the eluent, the title compound was obtained as a viscous, pale yellow oil (0.23 g, 66%).

$^1$H NMR (300 MHz, CDCl$_3$): δ 7.50 (s, 1H), 7.48 (d, 2H, J=8.5 Hz), 7.24 (d, 2H, J=8.5 Hz), 6.98 (s, 1H), 4.17 (q, 2H, J=7.0 Hz), 3.74 (t, 1H, J=5.8 Hz), 3.52 (s, 2H), 2.42 (s, 3H), 2.27-1.99 (m, 2H), 1.87-1.78 (m, 1H), 1.63-1.44 (m, 1H), 1.43 (s, 9H), 1.32 (s, 3H), 1.26 (s, 3H), 1.23 (t, 3H, buried).

6-(4-Carboxymethyl-phenylethynyl)-4,4,7-trimethyl-1,2,3,4-tetrahydro-naphthalene-1-carboxylic acid ethyl ester (Compound 57)

A solution of 6-(4-tert-butoxycarbonylmethyl-phenylethynyl)-4,4,7-trimethyl-1,2,3,4-tetrahydro-naphthalene-1-carboxylic acid ethyl ester (Intermediate 194, 0.23 g, 0.5 mmol) in 1,4-dioxane (1 mL) was treated with formic acid (3 mL) and the resulting reaction mixture was stirred at ambient temperature for 6 h. Water was added and the reaction mixture was extracted with ethyl acetate(×2). The combined organic phase was washed with water, dried over anhydrous magnesium sulfate, filtered and evaporated to an oil. Preparative reverse phase HPLC using 10% water in acetonitrile as the mobile phase afforded the title compound (0.15 g, 74%). $^1$H NMR (300 MHz, CDCl$_3$): δ 7.48 (s, 1H), 7.46 (br d, 2H), 7.23 (br d, 2H), 6.96 (s, 1H), 4.17 (q, 2H, J=7.0 Hz), 3.73 (t, 1H, J=5.8 Hz), 3.54 (br s, 2H), 2.40 (s, 3H), 2.29-1.95 (m, 2H), 1.85-1.77 (m, 1H), 1.62-1.44 (m, 1H), 1.31 (s, 3H), 1.26 (s, 3H), 1.25 (t, 3H, buried).

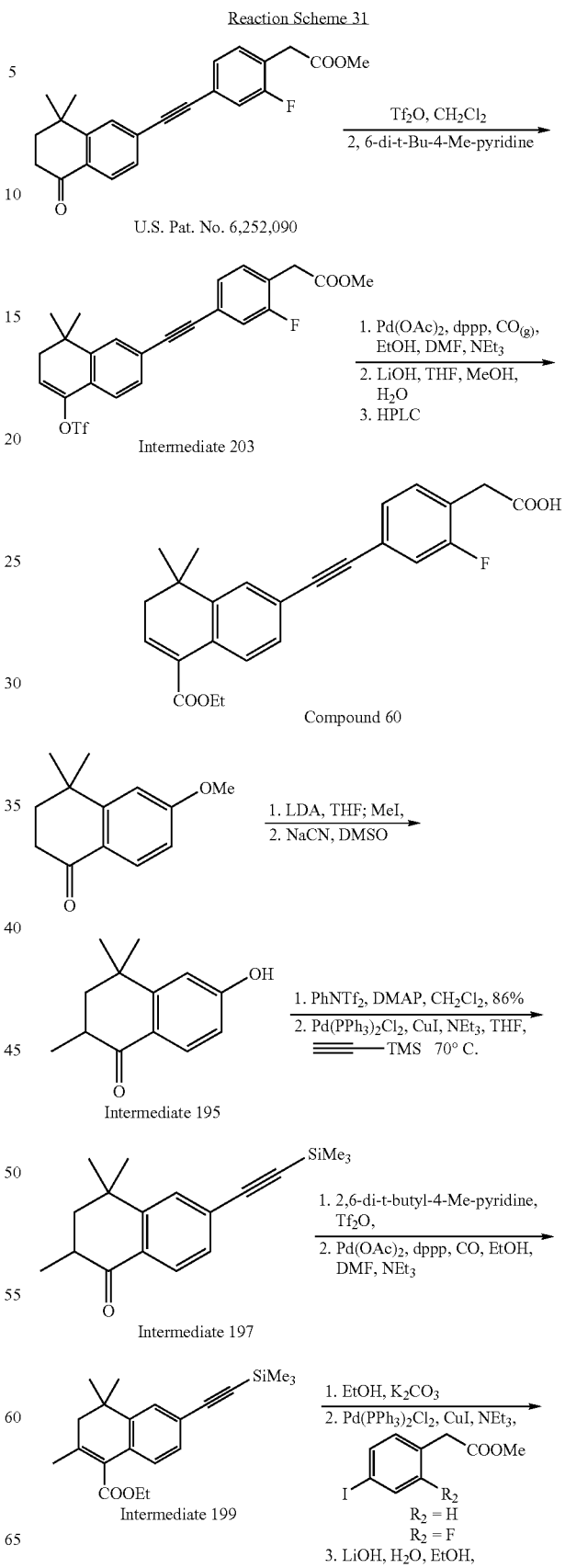

Reaction Scheme 31

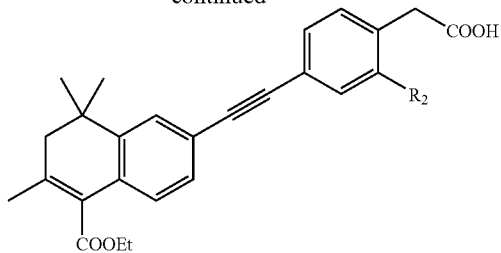

Compound 58 R$_2$ = H
Compound 59 R$_2$ = F

6-Hydroxy-2,4,4-trimethyl-3,4-dihydro-2H-naphthalen-1-one (Intermediate 195)

A solution 6-methoxy-2,4,4-trimethyl-3,4-dihydro-2H-naphthalen-1-one (described in Journal of Pharmaceutival Sciences, 1970, 59(6), p 869-870, Floyd et al. incorporated herein by reference; 1.2 g, 5.5 mmol) and sodium cyanide (2 g, 41 mmol) in anhydrous dimethylsulfoxide (15 mL) was heated at 230° C. for 24 h under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford the title compound, which was used as such for the next step (1 g, 89%).

Trifluoro-methanesulfonic acid 6,8,8-trimethyl-5-oxo-5,6,7,8-tetrahydro-naphthalen-2-yl ester (Intermediate 196)

A solution of 6-hydroxy-2,4,4-trimethyl-3,4-dihydro-2H-naphthalen-1-one (Intermediate 195, 1 g, 5 mmol) and 4-(dimethylamino)pyridine (1.22 g, 10 mmol) in anhydrous dichloromethane (10 mL) was treated with N-phenyltrifluoromethanesulfonimide (1.78 g, 10 mmol), and the resulting reaction mixture was stirred at ambient temperature for 2 h. Flash column chromatography of the reaction mixture over silica gel (230-400 mesh) using 5% ethyl acetate in hexane as the eluent afforded the title compound as a white solid (1.45 g, 86%).

$^1$H NMR (300 MHz, CDCl$_3$): δ 8.06 (d, 1H, J=8.5 Hz), 7.25 (d, 1H, J=2.0 Hz), 6.79 (dd, 1H, J=8.5, 2.0 Hz), 2.79 (m, 1H), 1.94 (m, 2H), 1.41 (s, 3H), 1.37 (s, 3H), 1.22 (d, 3H, J=6.7 Hz).

2,4,4-Trimethyl-6-trimethylsilanylethynyl-3,4-dihydro-2H-naphthalen-1-one (Intermediate 197)

Following General Procedure D and using trifluoro-methanesulfonic acid 6,8,8-trimethyl-5-oxo-5,6,7,8-tetrahydro-naphthalen-2-yl ester (Intermediate 196, 1.45 g, 4.3 mmol), triethyl amine (5 mL), copper(I)iodide (0.21 g, 0.26 mmol), trimethylsilyl acetylene (3 mL, 21 mmol) and dichlorobis(triphenylphosphine)palladium(II) (0.75 g, 1.07 mmol) followed by flash column chromatography over silica gel (230-400 mesh) using 5% ethyl acetate in hexane as the eluent, the title compound (1.28 g, ~100%) was obtained.

$^1$H NMR (300 MHz, CDCl$_3$): δ 7.64 (d, 1H, J=7.9 Hz), 7.22 (d, 1H, J=2.0 Hz), 7.08 (dd, 1H, J=7.9, 2.0 Hz), 2.50 (m, 1H), 1.94 (d, 2H, J=8.8 Hz)), 1.13 (s, 3H), 1.08 (s, 3H), 0.96 (d, 3H, J=6.8 Hz), 0.00 (s, 9H).

Trifluoro-methanesulfonic acid 2,4,4-trimethyl-6-trimethylsilanylethynyl-3,4-dihydro-naphthalen-1-yl ester (Intermediate 198)

A stirred, cooled (ice bath) solution of 2,4,4-trimethyl-6-trimethylsilanylethynyl-3,4-dihydro-2H-naphthalen-1-one (Intermediate 197, 1.28 g, 4.5 mmol) in anhydrous dichloromethane (10 mL) was treated with 2,6-di-t-butyl-4-methylpyridine (2.04 g, 9.91 mmol) and trifluoromethanesulfonic anhydride (1.52 mL, 9 mmol) and the resulting reaction mixture was stirrred at ambient temperature for 5 days at the end of which it was subjected to flash column chromatography on silica gel (230-400 mesh) using 5% ethyl acetate in hexane as the eluent to afford the title compound as an oil (1.59 g, 85%).

$^1$H NMR (300 MHz, CDCl$_3$): δ 7.09 (d, 1H, J=7.9 Hz), 7.07 (d, 1H, J=1.5 Hz), 6.98 (dd, 1H, J=7.9, 1.5 Hz), 2.04 (s, 2H), 1.72 (s, 3H), 1.03 (s, 6H), 0.00 (s, 9H).

2,4,4-Trimethyl-6-trimethylsilanylethynyl-3,4-dihydro-naphthalene-1-carboxylic acid ethyl este (Intermediate 199)

Following General Procedure E and using trifluoro-methanesulfonic acid 2,4,4-trimethyl-6-trimethylsilanylethynyl-3,4-dihydro-naphthalen-1-yl ester (Intermediate 198, 1.59 g, 3.8 mmol), palladium acetate (0.1 g, 0.45 mmol), 1,3-bis(diphenylphosphino)propane (0.1 g, 0.24 mmol), N,N-dimethylformamide (2.4 mL), ethanol (2.4 mL) and triethyl amine (2.4 mL) followed by flash column chromatography over silica gel (230-400 mesh) using 5% ethyl acetate in hexane as the eluent the title compound was obtained (0.31 g, 24%) as a yellow oil.

$^1$H NMR (300 MHz, CDCl$_3$): δ 7.12 (d, 1H, J=1.5 Hz), 7.01 (dd, 1H, J=8.2, 1.8 Hz), 6.77 (d, 1H, J=8.2 Hz), 4.10 (q, 2H, J=7.0 Hz), 1.93 (s, 2H), 1.73 (s, 3H), 1.08 (t, 3H, J=7.0 Hz), 0.99 (s, 6H), 0.00 (s, 9H).

6-Ethynyl-2,4,4-trimethyl-3,4-dihydro-naphthalene-1-carboxylic acid ethyl ester (Intermediate 200)

Following general procedure F and using 2,4,4-trimethyl-6-trimethylsilanylethynyl-3,4-dihydro-naphthalene-1-carboxylic acid ethyl ester (Intermediate 199, 0.31 g, 0.92 mmol), ethanol (2 mL) and potassium carbonate (0.3 g, 2.2 mmol), the title compound was obtained (0.26 g, >100%).

$^1$H NMR (300 MHz, CDCl$_3$): δ 7.32 (d, 1H, J=1.5 Hz), 7.20 (dd, 1H, J=8.2, 1.5 Hz), 6.96 (d, 1H, J=8.2 Hz), 4.27 (q, 2H, J=7.0 Hz), 3.00 (s, 1H), 2.10 (s, 2H), 1.90 (s, 3H), 1.27 (t, 3H, J=7.0 Hz), 1.16 (s, 6H).

6-(4-Methoxycarbonylmethyl-phenylethynyl)-2,4,4-trimethyl-3,4-dihydro-naphthalene-1-carboxylic acid ethyl ester (Intermediate 201)

Following General Procedure B and using 6-ethynyl-2,4,4-trimethyl-3,4-dihydro-naphthalene-1-carboxylic acid ethyl ester (Intermediate 200, 0.106 g, 0.38 mmol), 4-iodo phenyl acetic acid methyl ester (0.106 g, 0.38 mmol), triethyl amine (2 mL), copper(I)iodide (0.02 g, 0.105 mmol) and dichlorobis(triphenylphosphine)palladium(II) (0.07 g, 0.1 mmol) followed by flash column chromatography over silica gel (230-400 mesh) using 12-15% ethyl acetate in hexane as the eluent, the title compound was obtained as a pale yellow oil (0.075 g, 47%).

$^1$H NMR (300 MHz, CDCl$_3$): δ 7.49 (d, 2H, J=7.9 Hz), 7.45 (d, 1H, J=1.5 Hz), 7.32 (dd, 1H, J=7.9, 1.5 Hz), 7.26 (d,

2H, J=7.9 Hz), 7.07 (d, 1H, J=7.9 Hz), 4.37 (q, 2H, J=7.0 Hz), 3.70 (s, 3H), 3.63 (s, 2H), 2.22 (s, 2H), 2.00 (s, 3H), 1.38 (t, 3H, J=7.0 Hz), 1.27 (s, 6H).

6-(4-Carboxymethyl-phenylethynyl)-2,4,4-trimethyl-3,4-dihydro-naphthalene-1-carboxylic acid ethyl ester (Compound 58)

A solution of 6-(4-carboxymethyl-phenylethynyl)-2,4,4-trimethyl-3,4-dihydro-naphthalene-1-carboxylic acid ethyl ester (0.075 g, 0.18 mmol) in ethanol (2 mL) was treated with a 1M solution of lithium hydroxide (1 mL, 1 mmol) and the resulting reaction mixture was stirred at ambient temperature for 0.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product (0.055 g, 76%).

$^1$H NMR (300 MHz, CDCl$_3$): δ 7.48 (d, 2H, J=7.9 Hz), 7.44 (d, 1H, J=1.5 Hz), 7.31 (dd, 1H, J=7.9, 1.7 Hz), 7.23 (br d, 2H, J=7.7 Hz), 7.06 (d, 1H, J=7.9 Hz), 4.36 (q, 2H, J=7.0 Hz), 3.60 (br s, 2H), 2.20 (s, 2H), 1.99 (s, 3H), 1.37 (t, 3H, J=7.0 Hz), 1.26 (s, 6H).

6-(3-Fluoro-4-methoxycarbonylmethyl-phenylethynyl)-2,4,4-trimethyl-3,4-dihydro-naphthalene-1-carboxylic acid ethyl ester (Intermediate 202)

Following General Procedure B and using 6-ethynyl-2,4,4-trimethyl-3,4-dihydro-naphthalene-1-carboxylic acid ethyl ester (0.16 g, 0.59 mmol), 2-fluoro-4-iodo phenyl acetic acid methyl ester (Intermediate 200, 0.16 g, 0.56 mmol), triethyl amine (2 mL), copper(I)iodide (0.07 g, 0.37 mmol) and dichlorobis(triphenylphosphine)palladium(II) (0.1 μg, 0.16 mmol) followed by flash column chromatography over silica gel (230-400 mesh) using 12-15% ethyl acetate in hexane as the eluent, the title compound was obtained as a viscous oil (0.15 g, 58%).

$^1$H NMR (300 MHz, CDCl$_3$): δ 7.44 (d, 1H, J=1.5 Hz), 7.32 (dd, 1H, J=7.9, 1.5 Hz), 7.30-7.19 (m, 3H), 7.08 (d, 1H, J=7.9 Hz), 4.37 (q, 2H, J=7.0 Hz), 3.71 (s, 3H), 3.68 (s, 2H), 2.21 (s, 2H), 2.00 (s, 3H), 1.37 (t, 3H, J=7.0 Hz), 1.27 (s, 6H).

6-(4-Carboxymethyl-3-fluoro-phenylethynyl)-2,4,4-trimethyl-3,4-dihydro-naphthalene-1-carboxylic acid ethyl ester (Compound 59)

A solution of 6-(4-carboxymethyl-3-fluoro-phenylethynyl)-2,4,4-trimethyl-3,4-dihydro-naphthalene-1-carboxylic acid ethyl ester (Intermediate 202, 0.15 g, 0.35 mmol) in ethanol (2 mL) was treated with a 1M solution of lithium hydroxide (1 mL, 1 mmol) and the resulting reaction mixture was stirred at ambient temperature for 0.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product (0.1 g, 67%).

$^1$H NMR (300 MHz, CDCl$_3$): δ 7.44 (d, 1H, J=1.5 Hz), 7.32 (dd, 1H, J=8.2, 1.5 Hz), 7.22-7.18 (m, 3H), 7.07 (d, 1H, J=7.9 Hz), 4.36 (q, 2H, J=7.0 Hz), 3.66 (br s, 2H), 2.20 (s, 2H), 1.99 (s, 3H), 1.37 (t, 3H, J=7.0 Hz), 1.26 (s, 6H).

[4-(8,8-Dimethyl-5-trifluoromethanesulfonyloxy-7,8-dihydro-naphthalen-2-ylethynyl)-2-fluoro-phenyl]-acetic acid methyl ester (Intermediate 203)

A solution of [4-(8,8-dimethyl-5-oxo-5,6,7,8-tetrahydro-naphthalen-2-ylethynyl)-2-fluoro-phenyl]-acetic acid methyl ester (U.S. Pat. No. 6,252,090; 0.28 g, 0.77 mmol) in anhydrous dichloromethane (5 mL) was treated with 2,6-di-t-butyl-4-methylpyridine (0.189 g, 0.92 mmol) and trifluoromethanesulfonic anhydride (0.136 mL, 0.81 mmol) and the resulting reaction mixture was stirred at ambient temperature for 4 h at the end of which it was diluted with water and extracted with ethyl acetate. The organic extract was washed with water and brine, dried over anhydrous sodium sulfate, filtered and evaporated in vacuo to a residue that was subjected to flash column chromatography on silica gel (230-400 mesh) using 5% ethyl acetate in hexane as the eluent to afford the title compound as a pale orange oil (0.32 g, 84%).

$^1$H NMR (300 MHz, CDCl$_3$): δ 7.46-7.22(m, 6H), 6.00(t, J=4.8 Hz, 1H), 3.72(s, 3H), 3.70(s, 2H), 2.41(d, J=4.8 Hz, 2H), 1.33(s, 6H).

6-(3-Fluoro-4-methoxycarbonylmethyl-phenylethynyl)-4,4-dimethyl-3,4-dihydro-naphthalene-1-carboxylic acid ethyl ester (Intermediate 204)

Following General Procedure E and using [4-(8,8-dimethyl-5-trifluoromethanesulfonyloxy-7,8-dihydro-naphthalen-2-ylethynyl)-2-fluoro-phenyl]-acetic acid methyl ester (Intermediate 203, 0.32 g, 0.65 mmol), palladium acetate (0.015 g, 0.064 mmol), 1,3-bis(diphenylphosphino)propane (0.027 g, 0.064 mmol), N,N-dimethylformamide (5 mL), ethanol (2 mL) and triethyl amine (2 mL) followed by flash column chromatography over silica gel (230-400 mesh) using 5-15% ethyl acetate in hexane as the eluent the title compound was obtained (0.15 g, 55%) as a yellow oil.

$^1$H NMR (300 MHz, CDCl$_3$): δ 7.84(d, J=8.2 Hz, 1H), 7.47(d, J=1.7 Hz, 1H), 7.37(dd, J=8.2, 1.7 Hz, 1H), 7.30-7.15 (m, 3H), 7.08(t, J=4.8 Hz, 1H), 4.31(q, J=7.0 Hz, 2H), 3.71(s, 3H), 3.68(s, 2H), 2.34(d, J=4.8 Hz, 2H), 1.37(t, J=7.0 Hz, 3H), 1.28(s, 6H).

6-(4-Carboxymethyl-3-fluoro-phenylethynyl)-4,4-dimethyl-3,4-dihydro-naphthalene-1-carboxylic acid ethyl ester (Compound 60)

A solution of 6-(3-fluoro-4-methoxycarbonylmethyl-phenylethynyl)-4,4-dimethyl-3,4-dihydro-naphthalene-1-carboxylic acid ethyl ester (Intermediate 204, 0.15 g, 0.36 mmol) in ethanol (3 mL) and tetrahydrofuran (3 mL) was treated with a 2M solution of lithium hydroxide (1.5 mL, 3 mmol) and the resulting reaction mixture was stirred at ambient temperature for 1.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 5% water in acetonitrile as the mobile phase to afford the title product (0.04 g, 27%).

$^1$H NMR (300 MHz, CDCl$_3$): δ 7.81(d, J=8.2 Hz, 1H), 7.46(d, J=1.7 Hz, 1H), 7.37(dd, J=8.2 & 1.7 Hz, 1H), 7.27-7.09(m, 3H), 7.07(t, J=4.8 Hz, 1H), 4.31(q, J=7.0 Hz, 2H), 3.66(s, 2H), 2.33(d, J=4.8 Hz, 2H), 1.37(t, J=7.0 Hz, 3H), 1.27(s, 6H).

Reaction Scheme 32

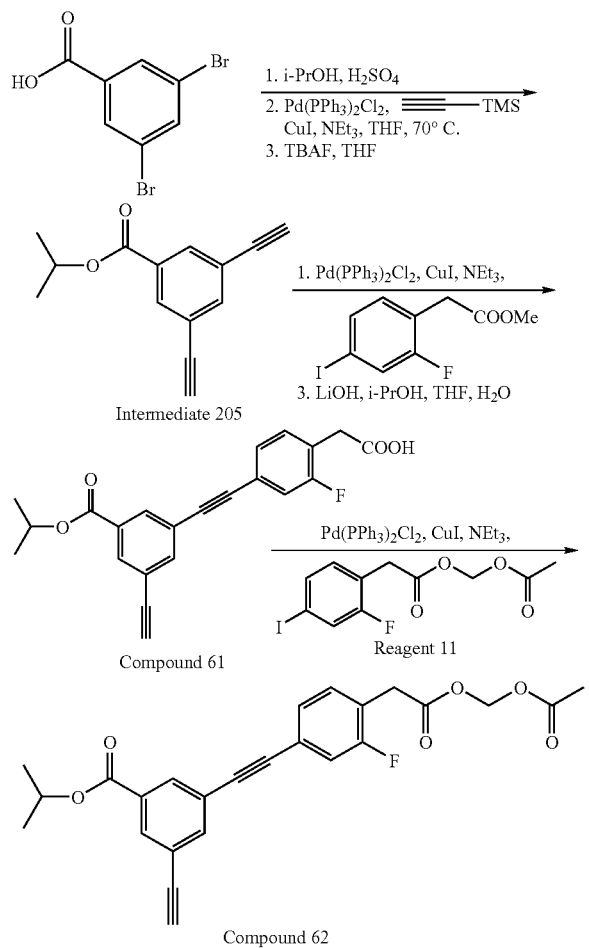

3,5-Dibromo-benzoic acid isopropyl ester (Intermediate 205)

A solution of 3,5-dibromobenzoic acid (Aldrich, 2.4 g, 8.6 mmol) in benzene (150 mL) and isopropanol (50 mL) was treated with concentrated sulfuric acid (2 mL) and heated to reflux overnight using a Dean-Stark water trap. The volatiles were evaporated in vacuo, the residue was diluted with water and extracted with diethyl ether. The organic phase was washed with water and saturated, aqueous sodium bicarbonate solution, dried over anhydrous magnesium sulfate, filtered and evaporated in vacuo to afford the title product as a clear oil that was used as such for the next step (2.7 g, ~100%).

3,5-Diethynyl-benzoic acid isopropyl ester (Intermediate 206)

Following General Procedure D and using 3,5-dibromo-benzoic acid isopropyl ester (Intermediate 205, 2.7 g, 8.6 mmol), triethyl amine (30 mL), copper(I)iodide (0.45 g, 2.4 mmol), trimethylsilyl acetylene (6.8 mL, 48 mmol) and dichlorobis(triphenylphosphine)palladium(II) (1.75 g, 2.4 mmol) followed by flash column chromatography over silica gel (230-400 mesh) using 3% ethyl acetate in hexane as the eluent, the intermediate 3,5-bis-trimethylsilanylethynyl-benzoic acid isopropyl ester was obtained. The intermediate (2.8 g, 7.85 mmol) was treated with a 1M solution of tetra-n-butyl ammonium fluoride in tetrahydrofuran (25 mL, 25 mmol) and the resulting reaction mixture was stirred in an ice bath for 1 h. Water was added and the reaction mixture was extracted with diethyl ether. The organic phase was washed with water and brine, dried over anhydrous sodium sulfate, filtered and evaporated to an oil that was redissolved in diethyl ether (10 mL) and treated with hexane (150 mL). The solid that precipitated out was filtered and dried to afford the title compound (1.3 g, 78%).

$^1$H NMR (300 MHz, CDCl$_3$): δ 8.08 (d, 1H, J=1.4 Hz), 7.73 (d, 1H, J=1.4 Hz), 5.23 (heptet, 1H, J=6.3 Hz), 3.13 (s, 2H), 1.35 (d, 6H, J=6.1 Hz).

3-Ethynyl-5-[3-fluoro-4-(3-trimethylsilanyl-propoxycarbonylmethyl)-phenylethynyl]-benzoic acid isopropyl ester (Intermediate 207)

Following General Procedure B and using 3,5-diethynyl-benzoic acid isopropyl ester (Intermediate 206, 0.36 g, 1.72 mmol), (2-fluoro-4-iodo-phenyl)-acetic acid 2-trimethylsilanyl-ethyl ester (0.132 g, 0.86 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230-400 mesh) using 5-10% ethyl acetate in hexane as the eluent, the title compound was obtained as a colorless oil (0.15 g, 37%).

$^1$H NMR (300 MHz, CDCl$_3$): δ 8.10 (m, 1H), 8.07(m, 1H), 7.75(m, 1H), 7.19-7.25(m, 3H), 5.24(hept, J=6.2 Hz, 1H), 4.19(t, J=8.5 Hz, 2H), 3.64(s, 2H), 3.14(s, 1H), 1.35(d, J=6.2 Hz, 6H), 0.97(t, J=8.5 Hz, 2H), 0.00(s, 9H).

3-(4-Carboxymethyl-3-fluoro-phenylethynyl)-5-ethynyl-benzoic acid isopropyl ester (Compound 61)

A solution of 3-ethynyl-5-[3-fluoro-4-(3-trimethylsilanyl-propoxycarbonylmethyl)-phenylethynyl]-benzoic acid isopropyl ester (Intermediate 207, 0.15 g, 0.32 mmol) in anhydrous dimethysulfoxide (4 mL) was treated with tetra-n-ethyl ammonium fluoride (0.19 mL, 1.3 mmol) and the resulting reaction mixture was stirred at ambient temperature for 5 min. Water was added and the reaction mixture was extracted with ethyl acetate. The organic phase was washed with water and brine, dried over anhydrous sodium sulfate, filtered and evaporated to an oil that was purified by recrystallization from ethyl acetate/hexane to afford the title compound as a white solid (0.045 g, 38%).

$^1$H NMR (300 MHz, CDCl$_3$): δ 8.13 (m, 1H), 8.10(m, 1H), 7.78(m, 1H), 7.23-7.30(m, 3H), 5.29(hept, J=6.4 Hz, 1H), 3.74(s, 2H), 3.15(s, 1H), 1.38(d, J=6.4 Hz, 6H).

3-(4-Acetoxymethoxycarbonylmethyl-3-fluoro-phenylethynyl)-5-ethynyl-benzoic acid isopropyl ester (Compound 62)

Following General Procedure B and using 3,5-diethynyl-benzoic acid isopropyl ester (Intermediate 206, 0.27 g, 1.27 mmol), (2-fluoro-4-iodo-phenyl)-acetic acid acetoxymethyl ester (0.224 g, 0.64 mmol), triethyl amine (8 mL), copper(I) iodide (0.019 g, 0.1 mmol) and dichlorobis(triphenylphosphine)palladium(II) (0.07 g, 0.1 mmol) followed by flash column chromatography over silica gel (230-400 mesh) using 2.5-20% ethyl acetate in hexane as the eluent, the title compound was obtained as an orange solid (0.09 g, 32%).

$^1$H NMR (300 MHz, CDCl$_3$): δ 8.13 (m, 1H), 8.10(m, 1H), 7.79 (m, 1H), 7.23-7.32(m, 3H), 5.78(s, 2H), 5.27(hept, J=6.4 Hz, 1H), 3.75(s, 2H), 3.15(s, 1H), 2.12 (s, 3H), 1.38(d, J=6.4 Hz, 6H).

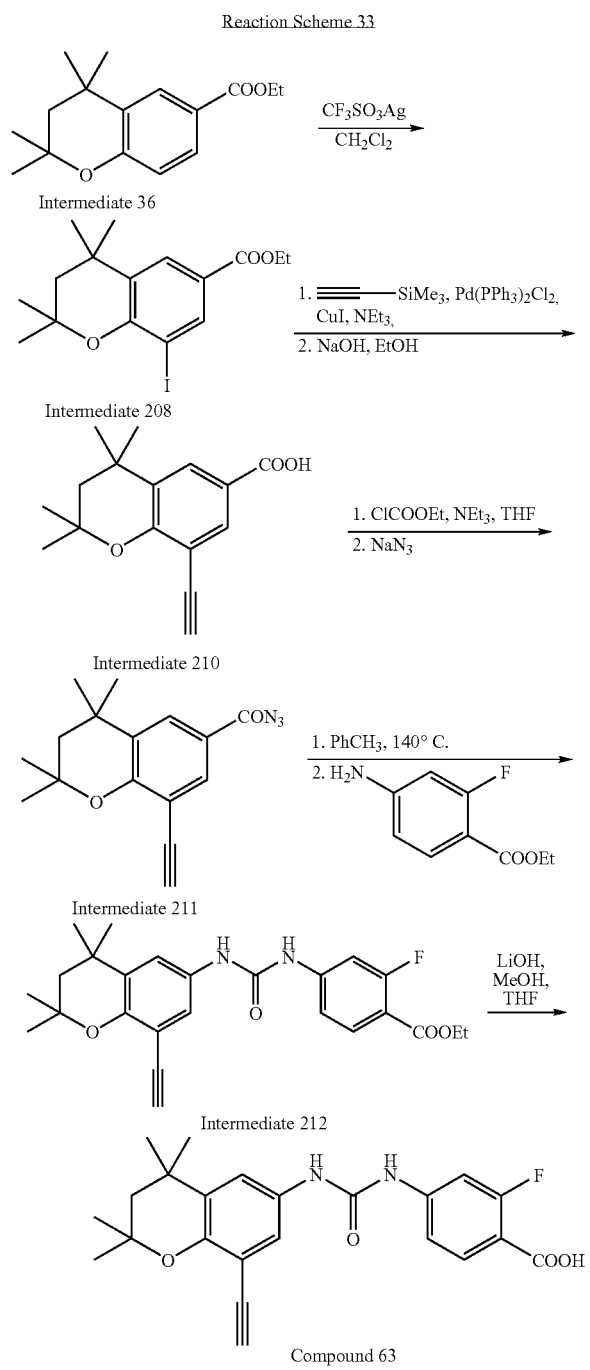

Reaction Scheme 33 drous magnesium sulfate, filtered and evaporated in vacuo to a residue which was subjected to flash column chromatography over silica gel (230-400 mesh) using 5-10% ethyl acetate in hexane as the eluent to afford the title compound (0.88 g, 81%) as a pale yellow oil.

$^1$H NMR (300 MHz, CDCl$_3$): δ 8.26 (d, 1H, J=2.0 Hz), 7.96 (d, 1H, J=2.0 Hz), 4.34(q, 2H, J=7.1 Hz), 1.87 (s, 2H), 1.40(s, 6H), 1.37 (s, 6H), 1.41-1.35(m, 3H).

Ethyl-8-trimethylsilanylethynyl-2,2,4,4-tetramethyl chroman-6-carboxylate (Intermediate 209)

A solution of ethyl-8-iodo-2,2,4,4-tetramethyl chroman-6-carboxylate (Intermediate 208, 0.88 g, 2.26 mmol) in triethyl amine (10 mL) was treated with copper(I)iodide (0.043 g, 0.226 mmol) and sparged with argon for 5 minutes. Trimethylsilyl acetylene (3 mL, 21.22 mmol) was then added followed by dichlorobis(triphenylphosphine)palladium(II) (0.159 g, 0.226 mmol). The resulting reaction mixture was heated at 70° C. overnight in a sealed tube. It was then cooled to ambient temperature, diluted with diethyl ether and filtered over a bed of celite. The filtrate was evaporated vacuo to an oil which was subjected to flash column chromatography over silica gel (230-400 mesh) using 10% ethyl acetate in hexane as the eluent to afford the title compound (0.803 g, 99%).

$^1$H NMR (300 MHz, CDCl$_3$): δ 7.93 (s, 1H), 7.92 (s, 1H), 4.32(q, 2H, J=7.0 Hz), 1.86 (s, 2H), 1.38(s, 6H), 1.34 (s, 6H), 1.38-1.34(m, 3H), 0.24(s, 9H).

8-Ethynyl-2,2,4,4-tetramethyl chroman-6-carboxylic acid (Intermediate 210)

A solution of ethyl-8-trimethylsilanylethynyl-2,2,4,4-tetramethylchroman-6-carboxylate (Intermediate 209, 0.525 g, 1.47 mmol) in ethanol (5 mL) was treated with 2N aqueous sodium hydroxide solution (5 mL, 10 mmol) and the resulting solution was adjusted to pH ~5 with 10% aqueous hydrochloric acid and extracted with ethyl acetate. The organic phase was dried over anhydrous magnesium sulfate, filtered and evaporated in vacuo to afford the title product as a brown solid (0.316 g, 84%).

$^1$H NMR (300 MHz, CDCl$_3$): δ 8.02(s, 2H), 3.23(s, 1H), 1.89 (s, 2H), 1.42(s, 6H), 1.38(s, 6H).

8-Ethynyl-2,2,4,4-tetramethyl-chroman-6-carboxylic acid azide (Intermediate 211)

A stirred, cooled (ice bath) solution of 8-ethynyl-2,2,4,4-tetramethyl-chroman-6-carboxylic acid (Intermediate 210, 0.52 g, 2 mmol) in anhydrous tetrahydrofuran (10 mL) under argon, was treated with triethyl amine (0.86 mL, 6 mmol) follwed by ethyl chloroformate (0.25 mL, 2.6 mmol) and the resulting reaction mixture was allowed to warm to ambient temperature and stirred for 2 h. Sodium azide 0.19 g, 3 mmol) was added and the reaction mixture was stirred overnight. The reaction mixture was then diluted with water and extracted with diethyl ether. The organic extract was dried over anhydrous magnesium sulfate, filtered and evaporated to a residue that was purified by flash column chromatography over silica gel (230-400 mesh) to afford the title compound as a yellow solid (0.32 g, 56%).

$^1$H NMR (300 MHz, CDCl$_3$): δ 7.96 (ABq, 2H, J=2.1 Hz), 3.24(s, 1H), 1.89 (s, 2H), 1.42 (s, 6H), 1.37 (s, 6H).

Ethyl-8-iodo-2,2,4,4-tetramethyl chroman-6-carboxylate (Intermediate 208)

A solution of ethyl-2,2,4,4-tetramethyl chroman-6-carboxylate (Intermediate 36, 0.733 g, 2.8 mmol) in anhydrous dichloromethane (10 mL) was treated with silver(I)trifluoromethanesulfonate (0.719 g, 2.8 mmol) and iodine (0.71 g, 2.8 mmol) and the resulting solution was stirred at ambient temperature for 4 h. The reaction mixture was treated with saturated, aqueous sodium thiosulfate solution and extracted with ethyl acetate. The organic phase was dried over anhy-

4-[3-(8-Ethynyl-2,2,4,4-tetramethyl-chroman-6-yl)-ureido]-2-fluoro-benzoic acid ethyl ester (Intermediate 212)

A solution of 8-ethynyl-2,2,4,4-tetramethyl-chroman-6-carboxylic acid azide (Intermediate 211, 0.104 g, 0.37 mmol) in anhydrous toluene was refluxed under argon overnight. Ethyl-4-amino-2-fluoro-benzoate (described in Teng et al, Journal of Medicinal Chemistry, 1996, 39, p3035-3038, 0.114 g, 0.622 mmol) was added and the reaction mixture was refluxed for 5.5 h. The reaction mixture was cooled to ambient temperature and subjected to flash column chromatography over silica gel (230-400 mesh) using 20-33% ethyl acetate in hexane as the eluent to afford the title compound contaminated with some ethyl-4-amino-2-fluoro-benzoate. It was used as such for the next step.

4-[3-(8-Ethynyl-2,2,4,4-tetramethyl-chroman-6-yl)-ureido]-2-fluoro-benzoic acid (Compound 63)

A solution of 4-[3-(8-ethynyl-2,2,4,4-tetramethyl-chroman-6-yl)-ureido]-2-fluoro-benzoic acid ethyl ester (Intermediate 212, 0.12 g) in methanol (2 mL), tetrahydrofuran (2 mL) and water (1 mL) was treated with lithium hydroxide (0.177 g, 4.2 mmol) and the resulting reaction mixture was stirred at ambient temperature overnight. The volatiles were evaporated in vacuo, the residue was diluted with water and neutralized with dilute hydrochloric acid and extracted with ethyl acetate. The organic phase was dried over anhydrous magnesium sulfate, filtered and evaporated to afford the title compound as a solid (0.07 g, 46% for two steps).
$^1$H NMR (300 MHz, $CD_3OD$): δ 7.86 (dd, 1H, J=8.8, 8.5 Hz), 7.53 (dd, 1H, J=13.7, 2.0 Hz), 7.42 (d, 1H, J=2.3 Hz), 7.28 (d, 1H, J=2.3 Hz), 7.14 (dd, 1H, J=2.0, 8.8 Hz), 3.50(s, 1H), 1.86 (s, 2H), 1.35 (s, 12H).

Alternatively, the composition can be pressurized and contain a compressed gas, such as nitrogen or a liquefied gas propellant. The liquefied propellant medium and indeed the total composition is preferably such that the active inhibitor does not dissolve therein to any substantial extent.

It is understood that modifications that do not substantially affect the activity of the various embodiments of this invention are also included within the definition of the invention provided herein. Accordingly, the following examples are intended to illustrate but not limit the present invention.

EXAMPLE I

Inhibition of Hamster Sebaceous Gland Differentiation by Blocking Retinoic Acid Receptor Signaling This example shows that inhibitors of CYP26B block sebaceous gland differentiation in hamsters.

Differentiation of hamster flank organ sebaceous gland is a model system for development of acne. To determine the effectiveness of selective CYP26B inhibitors for treating acne, such inhibitors were tested in this model system. To confirm that this model system can predict the effectiveness of a compound in reducing acne, 13-cis retinoic acid (acutane) was used as a positive control. As shown in FIG. 1, 13-cis retinoic acid was effective in reducing sebaceous gland differentiation in hamster flank organ.

For the hamster model system, male golden syrian hamsters were fed LabDiet#5002 rodent diet and housed individually on a 14/10 hr light/dark cycle. For treatment, the animals were randomized according to body weight and they were also weighed at each treatment so that the drug doses could be adjusted accordingly. The animals were treated daily by oral gavage, 6 days/week for 4 weeks. At the end of treatments, the animals were sacrificed by carbon dioxide inhalation. The flank organs were then excised and spread on a small piece of index card which was placed in a histology cassette for fixation in 10% buffered formaldehyde. The specimen was divided into 5 equally spaced portions to make paraffin blocks and one 5-micrometer H&E sections was prepared from each block. The two sections that contained the most sebaceous glands were used to determine the average acini area of the flank organ. A video camera attached to a standard microscope with the 4× objective was used to capture the images of the sebaceous glands. Computer programs Videoshop and NIH Image 1.63 were used to quantify the acini areas. All the recognizable sebaceous glands in the two sections were analyzed and the means were derived for comparison among various treatments. In all studies, blood samples were also collected for determining the levels of serum triglyceride using a triglyceride GPO Trinder kit from Sigma Chemicals (St. Louis, Mo.).

Figure 2:
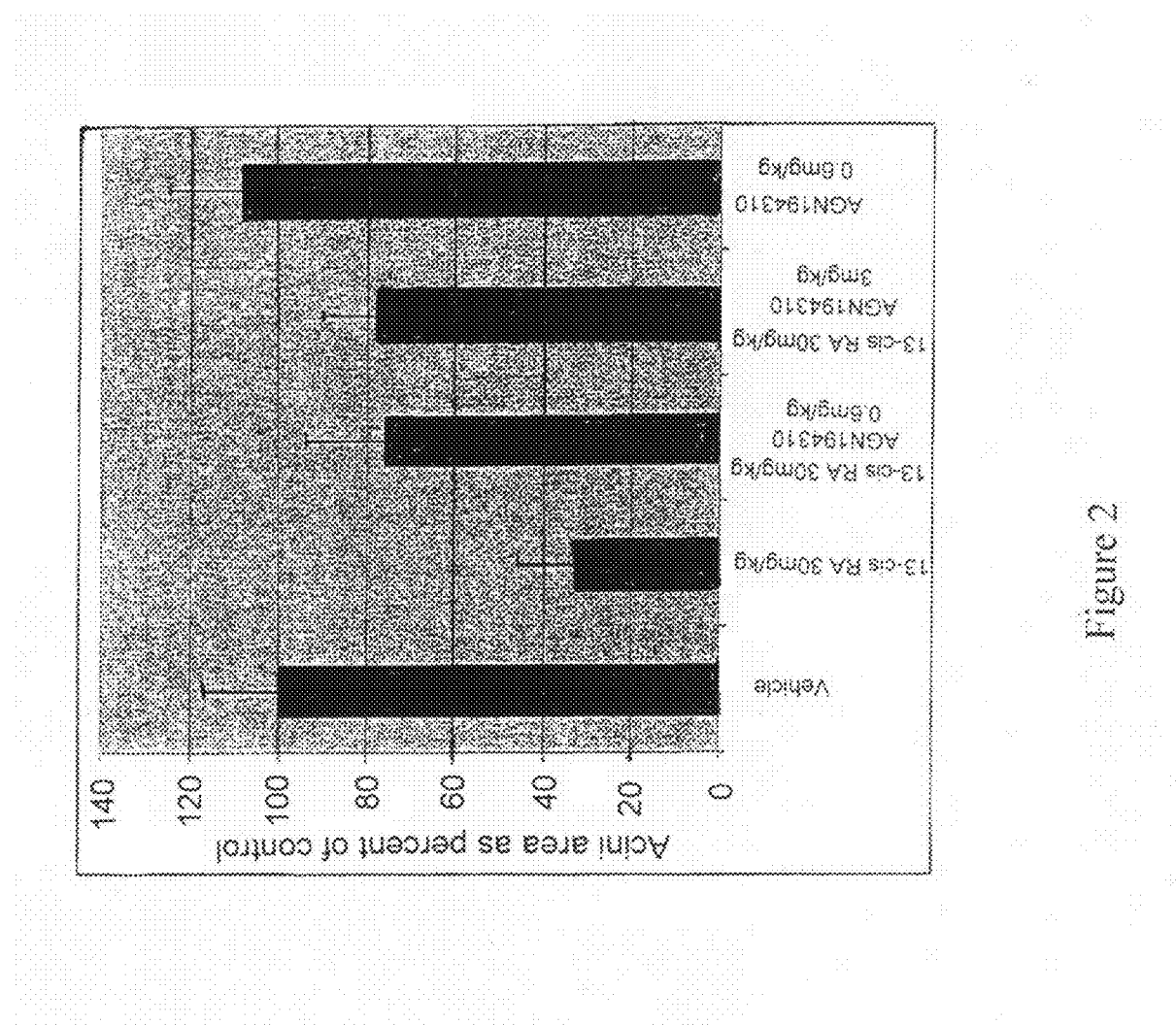
FIG. 2 shows that 13-cis retinoic acid activity on sebaceous gland differentiation can be blocked by a retinoic acid receptor antagonist.

To determine if retinoic acid receptor (RAR) signaling is required for 13-cis retinoic acid-induced reduction in differentiation of hamster flank organ sebaceous gland, an RAR pan-antagonist was tested. As shown in FIG. 2, RAR pan-antagonist (AGN194310) blocked the effect of 13-cis retinoic acid treatment on sebaceous gland differentiation.

Experimental results showing the effect of various retinoid compounds on differentiation of sebaceous gland in banister flank organ were generated. These results indicate that activation of retinoic acid receptor signaling is sufficient to reduce sebaceous gland differentiation. However, toxicity of RAR-agonists such as TTNPB was observed at effective doses. Inactive pro-drugs such as 13-cis retinoic acid and 4-oxo-13-cis RA, which have lower toxicity levels, appeared to be more effective.

Because CYP26 functions in cells to reduce retinoic acid receptor signaling, the effect of inhibiting CYP26 to increase retinoic acid receptor signaling, and thereby reduce differentiation of hamster sebaceous gland differentiation, was examined. The expression of CYP26A and CYP26B in hamster flank organ sebaceous gland was determined using Taqman RT-PCR. Hamsters were treated as described above and sacrificed at various time points (1 day to 3 weeks). The flank organs were excised and placed under a dissecting microscope. Sebaceous glands were removed and put into liquid nitrogen immediately. RNAs were isolated from the glands using Trizol reagents (Invitrogen; San Diego, Calif.) as described by the manufacturer. The RNAs were treated with DNase to remove contaminating genomic DNAs and further purified with the DNA-free kit (Ambion; Austin, Tex.). Quantitative RT-PCR was performed on an ABI 7700 machine using Invitrogen's Platinum qRT-PCR kit with CYP26-specific primers and probes.

As shown in Table 2, both CYP26A and CYP26B are expressed in hamster flank sebaceous gland, and expression of both is induced by 13-cis retinoic acid. CYP26B expression appears to be higher in cells at a later stage of differentiation.

Figure 3:
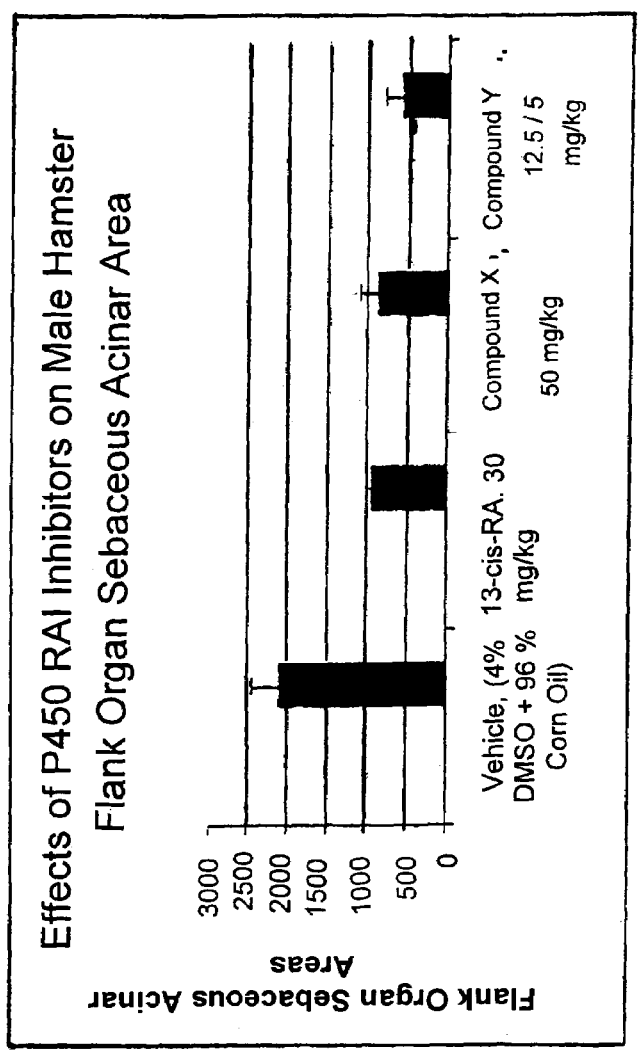
FIG. 3 shows that a selective CYP26A and a selective CYP26B inhibitor both are effective in reducing sebaceous gland differentiation in hamster flank organ.

As shown in FIG. 3 Compound X (AGN 198790, see Table 3) (50 mg/kg) and Compound Y (AGN 199713, see Table 3) (12.5 mg/kg) reduced hamster flank sebaceous gland differentiation at least as effectively as 13-cis retinoic acid (30 mg/kg). Compound X is a selective inhibitor of CYP26A that has at least 10-fold selectivity for CYP26A relative to CYP26B. Compound Y is a selective inhibitor of CYP26B that has at least 10-fold selectivity for CYP26B relative to CYP26A. The chemical structures of these compounds are shown in Table 3, below. Therefore, selective inhibitors of CYP26A or CYP26B are expected to effectively reduce or prevent acne.

TABLE 2

| Experiment | Sample | hacyp26b Ct | Relative to veh | hacyp26a Ct | Relative to Veh |
|---|---|---|---|---|---|
| HFO-9 | Veh 4d | 34.3 | 1× | 32.6 | 1× |
|  | 13cisRA 4d | 30.6 | 13× | 28.1 | 22.6× |
|  | Veh 1w | 33.3 | 1× | 33.4 | 1× |
|  | 13cisRA 1w#1 | 31.8 | 2.8× | 29.6 | 13.9× |
| Feb. 11, 2002 | 13cisRA 1w#2 | 30.5 | 7.0× | 29.8 | 12.1× |
|  | 13cisRA 2w#2 | 34.1 | 0.6× | 30.1 | 9.8× |
|  | 13cisRA 3w#1 | 36.7 | 0.1× | 33 | 1.3× |
|  | 13cisRA 3w#2 | 35.7 | 0.2× | 31.9 | 2.8× |
|  | No temp | 45 |  | 50 |  |

In summary, this example demonstrates that selective inhibitors of CYP26 are effective in reducing hamster flank sebaceous gland differentiation, a model system for development of acne.

EXAMPLE II

Cell-Based Method for Identifying CYP26 Inhibitors

This example describes a cell-based assay for identifying compounds that selectively inhibit CYP26A or CYP26B activity.

CYP26A and CYP26B stably transfected HeLa cells were maintained in 100 mm tissue culture dishes in MEM medium containing 10% FBS and 100 µg/ml hygromycin.

Exponentially growing cells were harvested by incubating in trypsin. Cells were then washed with 1×PBS and plated in a 48-well plate at 5×10$^5$ cells in 0.2 ml MEM medium containing 10% FBS and 0.05 µCi [$^3$H]-RA in the presence or absence of increasing concentrations of the test compounds. The compounds were diluted in 100% DMSO and then added to triplicate wells at final concentrations of 10, 1 or 0.1 µM. As a positive control for RA metabolism inhibition, cells were also incubated with ketoconazole at 100, 10 and 1 µM. Cells were incubated for 3 hours at 37° C. The retinoids were then extracted using a modified Bligh and Dyer procedure (Bligh and Dyer, supra (1959)), in which methylene-chloride, as opposed to chloroform, was used, and the aqueous soluble radioactivity quantified using a β-scintillation counter. ID$_{50}$ values represent the concentration of inhibitor required to inhibit RA metabolism by 50 percent and were derived manually from log-transformed data.

Table 3 shows a variety of compounds identified as inhibiting CYP26A or CYP26B selectively. The listed compounds were determined to have no substantial RAR. inhibiting activity. To determine selectivity of a CYP26A inhibitor, the ID$_{50}$ of the inhibitor with respect to CYP26A was divided by the ID$_{50}$ of the inhibitor with respect to CYP26B. To determine selectivity of a CYP26B inhibitor, the ID$_{50}$ of the inhibitor with respect to CYP26B was divided by the ID$_{50}$ of the inhibitor with respect to CYP26A.

TABLE 3

| AGN# | STRUCTURE | RAR EC$_{50}$/(Efficacy)/K$_d$ nM | | | CYP26 INHIBITION DATA | |
|---|---|---|---|---|---|---|
|  |  | α | β | γ | CYP26A Intact cells IC$_{50}$ µM | CYP26B Intact cells IC$_{50}$ µM |
| 198790 | 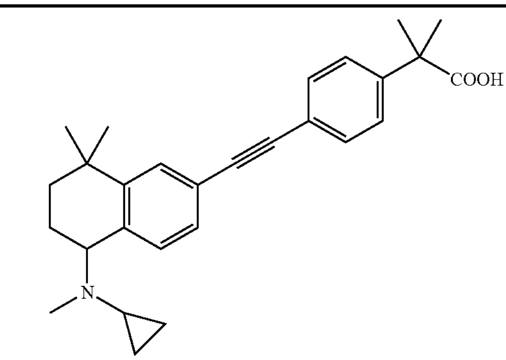 | NA >10K | WA (<5) >10K | NA >10K | 0.6 | >10 |
| 199713 | 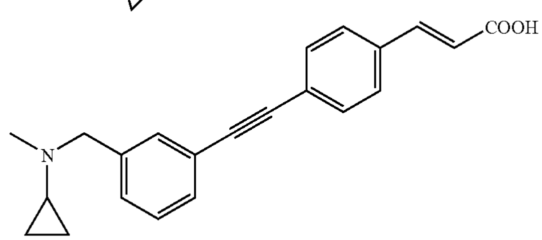 | NA >10K | WA (25) >10K | NA >10K | >10 | 0.6 |

Note:
WA = Weakly Active;
NA = Not Active

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating an individual having a retinoid responsive skin disorder selected from the group consisting of acne, psoriasis, eczema, atopic dermatitis, Pityriasis rubra pilaris, multiple basal cell carcinomasactinic keratoses, arsenic keratoses, ichthyoses, Darriers disease, lichen planus, glucocorticoid damage, microbial infection of the skin, excessive pigmentation of the skin, and photodamage of the skin, comprising administering to said individual an effective amount of a selective CYP26A inhibitor having a formula selected from:

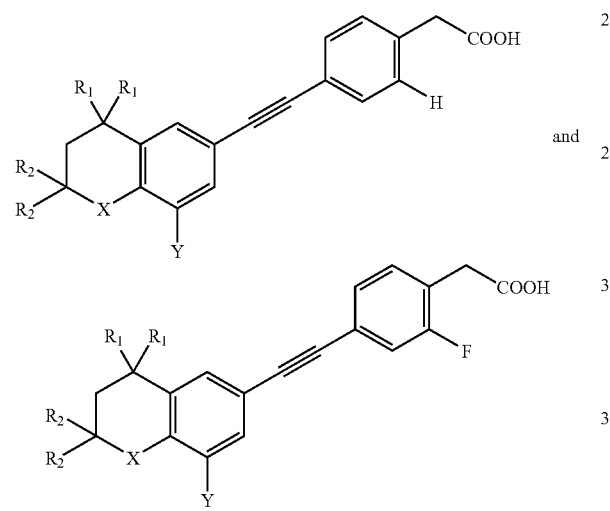

wherein,
$R_1=R_2=Me$;
$X=O$ or $S$; and
$Y=CH_2N(Me)(cyc-Pr)$, OR, COOR, wherein R=lower alkyl, cycloalkyl; or
$R_1=Me$;
$R_2=H$;
$X=H(C)CH_2N(Me)(cyc-Pr)$; and
$Y=OR$, COOR wherein R=lower alkyl, or cycloalkyl; or
$R_1=Me$;
$R_2=H$;
$X=C=O$; and
$Y=$alkenyl,
or a pharmaceutically acceptable salt, ester, amide, stereoisomer or racemic mixture thereof.

2. The method of claim 1, wherein said administering is oral administering.

3. The method of claim 1, wherein said inhibitor is administered peripherally.

4. The method of claim 1, wherein said individual is a human.

5. The method of claim 1, wherein the retinoid responsive skin disorder is acne, psoriasis or eczema.

6. A method for treating an individual having a retinoid responsive skin disorder selected from the group consisting of acne, psoriasis, eczema, atopic dermatitis, Pityriasis rubra pilaris, multiple basal cell carcinomasactinic keratoses, arsenic keratoses, ichthyoses, Darriers disease, lichen planus, glucocorticoid damage, microbial infection of the skin, excessive pigmentation of the skin, and photodamage of the skin, comprising administering to said individual an effective amount of a selective CYP26A selected from:

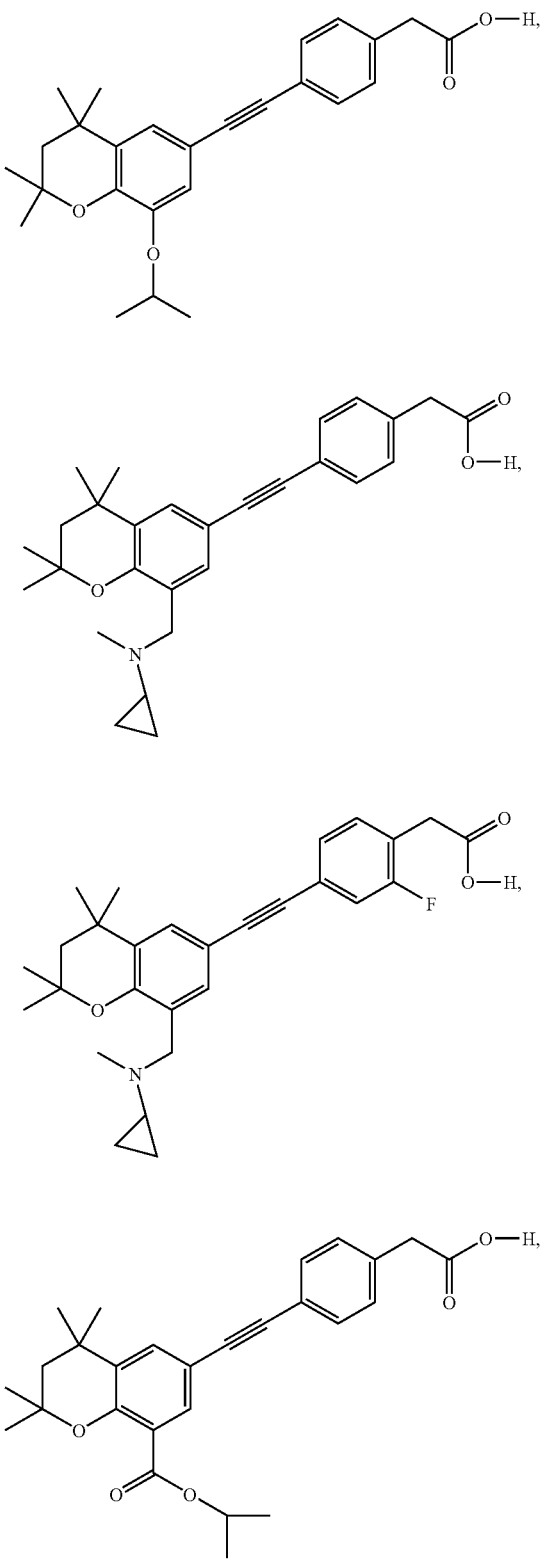

-continued
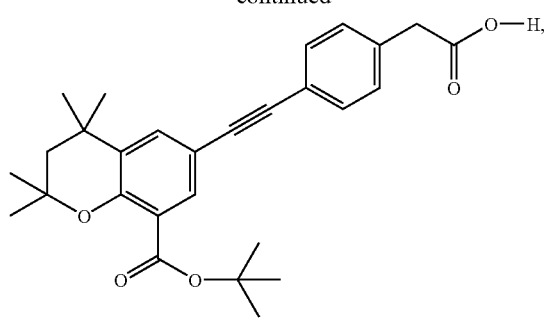
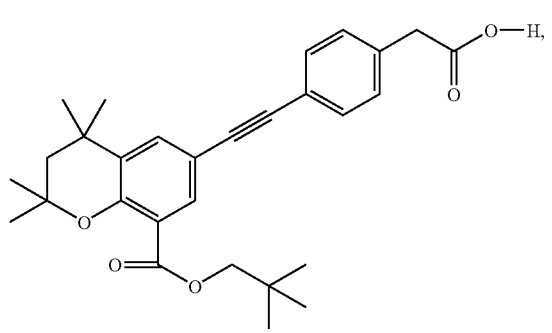
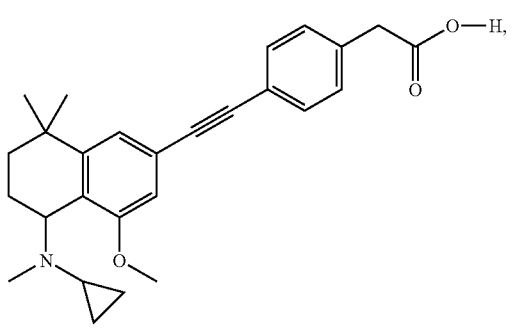
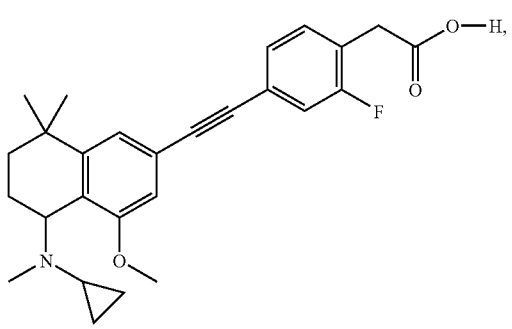
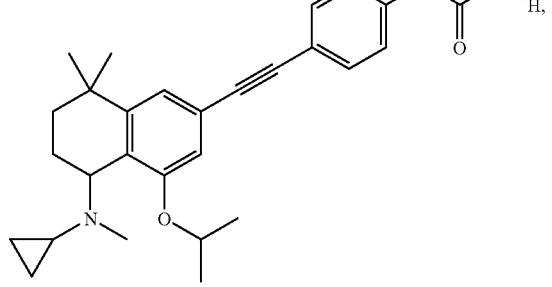
-continued
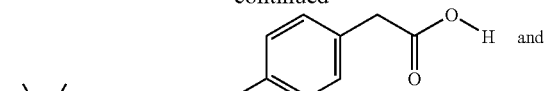
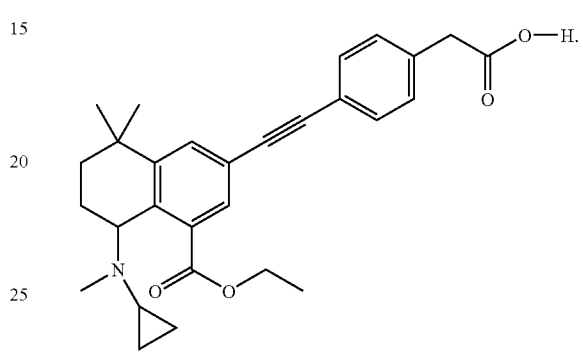
7. A method for treating an individual having acne, comprising administering to said individual an effective amount of a selective CYP26A inhibitor having a formula selected from:
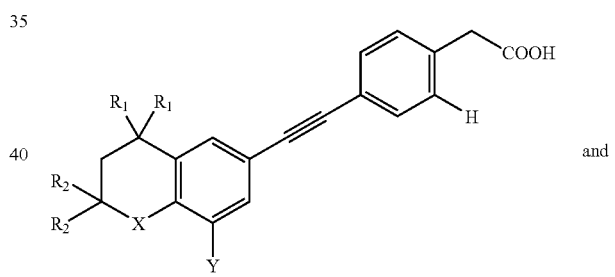
and
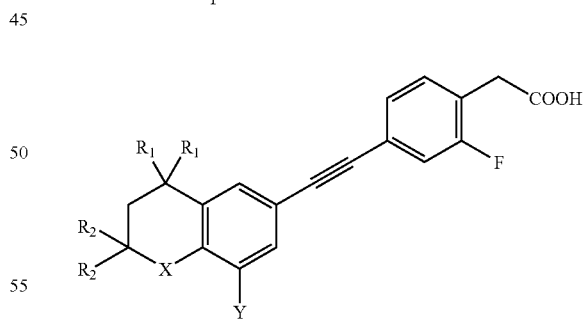
wherein,
R₁=R₂=Me;
X=O or S; and
Y=CH₂N(Me)(cyc-Pr), OR, COOR, wherein R=lower alkyl, cycloalkyl; or
R₁=Me;
R₂=H;
X=H(C)CM₂N(Me)(cyc-Pr); and Y=OR, COOR wherein R=lower alkyl, or cycloalkyl; or
R₁=Me;
R₂=H;
X=C=O; and
Y=alkenyl, or a pharmaceutically acceptable salt, ester, amide, stereoisomer or racemic mixture thereof.

8. The method of claim 7, wherein said administering is oral administering.

9. The method of claim 7, wherein said inhibitor is administered peripherally.

10. The method of claim 7, wherein said individual is a human.

11. The method of claim 7, wherein the acne is selected from the group consisting of superficial acne, deep acne, acne vulgaris, acne conglobata, acne fulminans, acne medicamentosa, comedonal acne and cystic acne.

12. A method for treating an individual having acne, comprising administering to said individual an effective amount of a selective CYP26A inhibitor selected from:

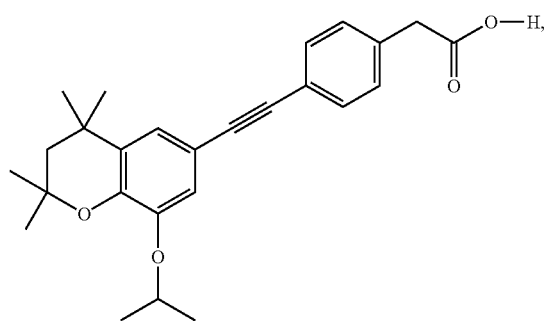

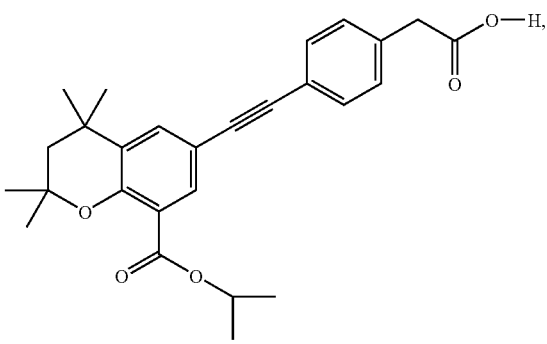

-continued

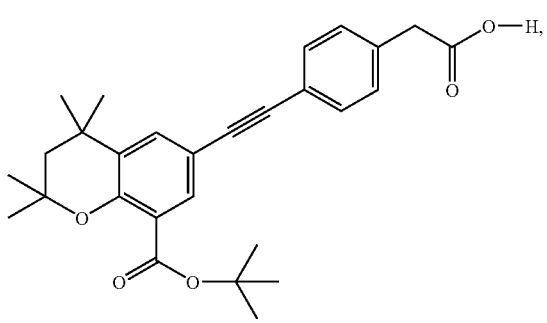

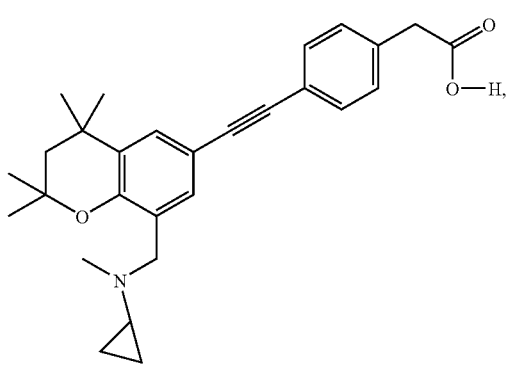

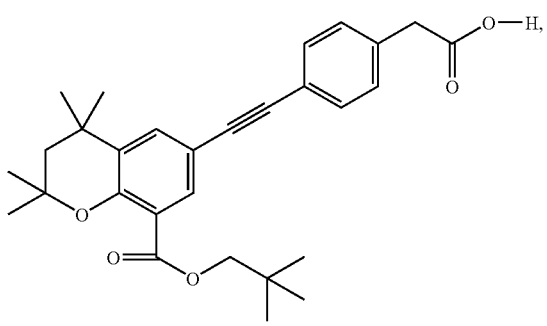

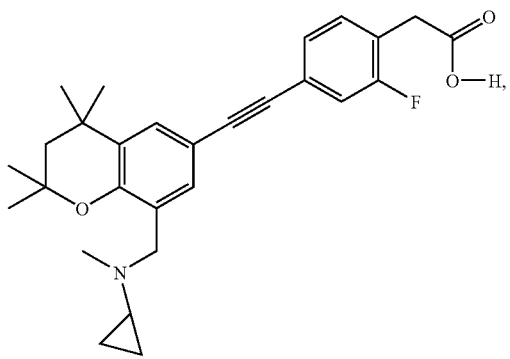

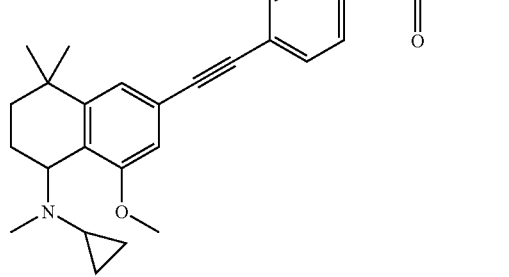

201
-continued
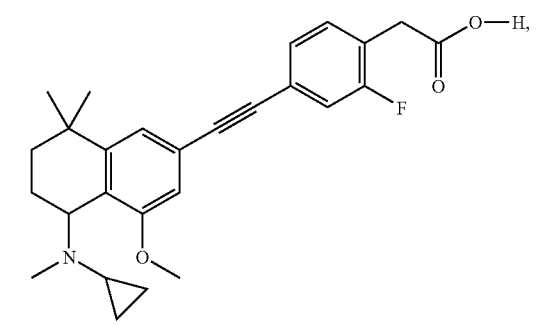
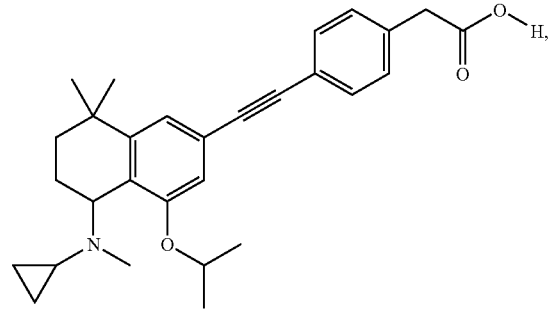
202
-continued
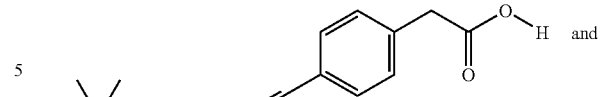
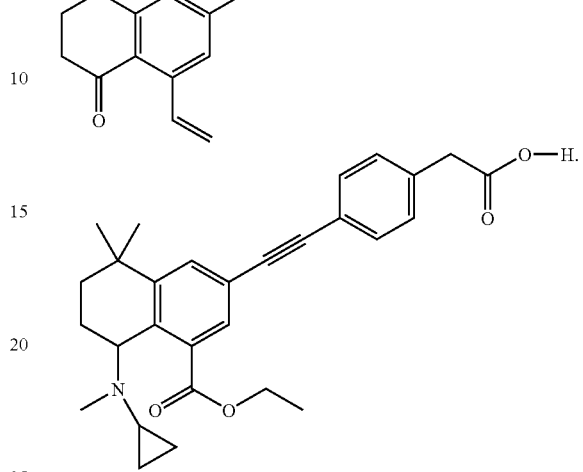
* * * * *